(12) United States Patent
Chang et al.

(10) Patent No.: US 8,506,948 B2
(45) Date of Patent: Aug. 13, 2013

(54) UCB-MSCS COMPRISING A TUMOR SUPPRESSOR GENE REDUCE THE SIZE OF AN IL-8 OR GRO-αEXPRESSING TUMOR

(75) Inventors: Jong Wook Chang, Seoul (KR); Dal Soo Kim, Seoul (KR); Yoon-Sun Yang, Seoul (KR); Won Il Oh, Seoul (KR)

(73) Assignee: Medipost Co., Ltd., Seoul (KR)

( * ) Notice: Subject to any disclaimer, the term of this patent is extended or adjusted under 35 U.S.C. 154(b) by 29 days.

(21) Appl. No.: 12/633,622

(22) Filed: Dec. 8, 2009

(65) Prior Publication Data
US 2010/0143261 A1 Jun. 10, 2010

Related U.S. Application Data

(63) Continuation-in-part of application No. PCT/KR2008/005026, filed on Aug. 27, 2008.

(60) Provisional application No. 60/972,966, filed on Sep. 17, 2007, provisional application No. 61/089,733, filed on Aug. 18, 2008.

(30) Foreign Application Priority Data

Aug. 29, 2007 (KR) .................. 10-2007-0087228
Jul. 10, 2008 (KR) .................. 10-2008-0067247

(51) Int. Cl.
*C12N 15/00* (2006.01)
*A01N 63/00* (2006.01)
*A61K 48/00* (2006.01)

(52) U.S. Cl.
USPC .................. 424/93.21; 435/455; 514/44 R

(58) Field of Classification Search
None
See application file for complete search history.

(56) References Cited

U.S. PATENT DOCUMENTS

2008/0241115 A1  10/2008  Suh et al.

FOREIGN PATENT DOCUMENTS

| EP | 1658853 A1 | 5/2006 |
|---|---|---|
| KR | 1020030069115 A | 8/2003 |
| KR | 10-2004-0022134 A | 3/2004 |
| KR | 100489248 B1 | 5/2005 |
| KR | 10-2007-0036289 A | 4/2007 |
| WO | 2005/005601 A2 | 1/2005 |
| WO | WO 2005/007176 | 1/2005 |
| WO | WO 2006/019357 A1 | 2/2006 |
| WO | 2007/011693 A2 | 1/2007 |
| WO | WO-2007037653 A1 | 4/2007 |
| WO | WO-2009028870 A2 | 3/2009 |
| WO | WO-2009028870 A3 | 3/2009 |

OTHER PUBLICATIONS

Miletic et al. Bystander Killing of Malignant Glioma by Bone Marrow-derived Tumor-Infiltrating Progenitor Cells Expressing a Suicide Gene Molecular Therapy, 2007, vol. 15, pp. 1373-1781.*
Furukawa et al. PTEN gene transfer suppresses the invasive potential of human malignant gliomas by regulating cell invasion-related molecules. Internat. J. Onocoloy, 2006, vol. 29, pp. 73-81.*
Tanaka et al. In vivo gene therapy of human bladder cancer with PTEN suppresses tumor growth, downregulates phosphorylated Akt, and increases sensitivity to doxorubicinGene Therapy, 2003, vol. 10, pp. 1636-1642.*
El-Badri et al. Cord Blood Mesenchymal Stem Cells: Potential Use in Neurological DisordersStem Cells Develop., 2006, vol. 15, 497-506.*
Rabin et al. A new xenograft model of myeloma bone disease demonstrating the efficacy of human mesenchymal stem cells expressing osteoprotegerin by lentiviral gene transfer. Leukemia, 2007, vol. 21, pp. 2181-2191.*
Erices et al. Mesenchymal progenitor cells in human umbilical cord blood. Brit. J. Haematol., 2000, vol. 109, pp. 235-242.*
Ringe et al.Towards in Situ Tissue Repair: Human Mesenchymal Stem Cells Express Chemokine Receptors CXCR1, CXCR2 and CCR2, and Migrate Upon Stimulation With CXCL8 but not CCL2. J. Cellular Biochem., 2007, vol. 101, pp. 135-146.*
Brat et al. The role of interleukin-8 and its receptors in gliomagenesis and tumoral angiogenesis. Neuro-Oncolocy, 2005, vol. 7, pp. 122-133.*
Kershaw et al. Redirecting Migration of T Cells to Chemokine Secreted from Tumors by Genetic Modification with CXCR2. Human Gene Therapy, 2002, vol. 13, pp. 1971-1980.*
Drappatz et al. Non-cytotoxic drugs as potential treatments for gliomas. Current Opinion in Neurology, 2004, vol. 17, pp. 663-673.*
van Meir et al. Interleukin-8 Is Produced in Neoplastic and Infectious Diseases of the Human Central Nervous System. Cancer Res, 1992, vol. 52, pp. 4297-4305.*
Korean Office Action issued in corresponding KR Application No. 10-2008-0067247, dated Jul. 26, 2010.
Australian Office Action issued in corresponding AU Application No. 2008-293208, dated Nov. 30, 2010.
Power et al., "Cell-based Delivery of Oncolytic Viruses: A New Strategic Alliance for a Biological Strike Against Cancer," The American Society of Gene Therapy, 2007, vol. 15., No. 4, pp. 660-665.
Trampe-Kieslich et al., "Migration of Somatic Cells from Umbilical Cord Blood Towards Glioma Cells," Acta Neuropathol, 2006, vol. 112, V990, pp. 361-362.
Jeong et al., "Differential Gene Expression Profiling of Human Umbilical Cord Blood-Derived Mesenchymal Stem Cells by DNA Microarray," Stem Cells, 2005, vol. 23, pp. 584-593.
Almici et al., "Umbilical Cord Blood as a Source of Hematopoietic Stem Cells: From Research to Clinical Application," Haematologica 1995, 80:473-479.
Australian Office Action mailed Jan. 17, 2012, in Australian Application No. 200829308.

(Continued)

*Primary Examiner* — Deborah Crouch
(74) *Attorney, Agent, or Firm* — Drinker Biddle & Reath LLP

(57) ABSTRACT

Provided is a gene therapy composition for transferring one of a therapeutic gene, a maker gene, or a mixture thereof to a cell that expresses interleukin-8 (IL-8) or GRO-α and induces tropism of mesenchymal stem cells isolated from umbilical cord blood and/or the mesenchymal stem cells expanded from said mesenchymal stem cells (UCB-MSCs), wherein the cell-treating composition includes UCB-MSCs. Provided is a composition for treating disease related to a cell expressing IL-8 or GRO-α, that is, a brain tumor in gene therapy, by using UCB-MSCs. Provided is a composition or kit for diagnosing brain tumors, preventing brain tumors, treating brain tumors, or monitoring brain tumor treatment progression by using UCB-MSCs.

15 Claims, 15 Drawing Sheets
(2 of 15 Drawing Sheet(s) Filed in Color)

(56) References Cited

OTHER PUBLICATIONS

Li et al., "Insulin-like growth factor 1 enhances the migratory capacity of mesenchymal stem cells," Biochemical and Biophysical Research Communications, No. 356, 2007, pp. 780-784.

Lijie et al., "Mesenchymal stem cells modified with angiopoietin-1 improve remodeling in a rat model of acute myocardial infarction," Biochemical and Biophysical Research Communications, No. 357, 2007, pp. 779-784.

Noiseux et al., "Mesenchymal Stem Cells Overexpressing Akt Dramatically Repair Infarcted Myocardium and Improve Cardiac Function Despite Infrequent Cellular Fusion or Differentiation," Molecular Therapy, vol. 14, No. 6, Dec. 2006, pp. 840-850.

López Ponte et al., "The In Vitro Migration Capacity of Human Bone Marrow Mesenchymal Stem Cells: Comparison of Chemokine and Growth Factor Chemotactic Activities," StemCells, 2007, No. 25, pp. 1737-1745.

Kähler et al., "Peripheral infusion of rat bone marrow derived endothelial progenitor cells leads to homing in acute lung injury," Respiratory Reasearch, Jul. 9, 2007, pp. 1-17.

Dwyer et al., "Monocyte Chemotactic Protein-1 Secreted by Primary Breast Tumors Stimulates Migration of Mesenchymal Stem Cells," Clin. Cancer Research, Sep. 1, 2007, vol. 13, No. 17, pp. 5020-5027.

Liu et al., "Chemokine Ligand 2 (CCL2) Induces Migration and Differentiation of Subventricular Zone Cells after Stroke," Journal of Neuroscience Research, vol. 85, 2007, pp. 2120-2125.

Brown et al., "Intravascular Delivery of Neural Stem Cell Lines to Target Intracranial and Extracranial Tumors of Neural and Non-Neural Origin," Human Gene Therapy, vol. 14, Dec. 10, 2003, pp. 1777-1785.

Ehtesham et al., "The Use on Interleukin 12-secreting Stem Cells for the Treatment of Intracranial Glioma," Cancer Research vol. 62, Oct. 15, 2002, pp. 5657-5663.

Ehtesham et al., "Induction of Glioblastoma Apoptosis Using Neural Stem Cell-mediated Delivery of Tumor Necrosis Factor-related Apoptosis-inducing Ligand," Cancer Research, vol. 62, Dec. 15, 2002, pp. 7170-7174.

Li et al., "Bcl-2 Engineered MSCs Inhibited Apoptosis and Improved Heart Function," Stem Cells, vol. 25, 2007, pp. 2118-2127.

Kanki-Horimoto et al., "Implantation of Mesenchymal Stem Cells Overexpressing Endothelial Notric Oxide Synthase Improves Right Venticular Impairments Caused by Pulmonary Hypertension," Circulation, 2006, 114(Suppl. I) pp. I-181 to I-185.

Yip et al., "Neural Stem Cells Biology My be Well Suited for Improving Brain Tumor Therapies," The Cancer Journal, vol. 9, No. 3, May/Jun. 2003, pp. 182-204.

Kim et al., "Human Neural Stem Cells Target Experimental Intracranial Medulloblastoma and Deliver a Therapeutic Gene Leading to Tumor Regression," Clin. Cancer Research, vol. 12, No. 18, Sep. 15, 2006, pp. 5550-5556.

Nakamizo et al., "Human Bone Marrow-Derived Mesenchymal Stem Cells in the Tratment of Gliomas." Cancer Research, vol. 65, No. 8, Apr. 15, 2005, pp. 3307-3318.

Barreda et al., "Flow cytometric analysis of PKH26-labeled goldfish kidney-derived macrophages," Developmental and Comparative Immunology, vol. 24, 2000, pp. 395-406.

Pittenger et al.,"Multilineage Potential of Adult Human Mesenchymal Stem Cells," Science, vol. 284, Apr. 2, 1999, pp. 143-147.

Lazarus et al., Ex vivo expansion and subsequent infusion of human bone marrow-derived stromal progenitor cells (mesenchymal progenitor cells): implications for therapeutic use, Bone Marrow Transplant, vol. 16, 1995, pp. 557-564.

Dehari et al., "Enhanced antitumor effect of RGD fiber-modified adenovirus for gene therapy of oral cancer," Cancer Gene Therapy, vol. 10, 2003, pp. 75-85.

Tsuda et al., "Efficent BMP2 Gene Transfer and Bone Formation of Mesenchymal Stem Cells by a Fiber-Mutant Adenoviral Vector," Molecular Therapy, vol. 7, No. 3, Mar. 2003, pp. 354-365.

Wu et al., "A novel therapeutic approach to 6-OHDA-induced Parkinson's disease in rats via supplementation of PTD-conjugated tyrosine hydroxylase," Biochemical and Biophysical Research Communications, vol. 346, 2006, pp. 1-6.

Le Blanc et al., "HLA expression and immunologic properties of differentiated and undifferentiated mesenchymal stem cells," Experimental Hematology, vol. 31, 2003, pp. 890-896.

Tse et al., "Suppression of Allogeneic T-cell Proliferation by Human Marrow Stromal Cells: Implications in Transplantation," Transplantation, vol. 75, No. 3, Feb. 15, 2003, pp. 389-397.

Weissleder et al., "Shedding light onto live molecular targets," Nature Medicine, vol. 9, No. 1, Jan. 2003, pp. 123-128.

Lewin et al., "Tat peptide-derivatized magnetic nanoparticles allow in vivo tracking and recovery of progenitor cells," Nature Biotechnology, vol. 18, Apr. 2000, pp. 410-414.

Campos et al., "Definition of Optimal Conditions for Collection and Cryopreservation of Umbilical Cord Hematopoietic Cells," Cryobiology,vol. 32, 1995,pp. 511-515.

Ali et al., "Defining umbilical cord blood stem cells," Stem Cell Discovery, vol. 2, No. 1, 2012, pp. 15-23.

Hwang et al., "Comparison of Cytokine Expression in Mesenchymal Stem Cells from Human Placenta, Cord Blood, and Bone Marrow," J. Korean Med. Sci., vol. 24, 2009, pp. 547-554.

Morita et al., "Induction and regulation of IL-8 and MCAF production in human brain tumor cell lines and brain tumor tissues," Eur. Cytokine Netw., vol. 4, No. 5, Sep./Oct. 1993, pp. 351-358 (Abstract only).

Boyle-Walsh et al., "RT-PCR detection of cytokine transcripts in a series of cultured human meninglomas," J. Pathology, vol. 178, No. 4, Apr. 1996, pp. 442-446 (Abstract only).

Green et al., "Cytokine expression in human anterior pituitary andenomas," Clin. Endocrinol. (Oxf.), vol. 45, No. 2, Aug. 1996; pp. 179-185 (Abstract only).

Wiegand et al,, "Analysis of cytokine levels in human lymphangiomas," In Vivo, vol. 22, No. 2, Mar./Apr. 2008, pp. 253-253 (Abstract only).

Kim et al., "Overexpression of CXC Chemokine Receptors Is Required for the Superior Glioma-Tracking Property of Umbilical Cord Blood-DErived Mesenchymal Stem Cells," Stem Cells and Development, vol. 18, No. 3, 2009, pp. 511-519.

International Preliminary Report on Patentability, including Written Opinion, dated Mar. 2, 2010 in PCT International Application No. PCT/KR2008/005026, filed Aug. 27, 2008.

Al-Nbaheen et al., "Human Stromal (Mesenchymal) Stem Cells from Bone Marrow, Adipose Tissue and Skin Exhibit Differences in Molecular Phenotype and Differentiation Potential," Stem Cell Rev. and Rep., Apr. 14, 2012 (published online).

Secco et al., "Gene Expression Profile of Mesenchymal Stem Cells from Paired Umbilical Cord Units: Cord is Different from Blood," Stem Cell Rev. and Rep., vol. 5, 2009, pp. 387-401.

Bochev et al., "Mesenchymal stem cells from human bone marrow or adipose tisse differently modulate mitogen-stimulated B-cell immunoglobukin production in vitro," Cell Biology International, vol. 32, 2008, pp. 384-393.

Ren et al., "Species Variation in the Mechanisms of Mesenchymal Stem Cell-Mediated Immunosuppression," Stem Cells, No. 27, 2009, pp. 1954-1962.

Hass et al., "Different populations and sources of human mesenchymal stem cells (MSC): A comparison of adult and neonatal tissue-derived MSC," Cell Communication and Signaling, 2011, 9:12, pp. 1-14.

Zhang et al., "Isolation and Characterization of Mesenchymal Stem Cells From Human Umbilical Cord Blood: Reevaluation of Critical Factors for Successful Isolation and High Ability to Proliferate and Differentiate to Chondrocytes as Compared to Mesenchymal Stem Cells From Bone Marrow and Adipose Tissue," Journal of Cellular Biochemistry, vol. 112, 2011, pp. 1206-1218.

Rebelatto et al., "Dissimilar Differentiation of Mesenchymal Stem Cells from Bone Marrow, Umbilical Cord Blood, and Adipose Tissue," Experimental Biology and Medicine, vol. 233, 2008, pp. 901-913.

Chang et al., "Disparate Mesenchyme-Lineage Tendencies in Mesenchymal Stem Cells from Human Bone Marrow and Umbilical Cord Blood," Stem Cells, vol. 24, 2006, pp. 679-685.

Kern et al., "Comparative Analysis of Mesenchymal Stem Cells from Bone Marrow, Umbilical Cord Blood, or Adipose Tissue," Stem Cells, vol. 24, 2006, pp. 1294-1301.

Bieback et al., "Comparing mesenchymal stromal cells from different human tissues: Bone marrow, adipose tissue and umbilical cord blood," Bio-Medical Materials and Engineering, vol. 18, 2008, pp. S71-S76.

Bieback et al., "Mesenchymal Stromal Cells from Umbilical Cord Blood," Current Stem Cell Research & Therapy, vol. 2. 2007: pp. 310-323.

Rojewski et al., "Phenotypic Characterization of Mesenchymal Stem Cells from Various Tissues," Transfusion Medicine and Hemotherapy, vol. 35, 2008, pp. 168-184.

Australian Patent Office, Australian Examiner's Report issued in corresponding AU Application No. 2008293208, dated Oct. 5, 2011.

European Patent Office, European Search Report issued in corresponding EP Application No. 08793529.2, dated Sep. 23, 2011.

Annotated *Wikipedia* entry for "Tumor suppressor gene".

Annotated *Wikipedia* entry for "Thymidine kinase".

U.S. Appl. No. 13/680,995, filed Nov. 19, 2012, Jong Wook Chang et al.

A. Nakamizo, et al., "Human Bone Marrow-Derived Mesenchymal Stem Cells in the Treatment of Gliomas," Cancer Research, Apr. 15, 2005, pp. 3307-3318, No. 65, American Association for Cancer Research.

Patent Examination Report No. 4 issued Aug. 3, 2012 in Australian Patent Application No. 2008293208.

Patent Examination Report No. 5 issued Aug. 28, 2012 in Australian Patent Application No. 2008293208.

Terai, M., et al., "Immortalization of Human Fetal Cells: The Life Span of Umbilical Cord Blood-derived Cells Can Be Prolonged without Manipulating $p16^{INK4a}$/RB Braking Pathway," *Mol. Biol. Cell* 16: 1491-99 (2005).

Resier, J., et al., "Potential of mesenchymal stem cells in gene therapy approaches for inherited and acquired diseases," *Expert Opin. Biol. Ther.* 5(12): 1571-84 (2005).

* cited by examiner

Primer sequence for target genes

| Target gene | Primer sequence | Annealing temperature (°C) | PCR product size (bp) |
|---|---|---|---|
| GAPDH | 5'-ACCACAGTCCATGCCATCAC -3' (SEQ ID NO:1)<br>5'-TCCACCACCCTGTTGCTGTA -3' (SEQ ID NO:2) | 55 | 452 |
| IL-8 | 5'-TCCTGATTTCTGCAGCTCTGTG-3' (SEQ ID NO:3)<br>5'- TGCTTGAAGTTTCACTGGCATC-3' (SEQ ID NO:4) | 55 | 300 |
| CXCR1 | 5'- GAGCCCGAATCTGACATTA-3' (SEQ ID NO:5)<br>5'- GCAGACACTGCAACACACCT-3' (SEQ ID NO:6) | 55 | 200 |
| CXCR2 | 5'- ATTCTGGGCATCCTTCACAG-3' (SEQ ID NO:7)<br>5'- TGCACTTAGGCAGGAGGTCT-3' (SEQ ID NO:8) | 55 | 202 |

UCB-MSCS COMPRISING A TUMOR SUPPRESSOR GENE REDUCE THE SIZE OF AN IL-8 OR GRO-αEXPRESSING TUMOR

CROSS REFERENCE TO RELATED APPLICATIONS

This application is a continuation-in-part of PCT International Application No. PCT/KR2008/005026, filed Aug. 27, 2008, which claims priority of:
i) Korean Patent Application No. 10-2007-0087228, filed Aug. 29, 2007; and
ii) Korean Patent Application No. 10-2008-0067247, filed Jul. 10, 2008, and which claims the benefit of:
a) U.S. Provisional Application No. 60/972,966 filed Sep. 17, 2007; and
b) U.S. Provisional Application No. 61/089,733, filed Aug. 18, 2008, the contents of all of which are incorporated herein by reference in their entirety.

REFERENCE TO A SEQUENCE LISTING

A sequence listing having SEQ ID NOs; 1-110 is incorporated by reference hereto.

TECHNICAL FIELD

The present invention relates to a gene therapy composition for transferring a therapeutical gene, a marker gene, or a product thereof to a cell that expresses interleukin-8 (IL-8) or GRO-α and induces tropism of umbilical cord blood-derived mesenchymal stem cells or mesenchymal stem cells isolated from umbilical cord blood and/or the mesenchymal stem cells expanded from said mesenchymal stem cells (UCB-MSCs), wherein the gene therapy composition includes UCB-MSCs.

The present invention also relates to preventing or treating disease related to a cell expressing IL-8 or GRO-α, or brain tumors in gene therapy, using the composition includes UCB-MSCs.

The present invention also relates to a composition or kit for diagnosing brain tumors, preventing brain tumors, treating brain tumors, or monitoring brain tumor treatment progression, using UCB-MSCs.

BACKGROUND ART

It is known that stem cells migrate toward sites of pathology. Recently, it was found that bone marrow-derived mesenchymal stem cells (BM-MSCs) have a tropism for tumors and migrate toward tumor sites. Such BM-MSCs that can migrate to sites of specific tumors may prove to be a useful tool in gene therapy. For example, BM-MSCs having a tropism for tumors can be used as vehicles for transferring a therapeutic suicide gene to tumor sites [see Ponte A. L. et al., *Stem Cells*, 25, 1737-1745 (2005); Kahler C. M. et al., *Respir Res* 8, 50 (2007)]. Despite this interesting phenomenon, the molecular mechanisms regulating MSCs trafficking to tumor are unclear.

Growing evidence over several years indicates that induction of BM-MSCs migration seems to be stimulated by several soluble factors. Recently, monocyte chemoattractant protein-1 (MCP-1) secreted from breast cancer cells has been shown to stimulate BM-MSCs migration [see Dwyer R. M. et al. *Clin Cancer Res* 13, 5020-5027 (2007)]. Furthermore, chemokine ligand2 (CCL2) and chemokine ligand10 (CCL-10) can induce the migration of neural progenitor cells to sites damaged within the middle cerebral artery occlusion (MCAo) stroke model [see *J Neurosci Res* 85, 2120-2125 (2007)]. An insulin-like growth factor-1 (IGF-1) markedly increased the rat BM-MSCs migratory response [see Li Y. et al. *Biochem Biophys Res Commun* 356, 780-784 (2007)]. Therefore, identifying the soluble factors that affect migration events of MSCs is important for understanding how MSCs migrate toward tumors or damaged tissues.

Genes introduced to BM-MSCs are over-expressed in vivo and show bioactivity. For example, BM-MSCs to which a human hAng1 gene is introduced stimulate generation of blood vessels in an infarction site of an acute myocardial infarction model animal [see Sun L. et al., *Biochemical Biophysical Research Communication* 357 (2007) 779-784], BM-MSCs overexpressing Akt surprisingly treat myocardial infarction and improve functions of heart [see Nicolas N. et al., *Molecular Therapy* 14(6), 840-850, 2006], Bcl-2 gene-modified BM-MSCs prevent apoptosis and improve functions of heart [see *Stem Cells* 25, 2118-2127 (2007)], and BM-MSCs overexpressing endothelial nitric oxide synthase recovers the damage of right ventricular caused by pulmonary hypertension [see Sachiko et al., *Circulation,* 114[suppl I]:I-181~I-185]. These results indicate that MSCs to which genes are introduced can be used as a tool in gene therapy.

Meanwhile, in general, cells of the central nervous system are well regulated, wherein the central nervous system consists of a brain and a spinal cord. However, when this regulation collapses, cells are continuously divided and tumors are formed. Tumors can be categorized as benign tumors or malignant tumors. The central nervous system has neurons, and glia cells that support and protect the neurons. Tumors generated in glia cells are known as glioma. Glioma accounts for 50% of primary brain tumors and accounts for 15% of primary spinal cord tumors. In addition, brain tumors include neural tumors, blood vessel tumors, and gland tumors. There is also a secondary brain tumor caused by other tumors developed in other sites of the body. The secondary brain tumor is the most common type of brain tumor Treating brain tumors are difficult due to the sites of the tumors. Brain tumors can be treated by physical surgery or chemotherapy. For physical surgery, when tumor sites are completely removed, complications are likely to occur. For chemotherapy, a high-concentration anticancer drug needs to be injected due to a brain-blood barrier, and thus, it seriously damages other organs. Recently, gene therapy has been used to treat brain tumors. In gene therapy, a gene is introduced for suppressing growth of cancer cells by using a virus vector. Since the virus vector does not have a selective migration capability toward a target cancer site, the virus vector is surface-modified to obtain such capability. However, there is a limit to migrate a sufficient amount of virus vectors to the target cancer site.

Research results on a homing effect, which is a phenomenon in which stem cells migrate toward a disease site, have been disclosed, indicating that stem cells can be useful delivery media for treating brain tumors. However, mechanisms regulating stem cells trafficking to tumors are unclear. It is known that neural stem cells have a tropism for a type of brain tumor, that is, malignant glioma. Based on this theory, research into a method of transferring genes to a brain tumor site by using neural stem cells that function as a vehicle is being conducted (see Yip S et al., *The Cancer J* 9(3), 189-204, 2003; Kim S K et al., *Clin Cancer Res* 12(18), 5550-5556, 2006). Yip et al. found that brain tumors can be treated with neural stem cells carrying an immune regulatory gene, an apoptosis promoting gene, a pro-drug converting enzyme, an oncolytic virus, etc. Brown et al. identified that brain tumors can be effectively treated by injecting a cytosine deaminase gene-containing vector into the brain, wherein the cytosine deaminase gene changes 5-fluorocytosine (5-FC) into 5-fluorouracil (5-FU), wherein 5-FU is an anticancer drug and 5-FC is a prodrug of 5-FU (see Brown A B et al., *Human Gene Ther.* 14(18), 1777-1785, 2003). Ehtesham et al. reported that growth of brain tumors was decreased by injecting neural stem cells treated for delivering interleukin-12 or a tumor necrosis factor-related apoptosis-inducing ligand (*Cancer Res* 62, 5657-5663, 2002; *Cancer Res* 62, 7170-7174, 2002). However, using neural stem cell in clinical experiments causes ethical problems related to how neural stem cells are taken, and immunological rejection caused by allogenic transplantation. Accordingly, there is a need to find other types of stem cells that do not cause these problems and can be easily obtained.

Akira et al. disclosed that BM-MSCs have a tropism for brain tumors (see *Cancer Res* 65(8), 3307-3316, 2005). BM-MSCs can be taken from patients. When BM-MSCs are injected through autologous transplantation, immunological rejection does not occur, which is an advantage for a clinical use. In a study, human BM-MSCs were injected into nude mice having skulls transplanted with human glioma cell lines through a carotid artery. As a result, the human BM-MSCs were found only in glioma and not in a normal part of the brain adjacent to glioma. In addition, even when human BM-MSCs were transplanted into a skull, human BM-MSCs migrated toward glioma. When human BM-MSCs were infected with an adenovirus vector containing cDNA of an IFN-beta gene and then the resultant vector was injected into a glioma-transplanted skull of a nude mouse through a carotid artery, the lifetime of the nude mouse was increased. WO07/037,653A1 discloses a composition for treating cancer, comprising BM-MSCs expressing a cytosine deaminase gene. In this case, however, since BM-MSCs are taken through a plurality of complex processes, subjects from which the BM-MSCs are taken suffer from mental and physical stress for a long period of time. Accordingly, there is a need to find other types of stem cells.

Unlike bone marrow, umbilical cord blood (UCB) having many MSCs can be easily taken from umbilical cords which were discarded in delivery processes. Also, the UCB storage industry is well established and thus, it is easy to find donors. Even when MSCs taken from other human-induced UCB are used, immunological rejection does not occur after transplantation. Accordingly, high immunological stability can be obtained. Therefore, it is very important to identify whether a disease such as a brain tumor can be treated based on tropism of UCB-MSCs. However, such attempts for identifying availability of UCB-MSCs have not yet been made. All the references cited in the present specification are incorporated by reference in their entity. Also, all the information disclosed in the present specification is used only to help understanding of the background of the present inventive concept and cannot be prior art.

DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 15 shows primer sequences used in Examples of the present invention.

DETAILED DESCRIPTION OF THE INVENTION

Technical Problem

Figure 1:
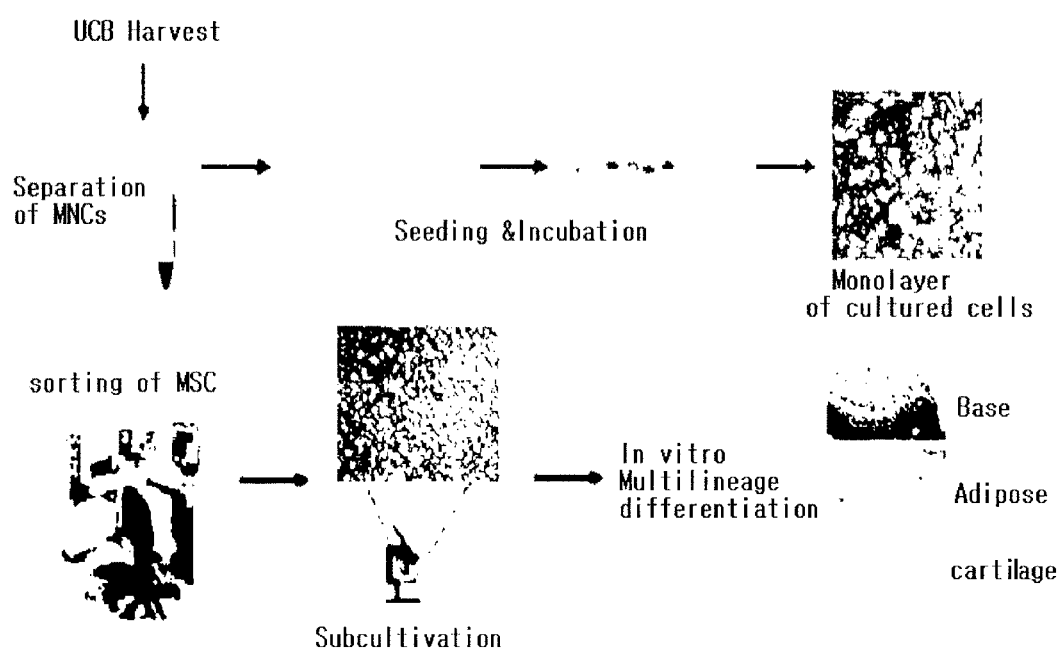
FIG. 1 is a view illustrating a process of collecting mesenchymal stem cells (MSCs)

Target gene therapy recently developed uses specific migration characteristics of mesenchymal stem cells (MSCs), in which therapeutical genes are introduced to MSCs and then the resultant MSCs are migrated to a disease site and the disease is treated. To develop gene therapy using tropism of MSCs, a molecular mechanism regulating the migration of MSCs toward disease site, for example tumors should be completely understood. However, the molecular mechanism has not yet been determined. Accordingly, the present inventive concept is to find out the molecular mechanism of UCB-MSCs migrating toward a disease site cell, for example, tumor cell and uses the molecular mechanism in gene therapy.

Although research into whether a disease condition, for example, tumor, including brain tumors can be treated with neural stem cells or bone marrow-derived mesenchymal stem cells (BM-MSCs) are being conducted, collecting neural stem cells and BM-MSCs may lead to ethical problems, immunological rejection, and mental and physical stress of a subject from which BM-MSCs are taken. Accordingly, the present inventive concept also provides a stem cell that can be taken without these problems described above and have better tropism for disease site for example, tumors such as brain tumors.

Technical Solution

The inventors of the present invention have conducted research in order to solve these problems, and found that mesenchymal stem cells isolated from umbilical cord blood and/or the mesenchymal stem cells expanded from said mesenchymal stem cells (UCB-MSCs) have a tropism for a cell expressing at least one selected from the group consisting of IL-8 and GRO-α, for example a tumor cell such as brain tumor cells and that UCB-MSCs have a stronger migration capability than mesenchymal stem cells isolated from bone marrow and/or the mesenchymal stem cells expanded from said mesenchymal stem cells (BM-MSCs). The inventors have provided a therapeutical application for treating a disease condition, for example a tumor cell such as brain tumor using UCB-MSCs.

Also, the inventors of the present invention found the tropism of UCB-MSCs is affected by interleukin-8 (IL-8) or GRO-α. Based on this finding, the inventors of the present invention provide a method of delivering a therapeutical gene or a product thereof to a cell that expresses IL-8 or GRO-α and induces the tropism of UCB-MSCs, and a therapeutical application thereof.

Advantageous Effects

Umbilical cord blood derived mesenchymal stem cells (UCB-MSCs) in the composition according to the present invention has a selective tropism for cells that express IL-8 or GRO-α and thus induce the tropism of UCB-MSCs or brain tumor cells. The tropism capability of the UCB-MSCs is better than that of other stem cells and thus, therapeutical genes or a product thereof can be more effectively delivered than when other conventional stem cells are used. Accordingly, a pharmaceutical composition or a kit comprising UCB-MSCs according to the present invention can be used to diagnose, prevent, and treat diseases related to cells expressing interleukin (IL)-8 or GRO-α or brain tumors.

Mode of Inventions

The inventors of the present invention have studied stem cells having an effective tropism for tumors, and surprisingly found that umbilical cord blood-derived mesenchymal stem cells (UCB-MSCs) have a strong tropism for brain tumors, specifically a stronger tropism for brain tumors than bone marrow-derived mesenchymal stem cells (BM-MSCs), which has never been known before. Also, the inventors found that at least one selected from the group consisting of interleukin-8 (IL-8) and GRO-α relates to the tropism of UCB-MSCs.

The inventors co-cultured UCB-MSCs and representative tumor cell lines to identify characteristics of the tropism of UCB-MSCs and cytokine related to those tumor cell lines. Specifically, UCB-MSCs, and one selected from human brain tumor cell lines, such as U-87 MG, LN18, U138, or U251 cells; human rectal cancer cell line such as LS-174T; human B lymphocyte such as NC37; mouse's fibroblast (NIH3T3); a gastric cancer cell line such as KATO III; a lung cancer cell line such as A549, and a liver cancer cell line such as PLC/PRF5 were co-cultured in a transwell chamber to measure mobility of UCB-MSCs. As a result, it was found that UCB-MSCs have a strong tropism for U-87 MG, LN18, U138, and U251 cells which are brain tumor cells (see FIGS. 3 and 4). UCB-MSCs also had tropism for a conditioned media that did not include U-87 MG cells and was obtained by culturing U-87 MG (see FIG. 4).

Figure 5:
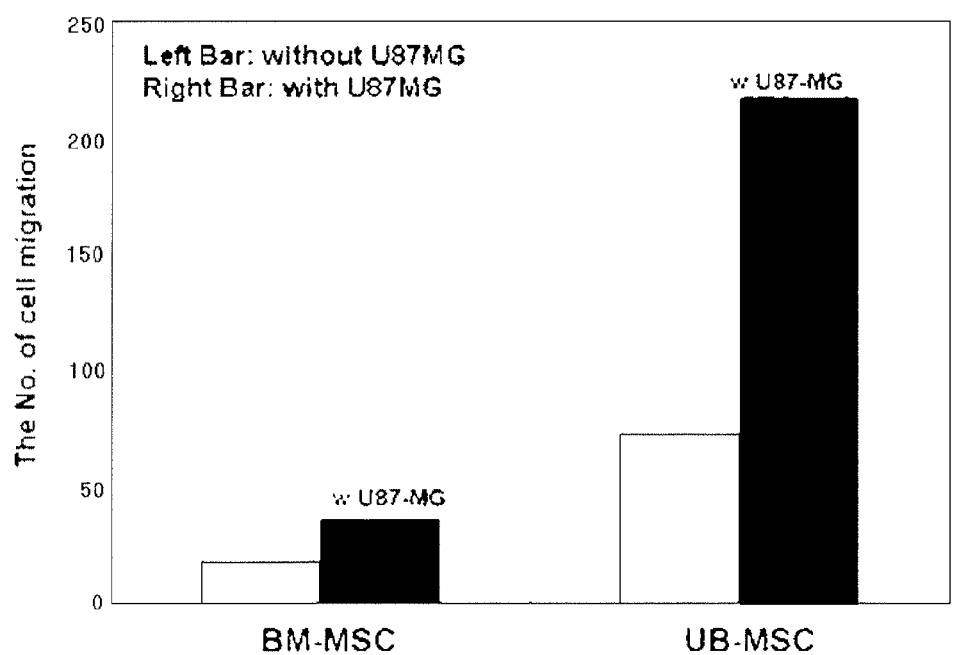
FIG. 5 is a graph for comparing tropisms of BM-MSCs and UCB-MSCs for U-87 MG cells, wherein each of PKH-labeled UCB-MSCs and PKH-labeled BM-MSCs placed in the upper compartment in the transwell chamber and U-87 MG cells placed in the lower compartment in the transwell chamber are co-cultured and the number of PKH-labeled UCB-MSCs migrated toward the lower compartment is compared with the number of PKH-labeled BM-MSCs, wherein a left bar indicates a case in which U-87 MG cells do not exist and a right bar indicates a case in which U-87 MG cells exist (the number of U-87 MG cells is $5\times10^5$, and in both cases, the number of MSCs is $1\times10^5$.
Figure 6:
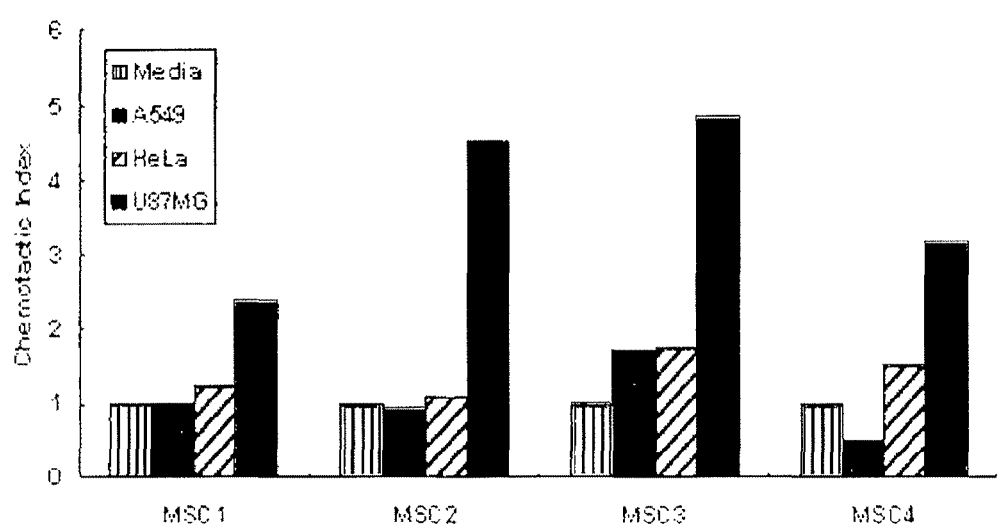
FIG. 6 is a graph of chemotactic indices of UCB-MSCs when UCB-MSCs are co-cultured with cancer cell lines (A549, HeLa, and U-87 MG cells)

Also, the tropism for a brain tumor cell line of UCB-MSCs was compared with that of BM-MSCs that is currently used as a source of stem cells. As a result, it was found that UCB-MSCs have a stronger tropism for a brain tumor cell line than BM-MSCs (FIG. 5). Also, the chemotactic index of UCB-MSCs was largest with respect to the brain tumor cell line among various cancer cell lines (FIG. 6). Such a high chemotactic index with respect to the brain tumor cell is an additional advantage of UCB-MSCs, in addition to the fact that UCB-MSCs can be obtained more easily and have more immunological stability than BM-MSCs, proving that UCB-MSCs are a very suitable medium for gene therapy of a brain tumor because a therapeutical gene can be efficiently transferred to the inside or neighboring portions of the brain tumor.

The tropism of UCB-MSCs in the transwell chamber may be derived by cytokines that are derived to be secreted in the co-culture of two cells. Thus, two cells were co-cultured in a transwell chamber to prepare a medium and then, the medium was analyzed using the cytokine array. As a result, it was identified that high levels of cytokines, such as IL-8 or GRO-α, were secreted in a medium in which UCB-MSCs and U-87 MG had been co-cultured (see FIG. 7). Accordingly, it is highly likely that these cytokines may derive a tropism of the UCB-MSCs.

The inventors of the present invention cultured UCB-MSCs alone, cultured U-87 MG alone, and co-cultured UCB-MSCs and U-87 MG, and then analyzed IL-8 mRNA levels of these cells using RT-PCR. As a result, UCB-MSCs did not express IL-8 in either the presence or absence of U-87 MG cells. However, U-87 MG expressed IL-8 constitutively in both the presence and absence of UCB-MSCs (see FIG. 8). Treatment of UCB-MSCs with IL-8 significantly enhanced its migration when compared to untreated cells (see (A) of FIG. 9). However, when UCB-MSCs were pre-incubated with anti-CXCR1 antibodies that are antibodies with respect to an IL-8 receptor and recombinant IL-8 was applied to UCB-MSCs, IL-8 mediated migration of UCB-MSCs were reduced in a dose-dependent manner by anti-CXCR1 treatment ((B) of FIG. 9). Anti-CXCR2 treatment also showed the same effect. Similarly, GRO-α treatment also enhanced UCB-MSCs migration when compared to untreated UCB-MSCs ((C) of FIG. 9). In contrast, there were no significant differences in UCB-MSCs migration in cultures treated with MCP-1 ((D) of FIG. 9). This data indicates that IL-8 and GRO-α participate in UCB-MSCs migration toward U-87 MG cells.

Figure 10:
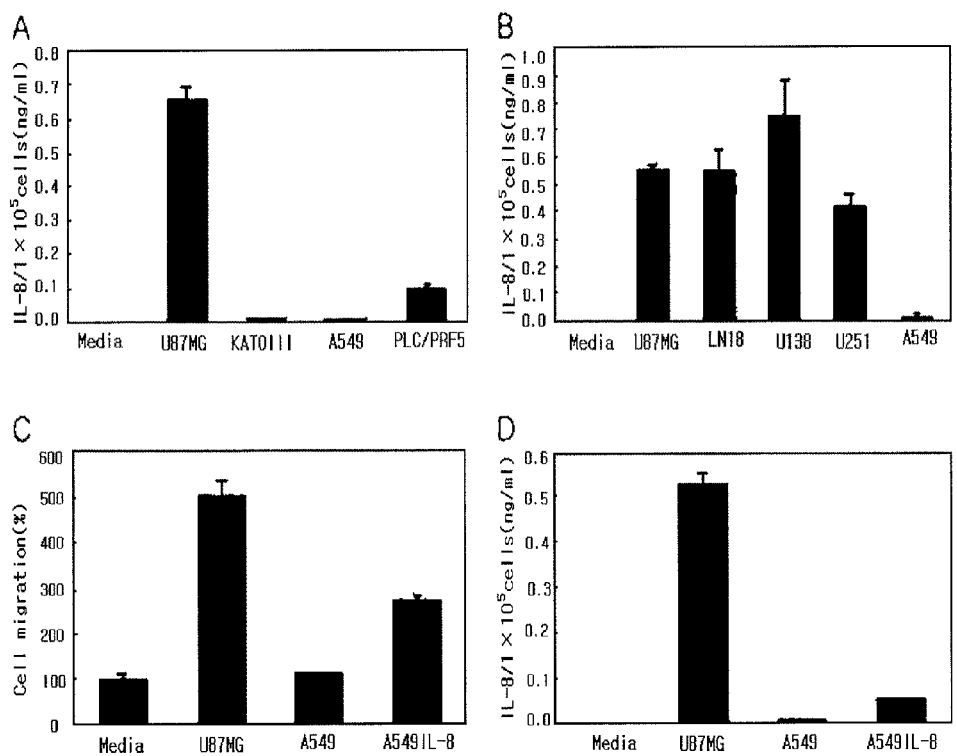
FIG. 10 consists of (A), (B), (C), and (D), wherein (A) and (B) are graphs of the amount of IL-8 secreted in the cultured media with U-87 MG, KATO III, A549, PLC/PRF5, LN18, U138, and U251 cells, measured by ELISA, (C) is a graph of cell migration when IL-8 gene is introduced to A549 cell secreting a low level of IL-8 and overexpressed, and (D) is a graph of the amount of IL-8 secreted in the media in the condition of (C), measured by ELISA.

The co-relationship between the concentration of IL-8 secreted by each cancer cell and UCB-MSCs migration was measured. As a result, U-87 MG, which migrated the highest concentration of UCB-MSCs, showed the highest IL-8 production (FIG. 10A). The inventor also measured IL-8 secretion level in various glioma cells. All tested glioma cell lines which were target cells of UCB-MSC tropism also showed high secretion level of IL-8 ((B) of FIG. 10). This data suggested that UCB-MSCs had a strong migration attraction toward IL-8 secreting cells. In order to identify this, IL-8 was artificially overexpressed in A549 that is a low level of IL-8 expressing human lung cancer cells and then, A549 overexpressing IL-8 and UCB-MSCs were co-cultured. As a result, it was found that although the UCB-MSCs had a poor migration attraction toward A549, UCB-MSCs had a strong migration attraction toward A549 overexpressing IL-8. Therefore, IL-8 could be a strong inducer of UCB-MSCs (see FIG. 10C).

The inventors of the present invention compared migration characteristics of BM-MSCs and UCB-MSCs with respect to U-87 MG cells or IL-8. As a result, it was found that UCB-MSCs migrate more strongly toward U-87 MG cells or IL-8 than BM-MSCs. UCB-MSCs migration is enhanced dramatically in response to IL-8 treatment, but BM-MSCs migration is weak in response to IL-8 treatment (see FIG. 11).

Figure 12:
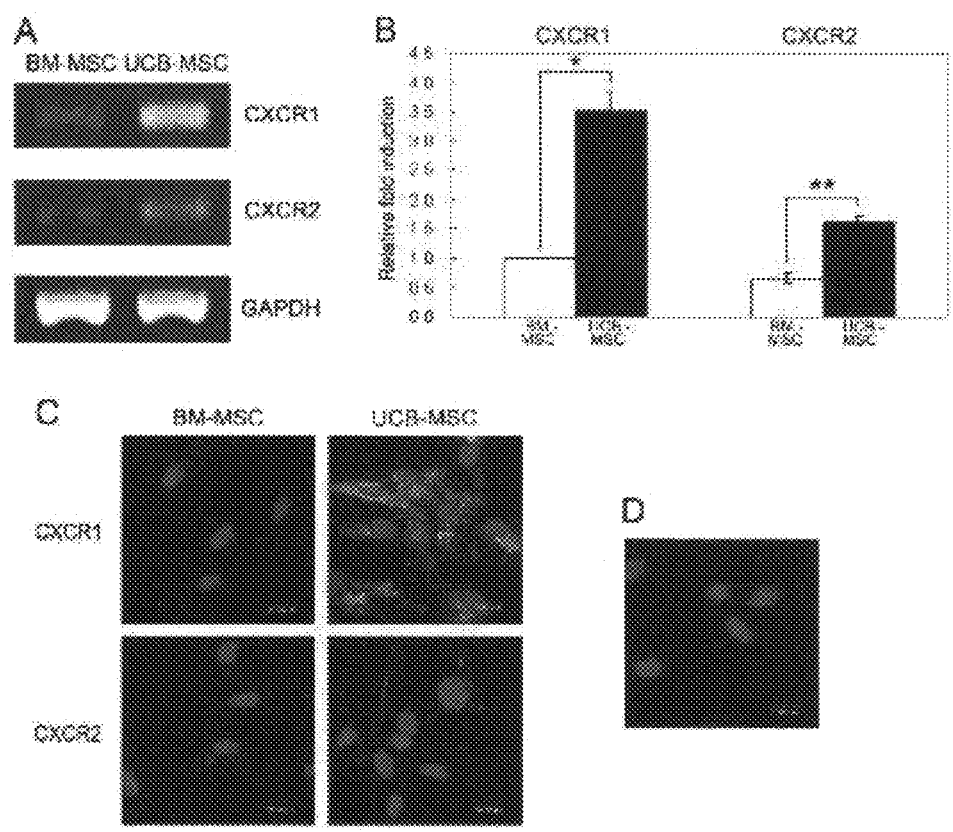
FIG. 12 show analysis results for comparing expression levels of CXC chemokine receptor 1 and CXC chemokine receptor 2 (CXCR1 and CXCR2), which are known as IL-8 receptors, in UCB-MSCs and BM-MSCs, by measuring mRNA and protein, wherein (A) shows analysis results when mRNA is separated from each of UCB-MSCs and BM-MSCs and RT-PCR was performed with CXCR1 and CXCR2 primers in UCB-MSCs and BM-MSCs, wherein the separated RNA was quantified with reference to GAPDH reacted with each sample, (B) is a graph of expression levels of CXCR1 and CXCR2 by measuring the band intensity of mRNA of each gel obtained from (A) with a densitometer (* and **, p<0.001; n=4), (C) shows analysis results of protein expression levels of CXCR1 and CXCR2 in UCB-MSCs and BM-MSCs by performing a immunostaining process and anti-CXCR1 and CXCR2 antibodies (×400), and (D) shows analysis results obtained by immunostaining UCB-MSCs and BM-MSCs with a secondary antibody only instead of anti-CXCR1 and CXCR2 antibodies to identify antigen specificity of the anti-CXCR1 and CXCR2 antibodies.

Expression levels of CXC chemokine receptor 1 (CXCR1) and CXC chemokine receptor 2 (CXCR2) in UCB-MSCs and BM-MSCs were compared by measuring mRNA and protein (see FIG. 12). RT-PCR analysis using total RNA isolated from UCB-MSCs and BM-MSCs reveal that the PCR product of both CXCR1 and CXCR2 has a higher intensity in UCB-MSCs when compared to BM-MSCs. In regard of protein expression of CXCR1 and CXCR2, CXCR1 and CXCR2 are highly expressed both in UCB-MSCs and BM-MSCs. Since IL-8 has a high affinity to CXCR1 and CXCR2, increased UCB-MSCs migration toward U-87 MG may be due to up-regulated expression of CXCR1 and CXCR2.

Figure 13:
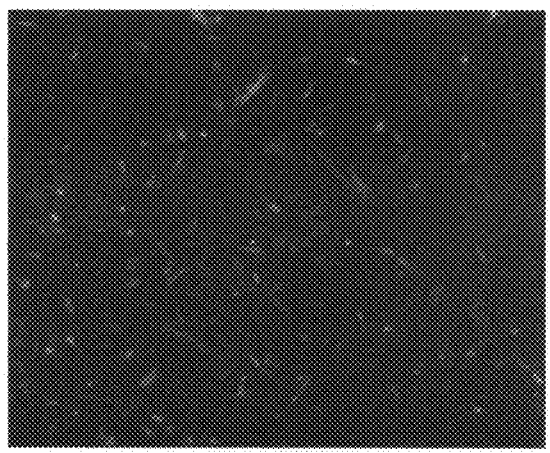
FIG. 13 is a fluorescent microscopic image of UCB-MSCs to which a gene coding green fluorescent protein (GFP) is introduced and overexpressed.

The inventors of the present invention performed an experiment of introducing a gene coding green fluorescent protein (GFP) into UCB-MSCs. As a result, it was found that GFP was successfully introduced and expressed (see FIG. 13). Also, it was found that UCB-MSCs overexpressing the gene coding GFP also have a tropism for U-87 MG (see FIG. 14). Such results show that UCB-MSCs to which a gene or a product thereof is introduced can be transferred to cells secreting IL-8 or GRO-α.

Based on the results described above, the present invention relates to a method of transferring a gene or product thereof to a cell expressing IL-8 or GRO-α by using UCB-MSCs. The present invention also relates to UCB-MSCs containing a therapeutical composition for transferring a therapeutical or marker gene or a product thereof to a cell that expresses IL-8 or GRO-α and drives tropism of UCB-MSCs. The present invention also relates to a therapeutical pharmaceutical composition, a kit, a use for preventing or treating brain tumors, and a treatment method of brain tumors, using UCB-MSCs. The present invention also relates to a composition, a kit for diagnosing brain tumors or monitoring the progression of brain tumor treatment and a diagnosing method of brain tumor or monitoring method of the progression of brain tumor treatment, using UCB-MSCs.

Specifically, the present inventive concept relates to:

[1] a pharmaceutical composition for preventing or treating brain tumors, wherein the pharmaceutical composition comprises a UCB-MSC;

[2] a pharmaceutical composition for preventing or treating brain tumors, wherein the pharmaceutical composition comprises a UCB-MSC, wherein the UCB-MSC functions as a carrier for gene therapy for brain tumors;

[3] a pharmaceutical composition for preventing or treating brain tumors, wherein the pharmaceutical composition comprises a UCB-MSC, wherein an anti-tumor gene is introduced to the UCB-MSC;

[4] a pharmaceutical composition for preventing or treating brain tumors, wherein the pharmaceutical composition comprises a UCB-MSC, wherein an anti-tumor gene is introduced to the UCB-MSC, wherein the anti-tumor gene is selected from a tumor suppressor gene, an apoptosis-inducing factor gene, a cell cycle regulatory gene, and an angiogenesis inhibitor gene;

[5] a pharmaceutical composition for preventing or treating brain tumors, wherein the pharmaceutical composition comprises a UCB-MSC, wherein an anti-tumor gene is introduced to the UCB-MSC, wherein the anti-tumor gene is selected from a tumor suppressor gene, an apoptosis inducing factor gene, a cell cycle regulatory gene, and an angiogenesis inhibitor gene, wherein the tumor suppressor gene may be selected from the group consisting of a gene of phosphatase and tensin homolog (PTEN), a gene of Maspin, a gene of RUNX3, a gene of Caveolin-1, a gene of nm23, a gene of Rb protein, a gene of Brush-1, a gene of inhibitor of tumor growth (ING-4), a gene of survivin, a gene of X chromosome linked inhibitor apoptosis protein (XIAP), a gene of neural apoptosis inhibitory protein (NAIP), and genes of proteins regulating these genes;

[6] a pharmaceutical composition for preventing or treating brain tumors, wherein the pharmaceutical composition comprises a UCB-MSC, wherein an anti-tumor gene is introduced to the UCB-MSC, wherein the anti-tumor gene is selected from a tumor suppressor gene, an apoptosis-inducing factor gene, a cell cycle regulatory gene, and an angiogenesis inhibitor gene, wherein the apoptosis-inducing factor gene may be selected from the group consisting of a gene of cytokine, a gene of interleukin, a gene of a tumor necrosis factor (TNF), a gene of interferon (INF-α, INF-β, INF-γ), a gene of a colony stimulating factor (CSFs), a gene of p53, a gene of Apaf-1, a gene of TRAIL, a gene of Caspase, a gene of Bax, a gene of Bad, a gene of FADD, a gene of JNK, a gene of p38 kinase, and genes of proteins regulating these genes;

[7] a pharmaceutical composition for preventing or treating brain tumors, wherein the pharmaceutical composition comprises a UCB-MSC, wherein an anti-tumor gene is introduced to the UCB-MSC, wherein the anti-tumor gene is selected from a tumor suppressor gene, an apoptosis-inducing factor gene, a cell cycle regulatory gene, and an angiogenesis inhibitor gene, wherein the cell cycle regulatory gene may be selected from the group consisting of a gene of cdc2, a gene of Cyclin (Cyclin A, Cyclin D, Cyclin E), a gene of cdc25C, a gene of WAF, a gene of INK4, a gene of CDK (CDK1, CDK2, CDK4, CDK6), a gene of Rb protein, a gene of E2F, an antisense or SiRNA thereof, and genes of proteins regulating these genes;

[8] a pharmaceutical composition for preventing or treating brain tumors, wherein the pharmaceutical composition comprises a UCB-MSC, wherein an anti-tumor gene is introduced to the UCB-MSC, wherein the anti-tumor gene is selected from a tumor suppressor gene, an apoptosis-inducing factor gene, a cell cycle regulatory gene, and an angiogenesis inhibitor gene, wherein the angiogenesis inhibitor gene may be selected from the group consisting of a gene of thrombospondin-1, a gene of endostatin, a gene of tumstatin, a gene of canstatin, a gene of vastatin, a gene of restin, a gene of a vascular endothelial growth inhibitor, a gene of maspin, a gene of angiopoietins, a gene of 16-kd prolactin fragment, and a gene of endorepellin;

[9] a pharmaceutical composition for preventing or treating brain tumors, wherein the pharmaceutical composition comprises a UCB-MSC, wherein a prodrug converting enzyme gene is introduced to the UCB-MSC;

[10] a pharmaceutical composition for preventing or treating brain tumors, wherein the pharmaceutical composition comprises a UCB-MSC, wherein a prodrug converting enzyme gene is introduced to the UCB-MSC, wherein the prodrug converting enzyme gene is selected from cytosine deaminase and CYP2B1 gene;

[11] a pharmaceutical composition for preventing or treating brain tumors, wherein the pharmaceutical composition comprises a UCB-MSC, wherein an antisense or SiRNA of a gene related to a brain tumor is introduced to the UCB-MSC;

[12] a pharmaceutical composition for preventing or treating brain tumors, wherein the pharmaceutical composition comprises a UCB-MSC, wherein an antisense or SiRNA of a gene related to a brain tumor is introduced to the UCB-MSC, wherein the gene related to a brain tumor may be selected from the group consisting of a gene of Ras family, a gene of c-myc, a gene of abl, a gene of erbB-1, a gene of EGF-R, a gene of Bax, a gene of Apaf-1 interacting protein (APIP), a gene of Wnt-1-induced secreted protein 1 (WISP-1), a gene of Wnt, a gene of Raf-1, a gene of Src, a gene of Akt, a gene of Erk-1,2 and a gene of BcL-2;

[13] a pharmaceutical composition for preventing or treating brain tumors, wherein the pharmaceutical composition comprises a UCB-MSC, wherein an oncolytic virus is introduced to the UCB-MSC;

[14] a pharmaceutical composition for preventing or treating brain tumors, wherein the pharmaceutical composition comprises a UCB-MSC, wherein an oncolytic virus is introduced to the UCB-MSC, wherein the oncolytic virus is selected from Herpes simplex virus and Reovirus type 3;

[15] any one of the pharmaceutical compositions for preventing or treating brain tumors described above, wherein the brain tumor is selected from the group consisting of Astrocytoma, Pilocytic astrocytoma, Low-grade Astrocytoma, Anaplastic Astrocytoma, Glioblastoma Multiforme, Brain Stem Glioma, Ependymoma, Subependymoma, Ganglioneuroma, Mixed Glioma, Oligodendroglioma, Optic Nerve Glioma, Acoustic Neuroma, Chordoma, CNS Lymphoma, Craniopharyngioma, Hemangioblastoma, Medulloblastoma, Meningioma, Pineal Tumors, Pituitary Tumors, Primitive Neuroectodermal Tumors, Rhabdoid Tumors, Schwannoma, Cysts, Neurofibromatosis, Pseudotumor Cerebri and Tuberous Sclerosis;

[16] a composition for diagnosing brain tumors or monitoring brain tumor treatment progression, wherein the composition includes a UCB-MSC;

[17] a composition for diagnosing brain tumors or monitoring brain tumor treatment progression, wherein the composition includes a UCB-MSC, wherein the UCB-MSC is labeled with a detectable marker;

[18] a composition for diagnosing brain tumors or monitoring brain tumor treatment progression, wherein the composition includes a UCB-MSC, wherein the UCB-MSC is labeled with a detectable marker, wherein the detectable marker is selected from luciferase-containing enzyme-based fluorescent detector and Tat peptide-derivatized magnetic nanoparticles;

[19] any one of the compositions for diagnosing brain tumors or monitoring brain tumor treatment progression, wherein the brain tumor is selected from the group consisting of Astrocytoma, Pilocytic astrocytoma, Low-grade Astrocytoma, Anaplastic Astrocytoma, Glioblastoma Multiforme, Brain Stem Glioma, Ependymoma, Subependymoma, Ganglioneuroma, Mixed Glioma, Oligodendroglioma, Optic Nerve Glioma, Acoustic Neuroma, Chordoma, CNS Lymphoma, Craniopharyngioma, Hemangioblastoma, Medulloblastoma, Meningioma, Pineal Tumors, Pituitary Tumors, Primitive Neuroectodermal Tumors, Rhabdoid Tumors, Schwannoma, Cysts, Neurofibromatosis, Pseudotumor Cerebri, and Tuberous Sclerosis;

[20] a kit for treating brain tumors, including: an expression vector having a prodrug converting enzyme gene; an UCB-MSC; and a prodrug of anticancer drug;

[21] a kit for treating brain tumors, including: an expression vector having a prodrug converting enzyme gene; an UCB-MSC; and a prodrug of anticancer drug, wherein the prodrug converting enzyme gene is selected from a cytosine deaminase gene and a CYP2B1 gene;

[22] a kit for treating brain tumors, including: an expression vector having a prodrug converting enzyme gene; an UCB-MSC; and a prodrug of anticancer drug, wherein the prodrug converting enzyme gene is selected from a cytosine deaminase gene and a CYP2B1 gene, wherein the UCB-MSC is transfected with the expression vector having a prodrug converting enzyme gene;

[23] any one of the kits described above, wherein the brain tumor is selected from the group consisting of Astrocytoma, Pilocytic astrocytoma, Low-grade Astrocytoma, Anaplastic Astrocytoma, Glioblastoma Multiforme, Brain Stem Glioma, Ependymoma, Subependymoma, Ganglioneuroma, Mixed Glioma, Oligodendroglioma, Optic Nerve Glioma, Acoustic Neuroma, Chordoma, CNS Lymphoma, Craniopharyngioma, Hemangioblastoma, Medulloblastoma, Meningioma, Pineal Tumors, Pituitary Tumors, Primitive Neuroectodermal Tumors, Rhabdoid Tumors, Schwannoma, Cysts, Neurofibromatosis, Pseudotumor Cerebri and Tuberous Sclerosis;

[24] a gene therapy composition for transferring a therapeutical gene or product thereof to a cell, wherein the gene therapy composition includes a UCB-MSC, wherein the cell expresses IL-8 or GRO-$\alpha$ and induces tropism of the UCB-MSC;

[25] a gene therapy composition for transferring a therapeutic gene or product thereof to a cell, wherein the gene therapy composition includes a UCB-MSC, wherein the cell expresses IL-8 or GRO-$\alpha$ and induces tropism of the UCB-MSC, wherein the UCB-MSC function as a carrier for gene therapy;

[26] a gene therapy composition for transferring a therapeutic gene or product thereof to a cell, wherein the gene therapy composition includes a UCB-MSC, wherein the cell expresses IL-8 or GRO-$\alpha$ and induces tropism of the UCB-MSC, wherein an anti-tumor gene is introduced to the UCB-MSC;

[27] a gene therapy composition for transferring a therapeutic gene or product thereof to a cell, wherein the gene therapy composition includes a UCB-MSC, wherein the cell expresses IL-8 or GRO-$\alpha$ and induces a tropism of the UCB-MSC, wherein an anti-tumor gene is introduced to the UCB-MSC, wherein the anti-tumor gene is selected from the group consisting of a tumor suppressor gene, an apoptosis-inducing factor gene, a cell cycle regulatory gene, and an angiogenesis inhibitor gene;

[28] a gene-treating composition for transferring a therapeutic gene or product thereof to a cell, wherein the gene therapy composition includes a UCB-MSC, wherein the cell expresses IL-8 or GRO-$\alpha$ and induces a tropism of the UCB-MSC, wherein an anti-tumor gene is introduced to the UCB-MSC, wherein the anti-tumor gene is selected from the group consisting of a tumor suppressor gene, an apoptosis-inducing factor gene, a cell cycle regulatory gene, and an angiogenesis inhibitor gene, wherein the tumor suppressor gene may be selected from the group consisting of a gene of phosphatase and tensin homolog (PTEN), a gene of Maspin, a gene of RUNX3, a gene of Caveolin-1, a gene of nm23, a gene of Rb protein, a gene of Brush-1, a gene of inhibitor of tumor growth (ING-4), a gene of survivin, a gene of X chromosome linked inhibitor apoptosis protein (XIAP), a gene of neural apoptosis inhibitory protein (NAIP), and genes of proteins regulating these genes;

[29] a gene therapy composition for transferring a therapeutic gene or product thereof to a cell, wherein the gene therapy composition includes a UCB-MSC, wherein the cell expresses IL-8 or GRO-$\alpha$ and induces a tropism of the UCB-MSC, wherein an anti-tumor gene is introduced to the UCB-MSC, wherein the anti-tumor gene is selected from the group consisting of a tumor suppressor gene, an apoptosis-inducing factor gene, a cell cycle regulatory gene, and an angiogenesis inhibitor gene, wherein the apoptosis-inducing factor gene may be selected from the group consisting of a gene of cytokine, a gene of interleukin, a gene of a tumor necrosis factor (TNF), a gene of interferon (INF-$\alpha$, INF-$\beta$, INF-$\gamma$), a gene of a colony stimulating factor (CSFs), a gene of p53, a gene of Apaf-1, a gene of TRAIL, a gene of Caspase, a gene of Bax, a gene of Bad, a gene of FADD, a gene of JNK, a gene of p38 kinase, and genes of proteins regulating these genes;

[30] a gene therapy composition for transferring a therapeutic gene or product thereof to a cell, wherein the gene therapy composition includes a UCB-MSC, wherein the cell expresses IL-8 or GRO-$\alpha$ and induces tropism of the UCB-MSC, wherein an anti-tumor gene is introduced to the UCB-MSC, wherein the anti-tumor gene is selected from the group consisting of a tumor suppressor gene, an apoptosis-inducing factor gene, a cell cycle regulatory gene, and an angiogenesis inhibitor gene, wherein the cell cycle regulatory gene may be selected from the group consisting of a gene of cdc2, a gene of Cyclin (Cyclin A, Cyclin D, Cyclin E), a gene of cdc25C, a gene of WAF, a gene of INK4, a gene of CDK (CDK1, CDK2, CDK4, CDK6), a gene of Rb protein, a gene of E2F, an antisense or SiRNA thereof, and genes of proteins regulating these genes;

[31] a gene therapy composition for transferring a therapeutic gene or product thereof to a cell, wherein the gene therapy composition includes a UCB-MSC, wherein the cell expresses IL-8 or GRO-$\alpha$ and induces a tropism of the UCB-MSC, wherein an anti-tumor gene is introduced to the UCB-MSC, wherein the anti-tumor gene is selected from the group consisting of a tumor suppressor gene, an apoptosis-inducing factor gene, a cell cycle regulatory gene, and an angiogenesis inhibitor gene, wherein the angiogenesis inhibitor gene may be selected from the group consisting of a gene of thrombospondin-1, a gene of endostatin, a gene of tumstatin, a gene of canstatin, a gene of vastatin, a gene of restin, a gene of a vascular endothelial growth inhibitor, a gene of maspin, a gene of angiopoietins, a gene of 16-kd prolactin fragment, and a gene of endorepellin;

[32] a gene therapy composition for transferring a therapeutic gene or product thereof to a cell, wherein the gene therapy composition includes a UCB-MSC, wherein the cell expresses IL-8 or GRO-$\alpha$ and induces a tropism of the UCB-MSC, wherein a prodrug converting enzyme gene is introduced to the UCB-MSC;

[33] a gene therapy composition for transferring a therapeutic gene or product thereof to a cell, wherein the gene therapy composition includes a UCB-MSC, wherein the cell expresses IL-8 or GRO-α and induces a tropism of the UCB-MSC, wherein a prodrug converting enzyme gene is introduced to the UCB-MSC, wherein the prodrug converting enzyme gene is selected from the group consisting of cytosine deaminase gene and a CYP2B1 gene;

[34] a gene therapy composition for transferring a therapeutic gene or product thereof to a cell, wherein the gene therapy composition includes a UCB-MSC, wherein the cell expresses IL-8 or GRO-α and induces a tropism of the UCB-MSC, wherein an antisense or SiRNA of a gene related to a tumor is introduced to the UCB-MSC;

[35] a gene therapy composition for transferring a therapeutic gene or product thereof to a cell, wherein the gene therapy composition includes a UCB-MSC, wherein the cell expresses IL-8 or GRO-α and induces a tropism of the UCB-MSC, wherein an antisense or SiRNA of a gene related to a tumor is introduced to the UCB-MSC, wherein the gene related to a tumor may be selected from the group consisting of a gene of Ras family, a gene of c-myc, a gene of abl, a gene of erbB-1, a gene of EGF-R, a gene of Bax, a gene of an Apaf-1 interacting protein (APIP), a gene of Wnt-1-induced secreted protein 1 (WISP-1), a gene of Wnt, a gene of Raf-1, a gene of Src, a gene of Akt, a gene of Erk-1,2 and a gene of BcL-2;

[36] a gene therapy composition for transferring a therapeutic gene or product thereof to a cell, wherein the gene-treating composition includes a UCB-MSC, wherein the cell expresses IL-8 or GRO-α and induces a tropism of the UCB-MSC, wherein an oncolytic virus is introduced to the UCB-MSC;

[37] a gene therapy composition for transferring a therapeutic gene or product thereof to a cell, wherein the gene therapy composition includes a UCB-MSC, wherein the cell expresses IL-8 or GRO-α and induces a tropism of the UCB-MSC, wherein a oncolytic virus is introduced to the UCB-MSC, wherein the oncolytic virus is selected from the group consisting of Herpes simplex virus and Reovirus type 3;

[38] a composition for diagnosing a disease occurring in a site including a cell or monitoring treatment progression of the disease, wherein the composition includes a UCB-MSC, wherein the cell expresses IL-8 or GRO-α and induces a tropism of the UCB-MSC;

[39] a composition for diagnosing a disease occurring in a site including a cell or monitoring treatment progression of the disease, wherein the composition includes a UCB-MSC, wherein the cell expresses IL-8 or GRO-α and induces a tropism of the UCB-MSC, wherein the UCB-MSC is labeled with a detectable marker; and

[40] a composition for diagnosing a disease occurring in a site including a cell or monitoring treatment progression of the disease, wherein the composition includes a UCB-MSC, wherein the cell expresses IL-8 or GRO-α and induces a tropism of the UCB-MSC, wherein the UCB-MSC is labeled with a detectable marker, wherein the detectable marker may be selected from the group consisting of a luciferase-containing enzyme based fluorescent detector and Tat peptide-derivatized magnetic nanoparticles.

An aspect of the present invention provides a method of preventing or treating a tumor comprising administering to a subject an effective dose of a composition comprising mesenchymal stem cells derived from umbilical cord blood (UCB-MSC).

In the method, the administration may be made by using any known method in the art. The administration may be made for example, by a parenteral administration. The parenteral administration includes an injection. The injection may be made intravascullary, intramuscularly, subcutaneously, intradermally, or intrathecally. The administration may be made systemically or locally. The local administration may include direct administration to the tumor tissue. The composition may be administered into the subject alone or in combination with any anti-cancer drug or prodrug known in the art.

Since UCB-MSCs do not express HLA-DR (Major Histocompatibility Complex class II) that is a major cause for immunological rejection when a tissue or organ is transplanted (see Le Blanc, K C, *Exp Hematol*, 31:890-896, 2003; and Tse W T et al., *Transplantation*, 75:389-397, 2003), immunological reactions, such as rejection, which are major problems of transplantation do not occur or can be minimized. Accordingly, UCB-MSCs included in the pharmaceutical composition or used in the method according to the present invention can be taken from, in addition to a self-derived UCB, another subject-derived UCB. According to the present invention, UCB-MSCs can be used after being cryopreserved.

The UCB-MSCs-containing pharmaceutical composition for gene therapy or for preventing or treating diseases according to the present invention may further include pharmaceutically acceptable additives, in addition to the effective component. The UCB-MSCs-containing pharmaceutical composition may be formed into a suitable formulation that can be administered to a body. The suitable formulation may be a non-oral administration formulation, such as an injectable formulation or a locally administrable formulation. For example, a sterilized solution or suspension that includes water or a pharmaceutically acceptable solvent can be non-orally administered in an injectable form. Specifically, water or the pharmaceutically acceptable solvent is appropriately combined with a pharmaceutically acceptable carrier or medium, thereby forming an injectable formulation in a conventionally acceptable unit dosage. Examples of the pharmaceutically acceptable carrier or medium may include sterile water, saline, vegetable oils, emulsifier, suspension, surfactant, stabilizer, excipient, vehicle, an antiseptic substance, a binder, etc.

The injectable formulation described above can be non-orally administered, specifically directly administered to a site of disease, by using a conventional method. Alternatively, the injectable formulation described above can be administered through a cerebrospinal fluid, a vein, or an artery supplying blood to the site of disease, preferably directly administered to neighboring portions of the site of disease in the brain or the spinal cord or the opposite portions thereto. For example, the injectable formulation described can be administered using a clinical method developed by Douglas Kondziolka in Pittsburgh in 1998. That is, a skull of a subject to be administered is cut to a diameter of about 1 cm, the size of a pea, and then a MSC solution mixed with a Hank's balanced salt solution (HBSS) is injected thereto. In this regard, the injecting the MSC solution is performed using an injector including a long needle and a stereotactic frame for accurately injecting the MSC solution into the brain.

The daily dose of UCB-MSCs may be $1 \times 10^4$ to $1 \times 10^7$ cells/kg body weight, preferably $5 \times 10^5$ to $5 \times 10^6$ cells/kg body weight. The daily dose may be administered at once or be divided for several treatments. However, according to the present invention, the administration dose of UCB-MSCs may vary according to the kinds of diseases to be treated, the severity of disease to be treated, administration routes, and the weight, age, and gender of a patient. Accordingly, the administration dose described above does not limit the scope of the present invention.

In the method, the UCB-MSC may be obtained by any known method in the art. For example, to isolate a monocyte including a MSC from an UCB, any known method such as the method disclosed in Korean Registered Patent No. 489248 filed by the applicant of the present application and registered can be used. For example, the isolating method may be a ficoll-Hypaque density gradient method, but is not limited thereto. Specifically, UCB taken from an umbilical vein after delivery and before the placenta is separated is centrifuged with a ficoll-hypaque gradient to obtain a monocyte, and then the monocyte is washed several times to remove impurities therefrom. The resultant monocyte can be directly used for isolation or culture of MSCs, or cryo preserved for a long period of time.

A MSC can be isolated from UCB and cultured using any known method (see Pittinger M F et al. *Science,* 284: 143-7, 1999; and Lazarus H M et al. *Bone Marrow Transplant,* 16: 557-64, 1995), such as a method disclosed in Korean Publicated Patent No. 2003-0069115.

First, the isolated UCB may be centrifuged with, for example, a ficoll-Hypaque gradient to separate monocytes including a hematopoietic cell and a MSC, and then, the monocyte may be washed several times to remove impurities therefrom. Then, monocytes may be seeded in an appropriate concentration in a culture dish to grow cells in a form of a single layer. These cells may be identified with a phase-contrast microscope. In the phase-contrast microscopic image, a colony of cells having a homogeneous spindle shape are MSCs. Then, when cells are cultured and grow, cells are sub-cultured and then multiplied until the number of the cells reaches a desired number.

The UCB-MSCs included in the composition or used in the method according to the present invention can be cryopreserved using known methods (see Campos et al., *Cryobiology* 35:921-924, 1995). A medium for the cryoporeserving process may include 10~20% fetal bovine serum (FBS) and 10% dimethylsulfoxide (DMSO). The cells may be suspended in the medium until the concentration of cells is about $1\times10^6$ to $5\times10^6$ cells per 1 mL of medium.

The cell suspension may be divided and each part may be loaded onto a glass or plastic ample for cryopreservation, and then, the sample may be sealed and loaded into a temperature-controlled programmed freezer. Cells may be frozen using a freezing program providing a temperature change of $-1°$ C./minute so that damage to cells can be reduced when frozen cells are thawed. When the temperature of the sample reaches $-90°$ C. or lower, the sample is moved to a liquid nitrogen storage tank having a temperature of $-150°$ C. or lower.

When the frozen cells are thawed, the sample is quickly moved from the liquid nitrogen storage tank to a water bath having a controlled temperature of 37° C. The thawed content in the ample is immediately moved to a culture dish containing a culture medium in a stabilized condition.

A culture medium for isolating and culturing a MSC may be a cell culture medium containing 10% to 30% of FBS. The cell culture medium may be any cell culture medium that is conventionally used in the art. Examples of the cell culture medium may include a medium selected from the group consisting of a DMEM medium, an MEM medium, a α-MEM medium, a McCoys 5A medium, an eagle's basal medium, a CMRL medium, a Glasgow minimum necessarily medium, a (Ham's) F-12 medium, an iscove's modified Dulbecco's medium (IMDM), a (Liebovitz') L-15 medium, a RPMI 1640 medium and a combination thereof. For example, the cell culture medium may be the DMEM medium. During culturing, cells may be suspended so that the concentration of cells is about $5\times10^3$ to $2\times10^4$ cells per 1 mL of the medium.

Also, the cell culture medium may further include one or more additives, if required. The additives may include at least one material selected from the group consisting of: a serum of fetal calf, horse or human; a penicillin G for preventing microorganism contamination; antibiotics such as streptomycin sulfate or gentamycin; antifungal agents such as amphotericin B or nystatin; and mixtures of at least two materials selected from the forgoing.

In the method, the UCB-MSCs may be genetically engineered so as to transfer a therapeutic drug for substantially inhibiting growth of brain tumor cells. Also, the UCB-MSCs may be genetically engineered so as to transfer a therapeutical gene or product thereof to cells secreting IL-8 or GRO-α. In this regard, the term "inhibiting" refers to inhibiting cell proliferation and growth, in addition necrosis and apoptosis. The therapeutical gene may be, for example, an anti-tumor gene, a gene of an enzyme converting a prodrug into a drug, an antisense or SiRNA of a gene related to a tumor, or oncolytic virus (see Yip S et al., *The Cancer J.* 9(3), 189-204, 2003).

The UCB-MSC may be for example, an UCB-MSC that an anti-tumor agent gene is introduced thereinto. The anti-tumor agent gene may be for example, an agent selected from the group consisting of a tumor suppressor gene, an apoptosis-inducing factor gene, a cell cycle regulatory factor gene and an angiogenesis inhibitor gene. The tumor suppressor gene may be a gene selected from the group consisting of a gene encoding phosphatase and tensin homolog (PTEN), a gene encoding Maspin, a gene encoding RUNX3, a gene encoding Caveolin-1, a gene encoding nm23, a gene encoding Rb protein, a gene encoding Brush-1, a gene encoding inhibitor of tumor growth (ING-4), a gene encoding survivin, a gene encoding X chromosome linked inhibitor apoptosis protein (XIAP), a gene encoding neural apoptosis inhibitory protein (NAIP), genes encoding proteins related to regulation of said genes and a combination thereof.

The PTEN gene was identified as a tumor suppressor that is mutated in a large number of cancers at high frequency. The protein encoded this gene is a phosphatidylinositol-3,4,5-trisphosphate 3-phosphatase. It contains a tensin like domain as well as a catalytic domain similar to that of the dual specificity protein tyrosine phosphatases. Unlike most of the protein tyrosine phosphatases, this protein preferentially dephosphorylates phosphoinositide substrates. It negatively regulates intracellular levels of phosphatidylinositol-3,4,5-trisphosphate in cells and functions as a tumor suppressor by negatively regulating AKT/PKB signaling pathway. The PTEN may have an amino acid sequence of SEQ ID NO: 9. The PTEN gene may have a nucleotide sequence encoding the amino acid sequence of SEQ ID NO: 9.

Maspin (mammary serine proteinase inhibitor), a member of the serpin superfamily, has a multitude of effects on cells and tissues at an assortment of developmental stages. Maspin has tumor suppressing activity against breast and prostate cancer. The Maspin may have an amino acid sequence of SEQ ID NO: 10. The Maspin gene may have a nucleotide sequence encoding the amino acid sequence of SEQ ID NO: 10.

RUNX3 (RUNT-related transcription factor 3) gene encodes a member of the runt domain-containing family of transcription factors. A heterodimer of this protein and a beta subunit forms a complex that binds to the core DNA sequence 5'-PYGPYGGT-3' found in a number of enhancers and promoters, and can either activate or suppress transcription. It also interacts with other transcription factors. It functions as a tumor suppressor, and the gene is frequently deleted or transcriptionally silenced in cancer. Multiple transcript variants encoding different isoforms have been found for this gene. The RUNX3 may have an amino acid sequence of SEQ ID NO: 11 (isoform 1) or 12 (isoform 2). The RUNX3 gene may have a nucleotide sequence encoding the amino acid sequence of SEQ ID NO: 11 or 12.

Caveolin 1 (CAV1), a scaffolding protein, is the main component of the caveolae plasma membranes found in most cell types. The protein links integrin subunits to the tyrosine kinase FYN, an initiating step in coupling integrins to the Ras-ERK pathway and promoting cell cycle progression. The gene is a tumor suppressor gene candidate and a negative regulator of the Ras-p42/44 MAP kinase cascade. CAV1 and CAV2 are located next to each other on chromosome 7 and express colocalizing proteins that form a stable hetero-oligomeric complex. By using alternative initiation codons in the same reading frame, two isoforms (alpha and beta) are encoded by a single transcript from caveolin 1 gene. The CAVEOLIN 1 may have an amino acid sequence of SEQ ID NO: 13. The CAVEOLIN 1 gene may have a nucleotide sequence encoding the amino acid sequence of SEQ ID NO: 13.

NM23 gene (NME1; nonmetastatic cells 1, protein expressed in) was identified because of its reduced mRNA transcript levels in highly metastatic cells. Nucleoside diphosphate kinase (NDK) exists as a hexamer composed of 'A' (encoded by this gene) and 'B' (encoded by NME2) isoforms. Mutations in this gene have been identified in aggressive neuroblastomas. Two transcript variants encoding different isoforms have been found for this gene. Co-transcription of this gene and the neighboring downstream gene (NME2) generates naturally-occurring transcripts (NME1-NME2), which encodes a fusion protein comprised of sequence sharing identity with each individual gene product. The NM23 may have an amino acid sequence of SEQ ID NO: 14 (isoform A) or 15 (isoform B). The NM23 gene may have a nucleotide sequence encoding the amino acid sequence of SEQ ID NO: 14 or 15.

The protein encoded by Rb (Retinoblastoma; Rb1) gene is a negative regulator of the cell cycle and was the first tumor suppressor gene found. The encoded protein also stabilizes constitutive heterochromatin to maintain the overall chromatin structure. The active, hypophosphorylated form of the protein binds transcription factor E2F1. Defects in this gene are a cause of childhood cancer retinoblastoma (RB), bladder cancer, and osteogenic sarcoma. The Rb may have an amino acid sequence of SEQ ID NO: 16. The Rb gene may have a nucleotide sequence encoding the amino acid sequence of SEQ ID NO: 16.

The protein encoded by Brush-1 (Myosin IA; MYO1A; BBMI) gene belongs to the myosin superfamily. Myosins are molecular motors that, upon interaction with actin filaments, utilize energy from ATP hydrolysis to generate mechanical force. Each myosin has a conserved N-terminal motor domain that contains both ATP-binding and actin-binding sequences. Following the motor domain is a light-chain-binding 'neck' region containing 1-6 copies of a repeat element, the IQ motif, that serves as a binding site for calmodulin or other members of the EF-hand superfamily of calcium-binding proteins. At the C-terminus, each myosin class has a distinct tail domain that serves in dimerization, membrane binding, protein binding, and/or enzymatic activities and targets each myosin to its particular subcellular location. The kidney epithelial cell line, LLC-PK1-CL4 (CL4), forms a well ordered brush border (BB) on its apical surface. Experiments indicate that the brush border population of the encoded protein turns over rapidly, while its head and tail domains interact transiently with the core actin and plasma membrane, respectively. A rapidly exchanging pool of the protein encoded by this gene envelops an actin core bundle that, by comparison, is static in structure. The Brush-1 may have an amino acid sequence of SEQ ID NO: 17. The Brush-1 gene may have a nucleotide sequence encoding the amino acid sequence of SEQ ID NO: 17.

ING4 (inhibitor of growth 4) gene encodes a tumor suppressor protein that contains a PHD-finger, which is a common motif in proteins involved in chromatin remodeling. This protein can bind TP53 and EP300/p300, a component of the histone acetyl transferase complex, suggesting its involvement in the TP53-dependent regulatory pathway. Multiple alternatively spliced transcript variants have been observed that encode distinct proteins. The ING4 may have an amino acid sequence of SEQ ID NO: 18 (isoform 1), 19 (isoform 3), 20 (isoform 4), 21 (isoform 5), 22 (isoform 6) or 23 (isoform 9). The ING4 gene may have a nucleotide sequence encoding the amino acid sequence of SEQ ID NO: 18, 19, 20, 21, 22 or 23.

Survivin (Baculoviral IAP repeat-containing protein 5; BIRC5) gene is a member of the inhibitor of apoptosis (IAP) gene family, which encodes negative regulatory proteins that prevent apoptotic cell death. IAP family members usually contain multiple baculovirus IAP repeat (BIR) domains, but this gene encodes proteins with only a single BIR domain. The encoded proteins also lack a C-terminus RING finger domain. Gene expression is high during fetal development and in most tumors yet low in adult tissues. Antisense transcripts are involved in the regulation of this gene's expression. At least four transcript variants encoding distinct isoforms have been found for this gene, but the full-length natures of only three of them have been determined. The Survivin may have an amino acid sequence of SEQ ID NO: 24 (isoform 1), 25 (isoform 2) or 26 (isoform 3). The Survivin gene may have a nucleotide sequence encoding the amino acid sequence of SEQ ID NO: 24, 25 or 26.

The protein encoded by XIAP (Inhibitor of apoptosis, X-linked; Baculoviral IAP repeat-containing protein 4; BIRC4) gene is a member of a family of proteins which inhibit apoptosis through binding to tumor necrosis factor receptor-associated factors TRAF1 and TRAF2. This protein inhibits apoptosis induced by menadione, a potent inducer of free radicals, and ICE. It also inhibits at least two members of the caspase family of cell-death proteases, caspase-3 and caspase-7. The XIAP may have an amino acid sequence of SEQ ID NO: 27. The XIAP gene may have a nucleotide sequence encoding the amino acid sequence of SEQ ID NO: 27.

NAIP (Neuronal apoptosis inhibitory protein; baculoviral IAP repeat-containing protein 1; BIRC) gene is part of a 500 kb inverted duplication on chromosome 5q13. This duplicated region contains at least four genes and repetitive elements which make it prone to rearrangements and deletions. The repetitiveness and complexity of the sequence have also caused difficulty in determining the organization of this genomic region. This copy of the gene is full length; additional copies with truncations and internal deletions are also present in this region of chromosome 5q13. It is thought that this gene is a modifier of spinal muscular atrophy caused by mutations in a neighboring gene, SMN1. The protein encoded by this gene contains regions of homology to two baculovirus inhibitor of apoptosis proteins, and it is able to suppress apoptosis induced by various signals. Alternatively spliced transcript variants encoding distinct isoforms have been found for this gene. The NAIP may have an amino acid sequence of SEQ ID NO: 28 (isoform 1) or SEQ ID NO: 29 (isoform 2). The NAIP gene may have a nucleotide sequence encoding the amino acid sequence of SEQ ID NO: 28 or 29.

The apoptosis inducing factor gene may be for example, a gene selected from the group consisting of a gene encoding cytokine, a gene encoding interleukin, a gene encoding a tumor necrosis factor (TNF), a gene encoding interferon (INF-α, INF-β, INF-γ), a gene encoding a colony stimulating factor (CSFs), a gene encoding p53, a gene encoding Apaf-1, a gene encoding TRAIL, a gene encoding Caspase, a gene encoding Bax, a gene encoding Bad, a gene encoding FADD, a gene encoding JNK, a gene encoding p38 kinase and genes encoding proteins related to regulation of said genes.

TNF (tumor necrosis factor) gene encodes a multifunctional proinflammatory cytokine that belongs to the tumor necrosis factor (TNF) superfamily. This cytokine is mainly secreted by macrophages. It can bind to, and thus functions through its receptors TNFRSF1A/TNFR1 and TNFRSF1B/TNFBR. This cytokine is involved in the regulation of a wide spectrum of biological processes including cell proliferation, differentiation, apoptosis, lipid metabolism, and coagulation. This cytokine has been implicated in a variety of diseases, including autoimmune diseases, insulin resistance, and cancer. Knockout studies in mice also suggested the neuroprotective function of this cytokine. The TNF may have an amino acid sequence of SEQ ID NO: 30. The TNF gene may have a nucleotide sequence encoding the amino acid sequence of SEQ ID NO: 30.

INF-α, leukocyte interferon is produced predominantly by B lymphocytes. Immune interferon (IFN-gamma; MIM 147570) is produced by mitogen- or antigen-stimulated T lymphocytes. INF-β is produced by fibroblast. The INF-α may have an amino acid sequence of SEQ ID NO: 31. The INF-α gene may have a nucleotide sequence encoding the amino acid sequence of SEQ ID NO: 31. The INF-β may have an amino acid sequence of SEQ ID NO: 32. The INF-β gene may have a nucleotide sequence encoding the amino acid sequence of SEQ ID NO: 32. INF-γ or type II interferon, is a cytokine critical for innate and adaptive immunity against viral and intracellular bacterial infections and for tumor control. Aberrant INF-γ expression is associated with a number of autoinflammatory and autoimmune diseases. The importance of INF-γ in the immune system stems in part from its ability to inhibit viral replication directly, but most importantly derives from its immunostimulatory and immunomodulatory effects. INF-γ is produced predominantly by natural killer (NK) and natural killer T (NKT) cells as part of the innate immune response, and by CD4 (MIM 186940) and CD8 (see MIM 186910) cytotoxic T lymphocyte (CTL) effector T cells once antigen-specific immunity develops. The INF-γ may have an amino acid sequence of SEQ ID NO: 33. The INF-γ gene may have a nucleotide sequence encoding the amino acid sequence of SEQ ID NO: 33.

The CSF may include CSF1, CSF2 or CSF3. CSF1 (COLONY-STIMULATING FACTOR 1) is a cytokine that controls the production, differentiation, and function of macrophages. The active form of the protein is found extracellularly as a disulfide-linked homodimer, and is thought to be produced by proteolytic cleavage of membrane-bound precursors. The encoded protein may be involved in development of the placenta. Four transcript variants encoding three different isoforms have been found for this gene. The CSF1 may have an amino acid sequence of SEQ ID NO: 34 (isoform a precursor), SEQ ID NO: 35 (isoform a precursor), SEQ ID NO: 36 (isoform b precursor) or SEQ ID NO: 37 (isoform c precursor). The CSF1 gene may have a nucleotide sequence encoding the amino acid sequence of SEQ ID NO: 34, 35, 36 or 37.

CSF2 is a cytokine that controls the production, differentiation, and function of granulocytes and macrophages. The active form of the protein is found extracellularly as a homodimer. CSF2 gene has been localized to a cluster of related genes at chromosome region 5q31, which is known to be associated with interstitial deletions in the 5q-syndrome and acute myelogenous leukemia. Other genes in the cluster include those encoding interleukins 4, 5, and 13. The CSF2 may have an amino acid sequence of SEQ ID NO: 38. The CSF2 gene may have a nucleotide sequence encoding the amino acid sequence of SEQ ID NO: 38.

CSF3 is a cytokine that controls the production, differentiation, and function of granulocytes. The active protein is found extracellularly. Three transcript variants encoding three different isoforms have been found for this gene. The CSF3 may have an amino acid sequence of SEQ ID NO: 39 (isoform a precursor), SEQ ID NO: 40 (isoform b precursor), or SEQ ID NO: 41 (isoform c). The CSF3 gene may have a nucleotide sequence encoding the amino acid sequence of SEQ ID NO: 39, 40, or 41.

P53 (Tumor protein p53; TP53) responds to diverse cellular stresses to regulate target genes that induce cell cycle arrest, apoptosis, senescence, DNA repair, or changes in metabolism. p53 protein is expressed at low level in normal cells and at a high level in a variety of transformed cell lines, where it's believed to contribute to transformation and malignancy. p53 is a DNA-binding protein containing transcription activation, DNA-binding, and oligomerization domains. It is postulated to bind to a p53-binding site and activate expression of downstream genes that inhibit growth and/or invasion, and thus function as a tumor suppressor. Mutants of p53 that frequently occur in a number of different human cancers fail to bind the consensus DNA binding site, and hence cause the loss of tumor suppressor activity. Alterations of this gene occur not only as somatic mutations in human malignancies, but also as germline mutations in some cancer-prone families with Li-Fraumeni syndrome. Multiple p53 variants due to alternative promoters and multiple alternative splicing have been found. These variants encode distinct isoforms, which can regulate p53 transcriptional activity. The p53 may have an amino acid sequence of SEQ ID NO: 42 (isoform a), SEQ ID NO: 43 (isoform a), SEQ ID NO: 44 (isoform b), SEQ ID NO: 45 (isoform c), SEQ ID NO: 46 (isoform d), SEQ ID NO: 47 (isoform e) or SEQ ID NO: 48 (isoform f). The p53 gene may have a nucleotide sequence encoding the amino acid sequence of SEQ ID NO: 42, 43, 44, 45, 46, 47 or 48.

APAF1 (apoptotic protease activating factor 1) is a cytoplasmic protein that initiates apoptosis. This protein contains several copies of the WD-40 domain, a caspase recruitment domain (CARD), and an ATPase domain (NB-ARC). Upon binding cytochrome c and dATP, this protein forms an oligomeric apoptosome. The apoptosome binds and cleaves caspase 9 preproprotein, releasing its mature, activated form. Activated caspase 9 stimulates the subsequent caspase cascade that commits the cell to apoptosis. Alternative splicing results in several transcript variants encoding different isoforms. The APAF1 may have an amino acid sequence of SEQ ID NO: 49 (isoform a), SEQ ID NO: 50 (isoform b), SEQ ID NO: 51 (isoform c), SEQ ID NO: 52 (isoform d), or SEQ ID NO: 53 (isoform e). The APAF1 gene may have a nucleotide sequence encoding the amino acid sequence of SEQ ID NO: 49, 50, 51, 52, or 53.

TRAIL (TNF-related apoptosis-inducing ligand; tumor necrosis factor ligand superfamily, member 10; TNFSF10) is a cytokine that belongs to the tumor necrosis factor (TNF) ligand family. This protein preferentially induces apoptosis in transformed and tumor cells, but does not appear to kill normal cells although it is expressed at a significant level in most normal tissues. This protein binds to several members of TNF receptor superfamily including TNFRSF10A/TRAILR1, TNFRSF10B/TRAILR2, TNFRSF10C/TRAILR3, TNFRSF10D/TRAILR4, and possibly also to TNFRSF11B/OPG. The activity of this protein may be modulated by binding to the decoy receptors TNFRSF10C/TRAILR3, TNFRSF10D/TRAILR4, and TNFRSF11B/OPG that cannot induce apoptosis. The binding of this protein to its receptors has been shown to trigger the activation of MAPK8/JNK, caspase 8, and caspase 3. The TRAIL may have an amino acid sequence of SEQ ID NO: 54. The TRAIL gene may have a nucleotide sequence encoding the amino acid sequence of SEQ ID NO: 54.

Caspase 3 (apoptosis-related cysteine protease; CASP3) is a protein which is a member of the cysteine-aspartic acid protease (caspase) family. Sequential activation of caspases plays a central role in the execution-phase of cell apoptosis. Caspases exist as inactive proenzymes which undergo proteolytic processing at conserved aspartic residues to produce two subunits, large and small, that dimerize to form the active enzyme. This protein cleaves and activates caspases 6, 7 and 9, and the protein itself is processed by caspases 8, 9 and 10. It is the predominant caspase involved in the cleavage of amyloid-beta 4A precursor protein, which is associated with neuronal death in Alzheimer's disease. Alternative splicing of this gene results in two transcript variants that encode the same protein. The Caspase 3 may have an amino acid sequence of SEQ ID NO: 55. The Caspase 3 gene may have a nucleotide sequence encoding the amino acid sequence of SEQ ID NO: 55.

BAX (BCL2-associated X protein) belongs to the BCL2 protein family. BCL2 family members form hetero- or homodimers and act as anti- or pro-apoptotic regulators that are involved in a wide variety of cellular activities. This protein forms a heterodimer with BCL2, and functions as an apoptotic activator. This protein is reported to interact with, and increase the opening of, the mitochondrial voltage-dependent anion channel (VDAC), which leads to the loss in membrane potential and the release of cytochrome c. The expression of this gene is regulated by the tumor suppressor P53 and has been shown to be involved in P53-mediated apoptosis. Multiple alternatively spliced transcript variants, which encode different isoforms, have been reported for this gene. The BAX may have an amino acid sequence of SEQ ID NO: 56. The BAX gene may have a nucleotide sequence encoding the amino acid sequence of SEQ ID NO: 56.

BAD (BCL2 antagonist of cell death) is a member of the BCL-2 family. BCL-2 family members are known to be regulators of programmed cell death. This protein positively regulates cell apoptosis by forming heterodimers with BCL-xL and BCL-2, and reversing their death repressor activity. Proapoptotic activity of this protein is regulated through its phosphorylation. Protein kinases AKT and MAP kinase, as well as protein phosphatase calcineurin were found to be involved in the regulation of this protein. Alternative splicing of this gene results in two transcript variants which encode the same isoform. The BAD may have an amino acid sequence of SEQ ID NO: 57. The BAD gene may have a nucleotide sequence encoding the amino acid sequence of SEQ ID NO: 57.

FADD (FAS-associated via death domain) is an adaptor molecule that interacts with various cell surface receptors and mediates cell apoptotic signals. Through its C-terminal death domain, this protein can be recruited by TNFRSF6/Fas-receptor, tumor necrosis factor receptor, TNFRSF25, and TNFSF10/TRAIL-receptor, and thus it participates in the death signaling initiated by these receptors. Interaction of this protein with the receptors unmasks the N-terminal effector domain of this protein, which allows it to recruit caspase-8, and thereby activate the cysteine protease cascade. Knockout studies in mice also suggest the importance of this protein in early T cell development. The FADD may have an amino acid sequence of SEQ ID NO: 58. The FADD gene may have a nucleotide sequence encoding the amino acid sequence of SEQ ID NO: 58.

JNK1 (C-jun kinase 1; mitogen-activated protein kinase 8; MAPK8) is a member of the MAP kinase family. MAP kinases act as an integration point for multiple biochemical signals, and are involved in a wide variety of cellular processes such as proliferation, differentiation, transcription regulation and development. This kinase is activated by various cell stimuli, and targets specific transcription factors, and thus mediates immediate-early gene expression in response to cell stimuli. The activation of this kinase by tumor-necrosis factor alpha (TNF-alpha) is found to be required for TNF-alpha induced apoptosis. This kinase is also involved in UV radiation induced apoptosis, which is thought to be related to cytochrome c-mediated cell death pathway. Studies of the mouse counterpart of this gene suggested that this kinase play a key role in T cell proliferation, apoptosis and differentiation. Four alternatively spliced transcript variants encoding distinct isoforms have been reported. The JNK1 may have an amino acid sequence of SEQ ID NO: 59 (JNK1 alpha1), SEQ ID NO: 60 (JNK1 alpha2), SEQ ID NO: 61 (JNK1 beta1) or SEQ ID NO: 62 (JNK1 beta2). The JNK1 gene may have a nucleotide sequence encoding the amino acid sequence of SEQ ID NO: 59, 60, 61 or 62.

P38 kinase (mitogen-activated protein kinase 14; MAPK14; p38 MAP KINASE; p38-ALPHA) is a member of the MAP kinase family. MAP kinases act as an integration point for multiple biochemical signals, and are involved in a wide variety of cellular processes such as proliferation, differentiation, transcription regulation and development. This kinase is activated by various environmental stresses and proinflammatory cytokines. The activation requires its phosphorylation by MAP kinase kinases (MKKs), or its autophosphorylation triggered by the interaction of MAP3K7IP1/TAB1 protein with this kinase. The substrates of this kinase include transcription regulator ATF2, MEF2C, and MAX, cell cycle regulator CDC25B, and tumor suppressor p53, which suggest the roles of this kinase in stress related transcription and cell cycle regulation, as well as in genotoxic stress response. Four alternatively spliced transcript variants of this gene encoding distinct isoforms have been reported. The p38 kinase may have an amino acid sequence of SEQ ID NO: 63 (isoform 1). The p38 kinase gene may have a nucleotide sequence encoding the amino acid sequence of SEQ ID NO: 63.

The cell cycle regulatory factor gene may be a gene selected from the group consisting of a gene encoding cdc2, a gene encoding Cyclin (Cyclin A, Cyclin D, Cyclin E), a gene encoding cdc25C, a gene encoding WAF, a gene encoding INK4, a gene encoding CDK (CDK1, CDK2, CDK4, CDK6), a gene encoding Rb protein, a gene encoding E2F, an antisense or siRNA thereof and genes encoding proteins related to the regulation of said genes.

CDC2 (cell division cycle 2, G1 to S and G2 to M; Cyclin-dependent kinase 1; CDK1) is a member of the Ser/Thr protein kinase family. This protein is a catalytic subunit of the highly conserved protein kinase complex known as M-phase promoting factor (MPF), which is essential for G1/S and G2/M phase transitions of eukaryotic cell cycle. Mitotic cyclins stably associate with this protein and function as regulatory subunits. The kinase activity of this protein is controlled by cyclin accumulation and destruction through the cell cycle. The phosphorylation and dephosphorylation of this protein also play important regulatory roles in cell cycle control. Alternatively spliced transcript variants encoding different isoforms have been found for this gene. The CDC2 may have an amino acid sequence of SEQ ID NO: 64 (isoform 2). The CDC2 gene may have a nucleotide sequence encoding the amino acid sequence of SEQ ID NO: 64.

Cyclin A (Cyclin A2; CCNA2) belongs to the highly conserved cyclin family, whose members are characterized by a dramatic periodicity in protein abundance through the cell cycle. Cyclins function as regulators of CDK kinases. Different cyclins exhibit distinct expression and degradation patterns which contribute to the temporal coordination of each mitotic event. In contrast to cyclin A1, which is present only in germ cells, this cyclin is expressed in all tissues tested. This cyclin binds and activates CDC2 or CDK2 kinases, and thus promotes both cell cycle G1/S and G2/M transitions. The Cyclin A may have an amino acid sequence of SEQ ID NO: 65. The Cyclin A gene may have a nucleotide sequence encoding the amino acid sequence of SEQ ID NO: 65.

The Cyclin D may include Cyclin D2, D3 or combination thereof. Cyclin D2 (CCND2) belongs to the highly conserved cyclin family, whose members are characterized by a dramatic periodicity in protein abundance through the cell cycle. Cyclins function as regulators of CDK kinases. Different cyclins exhibit distinct expression and degradation patterns which contribute to the temporal coordination of each mitotic event. This cyclin forms a complex with and functions as a regulatory subunit of CDK4 or CDK6, whose activity is required for cell cycle G1/S transition. This protein has been shown to interact with and be involved in the phosphorylation of tumor suppressor protein Rb. Knockout studies of the homologous gene in mouse suggest the essential roles of this gene in ovarian granulosa and germ cell proliferation. High level expression of this gene was observed in ovarian and testicular tumors. The Cyclin D2 may have an amino acid sequence of SEQ ID NO: 66. The Cyclin D2 gene may have a nucleotide sequence encoding the amino acid sequence of SEQ ID NO: 66. Cyclin D3 (CCND3) belongs to the highly conserved cyclin family, whose members are characterized by a dramatic periodicity in protein abundance through the cell cycle. Cyclins function as regulators of CDK kinases. Different cyclins exhibit distinct expression and degradation patterns which contribute to the temporal coordination of each mitotic event. This cyclin forms a complex with and functions as a regulatory subunit of CDK4 or CDK6, whose activity is required for cell cycle G1/S transition. This protein has been shown to interact with and be involved in the phosphorylation of tumor suppressor protein Rb. The CDK4 activity associated with this cyclin was reported to be necessary for cell cycle progression through G2 phase into mitosis after UV radiation. Several transcript variants encoding different isoforms have been found for this gene. The Cyclin D3 may have an amino acid sequence of SEQ ID NO: 67. The Cyclin D3 gene may have a nucleotide sequence encoding the amino acid sequence of SEQ ID NO: 67. The Cyclin E (CCNE; CYCLIN E1; CCNE1) belongs to the highly conserved cyclin family, whose members are characterized by a dramatic periodicity in protein abundance through the cell cycle. Cyclins function as regulators of CDK kinases. Different cyclins exhibit distinct expression and degradation patterns which contribute to the temporal coordination of each mitotic event. This cyclin forms a complex with and functions as a regulatory subunit of CDK2, whose activity is required for cell cycle G1/S transition. This protein accumulates at the G1-S phase boundary and is degraded as cells progress through S phase. Overexpression of this gene has been observed in many tumors, which results in chromosome instability, and thus may contribute to tumorigenesis. This protein was found to associate with, and be involved in, the phosphorylation of NPAT protein (nuclear protein mapped to the ATM locus), which participates in cell-cycle regulated histone gene expression and plays a critical role in promoting cell-cycle progression in the absence of pRB. Two alternatively spliced transcript variants of this gene, which encode distinct isoforms, have been described. Two additional splice variants were reported but detailed nucleotide sequence information is not yet available. The CYCLIN E may have an amino acid sequence of SEQ ID NO: 68. The Cyclin E gene may have a nucleotide sequence encoding the amino acid sequence of SEQ ID NO: 68.

CDC25C (cell division cycle 25C) gene is highly conserved during evolution and it plays a key role in the regulation of cell division. The CDC25C protein is a tyrosine phosphatase and belongs to the Cdc25 phosphatase family. It directs dephosphorylation of cyclin B-bound CDC2 and triggers entry into mitosis. It is also thought to suppress p53-induced growth arrest. Multiple alternatively spliced transcript variants of this gene have been described, however, the full-length nature of many of them is not known. The CDC25C may have an amino acid sequence of SEQ ID NO: 69 (isoform a) or SEQ ID NO: 70 (isoform b). The CDC25C gene may have a nucleotide sequence encoding the amino acid sequence of SEQ ID NO: 69 or 70.

WAF1 (wildtype p53-activated fragment 1; p21) is a potent cyclin-dependent kinase inhibitor. This protein binds to and inhibits the activity of cyclin-CDK2 or -CDK4 complexes, and thus functions as a regulator of cell cycle progression at G1. The expression of this gene is tightly controlled by the tumor suppressor protein p53, through which this protein mediates the p53-dependent cell cycle G1 phase arrest in response to a variety of stress stimuli. This protein can interact with proliferating cell nuclear antigen (PCNA), a DNA polymerase accessory factor, and plays a regulatory role in S phase DNA replication and DNA damage repair. This protein was reported to be specifically cleaved by CASP3-like caspases, which thus leads to a dramatic activation of CDK2, and may be instrumental in the execution of apoptosis following caspase activation. Two alternatively spliced variants, which encode an identical protein, have been reported. The WAF1 may have an amino acid sequence of SEQ ID NO: 71. The CDC25C gene may have a nucleotide sequence encoding the amino acid sequence of SEQ ID NO: 71.

INK4 (Cyclin-dependent kinase inhibitor 2A; CDKN2A) gene generates several transcript variants which differ in their first exons. At least three alternatively spliced variants encoding distinct proteins have been reported, two of which encode structurally related isoforms known to function as inhibitors of CDK4 kinase. The remaining transcript includes an alternate first exon located 20 Kb upstream of the remainder of the gene; this transcript contains an alternate open reading frame (ARF) that specifies a protein which is structurally unrelated to the products of the other variants. This ARF product functions as a stabilizer of the tumor suppressor protein p53 as it can interact with, and sequester, MDM1, a protein responsible for the degradation of p53. In spite of the structural and functional differences, the CDK inhibitor isoforms and the ARF product encoded by this gene, through the regulatory roles of CDK4 and p53 in cell cycle G1 progression, share a common functionality in cell cycle G1 control. This gene is frequently mutated or deleted in a wide variety of tumors, and is known to be an important tumor suppressor gene. The INK4 may have an amino acid sequence of SEQ ID NO: 72

(isoform 1), SEQ ID NO: 73 (isoform 3) or SEQ ID NO: 74 (isoform 4). The INK4 gene may have a nucleotide sequence encoding the amino acid sequence of SEQ ID NO: 72, 73 or 74.

CDK2 (Cyclin-dependent kinase 2) is a member of the Ser/Thr protein kinase family. This protein kinase is highly similar to the gene products of S. cerevisiae cdc28, and S. pombe cdc2. It is a catalytic subunit of the cyclin-dependent protein kinase complex, whose activity is restricted to the G1-S phase, and essential for cell cycle G1/S phase transition. This protein associates with and regulated by the regulatory subunits of the complex including cyclin A or E, CDK inhibitor p21Cip1 (CDKN1A) and p27Kip1 (CDKN1B). Its activity is also regulated by its protein phosphorylation. Two alternatively spliced variants and multiple transcription initiation sites of this gene have been reported. The CDK2 may have an amino acid sequence of SEQ ID NO: 75 (isoform 1) or SEQ ID NO: 76 (isoform 2). The CDK2 gene may have a nucleotide sequence encoding the amino acid sequence of SEQ ID NO: 75 or 76.

CDK4 (Cyclin-dependent kinase 4) is a member of the Ser/Thr protein kinase family. This protein is highly similar to the gene products of S. cerevisiae cdc28 and S. pombe cdc2. It is a catalytic subunit of the protein kinase complex that is important for cell cycle G1 phase progression. The activity of this kinase is restricted to the G1-S phase, which is controlled by the regulatory subunits D-type cyclins and CDK inhibitor p16(INK4a). This kinase was shown to be responsible for the phosphorylation of retinoblastoma gene product (Rb). Mutations in this gene as well as in its related proteins including D-type cyclins, p16 (INK4a) and Rb were all found to be associated with tumorigenesis of a variety of cancers. Multiple polyadenylation sites of this gene have been reported. The CDK4 may have an amino acid sequence of SEQ ID NO: 77. The CDK4 gene may have a nucleotide sequence encoding the amino acid sequence of SEQ ID NO: 77.

CDK6 (Cyclin-dependent kinase 6) is a member of the cyclin-dependent protein kinase (CDK) family. CDK family members are highly similar to the gene products of Saccharomyces cerevisiae cdc28, and Schizosaccharomyces pombe cdc2, and are known to be important regulators of cell cycle progression. This kinase is a catalytic subunit of the protein kinase complex that is important for cell cycle G1 phase progression and G1/S transition. The activity of this kinase first appears in mid-G1 phase, which is controlled by the regulatory subunits including D-type cyclins and members of INK4 family of CDK inhibitors. This kinase, as well as CDK4, has been shown to phosphorylate, and thus regulate the activity of, tumor suppressor protein Rb. The CDK6 may have an amino acid sequence of SEQ ID NO: 78. The CDK6 gene may have a nucleotide sequence encoding the amino acid sequence of SEQ ID NO: 78.

Transcription factor E2F (E2F Transcription factor 1; E2F1) is a member of the E2F family of transcription factors. The E2F family plays a crucial role in the control of cell cycle and action of tumor suppressor proteins and is also a target of the transforming proteins of small DNA tumor viruses. The E2F proteins contain several evolutionarily conserved domains found in most members of the family. These domains include a DNA binding domain, a dimerization domain which determines interaction with the differentiation regulated transcription factor proteins (DP), a transactivation domain enriched in acidic amino acids, and a tumor suppressor protein association domain which is embedded within the transactivation domain. This protein and another 2 members, E2F2 and E2F3, have an additional cyclin binding domain. This protein binds preferentially to retinoblastoma protein pRB in a cell-cycle dependent manner. It can mediate both cell proliferation and p53-dependent/independent apoptosis. The E2F may have an amino acid sequence of SEQ ID NO: 79. The E2F gene may have a nucleotide sequence encoding the amino acid sequence of SEQ ID NO: 79.

The angiogenesis inhibitor gene may be a gene selected from the group consisting of a gene encoding thrombospondin-1, a gene encoding endostatin, a gene encoding tumstatin, a gene encoding canstatin, a gene encoding vastatin, a gene encoding restin, a gene encoding a vascular endothelial growth factor inhibitor, a gene encoding maspin, a gene encoding angiopoietins, a gene encoding 16-kd prolactin fragment and a gene encoding endorepellin.

Thrombospondin I (THBS1, TSP1)) is a subunit of a disulfide-linked homotrimeric protein. This protein is an adhesive glycoprotein that mediates cell-to-cell and cell-to-matrix interactions. This protein can bind to fibrinogen, fibronectin, laminin, type V collagen and integrins alpha-V/beta-1. This protein has been shown to play roles in platelet aggregation, angiogenesis, and tumorigenesis. The thrombospondin 1 may have an amino acid sequence of SEQ ID NO: 80. The thrombospondin 1 gene may have a nucleotide sequence encoding the amino acid sequence of SEQ ID NO: 80.

Endostatin is contained in collagen, type XVIII, alpha-1 (COL18A1) which is the alpha chain of type XVIII collagen. This collagen is one of the multiplexins, extracellular matrix proteins that contain multiple triple-helix domains (collagenous domains) interrupted by non-collagenous domains. The proteolytically produced C-terminal fragment of type XVIII collagen is endostatin, a potent antiangiogenic protein. Mutations in this gene are associated with Knobloch syndrome. The main features of this syndrome involve retinal abnormalities, so type XVIII collagen may play an important role in retinal structure and in neural tube closure. Alternatively spliced transcript variants encoding different isoforms have been found for this gene. The Endostatin may have an amino acid sequence of SEQ ID NO: 81 (isoform 1) or 82 (isoform 2). The amino acid residues 1340-1510 of SEQ ID NO: 81 (isoform 1) or 1160-1330 residues of SEQ ID NO: 82 (isoform 2) is an endostatin like domain. The Endostatin gene may have a nucleotide sequence encoding the amino acid sequence of SEQ ID NO: 81 or 82.

Tumstatin is contained in collagen, type IV, alpha-3 (COL4A3). Type IV collagen, the major structural component of basement membranes, is a multimeric protein composed of 3 alpha subunits. These subunits are encoded by 6 different genes, alpha 1 through alpha 6, each of which can form a triple helix structure with 2 other subunits to form type IV collagen. This gene encodes alpha 3. In the Goodpasture syndrome, autoantibodies bind to the collagen molecules in the basement membranes of alveoli and glomeruli. The epitopes that elicit these autoantibodies are localized largely to the non-collagenous C-terminal domain of the protein. A specific kinase phosphorylates amino acids in this same C-terminal region and the expression of this kinase is upregulated during pathogenesis. There are multiple alternate transcripts that appear to be unique to this human alpha 3 gene and alternate splicing is restricted to the six exons that encode this C-terminal domain. This gene is also linked to an autosomal recessive form of Alport syndrome. The mutations contributing to this syndrome are also located within the exons that encode this C-terminal region. Like the other members of the type IV collagen gene family, this gene is organized in a head-to-head conformation with another type IV collagen gene so that each gene pair shares a common promoter. Some exons of this gene are interspersed with exons of an uncharacterized gene which is on the opposite strand. The tumstatin may have an amino acid sequence of SEQ ID NO: 83. The tumstatin gene may have a nucleotide sequence encoding the amino acid sequence of SEQ ID NO: 83.

Canstatin (alpha 2 type IV collagen preproprotein) is one of the six subunits of type IV collagen, the major structural component of basement membranes. The C-terminal portion of the protein, known as canstatin, is an inhibitor of angiogenesis and tumor growth. Like the other members of the type IV collagen gene family, this gene is organized in a head-to-head conformation with another type IV collagen gene so that each gene pair shares a common promoter. The canstatin may have an amino acid sequence of SEQ ID NO: 84. The canstatin gene may have a nucleotide sequence encoding the amino acid sequence of SEQ ID NO: 84.

The restin (RSN, Reed-Steinberg cell-expressed intermediate filament-associated protein) may have an amino acid sequence of SEQ ID NO: 85. The restin gene may have a nucleotide sequence encoding the amino acid sequence of SEQ ID NO: 85. VEGI (vascular endothelial growth inhibitor; tumor necrosis factor ligand superfamily, member 15; TNFSF15) is a cytokine that belongs to the tumor necrosis factor (TNF) ligand family. This protein is abundantly expressed in endothelial cells, but is not expressed in either B or T cells. The expression of this protein is inducible by TNF and IL-1 alpha. This cytokine is a ligand for receptor TNFRSF25 and decoy receptor TNFRSF21/DR6. It can activate NF-kappaB and MAP kinases, and acts as an autocrine factor to induce apoptosis in endothelial cells. This cytokine is also found to inhibit endothelial cell proliferation, and thus may function as an angiogenesis inhibitor. An additional isoform encoded by an alternatively spliced transcript variant has been reported but the sequence of this transcript has not been determined. The VEGI may have an amino acid sequence of SEQ ID NO: 86. The VEGI gene may have a nucleotide sequence encoding the amino acid sequence of SEQ ID NO: 86. Angiopoietins are proteins with important roles in vascular development and angiogenesis. All angiopoietins bind with similar affinity to an endothelial cell-specific tyrosine-protein kinase receptor. The protein encoded by this gene is a secreted glycoprotein that activates the receptor by inducing its tyrosine phosphorylation. It plays a critical role in mediating reciprocal interactions between the endothelium and surrounding matrix and mesenchyme. The protein also contributes to blood vessel maturation and stability, and may be involved in early development of the heart. Angiopoietin 1 may have an amino acid sequence of SEQ ID NO: 87. The angiopoietin 1 gene may have a nucleotide sequence encoding the amino acid sequence of SEQ ID NO: 87.

Prolactin (PRL) may have an amino acid sequence of SEQ ID NO: 88. The prolactin gene may have a nucleotide sequence encoding the amino acid sequence of SEQ ID NO: 88.

The endorepellin may have an amino acid sequence of SEQ ID NO: 89. The endorepeelin gene may have a nucleotide sequence encoding the amino acid sequence of SEQ ID NO: 89.

Further, the UCB-MSC may be for example, an UCB-MSC that a prodrug converting enzyme gene is introduced thereinto. The prodrug converting enzyme gene may be for example, a gene selected from cytosine deaminase gene, CYP2B1 gene and CYP2B6. The cytosine deaminase converte 5-FC into 5-FU that is an anticancer drug, or the cytochrome P-450 CYP2B1 enzyme, encoded by CYP2B1 gene, mediates the activation of at least one compounds selected from the group consisting of cyclophosphamide (CPA) and ifosfamide (IFO) to alkylating metabolites, which are anticancer drugs. The cytosine deaminase gene may include AICDA (activation-induced cytidine deaminase).

AICDA is a RNA-editing deaminase that is a member of the cytidine deaminase family. The protein is involved in somatic hypermutation, gene conversion, and class-switch recombination of immunoglobulin genes. Defects in this gene are the cause of autosomal recessive hyper-IgM immunodeficiency syndrome type 2 (HIGM2). The AICDA may have an amino acid sequence of SEQ ID NO: 90. The AICDA gene may have a nucleotide sequence encoding the amino acid sequence of SEQ ID NO: 90.

CYP2B6 (cytochrome P450, subfamily IIB, polypeptide 6) protein is a member of the cytochrome P450 superfamily of enzymes. The cytochrome P450 proteins are monooxygenases which catalyze many reactions involved in drug metabolism and synthesis of cholesterol, steroids and other lipids. This protein localizes to the endoplasmic reticulum and its expression is induced by phenobarbital. The enzyme is known to metabolize some xenobiotics, such as the anticancer drugs cyclophosphamide and ifosphamide. Transcript variants for this gene have been described; however, it has not been resolved whether these transcripts are in fact produced by this gene or by a closely related pseudogene, CYP2B7. Both the gene and the pseudogene are located in the middle of a CYP2A pseudogene found in a large cluster of cytochrome P450 genes from the CYP2A, CYP2B and CYP2F subfamilies on chromosome 19q. The CYP2B6 may have an amino acid sequence of SEQ ID NO: 91. The CYP2B6 gene may have a nucleotide sequence encoding the amino acid sequence of SEQ ID NO: 91.

In the method of the aspect of the present invention, the method further comprises administering a prodrug of an anticancer drug into the subject. The prodrug may be for example, 5-fluorocytosine (5-FC), which is a prodrug of 5-fluorouracil (5-FU), cyclophosphamide (CPA), ifosfamide (IFO) or a combination thereof.

The UCB-MSC may be for example, an UCB-MSC that an antisense or siRNA of a gene related to brain tumor is introduced thereinto. The gene related to brain tumor may be for example, a gene selected from the group consisting of a gene encoding a Ras family protein, a gene encoding c-myc, a gene encoding abl, a gene encoding erbB-1, a gene encoding EGFR, a gene encoding Bax, a gene encoding Apaf-1 interacting protein (APIP), a gene encoding Wnt-1-induced secreted protein 1 (WISP-1), a gene encoding Wnt, a gene encoding Raf-1, a gene encoding Src, a gene encoding Akt, a gene encoding Erk-1, 2 and a gene encoding BcL-2.

Myc (v-myc avian myelocytomatosis viral oncogene homolog) protein is a multifunctional, nuclear phosphoprotein that plays a role in cell cycle progression, apoptosis and cellular transformation. It functions as a transcription factor that regulates transcription of specific target genes. Mutations, overexpression, rearrangement and translocation of this gene have been associated with a variety of hematopoietic tumors, leukemias and lymphomas, including Burkitt lymphoma. There is evidence to show that alternative translation initiations from an upstream, in-frame non-AUG (CUG) and a downstream AUG start site result in the production of two isoforms with distinct N-termini. The synthesis of non-AUG initiated protein is suppressed in Burkitt's lymphomas, suggesting its importance in the normal function of this gene. The Myc may have an amino acid sequence of SEQ ID NO: 92. The Myc gene may have a nucleotide sequence encoding the amino acid sequence of SEQ ID NO: 92.

Abl (abetalipoproteinemia) protein is the large subunit of the heterodimeric microsomal triglyceride transfer protein. Protein disulfide isomerase (PDI) completes the heterodimeric microsomal triglyceride transfer protein, which has been shown to play a central role in lipoprotein assembly. Mutations in MTP can cause abetalipoproteinemia. The abl may have an amino acid sequence of SEQ ID NO: 93. The abl gene may have a nucleotide sequence encoding the amino acid sequence of SEQ ID NO: 93.

ErbB1 (epidermal growth factor receptor; EGFR) is a transmembrane glycoprotein that is a member of the protein kinase superfamily. This protein is a receptor for members of the epidermal growth factor family. EGFR is a cell surface protein that binds to epidermal growth factor. Binding of the protein to a ligand induces receptor dimerization and tyrosine autophosphorylation and leads to cell proliferation. Mutations in this gene are associated with lung cancer. The erbB1 may have an amino acid sequence of SEQ ID NO: 94 (isoform a precursor), SEQ ID NO: 95 (isoform d precursor) or SEQ ID NO: 96 (isoform b precursor). The erbB1 gene may have a nucleotide sequence encoding the amino acid sequence of SEQ ID NO: 94, 95 or 96.

APIP is an APAF1 (MIM 602233)-interacting protein that acts as a negative regulator of ischemic/hypoxic injury. The APIP may have an amino acid sequence of SEQ ID NO: 97. The APIP gene may have a nucleotide sequence encoding the amino acid sequence of SEQ ID NO: 97.

WISP1 (WNT1-inducible signaling pathway protein 1) is a member of the WNT1 inducible signaling pathway (WISP) protein subfamily, which belongs to the connective tissue growth factor (CTGF) family. WNT1 is a member of a family of cysteine-rich, glycosylated signaling proteins that mediate diverse developmental processes. The CTGF family members are characterized by four conserved cysteine-rich domains: insulin-like growth factor-binding domain, von Willebrand factor type C module, thrombospondin domain and C-terminal cysteine knot-like domain. This gene may be downstream in the WNT1 signaling pathway that is relevant to malignant transformation. It is expressed at a high level in fibroblast cells, and overexpressed in colon tumors. The encoded protein binds to decorin and biglycan, two members of a family of small leucine-rich proteoglycans present in the extracellular matrix of connective tissue, and possibly prevents the inhibitory activity of decorin and biglycan in tumor cell proliferation. It also attenuates p53-mediated apoptosis in response to DNA damage through activation of the Akt kinase. It is 83% identical to the mouse protein at the amino acid level. Alternative splicing of this gene generates 2 transcript variants. The WISP1 may have an amino acid sequence of SEQ ID NO: 98 (isoform 1 precursor) or SEQ ID NO: 99 (isoform 2 precursor). The WISP1 gene may have a nucleotide sequence encoding the amino acid sequence of SEQ ID NO: 98 or 99.

WNT1 (wingless-type MMTV integration site family, member 1) may have an amino acid sequence of SEQ ID NO: 100. The WNT1 gene may have a nucleotide sequence encoding the amino acid sequence of SEQ ID NO: 100. The WNT gene family consists of structurally related genes which encode secreted signaling proteins. These proteins have been implicated in oncogenesis and in several developmental processes, including regulation of cell fate and patterning during embryogenesis. This gene is a member of the WNT gene family. It is very conserved in evolution, and the protein encoded by this gene is known to be 98% identical to the mouse Wnt1 protein at the amino acid level. The studies in mouse indicate that the Wnt1 protein functions in the induction of the mesencephalon and cerebellum. This gene was originally considered as a candidate gene for Joubert syndrome, an autosomal recessive disorder with cerebellar hypoplasia as a leading feature. However, further studies suggested that the gene mutations might not have a significant role in Joubert syndrome. This gene is clustered with another family member, WNT10B, in the chromosome 12q13 region.

RAF1 (v-raf-1 murine leukemia viral oncogene homolog 1) is the cellular homolog of viral raf gene (v-raf). The protein is a MAP kinase kinase kinase (MAP3K), which functions downstream of the Ras family of membrane associated GTPases to which it binds directly. Once activated, the cellular RAF1 protein can phosphorylate to activate the dual specificity protein kinases MEK1 and MEK2, which in turn phosphorylate to activate the serine/threonine specific protein kinases, ERK1 and ERK2. Activated ERKs are pleiotropic effectors of cell physiology and play an important role in the control of gene expression involved in the cell division cycle, apoptosis, cell differentiation and cell migration. Mutations in this gene are associated with Noonan syndrome 5 and LEOPARD syndrome 2. Raf1 may have an amino acid sequence of SEQ ID NO: 101. The RAF1 gene may have a nucleotide sequence encoding the amino acid sequence of SEQ ID NO: 101.

Src (v-src avian sarcoma (SCHMIDT-RUPPIN A-2) viral oncogene) gene is highly similar to the v-src gene of Rous sarcoma virus. This proto-oncogene may play a role in the regulation of embryonic development and cell growth. The protein encoded by this gene is a tyrosine-protein kinase whose activity can be inhibited by phosphorylation by c-SRC kinase. Mutations in this gene could be involved in the malignant progression of colon cancer. Two transcript variants encoding the same protein have been found for this gene. SRC protein may have an amino acid sequence of SEQ ID NO: 102. The SRC gene may have a nucleotide sequence encoding the amino acid sequence of SEQ ID NO: 102.

Akt1 (v-ark murine thymoma viral oncogene homolog 1) protein may have an amino acid sequence of SEQ ID NO: 103. The Akt1 gene may have a nucleotide sequence encoding the amino acid sequence of SEQ ID NO: 103. The serine-threonine protein kinase encoded by the AKT1 gene is catalytically inactive in serum-starved primary and immortalized fibroblasts. AKT1 and the related AKT2 are activated by platelet-derived growth factor. The activation is rapid and specific, and it is abrogated by mutations in the pleckstrin homology domain of AKT1. It was shown that the activation occurs through phosphatidylinositol 3-kinase. In the developing nervous system AKT is a critical mediator of growth factor-induced neuronal survival. Survival factors can suppress apoptosis in a transcription-independent manner by activating the serine/threonine kinase AKT1, which then phosphorylates and inactivates components of the apoptotic machinery. Multiple alternatively spliced transcript variants have been found for this gene.

Erk1 (extracellular signal-regulated kinase 1; mitogen-activated protein kinase 3; MAPK3) protein is a member of the MAP kinase family. MAP kinases, also known as extracellular signal-regulated kinases (ERKs), act in a signaling cascade that regulates various cellular processes such as proliferation, differentiation, and cell cycle progression in response to a variety of extracellular signals. This kinase is activated by upstream kinases, resulting in its translocation to the nucleus where it phosphorylates nuclear targets. Alternatively spliced transcript variants encoding different protein isoforms have been described. Erk1 protein may have an amino acid sequence of SEQ ID NO: 104. The erk1 gene may have a nucleotide sequence encoding the amino acid sequence of SEQ ID NO: 104.

Erk2 (mitogen-activated protein kinase 1; MAPK1) protein is a member of the MAP kinase family. MAP kinases, also known as extracellular signal-regulated kinases (ERKs), act as an integration point for multiple biochemical signals, and are involved in a wide variety of cellular processes such as proliferation, differentiation, transcription regulation and development. The activation of this kinase requires its phosphorylation by upstream kinases. Upon activation, this kinase translocates to the nucleus of the stimulated cells, where it phosphorylates nuclear targets. Two alternatively spliced transcript variants encoding the same protein, but differing in the UTRs, have been reported for this gene. Erk2 protein may have an amino acid sequence of SEQ ID NO: $10^5$. The erk2 gene may have a nucleotide sequence encoding the amino acid sequence of SEQ ID NO: $10^5$.

BCL2 (B-cell CLL/lymphoma 2) gene encodes an integral outer mitochondrial membrane protein that blocks the apoptotic death of some cells such as lymphocytes. Constitutive expression of BCL2, such as in the case of translocation of BCL2 to Ig heavy chain locus, is thought to be the cause of follicular lymphoma. Two transcript variants, produced by alternate splicing, differ in their C-terminal ends. Bcl2 protein may have an amino acid sequence of SEQ ID NO: 106. The Bcl2 gene may have a nucleotide sequence encoding the amino acid sequence of SEQ ID NO: 106.

Further, the UCB-MSC may be for example, an UCB-MSC that an oncolytic virus is introduced thereinto. The oncolytic virus may be a gene selected from Herpes simplex virus and Reovirus type 3.

In the method, the gene introduced in the UCB-MSC may be in an expressionable state. The UCB-MSCs to which a desired gene is introduced in an expressionable state can be appropriately manufactured using techniques that are known in the art. For example, a vector including a desired gene is prepared (see Dehari H et al., *Cancer Gene Ther* 10, 75-85, 2003; WO07/037,653) and then the vector can be transduced ex vivo into primary culture MSCs. In this regard, examples of the vector include adenovirus vector, retrovirus vector, adeno-associated virus vector, herpes simplex virus vector, SV40 vector, poliomavirus vector, papillomavirus vector, picarnovirus vector, vaccinia virus vector, and lentivirus vector. For example, a method developed by Tsuda H et al. can be used (*Mol Ther* 2003, 7, 354-365). Specifically, one day before being infected with an adenovirus gene, MSCs for example, $5 \times 10^5$ cells may be inoculated into a culture dish. Then the MSCs and a solution including an adenovirus vector to which the adenovirus gene is introduced are incubated at 37° C. in a 5% $CO_2$ incubator for 1 hour, so that the MSCs are infected with the adenovirus gene. Then the infected MSCs are washed with a phosphoric acid buffer solution and then a conventional medium is applied thereto. Alternatively, without use of a virus vector, a desired gene can be introduced into UCB-MSCs by using a naked DNA and any method selected from a calcium-phosphate method, a cationic liposome method, and an electrophoration method. Alternatively, a fusion protein gene of protein transduction domain (PTD) and anti-tumor protein can be introduced to UCB-MSCs using the fusion protein gene-including vector (see Wu S P et al. *Biochem Biophys Res Commun.* 346(1), 1-6, 2006).

The vectors may further include a gene marker for an additional histological examination. The gene marker may be, for example, a gene for coding a chromogenic or fluorescent protein, such as lacZ or a green fluorescent protein (GFP), but is not limited thereto (see Yip S et al., *The Cancer J.* 9(3), 189-204, 2003).

In the method, a cell of the tumor may be a cell expressing at least one gene selected from a group of a gene encoding IL-8, a gene encoding GRO-α and a combination thereof. The tumor may be for example, a tumor selected from the group consisting of a brain tumor, a liver hepatoma, a breast cancer, a colon cancer, a B-cell neoplasm and a combination thereof.

The brain tumor may be a primary brain tumor or secondary brain tumor. The brain tumor may be for example, a tumor selected from the group consisting of astrocytoma, pilocytic astrocytoma, low-grade astrocytoma, anaplastic astrocytoma, glioblastoma multiforme, brain stem cell glioma, ependymoma, subependymoma, ganglioneuroma, mixed glioma, oligodendroglioma, optic nerve glioma, acoustic neuroma, chordoma, CNS lymphoma, craniopharyngioma, hemangioblastoma, medulloblastoma, meningioma, pineal tumors, pituitary tumors, primitive neuroectodermal tumors, rhabdoid tumors, schwannoma, cysts, neurofibromatosis, pseudotumor cerebri, tuberous sclerosis and a combination thereof. The B-cell neoplasm cell may be for example, a cell selected from the group consisting of a common B acute lymphoblastic leukemia cell, a precursor B acute lymphoblastic leukemia cell, a B-cell chronic lymphocytic leukemia cell, a mantle cell lymphoma cell, a Burkitt's lymphoma cell, a Follicular lymphoma cell and a combination thereof.

In the method, the subject may an animal. The animal may a mammal, for example, a human.

In the method, the method may further comprise enhancing the gene selected from the group consisting of a gene encoding IL-8 receptor and a gene encoding GRO-α receptor at the UCB-MSC. The enhancement of the expression may be achieved by at least one selected from the group consisting of activating the endogenous gene, introducing an exogenous gene and a combination thereof. The introduction of a foreign gene into the UCB-MSC may be made by a known method in the art. The enhancement of the expression level of an endogenous gene, for example, achieved by amplifying the number of the endogenous gene or upregulating the expression of the endogenous gene by using any known method in the art.

The IL-8 protein is a member of the CXC chemokine family. This chemokine is one of the major mediators of the inflammatory response. This chemokine is secreted by several cell types. It functions as a chemoattractant, and is also a potent angiogenic factor. This gene is believed to play a role in the pathogenesis of bronchiolitis, a common respiratory tract disease caused by viral infection. This gene and other ten members of the CXC chemokine gene family form a chemokine gene cluster in a region-mapped to chromosome 4q. The IL-8 protein may have an amino acid sequence of SEQ ID NO: 107. The IL-8 gene may have a nucleotide sequence encoding the amino acid sequence of SEQ ID NO: 107.

Chemokine (C-X-C motif) ligand 1 (CXCL1) is a small cytokine belonging to the CXC chemokine family that was previously called GRO1 oncogene, GRO-α, KC, Neutrophil-activating protein 3 (NAP-3) and melanoma growth stimulating activity, alpha (MSGA-α). In humans, this protein is encoded by CXCL1 gene. CXCL1 is secreted by human melanoma cells, has mitogenic properties and is implicated in melanoma pathogenesis. CXCL1 is expressed by macrophages, neutrophils and epithelial cells, and has neutrophil chemoattractant activity. CXCL1 plays a role in spinal cord development by inhibiting the migration of oligodendrocyte precursors and is involved in the processes of angiogenesis, inflammation, wound healing, and tumorigenesis. This chemokine elicits its effects by signaling through the chemokine receptor CXCR2. The gene for CXCL1 is located on human chromosome 4 amongst genes for other CXC chemokines. An initial study in mice showed evidence that CXCL1 decreased the severity of multiple sclerosis and may offer a neuro-protective function. The GROα protein may have an amino acid sequence of SEQ ID NO:108. The GROα gene may have a nucleotide sequence encoding the amino acid sequence of SEQ ID NO:108.

The IL-8 receptor may be for example, a receptor selected from a group consisting of CXCR1 and CXCR2. The GRO-α receptor may be a CXCR2.

The CXCR1 protein is a member of the G-protein-coupled receptor family. This protein is a receptor for interleukin 8 (IL8). It binds to IL8 with high affinity, and transduces the signal through a G-protein activated second messenger system. Knockout studies in mice suggested that this protein inhibits embryonic oligodendrocyte precursor migration in developing spinal cord. This gene, IL8RB, a gene encoding another high affinity IL8 receptor, as well as IL8RBP, a pseudogene of IL8RB, form a gene cluster in a region mapped to chromosome 2q33-q36. The CXCR1 protein may have an amino acid sequence of SEQ ID NO: 109. The CXCR1 gene may have a nucleotide sequence encoding the amino acid sequence of SEQ ID NO: 109.

The protein encoded by this gene is a member of the G-protein coupled receptor family. This protein is a receptor for interleukin 8 (IL8). It binds to IL8 with high affinity, and transduces the signal through a G-protein activated second messenger system. This receptor also binds to chemokine (C-X-C motif) ligand 1 (CXCL1/MGSA), a protein with melanoma growth stimulating activity, and has been shown to be a major component required for serum-dependent melanoma cell growth. In addition, it binds ligands CXCL2, CXCL3, and CXCL5. This receptor mediates neutrophil migration to sites of inflammation. The angiogenic effects of IL8 in intestinal microvascular endothelial cells are found to be mediated by this receptor. Knockout studies in mice suggested that this receptor controls the positioning of oligodendrocyte precursors in developing spinal cord by arresting their migration. This gene, IL8RA, a gene encoding another high affinity IL-8 receptor, as well as IL8RBP, a pseudogene of IL8RB, form a gene cluster in a region mapped to chromosome 2q33-q36. The CXCR2 protein may have an amino acid sequence of SEQ ID NO: 110. The CXCR2 gene may have a nucleotide sequence encoding the amino acid sequence of SEQ ID NO: 110.

In the method, the term "an effective dose" refers to that amount which provides a preventative or therapeutic effect for a tumor condition and administration regimen without causing serious toxic effects in the subject treated. The effective dose may be determined by a person having an ordinary skill in the art. For example, the effective dose may be $1 \times 10^4$ to $1 \times 10^7$ cells/kg body weight, preferably $5 \times 10^5$ to $5 \times 10^6$ cells/kg body weight.

Another aspect of the present invention provides a kit for identifying the location and the size of a brain tumor, comprising UCB-MSC, said UCB-MSC being labeled with a detectable marker. The UCB-MSC and a brain tumor may be an UCB-MSC and a brain tumor as described above in this specification, respectively. The detectable marker may be any marker capable of producing a detectable signal. The UCB-MSCs labeled with the detectable marker can be visualized by a state-of-the-art technique, and can be tracked in real time in a live animal. For example, the detectable marker may a marker selected from luciferase-containing enzyme-based fluorescent detector and Tat peptide-derivatized magnetic nanoparticles (Yip S et al., *The Cancer J.* 9(3), 189-204, 2003). If a stem cell expressing luciferase is used, the administered stem cell migrating to the site of disease can be tracked by identifying bioluminescence in real time and thus, diseases can be diagnosed and the site of disease can be identified (see Weissleder R et al., *Nat Med* 9, 123-128, 2003). The bioluminescence using luciferase may contain administering a luciferin, a substrate of luciferase to the subject. Tat peptide-derivatized magnetic nanoparticles are connected to UCB-MSCs using a method developed by Lewin et al. (see *Nat Biotech* 18, 410-414, 2000) and then administered in vivo. The administered UCB-MSCs can be tracked by magnetic resonance imaging (MRI) to the nanoparticles. Accordingly, UCB-MSCs labeled with the Tat peptide-derivatized magnetic nanoparticles can be administered in vivo and then, by identifying a location where UCB-MSCs gather, the tumor and the site of the tumor can be identified. In addition, UCB-MSCs labeled with the marker can be administered during the brain tumor treatment or after the brain tumor treatment to identify the location and size of the distribution of the administered UCB-MSCs.

Another aspect of the present invention provides a method of identifying the location and the size of a brain tumor of a subject, wherein the method comprises:
(a) administering to the subject an UCB-MSC;
(b) identifying the location and the size of the distribution of the administered UCB-MSC.

In the method of the another aspect of the present invention, the method includes administering to the subject an UCB-MSC.

The administration may be made by using any known method in the art. For example, the administration may be made by a parenteral administration. The parenteral administration includes an injection. The injection may be made intravascullary, intramuscularly, subcutaneously, intradermally, or intrathecally. the administration may be made systemically or locally. The local administration may include direct administration to the tumor tissue.

The subject may be an animal. The animal may be a mammal, for example, a human. The UCB-MSC may be an UCB-MSC as described herein above. The UCB-MSC may be labeled with a detectable marker and detected as described herein above.

In the method of the another aspect of the present invention, the method includes identifying the location and the size of the distribution of the administered UCB-MSC.

The identification of the location and the size of the distribution of the administered UCB-MSC may be made by detecting or measuring the signal from the administered UCB-MSC. The signal may be a signal derived from the detectable marker labeled. The signal may be a light or electrical signal. The light signal may include a visible light, UV or infrared light. The detection or measurement may be made by any known method for example, microscope observation, visual observation, or electronic or electrical detection.

Another aspect of the present invention provides a method of monitoring a progression of a tumor treatment in a subject who is received the brain tumor treatment, wherein the method comprises:
(a) first administering to the subject an UCB-MSC;
(b) identifying the location and the size of the distribution of the first administered UCB-MSC in the subject;
(c) second administering to the subject an UCB-MSC;
(d) identifying the location and the size of the distribution of the second administered UCB-MSC in the subject;
(e) comparing the location and the size of the distribution identified by (b) and (d),
wherein the subject receives a treatment of the tumor during the period starting from the first administration of the UCB-MSC to the second administration of the UCB-MSC.

In the method of another aspect of the present invention, the method includes first administering to the subject UCB- MSC. The administration may be made by using any known method in the art as described herein above. For example, the administration may be made by a parenteral administration. The parenteral administration includes an injection. The injection may be made intravascullary, intramuscularly, subcutaneously, intradermally, or intrathecally. the administration may be made systemically or locally. The local administration may include direct administration to the tumor tissue. The UCB-MSC may be an UCB-MSC as described in herein above. The UCB-MSC are labeled with a detectable marker and detected as described herein above. The detectable marker may be any marker capable of producing an detectable signal. For example, the detectable marker may a marker selected from luciferase-containing enzyme-based fluorescent detector and Tat peptide-derivatized magnetic nanoparticles (Yip S et al., *The Cancer J.* 9(3), 189-204, 2003). The subject may be an animal. The animal may be a mammal, for example, a human.

The method further includes identifying in the subject. The identification of the location and the size of the distribution of the first administered UCB-MSC may be made as described in the above in this specification.

The method further includes second administering to the subject UCB-MSC. The administration, the subject and UCB-MSC may be the same as described in the above in this specification. The first UCB-MSC and second UCB-MSC may be derived from the same or different sources of umbilical cords bloods. The second may be made in the same way or different way as the first administration.

The method further includes identifying the location and the size of the distribution of the second administered UCB-MSC in the subject. The identification of the location and the size of the distribution of the first administered UCB-MSC may be made as described in the above in this specification.

The method further includes comparing the location and the size of the distribution identified by (b) and (d). The comparison may be made for example, by visually comparing the visual data by (b) and (d) or by comparing the digital data by (b) and (d), respectively.

In the method, the treatment of the tumor may be any cancer therapy. The treatment may include for example, a treatment selected from the group consisting of chemotherapy, radiotherapy, surgery and a combination thereof.

In the method, if the identified location and the size of the distribution of the second administered UCB-MSC in the subject is smaller than that of the first administered UCB-MSC, the progression of the treatment may be determined as successful, or if the identified location and the size of the distribution of the second administered UCB-MSC in the subject is same or larger than that of the first administered UCB-MSC, the progression of the treatment may be determined as not successful.

Another aspect of the present invention provides a method for delivering a therapeutic gene to a site of a subject, the site comprising cells expressing at least one selected from the group consisting of IL-8 and GRO-α and inducing tropism of UCB-MSC toward the cells, wherein the method comprises the step of administering to the subject an effective dose of the UCB-MSC.

The method includes the step of administering to the subject an effective dose of the UCB-MSC. The administration, the subject and the UCB-MSC are as described in the above in this specification. The term "an effective dose" refers to that amount which delivers a therapeutic gene to a site of a subject comprising cells expressing at least one selected from the group consisting of IL-8 and GRO-α and inducing tropism of UCB-MSC toward the cells without causing serious toxic effects in the subject treated. The effective dose may be determined by a person having an ordinary skill in the art. For example, the effective dose may be $1 \times 10^4$-$1 \times 10^7$ cells/kg body weight.

The UCB-MSC may be an UCB-MSC which a therapeutic gene is introduced into the UCB-MSC. The therapeutic gene may be for example, a gene selected from the group consisting of a tumor suppressor gene, an apoptosis-inducing factor gene, a cell cycle regulatory gene and an angiogenesis inhibitor gene. Further, The UCB-MSC may be for example, an UCB-MSC that a prodrug converting enzyme gene is introduced to the UCB-MSC. The tumor suppressor gene, an apoptosis-inducing factor gene, a cell cycle regulatory gene, an angiogenesis inhibitor gene and prodrug converting enzyme gene may be the same as described in the above in this specification.

In the method of the another aspect of the present invention, the method may further comprise administering a prodrug of an anticancer drug into the subject. The prodrug may be for example, 5-fluorocytosine (5-FC), which is a prodrug of 5-fluorouracil (5-FU). The administration and the subject may be as described in the above in this specification.

The UCB-MSC may be for example, an UCB-MSC an antisense or siRNA of a gene related to brain tumor is introduced thereinto. The gene related to brain tumor may be a gene selected from the group consisting of a gene encoding a Ras family protein, a gene encoding c-myc, a gene encoding abl, a gene encoding erbB-1, a gene encoding EGFR, a gene encoding Bax, a gene encoding Apaf-1 interacting protein (APIP), a gene encoding Wnt-1-induced secreted protein 1 (WISP-1), a gene encoding Wnt, a gene encoding Raf-1, a gene encoding Src, a gene encoding Akt, a gene encoding Erk-1, 2 and a gene encoding BcL-2.

Further, the UCB-MSC may be for example, an UCB-MSC an oncolytic virus is introduced thereinto. The oncolytic virus may be a gene selected from Herpes simplex virus and Reovirus type 3.

In the method of the aspect of the present invention, the brain tumor may be for example, a tumor selected from the group consisting of astrocytoma, pilocytic astrocytoma, low-grade astrocytoma, anaplastic astrocytoma, glioblastoma multiforme, brain stem cell glioma, ependymoma, subependymoma, ganglioneuroma, mixed glioma, oligodendroglioma, optic nerve glioma, acoustic neuroma, chordoma, CNS lymphoma, craniopharyngioma, hemangioblastoma, medulloblastoma, meningioma, pineal tumors, pituitary tumors, primitive neuroectodermal tumors, rhabdoid tumors, schwannoma, cysts, neurofibromatosis, pseudotumor cerebri and tuberous sclerosis.

In the method of the aspect of the present invention, the subject may be an animal. The animal may be a mammal, for example, a human.

In the method, the cell expressing at least one selected from the group consisting of IL-8 and GRO-α and inducing tropism of UCB-MSC toward the cells may be for example, a cell selected from the group consisting of a brain tumor cell, a hepatoma cell, a breast cancer cell, a lung cell with an acute respiratory distress syndrome, a colon cancer cell, a B-cell neoplasm cell and a combination thereof.

The brain tumor may be for example, a tumor selected from the group consisting of astrocytoma, pilocytic astrocytoma, low-grade astrocytoma, anaplastic astrocytoma, glioblastoma multiforme, brain stem cell glioma, ependymoma, subependymoma, ganglioneuroma, mixed glioma, oligodendroglioma, optic nerve glioma, acoustic neuroma, chordoma, CNS lymphoma, craniopharyngioma, hemangioblastoma, medulloblastoma, meningioma, pineal tumors, pituitary tumors, primitive neuroectodermal tumors, rhabdoid tumors, schwannoma, cysts, neurofibromatosis, pseudotumor cerebri and tuberous sclerosis. The B-cell neoplasm cell may be for example, a cell selected from the group consisting of a common B acute lymphoblastic leukemia cell, a precursor B acute lymphoblastic leukemia cell, a B-cell chronic lymphocytic leukemia cell, a mantle cell lymphoma cell, a Burkitt's lymphoma cell, a Follicular lymphoma cell and a combination thereof.

Another aspect of the present invention provides a kit for identifying the location and the size of a site of a subject, the site comprising cells expressing at least one selected from the group consisting of IL-8 and GRO-α and inducing tropism of UCB-MSC toward the cells, wherein the kit comprises UCB-MSC, the UCB-MSC are labeled with a detectable marker. The UCB-MSC and the detectable marker are as described in the above in this specification. The labeled UCB-MSC may be detected as described in the above in this specification. The marker may be located within nucleoplasm, within cytoplasm, within a cellular organelle or on or within the cell membrane.

In the kit, the cells expressing at least one selected from the group consisting of IL-8 and GRO-α and inducing tropism of UCB-MSC toward the cells may be for example, a cell selected from the group consisting of a brain tumor cell, a hepatoma cell, a breast cancer cell, a lung cell with an acute respiratory distress syndrome, a colon cancer cell, a B-cell neoplasm cell and a combination thereof.

The brain tumor may be for example, a tumor selected from the group consisting of astrocytoma, pilocytic astrocytoma, low-grade astrocytoma, anaplastic astrocytoma, glioblastoma multiforme, brain stem cell glioma, ependymoma, subependymoma, ganglioneuroma, mixed glioma, oligodendroglioma, optic nerve glioma, acoustic neuroma, chordoma, CNS lymphoma, craniopharyngioma, hemangioblastoma, medulloblastoma, meningioma, pineal tumors, pituitary tumors, primitive neuroectodermal tumors, rhabdoid tumors, schwannoma, cysts, neurofibromatosis, pseudotumor cerebri and tuberous sclerosis. The B-cell neoplasm cell may be for example, a cell selected from the group consisting of a common B acute lymphoblastic leukemia cell, a precursor B acute lymphoblastic leukemia cell, a B-cell chronic lymphocytic leukemia cell, a mantle cell lymphoma cell, a Burkitt's lymphoma cell and a Follicular lymphoma cell.

Another aspect of the present invention provides a method of identifying the location and the size of a site of a subject, the site comprising cells expressing at least one selected from the group consisting of IL-8 and GRO-α and inducing tropism of UCB-MSC toward the cells, wherein the method comprises:
  (a) administering to the subject an UCB-MSC;
  (b) identifying the location and the size of the distribution of the administered UCB-MSC.

The method includes administering to the subject an UCB-MSC. The administration, the subject and the UCB-MSC may be the same as described in the above in this specification. The UCB-MSC may be labeled with a detectable marker and detected as described in the above in this specification. The marker may be located within nucleoplasm, within cytoplasm, within a celluar organelle or on or within the cell membrane.

The cell expressing at least one selected from the group consisting of IL-8 and GRO-α and inducing tropism of UCB-MSC toward the cell may be for example a cell selected from the group consisting of a brain tumor cell, a hepatoma cell, a breast cancer cell, a lung cell with an acute respiratory distress syndrome, a colon cancer cell and a B-cell neoplasm cell. The brain tumor and B-cell neoplasm cell are the same as described in the above in this specification.

Another aspect of the present invention provides a method of monitoring treatment progression of a disease occurred in a site of a subject, the site comprising cells expressing at least one selected from groups consisting of IL-8 and GRO-α and inducing tropism of UCB-MSC, wherein the method comprises:
  (a) first administering to the subject an UCB-MSC;
  (b) identifying the location and the size of the distribution of the first administered UCB-MSC in the subject;
  (c) second administering to the subject an UCB-MSC;
  (d) identifying the location and the size of the distribution of the second administered UCB-MSC in the subject; and
  (e) comparing the location and the size of the distribution identified by (b) and (d),
  wherein the subject receives a treatment of the disease during the period starting from the first administration of the UCB-MSC to the second administration of the UCB-MSC.

In the method of another aspect of the present invention, the method includes first administering to the subject an UCB-MSC. The administration, the subject and the UCB-MSC may be the same described in the above in this specification. The UCB-MSC are labeled with a detectable marker and detected as described in the above in this specification.

The method further includes identifying the location and the size of the distribution of the first administered UCB-MSC in the subject. The identification of the location and the size of the distribution of the first administered UCB-MSC may be made as described in the above in this specification.

The method further includes second administering to the subject UCB-MSC. The administration, the subject and UCB-MSC may be the same as described in the above in this specification. The first UCB-MSC and second UCB-MSC may be derived from the same or different sources of umbilical cords bloods. The second administration may be made in the same way or different way as the first administration. The second UCB-MSC may be labeled with a detectable marker. The detectable marker is as described in the above. The detectable marker used in the second UCB-MSC may be the same with or different from that used in the first UCB-MSC.

The method further includes identifying the location and the size of the distribution of the second administered UCB-MSC in the subject. The identification of the location and the size of the distribution of the first administered UCB-MSC may be made as described in the above in this specification.

The method further includes comparing the location and the size of the distribution identified by (b) and (d). The comparison may be made for example, by visually comparing the visual data from (b) and (d) or by comparing the digital data from (b) and (d), respectively.

In the method, the disease may be any disease caused by cells expressing, for example, overexpressing at least one selected from groups consisting of IL-8 and GRO-α and inducing tropism of UCB-MSC.

The treatment of the disease may be any cancer therapy. The treatment may include for example, a treatment selected from the group consisting of chemotherapy, radiotherapy, surgery and a combination thereof.

In the method, if the identified location and the size of the distribution of the second administered UCB-MSC in the subject is smaller than that of the first administered UCB-MSC, the progression of the treatment may be determined as successful, or if the identified location and the size of the distribution of the second administered UCB-MSC in the subject is same or larger than that of the first administered UCB-MSC, the progression of the treatment may be determined as not successful.

In the method, the cell expressing at least one selected from the group consisting of IL-8 and GRO-α and inducing tropism of UCB-MSC toward the cell may be for example, a cell selected from the group consisting of a brain tumor cell, a hepatoma cell, a breast cancer cell, a lung cell with an acute respiratory distress syndrome, a colon cancer cell and a B-cell neoplasm cell. The B-cell neoplasm cell may be for example a cell is selected from the group consisting of a common B acute lymphoblastic leukemia cell, a precursor B acute lymphoblastic leukemia cell, a B-cell chronic lymphocytic leukemia cell, a mantle cell lymphoma cell, a Burkitt's lymphoma cell and a Follicular lymphoma cell.

Another aspect of the present invention provides a method of delivering an anti-tumor agent to a site of a tumor in a subject, which comprises administering mesenchymal stem cells together with the anti-tumor agent to the site, wherein the mesenchymal stem cells (MSCs) are umbilical cord blood-derived MSCs ("UCB-MSC").

The administration and UCB-MSC may be as described in the above in this specification. The MSCs may be used in an amount of $1 \times 10^4$-$1 \times 10^7$ cells/kg body weight. The anti-tumor agent may be any anti-tumor known in the art. The anti-tumor agent may be an agent selected from the group consisting of a tumor suppressor gene, an apoptosis-inducing factor gene, a cell cycle regulatory factor gene and an angiogenesis inhibitor gene. The anti-tumor agent may admixed with the UCB-MSCs or carried within the UCB-MSCs. The introduction of the anti-tumor agent may be introduced into the UCB-MSCs by using any known introduction method of a foreign nucleic acid in the art. The introduction method may be for example, electroporation, transformation, transfection and bombardment.

In the method, the tumor may be a brain tumor. The brain tumor may be a tumor selected from the group consisting of astrocytoma, pilocytic astrocytoma, low-grade astrocytoma, anaplastic astrocytoma, glioblastoma multiforme, brain stem glioma, ependymoma, subependymoma, ganglioneuroma, mixed glioma, oligodendroglioma, optic nerve glioma, acoustic neuroma, chordoma, CNS lymphoma, craniopharyngioma, hemangioblastoma, medulloblastoma, meningioma, pineal tumors, pituitary tumors, primitive neuroectodermal tumors, rhabdoid tumors, schwannoma, cysts, neurofibromatosis, pseudotumor cerebri, tuberous sclerosis and a combination thereof.

The tumor suppressor gene may be a gene selected from the group consisting of phosphatase and tensin homolog gene (PTEN), Maspin gene, RUNX3 gene, Caveolin-1 gene, nm23 gene, Rb protein gene, Brush-1 gene, a gene encoding an inhibitor of tumor growth (ING-4), surviving gene, X chromosome linked inhibitor apoptosis protein (XIAP) gene, neural apoptosis inhibitory protein (NAIP) gene and genes encoding a protein related to regulating said genes. The apoptosis inducing factor gene may be a gene selected from the group consisting of a gene encoding cytokine, a gene encoding interleukin, a gene encoding a tumor necrosis factor (TNF), a gene encoding interferon (INF-α, INF-β, INF-γ), a gene encoding a colony stimulating factor (CSFs), a gene encoding p53, a gene encoding Apaf-1, a gene encoding TRAIL, a gene encoding Caspase, a gene encoding Bax, a gene encoding Bad, a gene encoding FADD, a gene encoding JNK, a gene encoding p38 kinase and genes encoding proteins related to regulating said genes. The cell cycle regulatory factor gene may be a gene selected from the group consisting of a gene encoding cdc2, a gene encoding Cyclin (Cyclin A, Cyclin D, Cyclin E), a gene encoding cdc25C, a gene encoding WAF, a gene encoding INK4, a gene encoding CDK (CDK1, CDK2, CDK4, CDK6), a gene encoding Rb protein, a gene encoding E2F, an antisense or siRNA thereof and genes encoding proteins related to regulating said genes. The angiogenesis inhibitor gene may be a gene selected from the group consisting of a gene encoding thrombospondin-1, a gene encoding endostatin, a gene encoding tumstatin, a gene encoding canstatin, a gene encoding vastatin, a gene encoding restin, a gene encoding a vascular endothelial growth factor inhibitor, a gene encoding maspin, a gene encoding angiopoietins, a gene encoding 16-kd prolactin fragment and a gene encoding endorepellin.

Further, the anti-tumor agent may be a prodrug converting enzyme gene.

Further, the anti-tumor agent may be for example, an antisense or siRNA of a gene related to a brain tumor. The gene related to brain tumor may be for example a gene selected from the group consisting of a gene encoding Ras family, a gene encoding c-myc, a gene encoding abl, a gene encoding erbB-1, a gene encoding EGF-R, a gene encoding Bax, a gene encoding Apaf-1 interacting protein (APIP), a gene encoding Wnt-1-induced secreted protein 1 (WISP-1), a gene encoding Wnt, a gene encoding Raf-1, a gene encoding Src, a gene encoding Akt, a gene encoding Erk-1,2 and a gene encoding BcL-2. The anti-tumor agent may be an oncolytic virus. The oncolytic virus may be a virus selected from Herpes simplex virus and Reovirus type 3.

In the present specification, the term "umbilical blood" refers to blood taken from an umbilical vein connecting a placenta to a fetus in all mammals including humans.

In the present specification, "The term "umbilical cord blood-derived mesenchymal stem cells ("UCB-MSC")" as used throughout the application is defined as mesenchymal stem cells that are isolated from UCB, expanded from the MSCs isolated from the UCB, or a mixture thereof, and a culture containing such expanded MSCs". The UCB-MSC may be derived from umbilical blood of mammals, preferably humans.

In the present specification, the term "treatment" refers to: preventing disease or disorder development in an animal, preferably a mammal, and more preferably humans which are not yet diagnosed with but susceptible to a disease; suppressing disease progression; and alleviating disease.

In the present specification, the term "brain tumor" refers to a malignant or benign tumor developing in the brain and the spinal cord and all kinds of tumors developing in a glial cell and a non-glial cell. In this regard, the brain tumor may be a primary brain tumor or a secondary brain tumor.

Meanwhile, terms which are not defined in the present specification may have meanings which are conventionally defined in the art.

It is noted that all the prior art referred to in the present specification is incorporated by reference in its entirety.

The present invention will be described in further detail with reference to the following examples. These examples are for illustrative purposes only and are not intended to limit the scope of the present inventive concept.

EXAMPLES

U-87 MG, A549, KATO III, PLC/PRF5, LN18, U138 and U251 cell lines were purchased from American Type Culture Collection (ATCC) and used in the present experiments. A549, KATOIII and PLC/PRF5 cells were cultured in RPMI containing 10-20% (v/v) FBS (HyClone, Logan, Utah, US) and Gentamicin at 37° C. in a 5% $CO_2$ incubator. U-87 MG CELLS, LN18, U138 and U251 cells were grown in an Eagle's minimum essential medium (MEM) containing 10-20% (v/v) FBS. Bone marrow-derived mesenchymal stem cell (BM-MSCs) was purchased from LONZA. BM-MSCs and established UCB-MSCs were cultured in α-MEM media containing 10-20% FBS.

Example 1

Preparation of Umbilical Cord Blood-Derived Mesenchymal Stem Cells (UCB-MSCS)

UCB samples were collected from the umbilical vein of deliveries, with informed maternal consent. Specifically, a 16-gauge needle of a UCB collection bag containing 44 mL of CPDA-1 anticoagulant (Greencross Co., Yongin, Kyungki-do, Korea) was inserted into the umbilical vein and UCB was collected by gravity. In all cases, UCB harvests were processed within 48 hours of collection, with viability of 90% or more.

Example 2

Isolation and Expansion of UCB-MSCs

UCB-MSCs prepared according to Example 1 were centrifuged with a Ficoll-Hypaque gradient (produced by Sigma Co., density: 1.077 g/mL), and then washed several times to remove impurities. 10 to 20% FBS (HyClone Co.)-containing a basic medium (α-MEM, Gibco BRL Co.) was added to the resultant product to suspend UCB-MSCs. The UCB-MSCs were portioned at a suitable concentration into each of 10 to 20% FBS-containing a basic media, and then cultivated at 37° C. in a 5% $CO_2$ incubator while the medium was altered twice in a week (FIG. 1). When the cultured cells formed a single layer, MSCs expanding in a spindle shape were identified with a phase-contrast microscope. Then, sub-cultivation was repeatedly performed until the MSCs expanded sufficiently.

Example 3

Preparation of UCB-MSCs Labeled with PKH-26

UCB-MSCs cultivated according to Example 2 were dyed with PKH-26 (Sigma Co.) using a method disclosed in a reference [Barreda D A et al., *Developmental and Comparative Immunology*, 24:395-406, 2000]. First, UCB-MSCs were separated from the cell culture dish by using Trypsin and then, $2 \times 10^7$ cells were washed with an FBS-free medium. The washed cells were collected using a centrifuge and then suspended in 1 mL of Diluent C in a kit provided by a manufacturer. Then the resultant cell suspension solution (2×) was mixed with 1 ml of the PKH fluorescent dye solution (2×) and then the mixture was reacted at 25☐ for 5 minutes. To terminate the labeling reaction, a medium containing an equal volume of fetal bovine serum (FBS) was added to the reaction product and then left to sit for 1 minute. Cells labeled with PKH26 were collected by centrifuging and then, washed with a 10 to 20% FBS-containing medium three times and used in experiments.

Example 4

Co-Culture of MSCs and Other Cell Lines in Transwell Chamber

Figure 2:
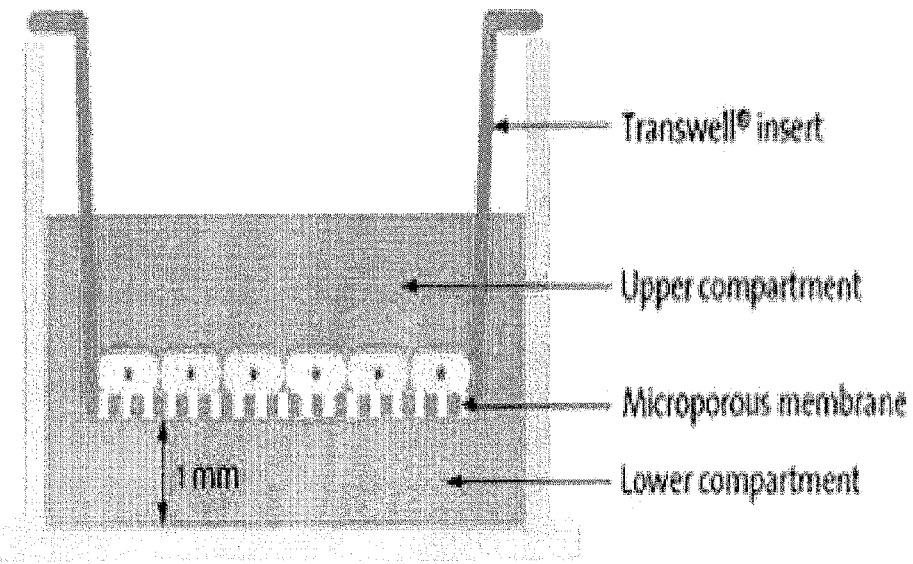
FIG. 2 is a schematic view of a transwell chamber that is used to co-culture umbilical cord blood derived mesenchymal stem cells (UCB-MSCs) and various cell lines according to the present invention.
Figure 3:
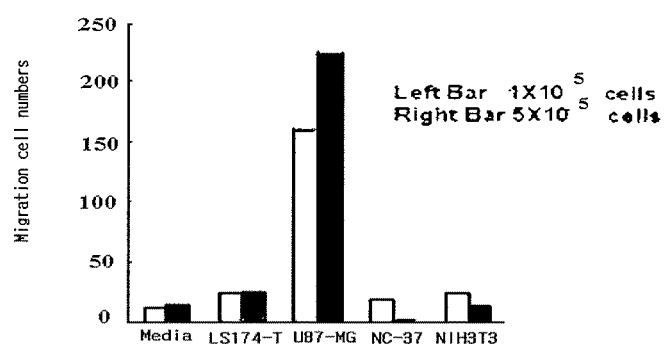
FIG. 3 is a graph of the number of UCB-MSCs migrated toward a lower compartment of a transwell chamber when PKH-labeled UCB-MSCs placed in an upper compartment of the transwell chamber and each of U-87 MG, LS174-T, NC-37, and NIH3T3 cells placed in the lower compartment of the transwell chamber are co-cultured, wherein: in (A), a left bar indicates a case in which the cell number of cell lines in the lower compartment in the transwell chamber is $1\times10^5$ cells and a right bar indicates a case in which the cell number of cell lines in the lower compartment in the transwell chamber is $5\times10^5$ cells, and in both cases, the number of UCB-MSCs is $1\times10^5$ cells and in (B), a left fluorescent microscopic image shows PKH26-labeled UCB-MSCs migrated toward the lower compartment of the transwell chamber when a human cell line-free medium only is used (control), and a right fluorescent microscopic image shows PKH26-labeled UCB-MSCs migrated toward the lower compartment of the transwell chamber when UCB-MSCs are co-cultured with U-87 MG cells.
Figure 3:
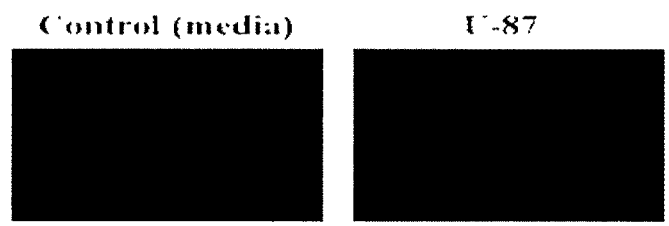
Figure 4:
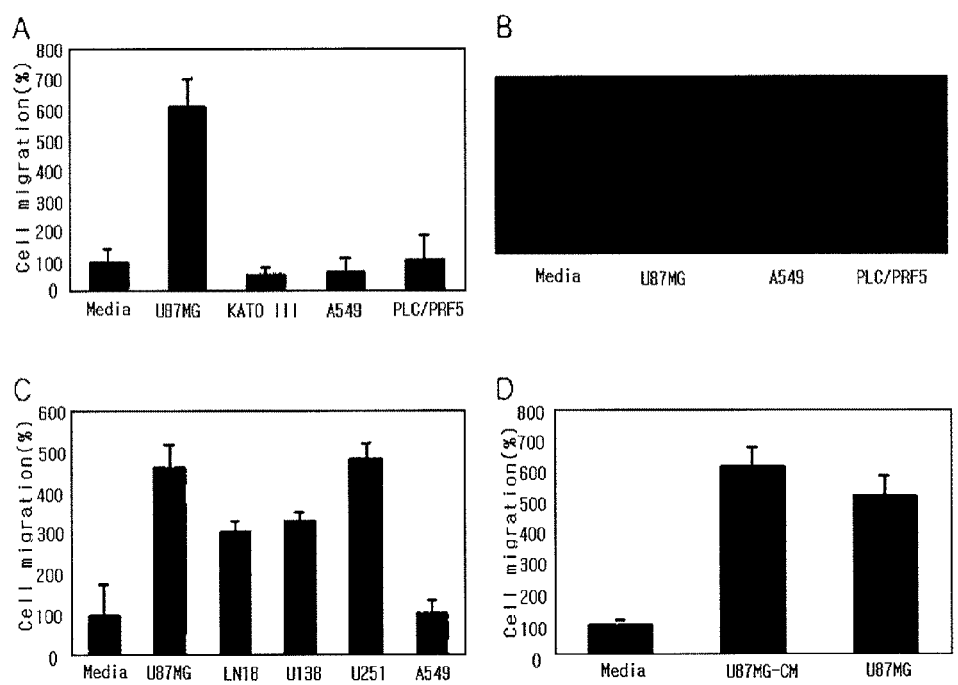
FIG. 4 is a graph of the number of UCB-MSCs migrated toward the lower compartment of the transwell chamber when PKH-labeled UCB-MSCs placed in the upper compartment of the transwell chamber and each of U-87 MG, KATO III, A549, PLC/PRF5, LN18, U138, and U251 cells placed in the lower compartment of the transwell chamber are co-cultured (A and C), wherein (B) is an fluorescent microscopic image of PKH26-labeled UCB-MSCs migrated toward the lower compartment, and (D) is a graph of the number of UCB-MSCs migrated when UCB-MSCs are co-cultured with U-87 MG cells, or with U-87 MG cells-free cultured-conditioned media which is prepared by culturing U-87 MG cells in media and then removing U-87 MG cells from the media.

Human UCB-MSCs (hUCB-MSCs) were dyed with PKH-26 (produced by Sigma). The dyed hUCB-MSCs and other tumor cell lines were co-cultured under a culture condition in a transwell chamber (FALCON) (MSC: cancer cell lines=1: 5). For a control group, cancer cell lines-free MSCs were cultured in the same condition as described above. The transwell chamber used in the co-culturing, as illustrated in FIG. 2, included a lower compartment and an upper compartment, wherein the lower compartment is separated from the upper compartment by a microporous membrane (8 μm size.) In the upper compartment, PKH26-labeled hUCB-MSCs were cultured; and in lower compartment, each of human brain tumor cell line U-87 MG, human rectal cancer cell line LS174-T, human B lymphocyte NC-37, and mouse's fibroblast NIH3T3 was cultured. After co-culturing for one day, two days, and three days each, the migration of PKH26-labeled UCB-MSCs was identified using a phase-contrast microscope (×100) and PKH26-labeled UCB-MSCs migrated was counted (FIG. 3). The same experiment was performed using KATO III, A549, PLC/PRF5, LN18, U138, and U251 which are tumor cell lines and the migration of PKH26-labeled UCB-MSCs was identified. The same experiment was performed in a condition in which a medium conditioned by U-87 MG cells was placed in the lower compartment (FIG. 4).

That is, PKH26-labeled UCB-MSCs were co-cultured with various tumor cell lines in a transwell chamber and then, PKH-labeled mesenchymal stem cells that have migrated into the lower compartment were counted. As a result, UCB-MSCs had a strong tropism for U-87 MG, LN18, U138, and U251 that are brain tumor cell lines, and a weak tropism for other tumor cells (FIGS. 3 and 4). In B of FIG. 3, the left image shows the case of the control group in which a human cell line-free medium was added instead of tumor cells, and the right image shows the case in which UCB-MSCs were co-cultured with U-87 MG cell. Referring to FIG. 3, the migration of many PKH26-labeled UCB-MSCs was identified. When the human cell line-free medium was used instead of tumor cells and cultured, the migration of PKH26-labeled UCB-MSCs was negligible (see the left image of B of FIG. 3). However, PKH26-labeled UCB-MSCs had a tropism for a conditioned medium that did not contain U-87 MG cells but U-87 MG cells had been cultured therein (see D of FIG. 4). Such results show that the conditioned medium contained soluble factors that function to attract UCB-MSCs toward U-87 MG cells.

Example 5

Comparison of Tropism of BM-MSCs for U-87 MG and Tropism of UCB-MSCs for U-87 MG A tropism of BM-MSCs for U-87 MG was compared to a tropism of UCB-MSCs for U-87 MG, using a transwell chamber. U-87 MG cancer cells or medium were placed in a lower compartment, and BM-MSCs and UCB-MSCs each were placed in an upper compartment. In all cases, the culturing was performed for two days. As a result, UCB-MSCs were found to have a stronger tropism for U-87 MG than BM-MSCs (FIG. 5).

Example 6

Comparison of Migrations of MSC

UCB-MSCs donated from four donors in the upper compartment and each of A549 that is lung cancer cell, HeLa that is cervical cancer cell, and U-87 MG that is brain cancer-glioma cell in the lower compartment were co-cultured in a transwell chamber. Then, chemotactic indices of UCB-MSCs in each case were compared (FIG. 6).

A549, HeLa, and U-87 MG cells were purchased from American type culture collection (ATCC). Each of A549 and U-87 cells was cultured in 10-20% bovine serum-containing RPMI1640, and HeLa was cultured in DMEM. In each case, the chemotactic index was calculated by dividing the number of UCB-MSCs migrated toward U-87 MG by the number of UCB-MSCs migrated in the control experiment. A tropism of UCB-MSCs for those cancer cells was analyzed. As a result, it was found that UCB-MSCs had the strongest tropism for U-87 MG that is a brain tumor cell line.

Example 7

Cytokine Array

MSCs and each of three kinds of human cells, including U-87 MG tumor cell, were co-cultured, and the cultured medium was collected. The cytokine profile from the cultured medium was examined by using a cytokine antibody array.

A film to which antibodies of various cytokine were attached was taken from a kit for a cytokine array purchased from R&D System Co. and was reacted with a blocking solution for one hour. Separately, amounts of the media prepared by co-culturing UCB-MSCs and each of three kinds of human cells, including U-87 MG tumor cell were adjusted to 1.5 mL or less, and each medium was mixed with the mixed antibodies of cyokines contained in the kit and an antigen-antibody reaction was induced for one hour. The medium in which the supplied cytokine antibodies were combined with secreted cytokines was reacted with the film that was subjected to the blocking for 4° C. for 12 hours. After the reaction, the film was placed in a washing solution and washed, and then washed with tertiary distilled water. Then the film was dried at room temperature. After repeating the washing and drying process two or three times, the film was reacted in a solution containing streptavidin-HRP for 30 minutes. Then the film was washed with a washing solution three times, reacted with a chromatic reagent, and then exposed to an X-ray film in the dark room.

Figure 7:
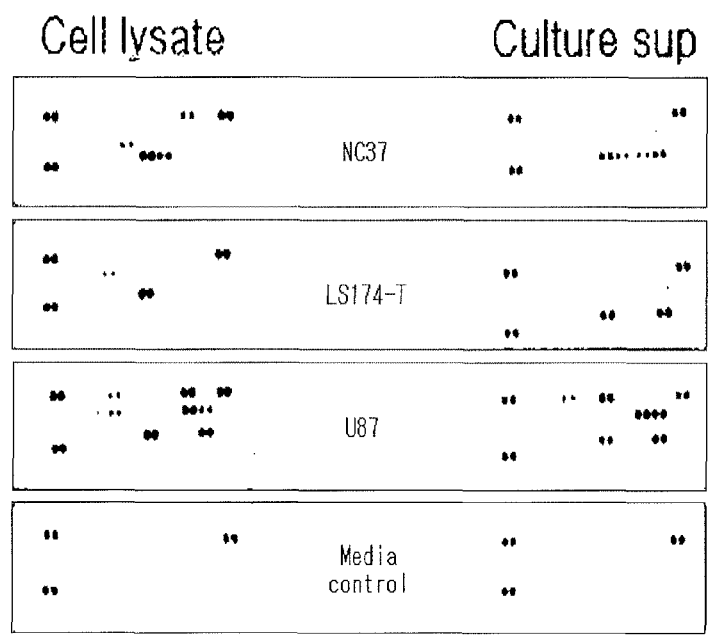
FIG. 7 shows results obtained by analyzing cell lysates and cell culture supernatants through a cytokine array after each of NC37, LS174-T, and U-87 MG cells is co-cultured with UCB-MSCs.

U-87 MG inducing strong tropism of UCB-MSCs secreted growth-related oncogene (GRO-alpha), IL-8, MCP-1, G-CSF, GM-DSF, IL-6, IL-1β, a migration inhibitory factor (MIF), and Serpin E1. Specifically the amounts of GRO-alpha and IL-8 were higher than those of MCP-1, G-CSF, GM-DSF, IL-6, IL-1β, a MIF, and Serpin E1. FIG. 7 shows results obtained by analyzing cell lysates and cell culture supernatants through a cytokine array. Array results and information about changed spots compared to the control group are shown in FIG. 1. In Table 1, cytokines in parentheses are cytokines that were derived by the co-culturing with tumor cells. It is highly likely that these cytokines may induce a tropism of UCB-MSCs.

TABLE 1

|  | Cell Lysate | Supernatants |
|---|---|---|
| NC37 | MIF+++ | MIF+++ |
|  | sICAM-1++ | Serpin E1+++ |
|  | MIP-1a++ | MIP-1a++ |
|  | IL-16++ | MIP-1b++ |
|  |  | IL-6+ |
|  |  | IL-8+ |
| LS174-T | MIF+++ | MIF+++ |
|  | IL-1ra++ | Serpin E1+++ |

TABLE 1-continued

|  | Cell Lysate | Supernatants |
|---|---|---|
|  | GROa+ | IL-6+ |
|  |  | IL-8+ |
| U-87 | sICAM-1+++ | (GROa+++) |
|  | IL-6+++ | IL-6+++ |
|  | MIF+++ | (IL-8+++) |
|  | Serpin E1+++ | Serpin E1+++ |
|  | IL-1ra++ | (G-CSF++) |
|  | IL-8++ | MIF++ |
|  | G-CSF++ | (MCP-1+) |
|  | IL-1a+ |  |
|  | IL-1b+ |  |

Figure 8:
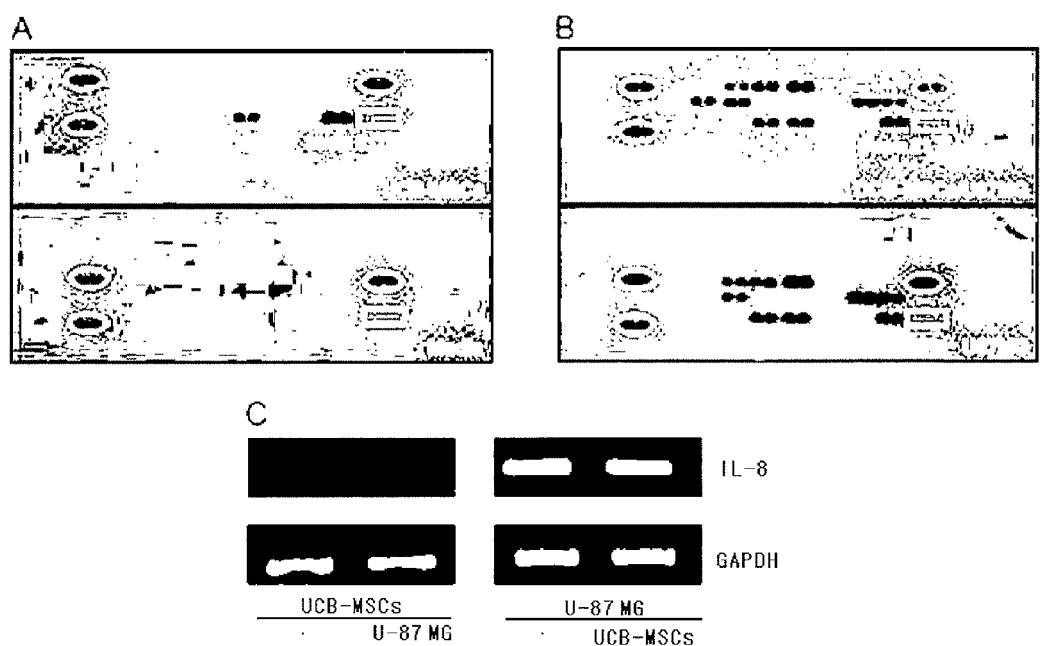
FIG. 8 shows analysis results obtained by collecting conditioned media in which UCB-MSCs were cultured alone, U-87 MG cells were cultured alone, and both of UCB-MSCs and U-87 MG cells were co-cultured, incubating the conditioned media on an array membrane, and then visualizing the incubated results with ECL reagents, wherein (A) shows cytokine antibody array analysis results from the conditioned media with UCB-MSCs and medium control, (B) shows analysis results when the conditioned media in which U-87 MG only is cultured is used and when the media in which a UCB-MSCs and U-87 MG are co-cultured is used, and (C) shows mRNA isolation results from UCB-MSCs (left) cultured with or without U-87 MG cells or UCB-MSCs, and from U-87 MG cells cultured with and without UCB-MSCs, wherein RP-PCT is performed with IL-8 specific primers and GAPDH is used as a control group.

Conditioned media collected from UCB-MSCs cultures only, U-87 MG cell cultures only, and the co-culture of both cells were prepared. Each conditioned medium was incubated on an array membrane, and then visualized by an ECL reagent. Then the visualized conditioned media were compared to each other (see FIG. 8). FIG. 8A shows cytokine antibody array analysis results from the medium prepared by culturing UCS-MSCs only and a control medium. FIG. 8B shows cytokine antibody array analysis results from the medium prepared by culturing the U-87 MG only, and the medium prepared by co-culturing UCB-MSCs and U-87 MG.

FIG. 8C shows results identified by isolating mRNA from UCB-MSCs cultured with and without U-87 MG (left) or from U-87 MG cultured with and without UCB-MSCs (right). RT-PCR was performed with IL-8 specific primers and GAPDH was used as a control. When the level of IL-8 mRNA was measured by RT-PCR, it was found that U-87 MG expresses IL-8 in both cases which U-87 MG cultured with and without UCB-MSCs.

Example 8

Effect of Cytokine With Respect to UCB-MSCs Migration

The effect of IL-8, GRO-α, MCP-1 (RND Systems, MN, USA) with respect to migration of UCB-MSCs was measured using a transwell migration assay. PHK-26-labelled UCB-MSCs were placed in the upper compartment and no cells were placed in the lower compartment. UCB-MSCs were cultured in an IL-8 free medium or in a medium containing different concentrations of recombinant humane IL-8 for 24 hours. As a result, it can be seen that UCB-MSCs migrated more when treated with IL-8 than when they were not treated with IL-8 (FIG. 9A).

IL-8 receptor on UCB-MSCs can be effectively blocked by anti-human CXC chemokine receptor 1 (CXCR1) antibodies. After pre-incubation of UCB-MSCs with anti-CXCR1 antibodies, recombinant IL-8 was again applied to UCB-MSCs. IL-8 mediated migration of UCB-MSCs was reduced, in a dose-dependant manner, by anti-CXCR1 treatment (FIG. 9B). Anti-CXCR2 treatment also showed the same effect.

Similarly, GRO-α treatment also enhanced UCB-MSCs migration when compared to untreated cells (FIG. 9C). GRO-α also belongs to the CC subfamily and can interact with the CXCR2 receptor [see Wuyts A. et al. *Eur J Biochem* 255, 67-73 (1998)].

Figure 9:
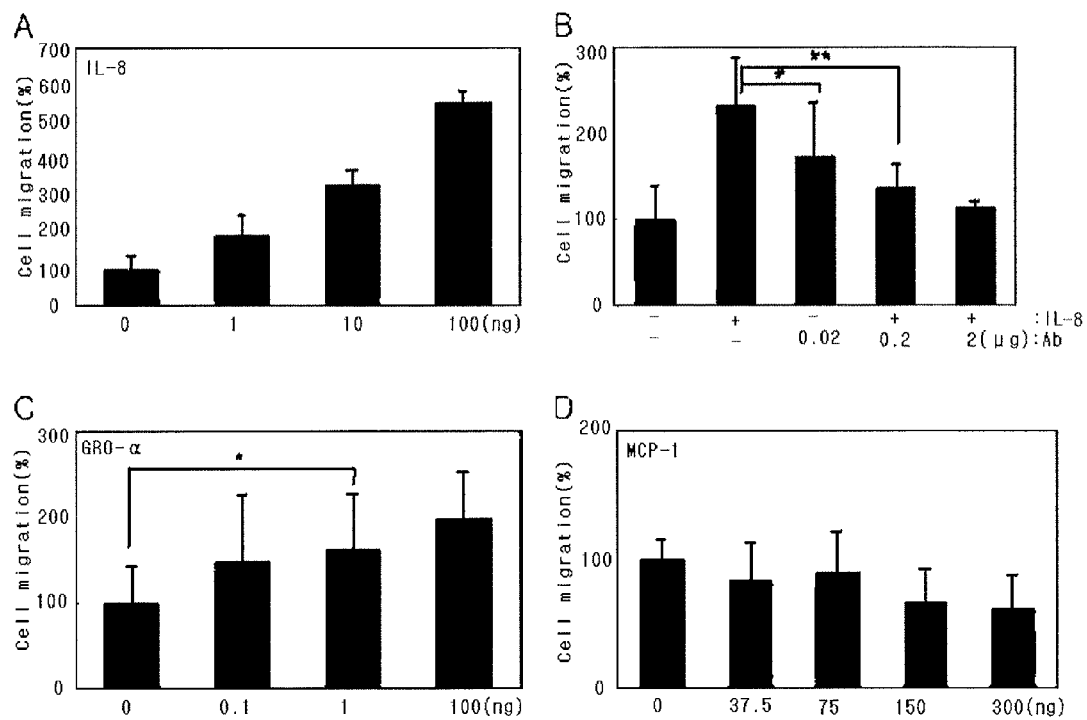
FIG. 9 is a graph for identifying the effect of IL-8 and GRO-α, among the cytokines analyzed with reference to FIG. 8, on MSC migration, wherein (A) is a graph of cell migration toward the lower compartment when MSCs are treated with a recombinant IL-8 protein for 0, 1, 10, and 100 ng for 24 hours, (B) is a graph of cell migration toward the lower compartment when UCB-MSCs are pre-treated with 0.02, 0.2, and 2 μg of a CXC chemokine receptor 1 (CXCR1) antibody that is known as a receptor of IL-8 in cells and then treated with 50 ng of IL-8 to promote the MSC migration. (*, p=0.007; **, p<0.001), (C) is a graph of cell migration toward the lower compartment when UCB-MSCs are treated with GRO-α (*,p<0.005), and (D) is a graph of cell migration when MSCs are treated with Monocyte chemoattractant protein-1 (MCP-1)

In contrast, significant differences were not found in UCB-MSCs migration in cultures treated with MCP-1 (FIG. 9 D). These data strongly indicate that IL-8 and GRO-α participate in migration of UCB-MSCs towards U-87 MG cells.

Example 9

UCB-MSCs Migrates Toward A549 Cell Overexpressing IL-8

The relationship between the concentration of IL-8 secreted from several cancer cells and UCB-MSCs migration toward each cancer cell was identified. FIG. 10A shows ELISA results indicating concentrations of IL-8 secreted in media in which U-87 MG (brain tumor), KATOIII (gastric cancer), A549 (lung cancer), and PLC/PRF5 (liver cancer) cells were cultured. In this regard, the concentration of IL-8 was measured per $1\times10^5$ cells. Among the cancer cell lines assayed, U-87 MG showed the highest IL-8 production. This data suggested that UCB-MSCs had a strong migration attraction toward IL-8 producing cells. In addition, other human brain tumor cells, that is, LN18, U138, and U251 cells, also showed the similar concentration level of IL-8 as that of U-87 MG (see FIG. 10B). Therefore, it can be seen that UCB-MSCs has a tropism for IL-8 secreted by brain tumor cells.

In order to know whether addition of IL-8 to cells expressing a lower level of IL-8 induces the migration of UCB-MSCs, IL-8 was overexpressed in A549 that is a human lung cancer cell. FIG. 10C shows migration results of UCB-MSCs after IL-8 gene was introduced to A549 cells that secrete a low level of IL-8 by using a lipofectamine reagent and then IL-8 was over-expressed. Referring to FIG. 10C, more UCB-MSCs migrated in A549 cells having over-expressed IL-8 than in A549 cells. Accordingly, it can be seen that IL-8 could be a strong inducer of UCB-MSCs migration. FIG. 10D shows the concentration of IL-8 secreted into a medium in a condition of C measured by ELISA.

Example 10

Comparison of Reaction of BM-MSCs and UCB-MSCs with Respect to IL-8

Figure 11:
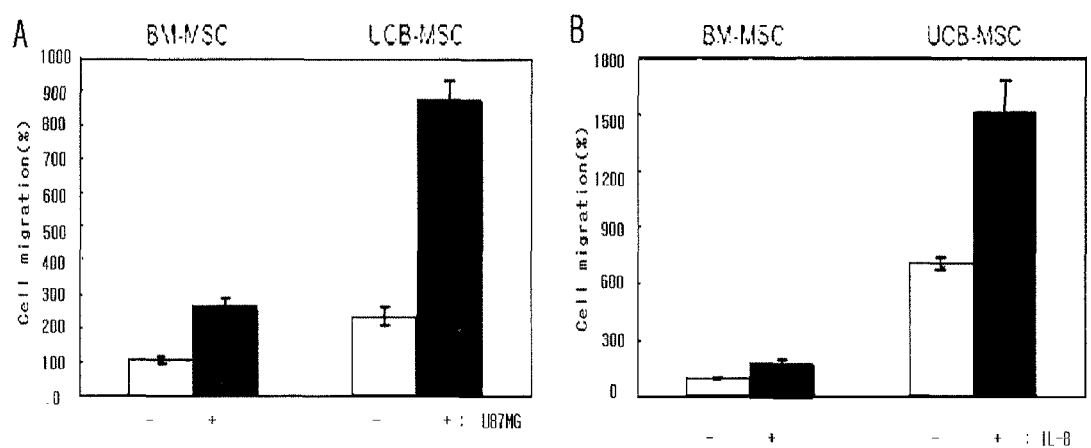
FIG. 11 are graphs for comparing tropisms of UCB-MSCs and BM-MSCs for U-87 MG cells, wherein (A) is a graph for comparing tropism of UCB-MSCs and BM-MSCs moved toward the lower compartment, with respect to U-87 MG cells, and (B) is a graph for comparing tropism of UCB-MSCs and BM-MSCs when UCB-MSCs and BM-MSCs are treated with IL-8 for 14 hours.

Since it is known that BM-MSCs migrate toward U-87 MG cells in vitro and in vivo, migration characteristics of BM-MSCs and UCB-MSCs with respect to U-87 MG cells were compared to those with respect to IL-8 (FIG. 11). A of FIG. 11 shows tropism characteristics of BM-MSCs and UCB-MSCs migrated toward the lower compartment B, that is, toward U-87 MG. B of FIG. 11 shows tropism characteristics of BM-MSCs and UCB-MSCs migrated toward the lower compartment B when they are treated with IL-8 for 14 hours. Referring to FIG. 11, more UCB-MSCs migrated than BM-MSCs. Therefore, it can be seen that UCB-MSCs strongly corresponded to IL-8 and migrated more, but BM-MSCs relatively weakly corresponded to IL-8.

Example 11

Expression Levels of the IL-8 Receptor CXCR1 and CXCR2 in UCB-MSCs

Expression levels of CXCR1 and CXCR2 which are IL-8 receptors in UCB-MSCs and BM-MSCs were compared by measuring mRNA and protein in each of CXCR1 and CXCR2. FIG. 12 A shows results of RT-PCR which was performed with CXCR1 and CXCR2 primers after mRNA was isolated in each of CXCR1 and CXCR2. GAPDH was included into each sample to assess the quantity of the isolated RNA. FIG. 12 B shows results of expression levels of CXCR1 and CXCR2 obtained by measuring each mRNA band intensity of gel obtained from FIG. 12A using a densitometer (* and **, $p<0.001$; n=4). As a result of RT-PCR analysis for all the RNA isolated from UCB-MSCs and BM-MSCs, the band density of the PCR product of CXCR1 and CXCR2 was higher in UCB-MSCs than in BM-MSCs. FIG. 12 C shows analysis results obtained by immunostaining UCB-MSCs and BM-MSCs with anti-CXCR1 and CXCR2 antibodies to identify expression levels of CXCR1 and CXCR2 (×400). Referring to C of FIG. 12, UCB-MSCs and BM-MSCs showed high expression levels of CXCR1 and CXCR2. Since IL-8 has high affinity to CXCR1 and CXCR2, increased UCB-MSCs migration toward U-87 MG may be due to up-regulated expression of CXCR1 and CXCR2. FIG. 12 D shows analysis results obtained by immunostaining UCB-MSCs and BM-MSCs with a secondary antibody only without anti-CXCR1 and CXCR2 antibodies to identify antigen specificity of the anti-CXCR1 and CXCR2 antibodies.

Example 12

Introduction of Gene into Umbilical Cord Blood Mesenchymal Stem Cell

As an example of an experiment in which a gene is introduced into UCB-MSCs, a green fluorescent protein (GFP) was overexpressed using an electroporation method with a human MSC neucleofector produced by amaxa biosystem Co. and an electroporation method. $4\times10^5$ cells of UCB-MSCs were cultured for two days and then placed in a mixture of 5 mg of a GFP encoding gene and 100 ml of a human MSC nucelofector for 15 minutes and the gene was introduced in an electroporator. The resultant UCB-MSCs were moved to a plate and after 24 hours, expression levels of GFP were identified with a fluorescent microscope. The GFP could be identified in a cytoplasm of each MSC (see FIG. 13).

Figure 14:
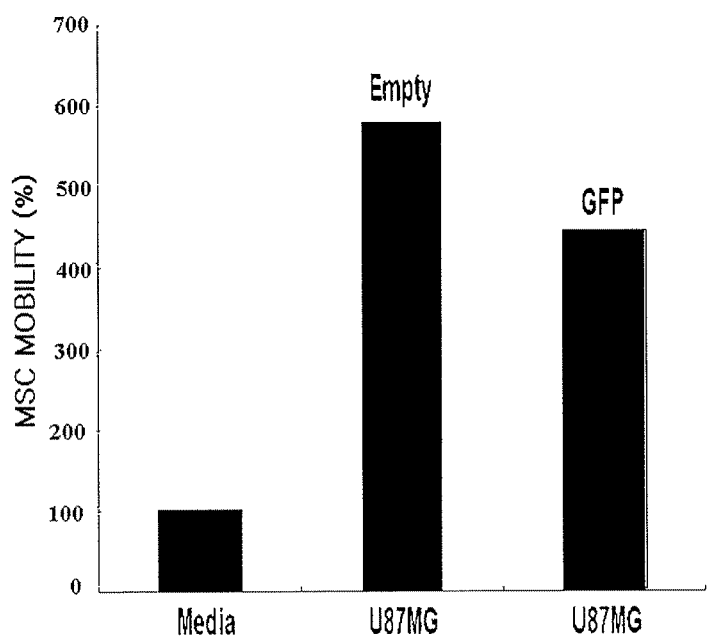
FIG. 14 shows results of an experiment in which each of the gene coding GFP and an empty gene is overexpressed in UCB-MSCs. Said UCB-MSCs are placed in a upper compartment in a transwell and U-87 MG cells are placed in a lower compartment in the transwell and cocultured for 24 hours, and then UCB-MSCs migrated toward the lower compartment are identified.

To test a tropism of UCB-MSCs to which the GFP encoding gene is introduced, each of a GFP encoding gene and an empty gene was overexpressed in UCB-MSCs and then, a tropism of the resultant UCB-MSCs for U-87 MG was identified. After the gene was introduced as described above, UCB-MSCs expressing GFP were placed in an upper compartment of a transwell chamber and U-87 MG was placed in a lower compartment of the transwell chamber, and then UCB-MSCs expressing GFP and U-87 MG were co-cultured for 24 hours. Among cells migrated toward the lower compartment, GFP positive cells were identified. As a result, it can be seen that UCB-MSCs overexpressing GFP due to introduction of a GFP gene had a strong tropism for U-87 MG (FIG. 14).

---

The invention claimed is:

1. A method of treating a tumor comprising administering to a subject an effective dose of a composition comprising mesenchymal stem cells derived from umbilical cord blood (UCB-MSC), wherein:
   a tumor cell expresses at least one gene selected from the group consisting of a gene encoding IL-8 and a gene encoding GRO-α,
   the tumor is selected from the group consisting of a brain tumor, a hepatoma, a breast cancer, and a colon cancer,
   the size of the tumor is diminished,
   an anti-tumor agent gene is introduced into the UCB-MSC, and
   the anti-tumor agent gene is selected from the group consisting of a tumor suppressor gene and an apoptosis-inducing factor gene.

2. The method of claim 1, wherein the tumor suppressor gene is selected from the group consisting of a gene encoding phosphatase and tensin homolog (PTEN), a gene encoding Maspin, a gene encoding RUNX3, a gene encoding Caveolin-1, a gene encoding nm23, a gene encoding retinoblastoma protein, a gene encoding Brush-1, a gene encoding inhibitor of tumor growth (ING-4), a gene encoding survivin, a gene encoding X chromosome linked inhibitor apoptosis protein (XIAP), a gene encoding neural apoptosis inhibitory protein (NAIP), and a gene encoding a protein related to regulation of one or more of said tumor suppressor genes.

3. The method of claim 1, wherein the brain tumor is selected from the group consisting of an astrocytoma, a pilocytic astrocytoma, a low-grade astrocytoma, an anaplastic astrocytoma, a glioblastoma multiforme, a brain stem cell glioma, an ependymoma, a suhependymoma, a ganglioneuroma, a mixed glioma, an oligodendroglioma, an optic nerve glioma, an acoustic neuroma, a chordoma, a central nervous system lymphoma, a craniopharyngioma, a hemangioblastoma, a medulloblastoma, a meningioma, a pineal tumor, a pituitary tumor, a primitive neuroectodermal tumor, a rhabdoid tumor, a schwannoma, a cyst, a neurofibroma, a pseudotumor cerebri, and a tuberous sclerosis tuber.

4. The method of claim 1, further comprises enhancing the expression level in the UCB-MSC of at least one gene selected from the group consisting of a gene encoding an IL-8 receptor and a gene encoding a GRO-α receptor.

5. The method of claim 4, wherein the gene encoding an IL-8 receptor is selected from the group consisting of a gene encoding CXCR1 and a gene encoding CXCR2.

6. The method of claim 4, wherein the gene encoding a GRO-α receptor is a gene encoding CXCR2.

7. The method of claim 4, wherein the enhancing the expression level in the UCB-MSC is achieved by at least one enhancement selected from the group consisting of activating the endogenous gene and introducing an exogenous gene.

8. A method for delivering a therapeutic gene to a site of a subject, the site comprising cells expressing at least one gene selected from the group consisting of a gene encoding IL-8 and a gene encoding GRO-α, and inducing tropism of mesenchymal stem cells derived from umbilical cord blood (UCB-MSC) toward the cells expressing the at least one gene, comprising administering to the subject an effective dose of the UCB-MSC, wherein:
   the cells expressing the at least one gene are selected from the group consisting of a brain tumor, a hepatoma, a breast cancer, and a colon cancer,
   the size of the tumor is diminished,
   the therapeutic gene is introduced into the UCB-MSC, and
   the therapeutic gene is selected from the group consisting of a tumor suppressor gene and an apoptosis-inducing factor gene.

9. The method of claim 8, wherein the tumor suppressor gene is selected from the group consisting of a gene encoding phosphatase and tensin homolog (PTEN), a gene encoding Maspin, a gene encoding RUNX3, a gene encoding Caveolin-1, a gene encoding nm23, a gene encoding retinoblastoma protein, a gene encoding Brush-1, a gene encoding inhibitor of tumor growth (ING-4), a gene encoding survivin, a gene encoding X chromosome linked inhibitor apoptosis protein (XIAP), a gene encoding neural apoptosis inhibitory protein (NAIP), and a gene encoding a protein related to regulation of one or more of said tumor suppressor genes.

10. The method of claim 8, wherein the apoptosis-inducing factor gene is selected from the group consisting of a gene encoding a cytokine, a gene encoding an interleukin, a gene encoding a tumor necrosis factor (TNF), a gene encoding an interferon, a gene encoding a colony stimulating factor (CSF), a gene encoding p53, a gene encoding Apaf-1, a gene encoding TRAIL, a gene encoding Caspase, a gene encoding Bax, a gene encoding Bad, a gene encoding FADD, a gene encoding JNK, a gene encoding p38 kinase, and a gene encoding a protein related to regulation of one or more of said apoptosis-inducing factor genes.

11. A method of delivering an anti-tumor agent to a site of a tumor in a subject, comprising administering mesenchymal stem cells together with the anti-tumor agent to the site, wherein:
   the mesenchymal stem cells are umbilical cord blood-derived mesenchymal stem cells (UCB-MSC),
   the tumor is a brain tumor,
   the size of the brain tumor is diminished,
   the anti-tumor agent is introduced into UCB-MSC, and
   the anti-tumor agent is selected from the group consisting of a tumor suppressor gene and an apoptosis-inducing factor gene.

12. The method according to claim 11, wherein the UCB-MSC are administered in an amount of $1 \times 10^4 - 1 \times 10^7$ cells/kg body weight.

13. The method according to claim 11, wherein the anti-tumor agent is admixed with the UCB-MSC.

14. The method according to claim 11, wherein the anti-tumor agent is carried within the UCB-MSC.

15. The method according to claim 11, wherein the tumor suppressor gene is selected from the group consisting of a gene encoding phosphatase and tensin homolog (PTEN), a gene encoding Maspin, a gene encoding RUNX3, a gene encoding Caveolin-1, a gene encoding nm23, a gene encoding retinoblastoma protein, a gene encoding Brush-1, a gene encoding an inhibitor of tumor growth (ING-4), a gene encoding survivin, a gene encoding X chromosome linked inhibitor apoptosis protein (XIAP), a gene encoding neural apoptosis inhibitory protein (NAIP), and a gene encoding a protein related to regulation of one or more of said tumor suppressor genes.

* * * * *

SEQUENCE LISTING

<160> NUMBER OF SEQ ID NOS: 110

<210> SEQ ID NO 1
<211> LENGTH: 20

```
<212> TYPE: DNA
<213> ORGANISM: Artificial Sequence
<220> FEATURE:
<223> OTHER INFORMATION: Synthetic construct

<400> SEQUENCE: 1
accacagtcc atgccatcac                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
tccaccaccc tgttgctgta                                               20

<210> SEQ ID NO 3
<211> LENGTH: 22
<212> TYPE: DNA
<213> ORGANISM: Artificial Sequence
<220> FEATURE:
<223> OTHER INFORMATION: Synthetic construct

<400> SEQUENCE: 3
tcctgatttc tgcagctctg tg                                            22

<210> SEQ ID NO 4
<211> LENGTH: 22
<212> TYPE: DNA
<213> ORGANISM: Artificial Sequence
<220> FEATURE:
<223> OTHER INFORMATION: Synthetic construct

<400> SEQUENCE: 4
tgcttgaagt ttcactggca tc                                            22

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
gagccccgaa tctgacatta                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
gcagacactg caacacacct                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
attctgggca tccttcacag                                               20
```

<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8
tgcacttagg caggaggtct                                           20

<210> SEQ ID NO 9
<211> LENGTH: 403
<212> TYPE: PRT
<213> ORGANISM: Homo sapiens

<400> SEQUENCE: 9

Met Thr Ala Ile Ile Lys Glu Ile Val Ser Arg Asn Lys Arg Arg Tyr
 1               5                  10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
 65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

```
Thr Lys Asn Asp Leu Asp Lys Ala Asn Lys Asp Lys Ala Asn Arg Tyr
            325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Thr Ser Val Thr Pro Asp
            355                 360                 365

Val Ser Asp Asn Glu Pro Asp His Tyr Arg Tyr Ser Asp Thr Thr Asp
370                 375                 380

Ser Asp Pro Glu Asn Gly Pro Phe Asp Glu Asp Gln His Thr Gln Ile
385                 390                 395                 400

Thr Lys Val

<210> SEQ ID NO 10
<211> LENGTH: 375
<212> TYPE: PRT
<213> ORGANISM: Homo sapiens

<400> SEQUENCE: 10

Met Asp Ala Leu Gln Leu Ala Asn Ser Ala Phe Ala Val Asp Leu Phe
1               5                   10                  15

Lys Gln Leu Cys Glu Lys Glu Pro Leu Gly Asn Val Leu Phe Ser Pro
            20                  25                  30

Ile Cys Leu Ser Thr Ser Leu Ser Leu Ala Gln Val Gly Ala Lys Gly
            35                  40                  45

Asp Thr Ala Asn Glu Ile Gly Gln Val Leu His Phe Glu Asn Val Lys
    50                  55                  60

Asp Val Pro Phe Gly Phe Gln Thr Val Thr Ser Asp Val Asn Lys Leu
65                  70                  75                  80

Ser Ser Phe Tyr Ser Leu Lys Leu Ile Lys Arg Leu Tyr Val Asp Lys
                85                  90                  95

Ser Leu Asn Leu Ser Thr Glu Phe Ile Ser Ser Thr Lys Arg Pro Tyr
            100                 105                 110

Ala Lys Glu Leu Glu Thr Val Asp Phe Lys Asp Lys Leu Glu Glu Thr
            115                 120                 125

Lys Gly Gln Ile Asn Asn Ser Ile Lys Asp Leu Thr Asp Gly His Phe
    130                 135                 140

Glu Asn Ile Leu Ala Asp Asn Ser Val Asn Asp Gln Thr Lys Ile Leu
145                 150                 155                 160

Val Val Asn Ala Ala Tyr Phe Val Gly Lys Trp Met Lys Lys Phe Ser
                165                 170                 175

Glu Ser Glu Thr Lys Glu Cys Pro Phe Arg Val Asn Lys Thr Asp Thr
            180                 185                 190

Lys Pro Val Gln Met Met Asn Met Glu Ala Thr Phe Cys Met Gly Asn
            195                 200                 205

Ile Asp Ser Ile Asn Cys Lys Ile Ile Glu Leu Pro Phe Gln Asn Lys
    210                 215                 220

His Leu Ser Met Phe Ile Leu Leu Pro Lys Asp Val Glu Asp Glu Ser
225                 230                 235                 240

Thr Gly Leu Glu Lys Ile Glu Lys Gln Leu Asn Ser Glu Ser Leu Ser
                245                 250                 255

Gln Trp Thr Asn Pro Ser Thr Met Ala Asn Ala Lys Val Lys Leu Ser
            260                 265                 270

Ile Pro Lys Phe Lys Val Glu Lys Met Ile Asp Pro Lys Ala Cys Leu
            275                 280                 285
```

```
Glu Asn Leu Gly Leu Lys His Ile Phe Ser Glu Asp Thr Ser Asp Phe
    290                 295                 300

Ser Gly Met Ser Glu Thr Lys Gly Val Ala Leu Ser Asn Val Ile His
305                 310                 315                 320

Lys Val Cys Leu Glu Ile Thr Glu Asp Gly Gly Asp Ser Ile Glu Val
                325                 330                 335

Pro Gly Ala Arg Ile Leu Gln His Lys Asp Glu Leu Asn Ala Asp His
            340                 345                 350

Pro Phe Ile Tyr Ile Ile Arg His Asn Lys Thr Arg Asn Ile Ile Phe
                355                 360                 365

Phe Gly Lys Phe Cys Ser Pro
370                 375

<210> SEQ ID NO 11
<211> LENGTH: 429
<212> TYPE: PRT
<213> ORGANISM: Homo sapiens

<400> SEQUENCE: 11

Met Ala Ser Asn Ser Ile Phe Asp Ser Phe Pro Thr Tyr Ser Pro Thr
1               5                   10                  15

Phe Ile Arg Asp Pro Ser Thr Ser Arg Arg Phe Thr Pro Pro Ser Pro
                20                  25                  30

Ala Phe Pro Cys Gly Gly Gly Gly Lys Met Gly Glu Asn Ser Gly
                35                  40                  45

Ala Leu Ser Ala Gln Ala Ala Val Gly Pro Gly Gly Arg Ala Arg Pro
            50                  55                  60

Glu Val Arg Ser Met Val Asp Val Leu Ala Asp His Ala Gly Glu Leu
65                  70                  75                  80

Val Arg Thr Asp Ser Pro Asn Phe Leu Cys Ser Val Leu Pro Ser His
                85                  90                  95

Trp Arg Cys Asn Lys Thr Leu Pro Val Ala Phe Lys Val Val Ala Leu
                100                 105                 110

Gly Asp Val Pro Asp Gly Thr Val Val Thr Val Met Ala Gly Asn Asp
            115                 120                 125

Glu Asn Tyr Ser Ala Glu Leu Arg Asn Ala Ser Ala Val Met Lys Asn
130                 135                 140

Gln Val Ala Arg Phe Asn Asp Leu Arg Phe Val Gly Arg Ser Gly Arg
145                 150                 155                 160

Gly Lys Ser Phe Thr Leu Thr Ile Thr Val Phe Thr Asn Pro Thr Gln
                165                 170                 175

Val Ala Thr Tyr His Arg Ala Ile Lys Val Thr Val Asp Gly Pro Arg
                180                 185                 190

Glu Pro Arg Arg His Arg Gln Lys Leu Glu Asp Gln Thr Lys Pro Phe
            195                 200                 205

Pro Asp Arg Phe Gly Asp Leu Glu Arg Leu Arg Met Arg Val Thr Pro
210                 215                 220

Ser Thr Pro Ser Pro Arg Gly Ser Leu Ser Thr Thr Ser His Phe Ser
225                 230                 235                 240

Ser Gln Pro Gln Thr Pro Ile Gln Gly Thr Ser Glu Leu Asn Pro Phe
                245                 250                 255

Ser Asp Pro Arg Gln Phe Asp Arg Ser Phe Pro Thr Leu Pro Thr Leu
                260                 265                 270

Thr Glu Ser Arg Phe Pro Asp Pro Arg Met His Tyr Pro Gly Ala Met
            275                 280                 285
```

```
Ser Ala Ala Phe Pro Tyr Ser Ala Thr Pro Ser Gly Thr Ser Ile Ser
    290                 295                 300

Ser Leu Ser Val Ala Gly Met Pro Ala Thr Ser Arg Phe His His Thr
305                 310                 315                 320

Tyr Leu Pro Pro Tyr Pro Gly Ala Pro Gln Asn Gln Ser Gly Pro
                325                 330                 335

Phe Gln Ala Asn Pro Ser Pro Tyr His Leu Tyr Tyr Gly Thr Ser Ser
                340                 345                 350

Gly Ser Tyr Gln Phe Ser Met Val Ala Gly Ser Ser Ser Gly Gly Asp
            355                 360                 365

Arg Ser Pro Thr Arg Met Leu Ala Ser Cys Thr Ser Ser Ala Ala Ser
        370                 375                 380

Val Ala Ala Gly Asn Leu Met Asn Pro Ser Leu Gly Gly Gln Ser Asp
385                 390                 395                 400

Gly Val Glu Ala Asp Gly Ser His Ser Asn Ser Pro Thr Ala Leu Ser
                405                 410                 415

Thr Pro Gly Arg Met Asp Glu Ala Val Trp Arg Pro Tyr
                420                 425

<210> SEQ ID NO 12
<211> LENGTH: 415
<212> TYPE: PRT
<213> ORGANISM: Homo sapiens

<400> SEQUENCE: 12

Met Arg Ile Pro Val Asp Pro Ser Thr Ser Arg Arg Phe Thr Pro Pro
1               5                   10                  15

Ser Pro Ala Phe Pro Cys Gly Gly Gly Gly Lys Met Gly Glu Asn
            20                  25                  30

Ser Gly Ala Leu Ser Ala Gln Ala Ala Val Gly Pro Gly Gly Arg Ala
        35                  40                  45

Arg Pro Glu Val Arg Ser Met Val Asp Val Leu Ala Asp His Ala Gly
    50                  55                  60

Glu Leu Val Arg Thr Asp Ser Pro Asn Phe Leu Cys Ser Val Leu Pro
65                  70                  75                  80

Ser His Trp Arg Cys Asn Lys Thr Leu Pro Val Ala Phe Lys Val Val
                85                  90                  95

Ala Leu Gly Asp Val Pro Asp Gly Thr Val Val Thr Val Met Ala Gly
            100                 105                 110

Asn Asp Glu Asn Tyr Ser Ala Glu Leu Arg Asn Ala Ser Ala Val Met
        115                 120                 125

Lys Asn Gln Val Ala Arg Phe Asn Asp Leu Arg Phe Val Gly Arg Ser
    130                 135                 140

Gly Arg Gly Lys Ser Phe Thr Leu Thr Ile Thr Val Phe Thr Asn Pro
145                 150                 155                 160

Thr Gln Val Ala Thr Tyr His Arg Ala Ile Lys Val Thr Val Asp Gly
                165                 170                 175

Pro Arg Glu Pro Arg Arg His Arg Gln Lys Leu Glu Asp Gln Thr Lys
            180                 185                 190

Pro Phe Pro Asp Arg Phe Gly Asp Leu Glu Arg Leu Arg Met Arg Val
        195                 200                 205

Thr Pro Ser Thr Pro Ser Pro Arg Gly Ser Leu Ser Thr Thr Ser His
    210                 215                 220

Phe Ser Ser Gln Pro Gln Thr Pro Ile Gln Gly Thr Ser Glu Leu Asn
225                 230                 235                 240
```

```
Pro Phe Ser Asp Pro Arg Gln Phe Asp Arg Ser Phe Pro Thr Leu Pro
                245                 250                 255

Thr Leu Thr Glu Ser Arg Phe Pro Asp Pro Arg Met His Tyr Pro Gly
            260                 265                 270

Ala Met Ser Ala Ala Phe Pro Tyr Ser Ala Thr Pro Ser Gly Thr Ser
        275                 280                 285

Ile Ser Ser Leu Ser Val Ala Gly Met Pro Ala Thr Ser Arg Phe His
    290                 295                 300

His Thr Tyr Leu Pro Pro Tyr Pro Gly Ala Pro Gln Asn Gln Ser
305                 310                 315                 320

Gly Pro Phe Gln Ala Asn Pro Ser Pro Tyr His Leu Tyr Tyr Gly Thr
                325                 330                 335

Ser Ser Gly Ser Tyr Gln Phe Ser Met Val Ala Gly Ser Ser Ser Gly
            340                 345                 350

Gly Asp Arg Ser Pro Thr Arg Met Leu Ala Ser Cys Thr Ser Ser Ala
        355                 360                 365

Ala Ser Val Ala Ala Gly Asn Leu Met Asn Pro Ser Leu Gly Gly Gln
    370                 375                 380

Ser Asp Gly Val Glu Ala Asp Gly Ser His Ser Asn Ser Pro Thr Ala
385                 390                 395                 400

Leu Ser Thr Pro Gly Arg Met Asp Glu Ala Val Trp Arg Pro Tyr
                405                 410                 415

<210> SEQ ID NO 13
<211> LENGTH: 178
<212> TYPE: PRT
<213> ORGANISM: Homo sapiens

<400> SEQUENCE: 13

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Asp Glu Leu Ser Glu Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Ile
    130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 14
<211> LENGTH: 177
<212> TYPE: PRT
```

<213> ORGANISM: Homo sapiens

<400> SEQUENCE: 14

Met Val Leu Leu Ser Thr Leu Gly Ile Val Phe Gln Gly Glu Gly Pro
1               5                   10                  15

Pro Ile Ser Ser Cys Asp Thr Gly Thr Met Ala Asn Cys Glu Arg Thr
                20                  25                  30

Phe Ile Ala Ile Lys Pro Asp Gly Val Gln Arg Gly Leu Val Gly Glu
            35                  40                  45

Ile Ile Lys Arg Phe Glu Gln Lys Gly Phe Arg Leu Val Gly Leu Lys
    50                  55                  60

Phe Met Gln Ala Ser Glu Asp Leu Leu Lys Glu His Tyr Val Asp Leu
65                  70                  75                  80

Lys Asp Arg Pro Phe Phe Ala Gly Leu Val Lys Tyr Met His Ser Gly
                85                  90                  95

Pro Val Val Ala Met Val Trp Glu Gly Leu Asn Val Val Lys Thr Gly
            100                 105                 110

Arg Val Met Leu Gly Glu Thr Asn Pro Ala Asp Ser Lys Pro Gly Thr
        115                 120                 125

Ile Arg Gly Asp Phe Cys Ile Gln Val Gly Arg Asn Ile Ile His Gly
130                 135                 140

Ser Asp Ser Val Glu Ser Ala Glu Lys Glu Ile Gly Leu Trp Phe His
145                 150                 155                 160

Pro Glu Glu Leu Val Asp Tyr Thr Ser Cys Ala Gln Asn Trp Ile Tyr
                165                 170                 175

Glu

<210> SEQ ID NO 15
<211> LENGTH: 152
<212> TYPE: PRT
<213> ORGANISM: Homo sapiens

<400> SEQUENCE: 15

Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
                20                  25                  30

Phe Arg Leu Val Gly Leu Lys Phe Met Gln Ala Ser Glu Asp Leu Leu
            35                  40                  45

Lys Glu His Tyr Val Asp Leu Lys Asp Arg Pro Phe Phe Ala Gly Leu
    50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
        115                 120                 125

Glu Ile Gly Leu Trp Phe His Pro Glu Glu Leu Val Asp Tyr Thr Ser
130                 135                 140

Cys Ala Gln Asn Trp Ile Tyr Glu
145                 150

<210> SEQ ID NO 16
<211> LENGTH: 928

```
<212> TYPE: PRT
<213> ORGANISM: Homo sapiens

<400> SEQUENCE: 16

Met Pro Pro Lys Thr Pro Arg Lys Thr Ala Thr Ala Ala Ala
1               5                   10                  15

Ala Ala Glu Pro Pro Ala Pro Pro Pro Pro Pro Glu Glu Asp
            20                  25                  30

Pro Glu Gln Asp Ser Gly Pro Glu Asp Leu Pro Leu Val Arg Leu Glu
            35                  40                  45

Phe Glu Glu Thr Glu Glu Pro Asp Phe Thr Ala Leu Cys Gln Lys Leu
    50                  55                          60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
            115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
            195                 200                 205

Glu Asp Asp Leu Val Ile Ser Phe Gln Leu Met Leu Cys Val Leu Asp
210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
            275                 280                 285

Lys Asn Val Tyr Phe Lys Asn Phe Ile Pro Phe Met Asn Ser Leu Gly
    290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
            340                 345                 350

Thr Gln Arg Thr Pro Arg Lys Ser Asn Leu Asp Glu Glu Val Asn Val
    355                 360                 365

Ile Pro Pro His Thr Pro Val Arg Thr Val Met Asn Thr Ile Gln Gln
370                 375                 380

Leu Met Met Ile Leu Asn Ser Ala Ser Asp Gln Pro Ser Glu Asn Leu
385                 390                 395                 400
```

-continued

```
Ile Ser Tyr Phe Asn Asn Cys Thr Val Asn Pro Lys Glu Ser Ile Leu
                405                 410                 415
Lys Arg Val Lys Asp Ile Gly Tyr Ile Phe Lys Glu Lys Phe Ala Lys
            420                 425                 430
Ala Val Gly Gln Gly Cys Val Glu Ile Gly Ser Gln Arg Tyr Lys Leu
        435                 440                 445
Gly Val Arg Leu Tyr Tyr Arg Val Met Glu Ser Met Leu Lys Ser Glu
    450                 455                 460
Glu Glu Arg Leu Ser Ile Gln Asn Phe Ser Lys Leu Leu Asn Asp Asn
465                 470                 475                 480
Ile Phe His Met Ser Leu Leu Ala Cys Ala Leu Glu Val Val Met Ala
                485                 490                 495
Thr Tyr Ser Arg Ser Thr Ser Gln Asn Leu Asp Ser Gly Thr Asp Leu
            500                 505                 510
Ser Phe Pro Trp Ile Leu Asn Val Leu Asn Leu Lys Ala Phe Asp Phe
        515                 520                 525
Tyr Lys Val Ile Glu Ser Phe Ile Lys Ala Glu Gly Asn Leu Thr Arg
    530                 535                 540
Glu Met Ile Lys His Leu Glu Arg Cys Glu His Arg Ile Met Glu Ser
545                 550                 555                 560
Leu Ala Trp Leu Ser Asp Ser Pro Leu Phe Asp Leu Ile Lys Gln Ser
                565                 570                 575
Lys Asp Arg Glu Gly Pro Thr Asp His Leu Glu Ser Ala Cys Pro Leu
            580                 585                 590
Asn Leu Pro Leu Gln Asn Asn His Thr Ala Ala Asp Met Tyr Leu Ser
        595                 600                 605
Pro Val Arg Ser Pro Lys Lys Lys Gly Ser Thr Thr Arg Val Asn Ser
    610                 615                 620
Thr Ala Asn Ala Glu Thr Gln Ala Thr Ser Ala Phe Gln Thr Gln Lys
625                 630                 635                 640
Pro Leu Lys Ser Thr Ser Leu Ser Leu Phe Tyr Lys Lys Val Tyr Arg
                645                 650                 655
Leu Ala Tyr Leu Arg Leu Asn Thr Leu Cys Glu Arg Leu Leu Ser Glu
            660                 665                 670
His Pro Glu Leu Glu His Ile Ile Trp Thr Leu Phe Gln His Thr Leu
        675                 680                 685
Gln Asn Glu Tyr Glu Leu Met Arg Asp Arg His Leu Asp Gln Ile Met
    690                 695                 700
Met Cys Ser Met Tyr Gly Ile Cys Lys Val Lys Asn Ile Asp Leu Lys
705                 710                 715                 720
Phe Lys Ile Ile Val Thr Ala Tyr Lys Asp Leu Pro His Ala Val Gln
                725                 730                 735
Glu Thr Phe Lys Arg Val Leu Ile Lys Glu Glu Tyr Asp Ser Ile
            740                 745                 750
Ile Val Phe Tyr Asn Ser Val Phe Met Gln Arg Leu Lys Thr Asn Ile
    755                 760                 765
Leu Gln Tyr Ala Ser Thr Arg Pro Pro Thr Leu Ser Pro Ile Pro His
    770                 775                 780
Ile Pro Arg Ser Pro Tyr Lys Phe Pro Ser Ser Pro Leu Arg Ile Pro
785                 790                 795                 800
Gly Gly Asn Ile Tyr Ile Ser Pro Leu Lys Ser Pro Tyr Lys Ile Ser
                805                 810                 815
Glu Gly Leu Pro Thr Pro Thr Lys Met Thr Pro Arg Ser Arg Ile Leu
            820                 825                 830
```

```
Val Ser Ile Gly Glu Ser Phe Gly Thr Ser Glu Lys Phe Gln Lys Ile
            835                 840                 845

Asn Gln Met Val Cys Asn Ser Asp Arg Val Leu Lys Arg Ser Ala Glu
        850                 855                 860

Gly Ser Asn Pro Pro Lys Pro Leu Lys Lys Leu Arg Phe Asp Ile Glu
865                 870                 875                 880

Gly Ser Asp Glu Ala Asp Gly Ser Lys His Leu Pro Gly Glu Ser Lys
            885                 890                 895

Phe Gln Gln Lys Leu Ala Glu Met Thr Ser Thr Arg Thr Arg Met Gln
            900                 905                 910

Lys Gln Lys Met Asn Asp Ser Met Asp Thr Ser Asn Lys Glu Glu Lys
            915                 920                 925

<210> SEQ ID NO 17
<211> LENGTH: 1043
<212> TYPE: PRT
<213> ORGANISM: Homo sapiens

<400> SEQUENCE: 17

Met Pro Leu Leu Glu Gly Ser Val Gly Val Glu Asp Leu Val Leu Leu
  1               5                  10                  15

Glu Pro Leu Val Glu Glu Ser Leu Leu Lys Asn Leu Gln Leu Arg Tyr
             20                  25                  30

Glu Asn Lys Glu Ile Tyr Thr Tyr Ile Gly Asn Val Val Ile Ser Val
         35                  40                  45

Asn Pro Tyr Gln Gln Leu Pro Ile Tyr Gly Pro Glu Phe Ile Ala Lys
 50                  55                  60

Tyr Gln Asp Tyr Thr Phe Tyr Glu Leu Lys Pro His Ile Tyr Ala Leu
 65                  70                  75                  80

Ala Asn Val Ala Tyr Gln Ser Leu Arg Asp Arg Asp Arg Asp Gln Cys
                 85                  90                  95

Ile Leu Ile Thr Gly Glu Ser Gly Ser Gly Lys Thr Glu Ala Ser Lys
            100                 105                 110

Leu Val Met Ser Tyr Val Ala Ala Val Cys Gly Lys Gly Glu Gln Val
            115                 120                 125

Asn Ser Val Lys Glu Gln Leu Leu Gln Ser Asn Pro Val Leu Glu Ala
        130                 135                 140

Phe Gly Asn Ala Lys Thr Ile Arg Asn Asn Asn Ser Ser Arg Phe Gly
145                 150                 155                 160

Lys Tyr Met Asp Ile Glu Phe Asp Phe Lys Gly Ser Pro Leu Gly Gly
                165                 170                 175

Val Ile Thr Asn Tyr Leu Leu Glu Lys Ser Arg Leu Val Lys Gln Leu
            180                 185                 190

Lys Gly Glu Arg Asn Phe His Ile Phe Tyr Gln Leu Leu Ala Gly Ala
        195                 200                 205

Asp Glu Gln Leu Leu Lys Ala Leu Lys Leu Glu Arg Asp Thr Thr Gly
    210                 215                 220

Tyr Ala Tyr Leu Asn His Glu Val Ser Arg Val Asp Gly Met Asp Asp
225                 230                 235                 240

Ala Ser Ser Phe Arg Ala Val Gln Ser Ala Met Ala Val Ile Gly Phe
                245                 250                 255

Ser Glu Glu Glu Ile Arg Gln Val Leu Glu Val Thr Ser Met Val Leu
            260                 265                 270

Lys Leu Gly Asn Val Leu Val Ala Asp Glu Phe Gln Ala Ser Gly Ile
        275                 280                 285
```

-continued

```
Pro Ala Ser Gly Ile Arg Asp Gly Arg Gly Val Arg Glu Ile Gly Glu
    290                 295                 300
Met Val Gly Leu Asn Ser Glu Glu Val Glu Arg Ala Leu Cys Ser Arg
305                 310                 315                 320
Thr Met Glu Thr Ala Lys Glu Lys Val Val Thr Ala Leu Asn Val Met
                325                 330                 335
Gln Ala Gln Tyr Ala Arg Asp Ala Leu Ala Lys Asn Ile Tyr Ser Arg
            340                 345                 350
Leu Phe Asp Trp Ile Val Asn Arg Ile Asn Glu Ser Ile Lys Val Gly
        355                 360                 365
Ile Gly Glu Lys Lys Lys Val Met Gly Val Leu Asp Ile Tyr Gly Phe
    370                 375                 380
Glu Ile Leu Glu Asp Asn Ser Phe Glu Gln Phe Val Ile Asn Tyr Cys
385                 390                 395                 400
Asn Glu Lys Leu Gln Gln Val Phe Ile Glu Met Thr Leu Lys Glu Glu
                405                 410                 415
Gln Glu Glu Tyr Lys Arg Glu Gly Ile Pro Trp Thr Lys Val Asp Tyr
            420                 425                 430
Phe Asp Asn Gly Ile Ile Cys Lys Leu Ile Glu His Asn Gln Arg Gly
        435                 440                 445
Ile Leu Ala Met Leu Asp Glu Glu Cys Leu Arg Pro Gly Val Val Ser
    450                 455                 460
Asp Ser Thr Phe Leu Ala Lys Leu Asn Gln Leu Phe Ser Lys His Gly
465                 470                 475                 480
His Tyr Glu Ser Lys Val Thr Gln Asn Ala Gln Arg Gln Tyr Asp His
                485                 490                 495
Thr Met Gly Leu Ser Cys Phe Arg Ile Cys His Tyr Ala Gly Lys Val
            500                 505                 510
Thr Tyr Asn Val Thr Ser Phe Ile Asp Lys Asn Asn Asp Leu Leu Phe
        515                 520                 525
Arg Asp Leu Leu Gln Ala Met Trp Lys Ala Gln His Pro Leu Leu Arg
    530                 535                 540
Ser Leu Phe Pro Glu Gly Asn Pro Lys Gln Ala Ser Leu Lys Arg Pro
545                 550                 555                 560
Pro Thr Ala Gly Ala Gln Phe Lys Ser Ser Val Ala Ile Leu Met Lys
                565                 570                 575
Asn Leu Tyr Ser Lys Ser Pro Asn Tyr Ile Arg Cys Ile Lys Pro Asn
            580                 585                 590
Glu His Gln Gln Arg Gly Gln Phe Ser Ser Asp Leu Val Ala Thr Gln
        595                 600                 605
Ala Arg Tyr Leu Gly Leu Leu Glu Asn Val Arg Val Arg Arg Ala Gly
    610                 615                 620
Tyr Ala His Arg Gln Gly Tyr Gly Pro Phe Leu Glu Arg Tyr Arg Leu
625                 630                 635                 640
Leu Ser Arg Ser Thr Trp Pro His Trp Asn Gly Gly Asp Arg Glu Gly
                645                 650                 655
Val Glu Lys Val Leu Gly Glu Leu Ser Met Ser Ser Gly Glu Leu Ala
            660                 665                 670
Phe Gly Lys Thr Lys Ile Phe Ile Arg Ser Pro Lys Thr Leu Phe Tyr
        675                 680                 685
Leu Glu Glu Gln Arg Arg Leu Arg Leu Gln Gln Leu Ala Thr Leu Ile
    690                 695                 700
Gln Lys Ile Tyr Arg Gly Trp Arg Cys Arg Thr His Tyr Gln Leu Met
```

```
                705                 710                 715                 720
Arg Lys Ser Gln Ile Leu Ile Ser Ser Trp Phe Arg Gly Asn Met Gln
                    725                 730                 735
Lys Lys Cys Tyr Gly Lys Ile Lys Ala Ser Val Leu Leu Ile Gln Ala
                    740                 745                 750
Phe Val Arg Gly Trp Lys Ala Arg Lys Asn Tyr Arg Lys Tyr Phe Arg
                    755                 760                 765
Ser Glu Ala Ala Leu Thr Leu Ala Asp Phe Ile Tyr Lys Ser Met Val
                    770                 775                 780
Gln Lys Phe Leu Leu Gly Leu Lys Asn Asn Leu Pro Ser Thr Asn Val
785                 790                 795                 800
Leu Asp Lys Thr Trp Pro Ala Ala Pro Tyr Lys Cys Leu Ser Thr Ala
                    805                 810                 815
Asn Gln Glu Leu Gln Gln Leu Phe Tyr Gln Trp Lys Cys Lys Arg Phe
                    820                 825                 830
Arg Asp Gln Leu Ser Pro Lys Gln Val Glu Ile Leu Arg Glu Lys Leu
                    835                 840                 845
Cys Ala Ser Glu Leu Phe Lys Gly Lys Lys Ala Ser Tyr Pro Gln Ser
850                 855                 860
Val Pro Ile Pro Phe Cys Gly Asp Tyr Ile Gly Leu Gln Gly Asn Pro
865                 870                 875                 880
Lys Leu Gln Lys Leu Lys Gly Glu Glu Gly Pro Val Leu Met Ala
                    885                 890                 895
Glu Ala Val Lys Lys Val Asn Arg Gly Asn Gly Lys Thr Ser Ser Arg
                    900                 905                 910
Ile Leu Leu Leu Thr Lys Gly His Val Ile Leu Thr Asp Thr Lys Lys
                    915                 920                 925
Ser Gln Ala Lys Ile Val Ile Gly Leu Asp Asn Val Ala Gly Val Ser
                    930                 935                 940
Val Thr Ser Leu Lys Asp Gly Leu Phe Ser Leu His Leu Ser Glu Met
945                 950                 955                 960
Ser Ser Val Gly Ser Lys Gly Asp Phe Leu Leu Val Ser Glu His Val
                    965                 970                 975
Ile Glu Leu Leu Thr Lys Met Tyr Arg Ala Val Leu Asp Ala Thr Gln
                    980                 985                 990
Arg Gln Leu Thr Val Thr Val Thr Glu Lys Phe Ser Val Arg Phe Lys
                    995                 1000                1005
Glu Asn Ser Val Ala Val Lys Val Val Gln Gly Pro Ala Gly Gly Asp
            1010                1015                1020
Asn Ser Lys Leu Arg Tyr Lys Lys Gly Ser His Cys Leu Glu Val
1025                1030                1035                1040
Thr Val Gln

<210> SEQ ID NO 18
<211> LENGTH: 248
<212> TYPE: PRT
<213> ORGANISM: Homo sapiens

<400> SEQUENCE: 18

Met Ala Ala Gly Met Tyr Leu Glu His Tyr Leu Asp Ser Ile Glu Asn
1               5                   10                  15
Leu Pro Phe Glu Leu Gln Arg Asn Phe Gln Leu Met Arg Asp Leu Asp
                20                  25                  30
Gln Arg Thr Glu Asp Leu Lys Ala Glu Ile Asp Lys Leu Ala Thr Glu
                35                  40                  45
```

Tyr Met Ser Ser Ala Arg Ser Leu Ser Ser Glu Glu Lys Leu Ala Leu
             50                  55                  60

Leu Lys Gln Ile Gln Glu Ala Tyr Gly Lys Cys Lys Glu Phe Gly Asp
 65                  70                  75                  80

Asp Lys Val Gln Leu Ala Met Gln Thr Tyr Glu Met Val Asp Lys His
                 85                  90                  95

Ile Arg Arg Leu Asp Thr Asp Leu Ala Arg Phe Glu Ala Asp Leu Lys
                100                 105                 110

Glu Lys Gln Ile Glu Ser Ser Asp Tyr Asp Ser Ser Ser Lys Gly
            115                 120                 125

Lys Lys Ser Arg Thr Gln Lys Glu Lys Ala Ala Arg Ala Arg Ser
130                 135                 140

Lys Gly Lys Asn Ser Asp Glu Glu Ala Pro Lys Thr Ala Gln Lys Lys
145                 150                 155                 160

Leu Lys Leu Val Arg Thr Ser Pro Glu Tyr Gly Met Pro Ser Val Thr
                165                 170                 175

Phe Gly Ser Val His Pro Ser Asp Val Leu Asp Met Pro Val Asp Pro
                180                 185                 190

Asn Glu Pro Thr Tyr Cys Leu Cys His Gln Val Ser Tyr Gly Glu Met
            195                 200                 205

Ile Gly Cys Asp Asn Pro Asp Cys Ser Ile Glu Trp Phe His Phe Ala
210                 215                 220

Cys Val Gly Leu Thr Thr Lys Pro Arg Gly Lys Trp Phe Cys Pro Arg
225                 230                 235                 240

Cys Ser Gln Glu Arg Lys Lys Lys
            245

<210> SEQ ID NO 19
<211> LENGTH: 246
<212> TYPE: PRT
<213> ORGANISM: Homo sapiens

<400> SEQUENCE: 19

Met Ala Ala Gly Met Tyr Leu Glu His Tyr Leu Asp Ser Ile Glu Asn
 1               5                  10                  15

Leu Pro Phe Glu Leu Gln Arg Asn Phe Gln Leu Met Arg Asp Leu Asp
                20                  25                  30

Gln Arg Thr Glu Asp Leu Lys Ala Glu Ile Asp Lys Leu Ala Thr Glu
             35                  40                  45

Tyr Met Ser Ser Ala Arg Ser Leu Ser Ser Glu Glu Lys Leu Ala Leu
             50                  55                  60

Leu Lys Gln Ile Gln Glu Ala Tyr Gly Lys Cys Lys Glu Phe Gly Asp
 65                  70                  75                  80

Asp Lys Val Gln Leu Ala Met Gln Thr Tyr Glu Met Val Asp Lys His
                 85                  90                  95

Ile Arg Arg Leu Asp Thr Asp Leu Ala Arg Phe Glu Ala Asp Leu Lys
                100                 105                 110

Glu Lys Gln Ile Glu Ser Ser Asp Tyr Asp Ser Ser Ser Lys Glu
            115                 120                 125

Gly Arg Thr Gln Lys Glu Lys Lys Ala Ala Arg Ala Arg Ser Lys Gly
130                 135                 140

Lys Asn Ser Asp Glu Glu Ala Pro Lys Thr Ala Gln Lys Lys Leu Lys
145                 150                 155                 160

Leu Val Arg Thr Ser Pro Glu Tyr Gly Met Pro Ser Val Thr Phe Gly
                165                 170                 175

```
Ser Val His Pro Ser Asp Val Leu Asp Met Pro Val Asp Pro Asn Glu
            180                 185                 190
Pro Thr Tyr Cys Leu Cys His Gln Val Ser Tyr Gly Glu Met Ile Gly
        195                 200                 205
Cys Asp Asn Pro Asp Cys Ser Ile Glu Trp Phe His Phe Ala Cys Val
    210                 215                 220
Gly Leu Thr Thr Lys Pro Arg Gly Lys Trp Phe Cys Pro Arg Cys Ser
225                 230                 235                 240
Gln Glu Arg Lys Lys Lys
                245

<210> SEQ ID NO 20
<211> LENGTH: 245
<212> TYPE: PRT
<213> ORGANISM: Homo sapiens

<400> SEQUENCE: 20

Met Ala Ala Gly Met Tyr Leu Glu His Tyr Leu Asp Ser Ile Glu Asn
  1               5                  10                  15
Leu Pro Phe Glu Leu Gln Arg Asn Phe Gln Leu Met Arg Asp Leu Asp
             20                  25                  30
Gln Arg Thr Glu Asp Leu Lys Ala Glu Ile Asp Lys Leu Ala Thr Glu
         35                  40                  45
Tyr Met Ser Ser Ala Arg Ser Leu Ser Ser Glu Glu Lys Leu Ala Leu
     50                  55                  60
Leu Lys Gln Ile Gln Glu Ala Tyr Gly Lys Cys Lys Glu Phe Gly Asp
 65                  70                  75                  80
Asp Lys Val Gln Leu Ala Met Gln Thr Tyr Glu Met Val Asp Lys His
                 85                  90                  95
Ile Arg Arg Leu Asp Thr Asp Leu Ala Arg Phe Glu Ala Asp Leu Lys
            100                 105                 110
Glu Lys Gln Ile Glu Ser Ser Asp Tyr Asp Ser Ser Ser Lys Gly
        115                 120                 125
Arg Thr Gln Lys Glu Lys Lys Ala Ala Arg Ala Arg Ser Lys Gly Lys
    130                 135                 140
Asn Ser Asp Glu Glu Ala Pro Lys Thr Ala Gln Lys Lys Leu Lys Leu
145                 150                 155                 160
Val Arg Thr Ser Pro Glu Tyr Gly Met Pro Ser Val Thr Phe Gly Ser
                165                 170                 175
Val His Pro Ser Asp Val Leu Asp Met Pro Val Asp Pro Asn Glu Pro
            180                 185                 190
Thr Tyr Cys Leu Cys His Gln Val Ser Tyr Gly Glu Met Ile Gly Cys
        195                 200                 205
Asp Asn Pro Asp Cys Ser Ile Glu Trp Phe His Phe Ala Cys Val Gly
    210                 215                 220
Leu Thr Thr Lys Pro Arg Gly Lys Trp Phe Cys Pro Arg Cys Ser Gln
225                 230                 235                 240
Glu Arg Lys Lys Lys
                245

<210> SEQ ID NO 21
<211> LENGTH: 225
<212> TYPE: PRT
<213> ORGANISM: Homo sapiens

<400> SEQUENCE: 21
```

```
Met Ala Gly Met Tyr Leu Glu His Tyr Leu Asp Asn Leu Lys Ala
1               5                   10                  15

Glu Ile Asp Lys Leu Ala Thr Glu Tyr Met Ser Ser Ala Arg Ser Leu
            20                  25                  30

Ser Ser Glu Glu Lys Leu Ala Leu Leu Lys Gln Ile Gln Glu Ala Tyr
        35                  40                  45

Gly Lys Cys Lys Glu Phe Gly Asp Asp Lys Val Gln Leu Ala Met Gln
    50                  55                  60

Thr Tyr Glu Met Val Asp Lys His Ile Arg Arg Leu Asp Thr Asp Leu
65                  70                  75                  80

Ala Arg Phe Glu Ala Asp Leu Lys Glu Lys Gln Ile Glu Ser Ser Asp
                85                  90                  95

Tyr Asp Ser Ser Ser Lys Gly Lys Lys Gly Arg Thr Gln Lys
            100                 105                 110

Glu Lys Lys Ala Ala Arg Ala Arg Ser Lys Gly Lys Asn Ser Asp Glu
        115                 120                 125

Glu Ala Pro Lys Thr Ala Gln Lys Lys Leu Lys Leu Val Arg Thr Ser
    130                 135                 140

Pro Glu Tyr Gly Met Pro Ser Val Thr Phe Gly Ser Val His Pro Ser
145                 150                 155                 160

Asp Val Leu Asp Met Pro Val Asp Pro Asn Glu Pro Thr Tyr Cys Leu
                165                 170                 175

Cys His Gln Val Ser Tyr Gly Glu Met Ile Gly Cys Asp Asn Pro Asp
            180                 185                 190

Cys Ser Ile Glu Trp Phe His Phe Ala Cys Val Gly Leu Thr Thr Lys
        195                 200                 205

Pro Arg Gly Lys Trp Phe Cys Pro Arg Cys Ser Gln Glu Arg Lys Lys
210                 215                 220

Lys
225

<210> SEQ ID NO 22
<211> LENGTH: 179
<212> TYPE: PRT
<213> ORGANISM: Homo sapiens

<400> SEQUENCE: 22

Met Ala Ala Gly Met Tyr Leu Glu His Tyr Leu Asp Ser Ile Glu Asn
1               5                   10                  15

Leu Pro Phe Glu Leu Gln Arg Asn Phe Gln Leu Met Arg Asp Leu Asp
            20                  25                  30

Gln Arg Thr Glu Asp Leu Lys Ala Glu Ile Asp Lys Leu Ala Thr Glu
        35                  40                  45

Tyr Met Ser Ser Ala Arg Ser Leu Ser Ser Glu Glu Lys Leu Ala Leu
    50                  55                  60

Leu Lys Gln Ile Gln Glu Ala Tyr Gly Lys Cys Lys Glu Phe Gly Asp
65                  70                  75                  80

Asp Lys Val Gln Leu Ala Met Gln Thr Tyr Glu Met Val Asp Lys His
                85                  90                  95

Ile Arg Arg Leu Asp Thr Asp Leu Ala Arg Phe Glu Ala Asp Leu Lys
            100                 105                 110

Glu Lys Gln Ile Glu Ser Ser Asp Tyr Asp Ser Ser Ser Ser Lys Gly
        115                 120                 125

Lys Lys Lys Gly Arg Thr Gln Lys Glu Lys Lys Ala Ala Arg Ala Arg
    130                 135                 140
```

```
Ser Lys Gly Lys Asn Ser Asp Glu Glu Ala Pro Lys Thr Ala Gln Lys
145                 150                 155                 160

Lys Leu Lys Leu Val Arg Thr Val Pro Leu Ser Gly Ser Ile Leu Pro
                165                 170                 175

Val Trp Gly

<210> SEQ ID NO 23
<211> LENGTH: 249
<212> TYPE: PRT
<213> ORGANISM: Homo sapiens

<400> SEQUENCE: 23

Met Ala Ala Gly Met Tyr Leu Glu His Tyr Leu Asp Ser Ile Glu Asn
 1               5                  10                  15

Leu Pro Phe Glu Leu Gln Arg Asn Phe Gln Leu Met Arg Asp Leu Asp
            20                  25                  30

Gln Arg Thr Glu Asp Leu Lys Ala Glu Ile Asp Lys Leu Ala Thr Glu
        35                  40                  45

Tyr Met Ser Ser Ala Arg Ser Leu Ser Ser Glu Glu Lys Leu Ala Leu
    50                  55                  60

Leu Lys Gln Ile Gln Glu Ala Tyr Gly Lys Cys Lys Glu Phe Gly Asp
65                  70                  75                  80

Asp Lys Val Gln Leu Ala Met Gln Thr Tyr Glu Met Val Asp Lys His
                85                  90                  95

Ile Arg Arg Leu Asp Thr Asp Leu Ala Arg Phe Glu Ala Asp Leu Lys
            100                 105                 110

Glu Lys Gln Ile Glu Ser Ser Asp Tyr Asp Ser Ser Ser Lys Gly
        115                 120                 125

Lys Lys Lys Gly Arg Thr Gln Lys Glu Lys Ala Ala Arg Ala Arg
    130                 135                 140

Ser Lys Gly Lys Asn Ser Asp Glu Glu Ala Pro Lys Thr Ala Gln Lys
145                 150                 155                 160

Lys Leu Lys Leu Val Arg Thr Ser Pro Glu Tyr Gly Met Pro Ser Val
                165                 170                 175

Thr Phe Gly Ser Val His Pro Ser Asp Val Leu Asp Met Pro Val Asp
            180                 185                 190

Pro Asn Glu Pro Thr Tyr Cys Leu Cys His Gln Val Ser Tyr Gly Glu
        195                 200                 205

Met Ile Gly Cys Asp Asn Pro Asp Cys Ser Ile Glu Trp Phe His Phe
    210                 215                 220

Ala Cys Val Gly Leu Thr Thr Lys Pro Arg Gly Lys Trp Phe Cys Pro
225                 230                 235                 240

Arg Cys Ser Gln Glu Arg Lys Lys Lys
                245

<210> SEQ ID NO 24
<211> LENGTH: 142
<212> TYPE: PRT
<213> ORGANISM: Homo sapiens

<400> SEQUENCE: 24

Met Gly Ala Pro Thr Leu Pro Pro Ala Trp Gln Pro Phe Leu Lys Asp
 1               5                  10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45
```

```
Glu Asn Glu Pro Asp Leu Ala Gln Cys Phe Phe Cys Phe Lys Glu Leu
        50                  55                  60

Glu Gly Trp Glu Pro Asp Asp Pro Ile Glu His Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Glu Phe Glu Glu Thr Ala
        115                 120                 125

Glu Lys Val Arg Arg Ala Ile Glu Gln Leu Ala Ala Met Asp
        130                 135                 140
```

<210> SEQ ID NO 25
<211> LENGTH: 137
<212> TYPE: PRT
<213> ORGANISM: Homo sapiens

<400> SEQUENCE: 25

```
Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Met Gln Arg Lys Pro Thr Ile
65                  70                  75                  80

Arg Arg Lys Asn Leu Arg Lys Leu Arg Arg Lys Cys Ala Val Pro Ser
                85                  90                  95

Ser Ser Trp Leu Pro Trp Ile Glu Ala Ser Gly Arg Ser Cys Leu Val
            100                 105                 110

Pro Glu Trp Leu His His Phe Gln Gly Leu Phe Pro Gly Ala Thr Ser
        115                 120                 125

Leu Pro Val Gly Pro Leu Ala Met Ser
        130                 135
```

<210> SEQ ID NO 26
<211> LENGTH: 165
<212> TYPE: PRT
<213> ORGANISM: Homo sapiens

<400> SEQUENCE: 26

```
Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Gly Pro Gly Thr Val Ala
65                  70                  75                  80

Tyr Ala Cys Asn Thr Ser Thr Leu Gly Gly Arg Gly Gly Arg Ile Thr
                85                  90                  95
```

```
Arg Glu Glu His Lys Lys His Ser Ser Gly Cys Ala Phe Leu Ser Val
            100                 105                 110

Lys Lys Gln Phe Glu Glu Leu Thr Leu Gly Glu Phe Leu Lys Leu Asp
        115                 120                 125

Arg Glu Arg Ala Lys Asn Lys Ile Ala Lys Thr Asn Asn Lys Lys
130                 135                 140

Lys Glu Phe Glu Glu Thr Ala Glu Lys Val Arg Arg Ala Ile Glu Gln
145                 150                 155                 160

Leu Ala Ala Met Asp
                165

<210> SEQ ID NO 27
<211> LENGTH: 497
<212> TYPE: PRT
<213> ORGANISM: Homo sapiens

<400> SEQUENCE: 27

Met Thr Phe Asn Ser Phe Glu Gly Ser Lys Thr Cys Val Pro Ala Asp
1               5                   10                  15

Ile Asn Lys Glu Glu Glu Phe Val Glu Phe Asn Arg Leu Lys Thr
            20                  25                  30

Phe Ala Asn Phe Pro Ser Gly Ser Pro Val Ser Ala Ser Thr Leu Ala
        35                  40                  45

Arg Ala Gly Phe Leu Tyr Thr Gly Glu Gly Asp Thr Val Arg Cys Phe
    50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
130                 135                 140

Gln Val Val Asp Ile Ser Asp Thr Ile Tyr Pro Arg Asn Pro Ala Met
145                 150                 155                 160

Tyr Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Cys Gly Gly Lys Leu Lys
        195                 200                 205

Asn Trp Glu Pro Cys Asp Arg Ala Trp Ser Glu His Arg Arg His Phe
210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
        275                 280                 285

Phe Tyr Ala Leu Gly Glu Gly Asp Lys Val Lys Cys Phe His Cys Gly
290                 295                 300
```

```
Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Glu Gln Lys Gly Gln
            325                 330                 335

Glu Tyr Ile Asn Asn Ile His Leu Thr His Ser Leu Glu Glu Cys Leu
                340                 345                 350

Val Arg Thr Thr Glu Lys Thr Pro Ser Leu Thr Arg Arg Ile Asp Asp
            355                 360                 365

Thr Ile Phe Gln Asn Pro Met Val Gln Glu Ala Ile Arg Met Gly Phe
370                 375                 380

Ser Phe Lys Asp Ile Lys Lys Ile Met Glu Glu Lys Ile Gln Ile Ser
385                 390                 395                 400

Gly Ser Asn Tyr Lys Ser Leu Glu Val Leu Val Ala Asp Leu Val Asn
            405                 410                 415

Ala Gln Lys Asp Ser Met Gln Asp Glu Ser Ser Gln Thr Ser Leu Gln
            420                 425                 430

Lys Glu Ile Ser Thr Glu Glu Gln Leu Arg Arg Leu Gln Glu Lys
            435                 440                 445

Leu Cys Lys Ile Cys Met Asp Arg Asn Ile Ala Ile Val Phe Val Pro
450                 455                 460

Cys Gly His Leu Val Thr Cys Lys Gln Cys Ala Glu Ala Val Asp Lys
465                 470                 475                 480

Cys Pro Met Cys Tyr Thr Val Ile Thr Phe Lys Gln Lys Ile Phe Met
            485                 490                 495

Ser

<210> SEQ ID NO 28
<211> LENGTH: 1403
<212> TYPE: PRT
<213> ORGANISM: Homo sapiens

<400> SEQUENCE: 28

Met Ala Thr Gln Gln Lys Ala Ser Asp Glu Arg Ile Ser Gln Phe Asp
1               5                   10                  15

His Asn Leu Leu Pro Glu Leu Ser Ala Leu Leu Gly Leu Asp Ala Val
                20                  25                  30

Gln Leu Ala Lys Glu Leu Glu Glu Glu Gln Lys Glu Arg Ala Lys
            35                  40                  45

Met Gln Lys Gly Tyr Asn Ser Gln Met Arg Ser Glu Ala Lys Arg Leu
    50                  55                  60

Lys Thr Phe Val Thr Tyr Glu Pro Tyr Ser Ser Trp Ile Pro Gln Glu
65                  70                  75                  80

Met Ala Ala Ala Gly Phe Tyr Phe Thr Gly Val Lys Ser Gly Ile Gln
                85                  90                  95

Cys Phe Cys Cys Ser Leu Ile Leu Phe Gly Ala Gly Leu Thr Arg Leu
                100                 105                 110

Pro Ile Glu Asp His Lys Arg Phe His Pro Asp Cys Gly Phe Leu Leu
            115                 120                 125

Asn Lys Asp Val Gly Asn Ile Ala Lys Tyr Asp Ile Arg Val Lys Asn
        130                 135                 140

Leu Lys Ser Arg Leu Arg Gly Gly Lys Met Arg Tyr Gln Glu Glu Glu
145                 150                 155                 160

Ala Arg Leu Ala Ser Phe Arg Asn Trp Pro Phe Tyr Val Gln Gly Ile
                165                 170                 175

Ser Pro Cys Val Leu Ser Glu Ala Gly Phe Val Phe Thr Gly Lys Gln
```

```
                          180                 185                 190
Asp Thr Val Gln Cys Phe Ser Cys Gly Gly Cys Leu Gly Asn Trp Glu
            195                 200                 205
Glu Gly Asp Asp Pro Trp Lys Glu His Ala Lys Trp Phe Pro Lys Cys
            210                 215                 220
Glu Phe Leu Arg Ser Lys Lys Ser Ser Glu Glu Ile Thr Gln Tyr Ile
225                 230                 235                 240
Gln Ser Tyr Lys Gly Phe Val Asp Ile Thr Gly Glu His Phe Val Asn
                245                 250                 255
Ser Trp Val Gln Arg Glu Leu Pro Met Ala Ser Ala Tyr Cys Asn Asp
                260                 265                 270
Ser Ile Phe Ala Tyr Glu Glu Leu Arg Leu Asp Ser Phe Lys Asp Trp
            275                 280                 285
Pro Arg Glu Ser Ala Val Gly Val Ala Ala Leu Ala Lys Ala Gly Leu
            290                 295                 300
Phe Tyr Thr Gly Ile Lys Asp Ile Val Gln Cys Phe Ser Cys Gly Gly
305                 310                 315                 320
Cys Leu Glu Lys Trp Gln Glu Gly Asp Asp Pro Leu Asp Asp His Thr
                325                 330                 335
Arg Cys Phe Pro Asn Cys Pro Phe Leu Gln Asn Met Lys Ser Ser Ala
            340                 345                 350
Glu Val Thr Pro Asp Leu Gln Ser Arg Gly Leu Cys Glu Leu Leu
            355                 360                 365
Glu Thr Thr Ser Glu Ser Asn Leu Glu Asp Ser Ile Ala Val Gly Pro
            370                 375                 380
Ile Val Pro Glu Met Ala Gln Gly Glu Ala Gln Trp Phe Gln Glu Ala
385                 390                 395                 400
Lys Asn Leu Asn Glu Gln Leu Arg Ala Ala Tyr Thr Ser Ala Ser Phe
                405                 410                 415
Arg His Met Ser Leu Leu Asp Ile Ser Ser Asp Leu Ala Thr Asp His
                420                 425                 430
Leu Leu Gly Cys Asp Leu Ser Ile Ala Ser Lys His Ile Ser Lys Pro
            435                 440                 445
Val Gln Glu Pro Leu Val Leu Pro Glu Val Phe Gly Asn Leu Asn Ser
            450                 455                 460
Val Met Cys Val Glu Gly Glu Ala Gly Ser Gly Lys Thr Val Leu Leu
465                 470                 475                 480
Lys Lys Ile Ala Phe Leu Trp Ala Ser Gly Cys Cys Pro Leu Leu Asn
                485                 490                 495
Arg Phe Gln Leu Val Phe Tyr Leu Ser Leu Ser Ser Thr Arg Pro Asp
            500                 505                 510
Glu Gly Leu Ala Ser Ile Ile Cys Asp Gln Leu Leu Glu Lys Glu Gly
            515                 520                 525
Ser Val Thr Glu Met Cys Val Arg Asn Ile Ile Gln Gln Leu Lys Asn
            530                 535                 540
Gln Val Leu Phe Leu Leu Asp Asp Tyr Lys Glu Ile Cys Ser Ile Pro
545                 550                 555                 560
Gln Val Ile Gly Lys Leu Ile Gln Lys Asn His Leu Ser Arg Thr Cys
                565                 570                 575
Leu Leu Ile Ala Val Arg Thr Asn Arg Ala Arg Asp Ile Arg Arg Tyr
                580                 585                 590
Leu Glu Thr Ile Leu Glu Ile Lys Ala Phe Pro Phe Tyr Asn Thr Val
            595                 600                 605
```

-continued

Cys Ile Leu Arg Lys Leu Phe Ser His Asn Met Thr Arg Leu Arg Lys
610                 615                 620

Phe Met Val Tyr Phe Gly Lys Asn Gln Ser Leu Gln Lys Ile Gln Lys
625                 630                 635                 640

Thr Pro Leu Phe Val Ala Ala Ile Cys Ala His Trp Phe Gln Tyr Pro
            645                 650                 655

Phe Asp Pro Ser Phe Asp Asp Val Ala Val Phe Lys Ser Tyr Met Glu
            660                 665                 670

Arg Leu Ser Leu Arg Asn Lys Ala Thr Ala Glu Ile Leu Lys Ala Thr
            675                 680                 685

Val Ser Ser Cys Gly Glu Leu Ala Leu Lys Gly Phe Phe Ser Cys Cys
690                 695                 700

Phe Glu Phe Asn Asp Asp Asp Leu Ala Glu Ala Gly Val Asp Glu Asp
705                 710                 715                 720

Glu Asp Leu Thr Met Cys Leu Met Ser Lys Phe Thr Ala Gln Arg Leu
            725                 730                 735

Arg Pro Phe Tyr Arg Phe Leu Ser Pro Ala Phe Gln Glu Phe Leu Ala
            740                 745                 750

Gly Met Arg Leu Ile Glu Leu Leu Asp Ser Asp Arg Gln Glu His Gln
            755                 760                 765

Asp Leu Gly Leu Tyr His Leu Lys Gln Ile Asn Ser Pro Met Met Thr
770                 775                 780

Val Ser Ala Tyr Asn Asn Phe Leu Asn Tyr Val Ser Ser Leu Pro Ser
785                 790                 795                 800

Thr Lys Ala Gly Pro Lys Ile Val Ser His Leu Leu His Leu Val Asp
            805                 810                 815

Asn Lys Glu Ser Leu Glu Asn Ile Ser Glu Asn Asp Asp Tyr Leu Lys
            820                 825                 830

His Gln Pro Glu Ile Ser Leu Gln Met Gln Leu Leu Arg Gly Leu Trp
            835                 840                 845

Gln Ile Cys Pro Gln Ala Tyr Phe Ser Met Val Ser Glu His Leu Leu
850                 855                 860

Val Leu Ala Leu Lys Thr Ala Tyr Gln Ser Asn Thr Val Ala Ala Cys
865                 870                 875                 880

Ser Pro Phe Val Leu Gln Phe Leu Gln Gly Arg Thr Leu Thr Leu Gly
            885                 890                 895

Ala Leu Asn Leu Gln Tyr Phe Asp His Pro Glu Ser Leu Ser Leu
            900                 905                 910

Leu Arg Ser Ile His Phe Pro Ile Arg Gly Asn Lys Thr Ser Pro Arg
            915                 920                 925

Ala His Phe Ser Val Leu Glu Thr Cys Phe Asp Lys Ser Gln Val Pro
            930                 935                 940

Thr Ile Asp Gln Asp Tyr Ala Ser Ala Phe Glu Pro Met Asn Glu Trp
945                 950                 955                 960

Glu Arg Asn Leu Ala Glu Lys Glu Asp Asn Val Lys Ser Tyr Met Asp
            965                 970                 975

Met Gln Arg Arg Ala Ser Pro Asp Leu Ser Thr Gly Tyr Trp Lys Leu
            980                 985                 990

Ser Pro Lys Gln Tyr Lys Ile Pro Cys Leu Glu Val Asp Val Asn Asp
            995                 1000                1005

Ile Asp Val Val Gly Gln Asp Met Leu Glu Ile Leu Met Thr Val Phe
    1010                1015                1020

Ser Ala Ser Gln Arg Ile Glu Leu His Leu Asn His Ser Arg Gly Phe
1025                1030                1035                1040

Ile Glu Ser Ile Arg Pro Ala Leu Glu Leu Ser Lys Ala Ser Val Thr
            1045                1050                1055

Lys Cys Ser Ile Ser Lys Leu Glu Leu Ser Ala Ala Glu Gln Glu Leu
        1060                1065                1070

Leu Leu Thr Leu Pro Ser Leu Glu Ser Leu Glu Val Ser Gly Thr Ile
    1075                1080                1085

Gln Ser Gln Asp Gln Ile Phe Pro Asn Leu Asp Lys Phe Leu Cys Leu
    1090                1095                1100

Lys Glu Leu Ser Val Asp Leu Glu Gly Asn Ile Asn Val Phe Ser Val
1105                1110                1115                1120

Ile Pro Glu Glu Phe Pro Asn Phe His His Met Glu Lys Leu Leu Ile
            1125                1130                1135

Gln Ile Ser Ala Glu Tyr Asp Pro Ser Lys Leu Val Lys Leu Ile Gln
        1140                1145                1150

Asn Ser Pro Asn Leu His Val Phe His Leu Lys Cys Asn Phe Phe Ser
    1155                1160                1165

Asp Phe Gly Ser Leu Met Thr Met Leu Val Ser Cys Lys Lys Leu Thr
    1170                1175                1180

Glu Ile Lys Phe Ser Asp Ser Phe Phe Gln Ala Val Pro Phe Val Ala
1185                1190                1195                1200

Ser Leu Pro Asn Phe Ile Ser Leu Lys Ile Leu Asn Leu Glu Gly Gln
            1205                1210                1215

Gln Phe Pro Asp Glu Glu Thr Ser Glu Lys Phe Ala Tyr Ile Leu Gly
        1220                1225                1230

Ser Leu Ser Asn Leu Glu Glu Leu Ile Leu Pro Thr Gly Asp Gly Ile
    1235                1240                1245

Tyr Arg Val Ala Lys Leu Ile Ile Gln Gln Cys Gln Gln Leu His Cys
    1250                1255                1260

Leu Arg Val Leu Ser Phe Phe Lys Thr Leu Asn Asp Asp Ser Val Val
1265                1270                1275                1280

Glu Ile Ala Lys Val Ala Ile Ser Gly Gly Phe Gln Lys Leu Glu Asn
            1285                1290                1295

Leu Lys Leu Ser Ile Asn His Lys Ile Thr Glu Gly Tyr Arg Asn
        1300                1305                1310

Phe Phe Gln Ala Leu Asp Asn Met Pro Asn Leu Gln Glu Leu Asp Ile
    1315                1320                1325

Ser Arg His Phe Thr Glu Cys Ile Lys Ala Gln Ala Thr Thr Val Lys
    1330                1335                1340

Ser Leu Ser Gln Cys Val Leu Arg Leu Pro Arg Leu Ile Arg Leu Asn
1345                1350                1355                1360

Met Leu Ser Trp Leu Leu Asp Ala Asp Asp Ile Ala Leu Leu Asn Val
            1365                1370                1375

Met Lys Glu Arg His Pro Gln Ser Lys Tyr Leu Thr Ile Leu Gln Lys
        1380                1385                1390

Trp Ile Leu Pro Phe Ser Pro Ile Ile Gln Lys
    1395                1400

<210> SEQ ID NO 29
<211> LENGTH: 1241
<212> TYPE: PRT
<213> ORGANISM: Homo sapiens

<400> SEQUENCE: 29

Met Pro Leu His Ile Gly Asp Phe Val Trp Asp Ser Lys Val His Ser
1               5                   10                  15

```
Leu Gln Ser Ser Leu Asn Ile Phe Ser Leu Pro Thr Lys Gly Arg
            20                  25                  30
Thr Glu His Leu Phe Phe Ser His Ile Leu Ser Phe His Trp Pro Ala
         35                  40                  45
Phe Ser Ser Ile Arg Leu Glu Leu Trp Ile Asn Leu Arg Cys Glu Phe
 50                  55                  60
Leu Arg Ser Lys Lys Ser Ser Glu Glu Ile Thr Gln Tyr Ile Gln Ser
 65                  70                  75                  80
Tyr Lys Gly Phe Val Asp Ile Thr Gly Glu His Phe Val Asn Ser Trp
                 85                  90                  95
Val Gln Arg Glu Leu Pro Met Ala Ser Ala Tyr Cys Asn Asp Ser Ile
                100                 105                 110
Phe Ala Tyr Glu Glu Leu Arg Leu Asp Ser Phe Lys Asp Trp Pro Arg
            115                 120                 125
Glu Ser Ala Val Gly Val Ala Ala Leu Ala Lys Ala Gly Leu Phe Tyr
130                 135                 140
Thr Gly Ile Lys Asp Ile Val Gln Cys Phe Ser Cys Gly Gly Cys Leu
145                 150                 155                 160
Glu Lys Trp Gln Glu Gly Asp Asp Pro Leu Asp Asp His Thr Arg Cys
                165                 170                 175
Phe Pro Asn Cys Pro Phe Leu Gln Asn Met Lys Ser Ser Ala Glu Val
            180                 185                 190
Thr Pro Asp Leu Gln Ser Arg Gly Glu Leu Cys Glu Leu Leu Glu Thr
            195                 200                 205
Thr Ser Glu Ser Asn Leu Glu Asp Ser Ile Ala Val Gly Pro Ile Val
210                 215                 220
Pro Glu Met Ala Gln Gly Glu Ala Gln Trp Phe Gln Glu Ala Lys Asn
225                 230                 235                 240
Leu Asn Glu Gln Leu Arg Ala Ala Tyr Thr Ser Ala Ser Phe Arg His
                245                 250                 255
Met Ser Leu Leu Asp Ile Ser Ser Asp Leu Ala Thr Asp His Leu Leu
            260                 265                 270
Gly Cys Asp Leu Ser Ile Ala Ser Lys His Ile Ser Lys Pro Val Gln
            275                 280                 285
Glu Pro Leu Val Leu Pro Glu Val Phe Gly Asn Leu Asn Ser Val Met
            290                 295                 300
Cys Val Glu Gly Glu Ala Gly Ser Gly Lys Thr Val Leu Leu Lys Lys
305                 310                 315                 320
Ile Ala Phe Leu Trp Ala Ser Gly Cys Cys Pro Leu Leu Asn Arg Phe
                325                 330                 335
Gln Leu Val Phe Tyr Leu Ser Leu Ser Ser Thr Arg Pro Asp Glu Gly
            340                 345                 350
Leu Ala Ser Ile Ile Cys Asp Gln Leu Leu Lys Glu Gly Ser Val
            355                 360                 365
Thr Glu Met Cys Val Arg Asn Ile Ile Gln Gln Leu Lys Asn Gln Val
            370                 375                 380
Leu Phe Leu Leu Asp Asp Tyr Lys Glu Ile Cys Ser Ile Pro Gln Val
385                 390                 395                 400
Ile Gly Lys Leu Ile Gln Lys Asn His Leu Ser Arg Thr Cys Leu Leu
                405                 410                 415
Ile Ala Val Arg Thr Asn Arg Ala Arg Asp Ile Arg Arg Tyr Leu Glu
            420                 425                 430
Thr Ile Leu Glu Ile Lys Ala Phe Pro Phe Tyr Asn Thr Val Cys Ile
```

```
                435                 440                 445
Leu Arg Lys Leu Phe Ser His Asn Met Thr Arg Leu Arg Lys Phe Met
450                 455                 460
Val Tyr Phe Gly Lys Asn Gln Ser Leu Gln Lys Ile Gln Lys Thr Pro
465                 470                 475                 480
Leu Phe Val Ala Ala Ile Cys Ala His Trp Phe Gln Tyr Pro Phe Asp
                485                 490                 495
Pro Ser Phe Asp Asp Val Ala Val Phe Lys Ser Tyr Met Glu Arg Leu
                500                 505                 510
Ser Leu Arg Asn Lys Ala Thr Ala Glu Ile Leu Lys Ala Thr Val Ser
                515                 520                 525
Ser Cys Gly Glu Leu Ala Leu Lys Gly Phe Ser Cys Cys Phe Glu
530                 535                 540
Phe Asn Asp Asp Asp Leu Ala Glu Ala Gly Val Asp Glu Asp Glu Asp
545                 550                 555                 560
Leu Thr Met Cys Leu Met Ser Lys Phe Thr Ala Gln Arg Leu Arg Pro
                565                 570                 575
Phe Tyr Arg Phe Leu Ser Pro Ala Phe Gln Glu Phe Leu Ala Gly Met
                580                 585                 590
Arg Leu Ile Glu Leu Leu Asp Ser Asp Arg Gln Glu His Gln Asp Leu
                595                 600                 605
Gly Leu Tyr His Leu Lys Gln Ile Asn Ser Pro Met Met Thr Val Ser
                610                 615                 620
Ala Tyr Asn Asn Phe Leu Asn Tyr Val Ser Ser Leu Pro Ser Thr Lys
625                 630                 635                 640
Ala Gly Pro Lys Ile Val Ser His Leu Leu His Leu Val Asp Asn Lys
                645                 650                 655
Glu Ser Leu Glu Asn Ile Ser Glu Asn Asp Asp Tyr Leu Lys His Gln
                660                 665                 670
Pro Glu Ile Ser Leu Gln Met Gln Leu Leu Arg Gly Leu Trp Gln Ile
                675                 680                 685
Cys Pro Gln Ala Tyr Phe Ser Met Val Ser Glu His Leu Leu Val Leu
690                 695                 700
Ala Leu Lys Thr Ala Tyr Gln Ser Asn Thr Val Ala Ala Cys Ser Pro
705                 710                 715                 720
Phe Val Leu Gln Phe Leu Gly Arg Thr Leu Thr Leu Gly Ala Leu
                725                 730                 735
Asn Leu Gln Tyr Phe Phe Asp His Pro Glu Ser Leu Ser Leu Leu Arg
                740                 745                 750
Ser Ile His Phe Pro Ile Arg Gly Asn Lys Thr Ser Pro Arg Ala His
                755                 760                 765
Phe Ser Val Leu Glu Thr Cys Phe Asp Lys Ser Gln Val Pro Thr Ile
770                 775                 780
Asp Gln Asp Tyr Ala Ser Ala Phe Glu Pro Met Asn Glu Trp Glu Arg
785                 790                 795                 800
Asn Leu Ala Glu Lys Glu Asp Asn Val Lys Ser Tyr Met Asp Met Gln
                805                 810                 815
Arg Arg Ala Ser Pro Asp Leu Ser Thr Gly Tyr Trp Lys Leu Ser Pro
                820                 825                 830
Lys Gln Tyr Lys Ile Pro Cys Leu Glu Val Asp Val Asn Asp Ile Asp
                835                 840                 845
Val Val Gly Gln Asp Met Leu Glu Leu Met Thr Val Phe Ser Ala
850                 855                 860
```

```
Ser Gln Arg Ile Glu Leu His Leu Asn His Ser Arg Gly Phe Ile Glu
865                 870                 875                 880

Ser Ile Arg Pro Ala Leu Glu Leu Ser Lys Ala Ser Val Thr Lys Cys
            885                 890                 895

Ser Ile Ser Lys Leu Glu Leu Ser Ala Ala Glu Gln Glu Leu Leu Leu
        900                 905                 910

Thr Leu Pro Ser Leu Glu Ser Leu Glu Val Ser Gly Thr Ile Gln Ser
    915                 920                 925

Gln Asp Gln Ile Phe Pro Asn Leu Asp Lys Phe Leu Cys Leu Lys Glu
930                 935                 940

Leu Ser Val Asp Leu Glu Gly Asn Ile Asn Val Phe Ser Val Ile Pro
945                 950                 955                 960

Glu Glu Phe Pro Asn Phe His His Met Glu Lys Leu Leu Ile Gln Ile
                965                 970                 975

Ser Ala Glu Tyr Asp Pro Ser Lys Leu Val Lys Leu Ile Gln Asn Ser
            980                 985                 990

Pro Asn Leu His Val Phe His Leu Lys Cys Asn Phe Phe Ser Asp Phe
        995                 1000                1005

Gly Ser Leu Met Thr Met Leu Val Ser Cys Lys Lys Leu Thr Glu Ile
    1010                1015                1020

Lys Phe Ser Asp Ser Phe Phe Gln Ala Val Pro Phe Val Ala Ser Leu
1025                1030                1035                1040

Pro Asn Phe Ile Ser Leu Lys Ile Leu Asn Leu Glu Gly Gln Gln Phe
                1045                1050                1055

Pro Asp Glu Glu Thr Ser Glu Lys Phe Ala Tyr Ile Leu Gly Ser Leu
            1060                1065                1070

Ser Asn Leu Glu Glu Leu Ile Leu Pro Thr Gly Asp Gly Ile Tyr Arg
        1075                1080                1085

Val Ala Lys Leu Ile Ile Gln Gln Cys Gln Gln Leu His Cys Leu Arg
    1090                1095                1100

Val Leu Ser Phe Phe Lys Thr Leu Asn Asp Asp Ser Val Val Glu Ile
1105                1110                1115                1120

Ala Lys Val Ala Ile Ser Gly Gly Phe Gln Lys Leu Glu Asn Leu Lys
                1125                1130                1135

Leu Ser Ile Asn His Lys Ile Thr Glu Glu Gly Tyr Arg Asn Phe Phe
            1140                1145                1150

Gln Ala Leu Asp Asn Met Pro Asn Leu Gln Glu Leu Asp Ile Ser Arg
        1155                1160                1165

His Phe Thr Glu Cys Ile Lys Ala Gln Ala Thr Thr Val Lys Ser Leu
    1170                1175                1180

Ser Gln Cys Val Leu Arg Leu Pro Arg Leu Ile Arg Leu Asn Met Leu
1185                1190                1195                1200

Ser Trp Leu Leu Asp Ala Asp Asp Ile Ala Leu Leu Asn Val Met Lys
                1205                1210                1215

Glu Arg His Pro Gln Ser Lys Tyr Leu Thr Ile Leu Gln Lys Trp Ile
            1220                1225                1230

Leu Pro Phe Ser Pro Ile Ile Gln Lys
        1235                1240

<210> SEQ ID NO 30
<211> LENGTH: 233
<212> TYPE: PRT
<213> ORGANISM: Homo sapiens

<400> SEQUENCE: 30
```

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
        130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
210                 215                 220

Gln Val Tyr Phe Gly Ile Ile Ala Leu
225                 230

<210> SEQ ID NO 31
<211> LENGTH: 189
<212> TYPE: PRT
<213> ORGANISM: Homo sapiens

<400> SEQUENCE: 31

Met Ala Ser Pro Phe Ala Leu Leu Met Val Leu Val Val Leu Ser Cys
1               5                   10                  15

Lys Ser Ser Cys Ser Leu Gly Cys Asp Leu Pro Glu Thr His Ser Leu
                20                  25                  30

Asp Asn Arg Arg Thr Leu Met Leu Leu Ala Gln Met Ser Arg Ile Ser
            35                  40                  45

Pro Ser Ser Cys Leu Met Asp Arg His Asp Phe Gly Phe Pro Gln Glu
        50                  55                  60

Glu Phe Asp Gly Asn Gln Phe Gln Lys Ala Pro Ala Ile Ser Val Leu
65                  70                  75                  80

His Glu Leu Ile Gln Gln Ile Phe Asn Leu Phe Thr Thr Lys Asp Ser
            85                  90                  95

Ser Ala Ala Trp Asp Glu Asp Leu Leu Asp Lys Phe Cys Thr Glu Leu
        100                 105                 110

Tyr Gln Gln Leu Asn Asp Leu Glu Ala Cys Val Met Gln Glu Glu Arg
        115                 120                 125

Val Gly Glu Thr Pro Leu Met Asn Ala Asp Ser Ile Leu Ala Val Lys
        130                 135                 140

```
Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Leu Ser Thr Asn Leu Gln Glu Arg Leu Arg Arg Lys Glu
            180                 185

<210> SEQ ID NO 32
<211> LENGTH: 187
<212> TYPE: PRT
<213> ORGANISM: Homo sapiens

<400> SEQUENCE: 32

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 33
<211> LENGTH: 166
<212> TYPE: PRT
<213> ORGANISM: Homo sapiens

<400> SEQUENCE: 33

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
```

-continued

```
                100                 105                 110
Asp Asp Phe Glu Lys Leu Thr Asn Tyr Ser Val Thr Asp Leu Asn Val
            115                 120                 125

Gln Arg Lys Ala Ile His Glu Leu Ile Gln Val Met Ala Glu Leu Ser
        130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 34
<211> LENGTH: 554
<212> TYPE: PRT
<213> ORGANISM: Homo sapiens

<400> SEQUENCE: 34

Met Thr Ala Pro Gly Ala Ala Gly Arg Cys Pro Pro Thr Thr Trp Leu
 1               5                  10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
```

Thr Glu Leu Ser Pro Ser Arg Pro Gly Gly Ser Met Gln Thr Glu
305                 310                 315                 320

Pro Ala Arg Pro Ser Asn Phe Leu Ser Ala Ser Ser Pro Leu Pro Ala
                325                 330                 335

Ser Ala Lys Gly Gln Gln Pro Ala Asp Val Thr Gly Thr Ala Leu Pro
            340                 345                 350

Arg Val Gly Pro Val Arg Pro Thr Gly Gln Asp Trp Asn His Thr Pro
        355                 360                 365

Gln Lys Thr Asp His Pro Ser Ala Leu Leu Arg Asp Pro Pro Glu Pro
    370                 375                 380

Gly Ser Pro Arg Ile Ser Ser Leu Arg Pro Gln Gly Leu Ser Asn Pro
385                 390                 395                 400

Ser Thr Leu Ser Ala Gln Pro Gln Leu Ser Arg Ser His Ser Ser Gly
                405                 410                 415

Ser Val Leu Pro Leu Gly Glu Leu Glu Gly Arg Arg Ser Thr Arg Asp
            420                 425                 430

Arg Arg Ser Pro Ala Glu Pro Glu Gly Gly Pro Ala Ser Glu Gly Ala
        435                 440                 445

Ala Arg Pro Leu Pro Arg Phe Asn Ser Val Pro Leu Thr Asp Thr Gly
    450                 455                 460

His Glu Arg Gln Ser Glu Gly Ser Ser Pro Gln Leu Gln Glu Ser
465                 470                 475                 480

Val Phe His Leu Leu Val Pro Ser Val Ile Leu Val Leu Leu Ala Val
                485                 490                 495

Gly Gly Leu Leu Phe Tyr Arg Trp Arg Arg Ser His Gln Glu Pro
            500                 505                 510

Gln Arg Ala Asp Ser Pro Leu Glu Gln Pro Glu Gly Ser Pro Leu Thr
        515                 520                 525

Gln Asp Asp Arg Gln Val Glu Leu Pro Val
    530                 535                 540

545                 550

<210> SEQ ID NO 35
<211> LENGTH: 554
<212> TYPE: PRT
<213> ORGANISM: Homo sapiens

<400> SEQUENCE: 35

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
                20                  25                  30

Glu Glu Val Ser Glu Tyr Cys Ser His Met Ile Gly Ser Gly His Leu
            35                  40                  45

Gln Ser Leu Gln Arg Leu Ile Asp Ser Gln Met Glu Thr Ser Cys Gln
        50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln

-continued

```
            130                 135                 140
Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
                180                 185                 190

Tyr Pro Lys Ala Ile Pro Ser Ser Asp Pro Ala Ser Val Ser Pro His
                195                 200                 205

Gln Pro Leu Ala Pro Ser Met Ala Pro Val Ala Gly Leu Thr Trp Glu
                210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
                260                 265                 270

Thr Ile Gly Gly Ser Pro Gln Pro Arg Pro Ser Val Gly Ala Phe Asn
                275                 280                 285

Pro Gly Met Glu Asp Ile Leu Asp Ser Ala Met Gly Thr Asn Trp Val
                290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
                340                 345                 350

Ser Ala Lys Gly Gln Gln Pro Ala Asp Val Thr Gly Thr Ala Leu Pro
                355                 360                 365

Arg Val Gly Pro Val Arg Pro Thr Gly Gln Asp Trp Asn His Thr Pro
                370                 375                 380

Gln Lys Thr Asp His Pro Ser Ala Leu Leu Arg Asp Pro Pro Glu Pro
385                 390                 395                 400

Gly Ser Pro Arg Ile Ser Ser Leu Arg Pro Gln Gly Leu Ser Asn Pro
                405                 410                 415

Ser Thr Leu Ser Ala Gln Pro Gln Leu Ser Arg Ser His Ser Ser Gly
                420                 425                 430

Ser Val Leu Pro Leu Gly Glu Leu Glu Gly Arg Arg Ser Thr Arg Asp
                435                 440                 445

Arg Arg Ser Pro Ala Glu Pro Glu Gly Gly Pro Ala Ser Glu Gly Ala
450                 455                 460

Ala Arg Pro Leu Pro Arg Phe Asn Ser Val Pro Leu Thr Asp Thr Gly
465                 470                 475                 480

His Glu Arg Gln Ser Glu Gly Ser Ser Pro Gln Leu Gln Glu Ser
                485                 490                 495

Val Phe His Leu Leu Val Pro Ser Val Ile Leu Val Leu Leu Ala Val
                500                 505                 510

Gly Gly Leu Leu Phe Tyr Arg Trp Arg Arg Arg Ser His Gln Glu Pro
                515                 520                 525

Gln Arg Ala Asp Ser Pro Leu Glu Gln Pro Glu Gly Ser Pro Leu Thr
                530                 535                 540

Gln Asp Asp Arg Gln Val Glu Leu Pro Val
545                 550
```

<210> SEQ ID NO 36
<211> LENGTH: 438
<212> TYPE: PRT
<213> ORGANISM: Homo sapiens

<400> SEQUENCE: 36

```
Met Thr Ala Pro Gly Ala Ala Gly Arg Cys Pro Pro Thr Thr Trp Leu
 1               5                  10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly His Glu Arg Gln
        355                 360                 365

Ser Glu Gly Ser Ser Ser Pro Gln Leu Gln Glu Ser Val Phe His Leu
    370                 375                 380
```

```
Leu Val Pro Ser Val Ile Leu Val Leu Leu Ala Val Gly Gly Leu Leu
385                 390                 395                 400

Phe Tyr Arg Trp Arg Arg Ser His Gln Glu Pro Gln Arg Ala Asp
            405                 410                 415

Ser Pro Leu Glu Gln Pro Glu Gly Ser Pro Leu Thr Gln Asp Asp Arg
        420                 425                 430

Gln Val Glu Leu Pro Val
        435
```

<210> SEQ ID NO 37
<211> LENGTH: 256
<212> TYPE: PRT
<213> ORGANISM: Homo sapiens

<400> SEQUENCE: 37

```
Met Thr Ala Pro Gly Ala Gly Arg Cys Pro Pro Thr Thr Trp Leu
1               5                   10                  15

Gly Ser Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Gly His Glu Arg Gln Ser Glu Gly Ser Ser Ser
            180                 185                 190

Pro Gln Leu Gln Glu Ser Val Phe His Leu Leu Val Pro Ser Val Ile
        195                 200                 205

Leu Val Leu Leu Ala Val Gly Gly Leu Leu Phe Tyr Arg Trp Arg Arg
    210                 215                 220

Arg Ser His Gln Glu Pro Gln Arg Ala Asp Ser Pro Leu Glu Gln Pro
225                 230                 235                 240

Glu Gly Ser Pro Leu Thr Gln Asp Asp Arg Gln Val Glu Leu Pro Val
                245                 250                 255
```

<210> SEQ ID NO 38
<211> LENGTH: 144
<212> TYPE: PRT
<213> ORGANISM: Homo sapiens

<400> SEQUENCE: 38

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
```

```
                 20                  25                  30
Val Asn Ala Ile Gln Glu Ala Arg Arg Leu Leu Asn Leu Ser Arg Asp
                 35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
                115                 120                 125

Asp Phe Leu Leu Val Ile Pro Phe Asp Cys Trp Glu Pro Val Gln Glu
                130                 135                 140
```

<210> SEQ ID NO 39
<211> LENGTH: 207
<212> TYPE: PRT
<213> ORGANISM: Homo sapiens

<400> SEQUENCE: 39

```
Met Ala Gly Pro Ala Thr Gln Ser Pro Met Lys Leu Met Ala Leu Gln
 1               5                  10                  15

Leu Leu Leu Trp His Ser Ala Leu Trp Thr Val Gln Glu Ala Thr Pro
                 20                  25                  30

Leu Gly Pro Ala Ser Ser Leu Pro Gln Ser Phe Leu Leu Lys Cys Leu
                 35                  40                  45

Glu Gln Val Arg Lys Ile Gln Gly Asp Gly Ala Ala Leu Gln Glu Lys
 50                  55                  60

Leu Val Ser Glu Cys Ala Thr Tyr Lys Leu Cys His Pro Glu Glu Leu
 65                  70                  75                  80

Val Leu Leu Gly His Ser Leu Gly Ile Pro Trp Ala Pro Leu Ser Ser
                 85                  90                  95

Cys Pro Ser Gln Ala Leu Gln Leu Ala Gly Cys Leu Ser Gln Leu His
                100                 105                 110

Ser Gly Leu Phe Leu Tyr Gln Gly Leu Leu Gln Ala Leu Glu Gly Ile
                115                 120                 125

Ser Pro Glu Leu Gly Pro Thr Leu Asp Thr Leu Gln Leu Asp Val Ala
                130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
                180                 185                 190

Phe Leu Glu Val Ser Tyr Arg Val Leu Arg His Leu Ala Gln Pro
                195                 200                 205
```

<210> SEQ ID NO 40
<211> LENGTH: 204
<212> TYPE: PRT
<213> ORGANISM: Homo sapiens

<400> SEQUENCE: 40

```
Met Ala Gly Pro Ala Thr Gln Ser Pro Met Lys Leu Met Ala Leu Gln
 1               5                  10                  15
```

```
Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
 50                  55                  60

Leu Cys Ala Thr Tyr Lys Leu Cys His Pro Glu Glu Leu Val Leu Leu
 65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200

<210> SEQ ID NO 41
<211> LENGTH: 200
<212> TYPE: PRT
<213> ORGANISM: Homo sapiens

<400> SEQUENCE: 41

Met Ser Pro Glu Pro Ala Leu Ser Pro Ala Leu Gln Leu Leu Leu Trp
 1               5                  10                  15

His Ser Ala Leu Trp Thr Val Gln Glu Ala Thr Pro Leu Gly Pro Ala
            20                  25                  30

Ser Ser Leu Pro Gln Ser Phe Leu Leu Lys Cys Leu Glu Gln Val Arg
        35                  40                  45

Lys Ile Gln Gly Asp Gly Ala Ala Leu Gln Glu Lys Leu Cys Ala Thr
 50                  55                  60

Tyr Lys Leu Cys His Pro Glu Glu Leu Val Leu Leu Gly His Ser Leu
 65                  70                  75                  80

Gly Ile Pro Trp Ala Pro Leu Ser Ser Cys Pro Ser Gln Ala Leu Gln
                85                  90                  95

Leu Ala Gly Cys Leu Ser Gln Leu His Ser Gly Leu Phe Leu Tyr Gln
            100                 105                 110

Gly Leu Leu Gln Ala Leu Glu Gly Ile Ser Pro Glu Leu Gly Pro Thr
        115                 120                 125

Leu Asp Thr Leu Gln Leu Asp Val Ala Asp Phe Ala Thr Thr Ile Trp
130                 135                 140

Gln Gln Met Glu Glu Leu Gly Met Ala Pro Ala Leu Gln Pro Thr Gln
145                 150                 155                 160

Gly Ala Met Pro Ala Phe Ala Ser Ala Phe Gln Arg Arg Ala Gly Gly
                165                 170                 175

Val Leu Val Ala Ser His Leu Gln Ser Phe Leu Glu Val Ser Tyr Arg
            180                 185                 190
```

```
Val Leu Arg His Leu Ala Gln Pro
        195                 200
```

<210> SEQ ID NO 42
<211> LENGTH: 393
<212> TYPE: PRT
<213> ORGANISM: Homo sapiens

<400> SEQUENCE: 42

```
Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365
```

```
Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 43
<211> LENGTH: 393
<212> TYPE: PRT
<213> ORGANISM: Homo sapiens

<400> SEQUENCE: 43

Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
 50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350
```

Ala Gln Ala Gly Lys Glu Pro Gly Gly Ser Arg Ala His Ser Ser His
        355                 360                 365

Leu Lys Ser Lys Gly Gln Ser Thr Ser Arg His Lys Lys Leu Met
    370                 375                 380

Phe Lys Thr Glu Gly Pro Asp Ser Asp
385                 390

<210> SEQ ID NO 44
<211> LENGTH: 341
<212> TYPE: PRT
<213> ORGANISM: Homo sapiens

<400> SEQUENCE: 44

Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
                 20                  25                  30

Ser Pro Leu Pro Ser Gln Ala Met Asp Asp Leu Met Leu Ser Pro Asp
             35                  40                  45

Asp Ile Glu Gln Trp Phe Thr Glu Asp Pro Gly Pro Asp Glu Ala Pro
         50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Asp Gln Thr Ser Phe
                325                 330                 335

```
Gln Lys Glu Asn Cys
            340

<210> SEQ ID NO 45
<211> LENGTH: 346
<212> TYPE: PRT
<213> ORGANISM: Homo sapiens

<400> SEQUENCE: 45

Met Glu Glu Pro Gln Ser Asp Pro Ser Val Glu Pro Leu Ser Gln
  1               5                  10                  15

Glu Thr Phe Ser Asp Leu Trp Lys Leu Leu Pro Glu Asn Asn Val Leu
                 20                  25                  30

Ser Pro Leu Pro Ser Gln Ala Met Asp Asp Leu Met Leu Ser Pro Asp
             35                  40                  45

Asp Ile Glu Gln Trp Phe Thr Glu Asp Pro Gly Pro Asp Glu Ala Pro
         50                  55                  60

Arg Met Pro Glu Ala Ala Pro Pro Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
            130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
        210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
        290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Met Leu Leu Asp Leu
                325                 330                 335

Arg Trp Cys Tyr Phe Leu Ile Asn Ser Ser
            340                 345

<210> SEQ ID NO 46
```

```
<211> LENGTH: 261
<212> TYPE: PRT
<213> ORGANISM: Homo sapiens

<400> SEQUENCE: 46

Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Ile Arg Gly Arg Glu Arg Phe Glu Met
        195                 200                 205

Phe Arg Glu Leu Asn Glu Ala Leu Glu Leu Lys Asp Ala Gln Ala Gly
    210                 215                 220

Lys Glu Pro Gly Gly Ser Arg Ala His Ser Ser His Leu Lys Ser Lys
225                 230                 235                 240

Lys Gly Gln Ser Thr Ser Arg His Lys Lys Leu Met Phe Lys Thr Glu
                245                 250                 255

Gly Pro Asp Ser Asp
            260

<210> SEQ ID NO 47
<211> LENGTH: 209
<212> TYPE: PRT
<213> ORGANISM: Homo sapiens

<400> SEQUENCE: 47

Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80
```

```
Arg His Ser Val Val Pro Tyr Glu Pro Pro Glu Val Gly Ser Asp
             85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Asp Gln Thr Ser Phe Gln Lys Glu Asn
        195                 200                 205

Cys

<210> SEQ ID NO 48
<211> LENGTH: 214
<212> TYPE: PRT
<213> ORGANISM: Homo sapiens

<400> SEQUENCE: 48

Met Phe Cys Gln Leu Ala Lys Thr Cys Pro Val Gln Leu Trp Val Asp
  1               5                  10                  15

Ser Thr Pro Pro Pro Gly Thr Arg Val Arg Ala Met Ala Ile Tyr Lys
             20                  25                  30

Gln Ser Gln His Met Thr Glu Val Val Arg Arg Cys Pro His His Glu
         35                  40                  45

Arg Cys Ser Asp Ser Asp Gly Leu Ala Pro Pro Gln His Leu Ile Arg
     50                  55                  60

Val Glu Gly Asn Leu Arg Val Glu Tyr Leu Asp Asp Arg Asn Thr Phe
 65                  70                  75                  80

Arg His Ser Val Val Val Pro Tyr Glu Pro Pro Glu Val Gly Ser Asp
             85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Met Leu Leu Asp Leu Arg Trp Cys Tyr
        195                 200                 205

Phe Leu Ile Asn Ser Ser
    210

<210> SEQ ID NO 49
<211> LENGTH: 1237
<212> TYPE: PRT
```

<213> ORGANISM: Homo sapiens

<400> SEQUENCE: 49

```
Met Asp Ala Lys Ala Arg Asn Cys Leu Leu Gln His Arg Glu Ala Leu
  1               5                  10                  15
Glu Lys Asp Ile Lys Thr Ser Tyr Ile Met Asp His Met Ile Ser Asp
             20                  25                  30
Gly Phe Leu Thr Ile Ser Glu Glu Lys Val Arg Asn Glu Pro Thr
         35                  40                  45
Gln Gln Gln Arg Ala Ala Met Leu Ile Lys Met Ile Leu Lys Lys Asp
 50                  55                  60
Asn Asp Ser Tyr Val Ser Phe Tyr Asn Ala Leu Leu His Glu Gly Tyr
 65                  70                  75                  80
Lys Asp Leu Ala Ala Leu Leu His Asp Gly Ile Pro Val Val Ser Ser
                 85                  90                  95
Ser Ser Val Arg Thr Val Leu Cys Glu Gly Gly Val Pro Gln Arg Pro
            100                 105                 110
Val Val Phe Val Thr Arg Lys Lys Leu Val Asn Ala Ile Gln Gln Lys
            115                 120                 125
Leu Ser Lys Leu Lys Gly Glu Pro Gly Trp Val Thr Ile His Gly Met
130                 135                 140
Ala Gly Cys Gly Lys Ser Val Leu Ala Ala Glu Ala Val Arg Asp His
145                 150                 155                 160
Ser Leu Leu Glu Gly Cys Phe Pro Gly Gly Val His Trp Val Ser Val
                165                 170                 175
Gly Lys Gln Asp Lys Ser Gly Leu Leu Met Lys Leu Gln Asn Leu Cys
            180                 185                 190
Thr Arg Leu Asp Gln Asp Glu Ser Phe Ser Gln Arg Leu Pro Leu Asn
            195                 200                 205
Ile Glu Glu Ala Lys Asp Arg Leu Arg Ile Leu Met Leu Arg Lys His
        210                 215                 220
Pro Arg Ser Leu Leu Ile Leu Asp Asp Val Trp Asp Ser Trp Val Leu
225                 230                 235                 240
Lys Ala Phe Asp Ser Gln Cys Gln Ile Leu Thr Thr Arg Asp Lys
                245                 250                 255
Ser Val Thr Asp Ser Val Met Gly Pro Lys Tyr Val Pro Val Glu
            260                 265                 270
Ser Ser Leu Gly Lys Glu Lys Gly Leu Glu Ile Leu Ser Leu Phe Val
            275                 280                 285
Asn Met Lys Lys Ala Asp Leu Pro Glu Gln Ala His Ser Ile Ile Lys
        290                 295                 300
Glu Cys Lys Gly Ser Pro Leu Val Val Ser Leu Ile Gly Ala Leu Leu
305                 310                 315                 320
Arg Asp Phe Pro Asn Arg Trp Glu Tyr Tyr Leu Lys Gln Leu Gln Asn
                325                 330                 335
Lys Gln Phe Lys Arg Ile Arg Lys Ser Ser Tyr Asp Tyr Glu Ala
            340                 345                 350
Leu Asp Glu Ala Met Ser Ile Ser Val Glu Met Leu Arg Glu Asp Ile
            355                 360                 365
Lys Asp Tyr Tyr Thr Asp Leu Ser Ile Leu Gln Lys Asp Val Lys Val
        370                 375                 380
Pro Thr Lys Val Leu Cys Ile Leu Trp Asp Met Glu Thr Glu Glu Val
385                 390                 395                 400
Glu Asp Ile Leu Gln Glu Phe Val Asn Lys Ser Leu Leu Phe Cys Asp
```

-continued

```
                405                 410                 415
Arg Asn Gly Lys Ser Phe Arg Tyr Tyr Leu His Asp Leu Gln Val Asp
            420                 425                 430

Phe Leu Thr Glu Lys Asn Cys Ser Gln Leu Gln Asp Leu His Lys Lys
            435                 440                 445

Ile Ile Thr Gln Phe Gln Arg Tyr His Gln Pro His Thr Leu Ser Pro
450                 455                 460

Asp Gln Glu Asp Cys Met Tyr Trp Tyr Asn Phe Leu Ala Tyr His Met
465                 470                 475                 480

Ala Ser Ala Lys Met His Lys Glu Leu Cys Ala Leu Met Phe Ser Leu
            485                 490                 495

Asp Trp Ile Lys Ala Lys Thr Glu Leu Val Gly Pro Ala His Leu Ile
            500                 505                 510

His Glu Phe Val Glu Tyr Arg His Ile Leu Asp Glu Lys Asp Cys Ala
            515                 520                 525

Val Ser Glu Asn Phe Gln Glu Phe Leu Ser Leu Asn Gly His Leu Leu
530                 535                 540

Gly Arg Gln Pro Phe Pro Asn Ile Val Gln Leu Gly Leu Cys Glu Pro
545                 550                 555                 560

Glu Thr Ser Glu Val Tyr Gln Gln Ala Lys Leu Gln Ala Lys Gln Glu
            565                 570                 575

Val Asp Asn Gly Met Leu Tyr Leu Glu Trp Ile Asn Lys Lys Asn Ile
            580                 585                 590

Thr Asn Leu Ser Arg Leu Val Val Arg Pro His Thr Asp Ala Val Tyr
            595                 600                 605

His Ala Cys Phe Ser Glu Asp Gly Gln Arg Ile Ala Ser Cys Gly Ala
            610                 615                 620

Asp Lys Thr Leu Gln Val Phe Lys Ala Glu Thr Gly Glu Lys Leu Leu
625                 630                 635                 640

Glu Ile Lys Ala His Glu Asp Glu Val Leu Cys Cys Ala Phe Ser Thr
            645                 650                 655

Asp Asp Arg Phe Ile Ala Thr Cys Ser Val Asp Lys Lys Val Lys Ile
            660                 665                 670

Trp Asn Ser Met Thr Gly Glu Leu Val His Thr Tyr Asp Glu His Ser
            675                 680                 685

Glu Gln Val Asn Cys Cys His Phe Thr Asn Ser Ser His His Leu Leu
            690                 695                 700

Leu Ala Thr Gly Ser Ser Asp Cys Phe Leu Lys Leu Trp Asp Leu Asn
705                 710                 715                 720

Gln Lys Glu Cys Arg Asn Thr Met Phe Gly His Thr Asn Ser Val Asn
            725                 730                 735

His Cys Arg Phe Ser Pro Asp Asp Lys Leu Leu Ala Ser Cys Ser Ala
            740                 745                 750

Asp Gly Thr Leu Lys Leu Trp Asp Ala Thr Ser Ala Asn Glu Arg Lys
            755                 760                 765

Ser Ile Asn Val Lys Gln Phe Phe Leu Asn Leu Glu Asp Pro Gln Glu
770                 775                 780

Asp Met Glu Val Ile Val Lys Cys Cys Ser Trp Ser Ala Asp Gly Ala
785                 790                 795                 800

Arg Ile Met Val Ala Ala Lys Asn Lys Ile Phe Leu Phe Asp Ile His
            805                 810                 815

Thr Ser Gly Leu Leu Gly Glu Ile His Thr Gly His His Ser Thr Ile
            820                 825                 830
```

-continued

Gln Tyr Cys Asp Phe Ser Pro Gln Asn His Leu Ala Val Val Ala Leu
    835                 840                 845

Ser Gln Tyr Cys Val Glu Leu Trp Asn Thr Asp Ser Arg Ser Lys Val
    850                 855                 860

Ala Asp Cys Arg Gly His Leu Ser Trp Val His Gly Val Met Phe Ser
865                 870                 875                 880

Pro Asp Gly Ser Ser Phe Leu Thr Ser Ser Asp Asp Gln Thr Ile Arg
                885                 890                 895

Leu Trp Glu Thr Lys Lys Val Cys Lys Asn Ser Ala Val Met Leu Lys
            900                 905                 910

Gln Glu Val Asp Val Val Phe Gln Glu Asn Val Met Val Leu Ala
        915                 920                 925

Val Asp His Ile Arg Arg Leu Gln Leu Ile Asn Gly Arg Thr Gly Gln
    930                 935                 940

Ile Asp Tyr Leu Thr Glu Ala Gln Val Ser Cys Cys Cys Leu Ser Pro
945                 950                 955                 960

His Leu Gln Tyr Ile Ala Phe Gly Asp Glu Asn Gly Ala Ile Glu Ile
                965                 970                 975

Leu Glu Leu Val Asn Asn Arg Ile Phe Gln Ser Arg Phe Gln His Lys
            980                 985                 990

Lys Thr Val Trp His Ile Gln Phe Thr Ala Asp Glu Lys Thr Leu Ile
        995                 1000                1005

Ser Ser Ser Asp Asp Ala Glu Ile Gln Val Trp Asn Trp Gln Leu Asp
    1010                1015                1020

Lys Cys Ile Phe Leu Arg Gly His Gln Glu Thr Val Lys Asp Phe Arg
1025                1030                1035                1040

Leu Leu Lys Asn Ser Arg Leu Leu Ser Trp Ser Phe Asp Gly Thr Val
                1045                1050                1055

Lys Val Trp Asn Ile Ile Thr Gly Asn Lys Glu Lys Asp Phe Val Cys
            1060                1065                1070

His Gln Gly Thr Val Leu Ser Cys Asp Ile Ser His Asp Ala Thr Lys
        1075                1080                1085

Phe Ser Ser Thr Ser Ala Asp Lys Thr Ala Lys Ile Trp Ser Phe Asp
    1090                1095                1100

Leu Leu Leu Pro Leu His Glu Leu Arg Gly His Asn Gly Cys Val Arg
1105                1110                1115                1120

Cys Ser Ala Phe Ser Val Asp Ser Thr Leu Leu Ala Thr Gly Asp Asp
                1125                1130                1135

Asn Gly Glu Ile Arg Ile Trp Asn Val Ser Asn Gly Glu Leu Leu His
            1140                1145                1150

Leu Cys Ala Pro Leu Ser Glu Glu Gly Ala Ala Thr His Gly Gly Trp
        1155                1160                1165

Val Thr Asp Leu Cys Phe Ser Pro Asp Gly Lys Met Leu Ile Ser Ala
    1170                1175                1180

Gly Gly Tyr Ile Lys Trp Trp Asn Val Val Thr Gly Glu Ser Ser Gln
1185                1190                1195                1200

Thr Phe Tyr Thr Asn Gly Thr Asn Leu Lys Lys Ile His Val Ser Pro
                1205                1210                1215

Asp Phe Lys Thr Tyr Val Thr Val Asp Asn Leu Gly Ile Leu Tyr Ile
            1220                1225                1230

Leu Gln Thr Leu Glu
    1235

<210> SEQ ID NO 50

```
<211> LENGTH: 1194
<212> TYPE: PRT
<213> ORGANISM: Homo sapiens

<400> SEQUENCE: 50

Met Asp Ala Lys Ala Arg Asn Cys Leu Leu Gln His Arg Glu Ala Leu
  1               5                  10                  15

Glu Lys Asp Ile Lys Thr Ser Tyr Ile Met Asp His Met Ile Ser Asp
             20                  25                  30

Gly Phe Leu Thr Ile Ser Glu Glu Lys Val Arg Asn Glu Pro Thr
         35                  40                  45

Gln Gln Gln Arg Ala Ala Met Leu Ile Lys Met Ile Leu Lys Lys Asp
     50                  55                  60

Asn Asp Ser Tyr Val Ser Phe Tyr Asn Ala Leu Leu His Gly Tyr
 65                  70                  75                  80

Lys Asp Leu Ala Ala Leu Leu His Asp Gly Ile Pro Val Val Ser Ser
                 85                  90                  95

Ser Ser Val Arg Thr Val Leu Cys Glu Gly Val Pro Gln Arg Pro
                100                 105                 110

Val Val Phe Val Thr Arg Lys Lys Leu Val Asn Ala Ile Gln Gln Lys
            115                 120                 125

Leu Ser Lys Leu Lys Gly Glu Pro Gly Trp Val Thr Ile His Gly Met
    130                 135                 140

Ala Gly Cys Gly Lys Ser Val Leu Ala Ala Glu Ala Val Arg Asp His
145                 150                 155                 160

Ser Leu Leu Glu Gly Cys Phe Pro Gly Gly Val His Trp Val Ser Val
                165                 170                 175

Gly Lys Gln Asp Lys Ser Gly Leu Leu Met Lys Leu Gln Asn Leu Cys
            180                 185                 190

Thr Arg Leu Asp Gln Asp Glu Ser Phe Ser Gln Arg Leu Pro Leu Asn
        195                 200                 205

Ile Glu Glu Ala Lys Asp Arg Leu Arg Ile Leu Met Leu Arg Lys His
    210                 215                 220

Pro Arg Ser Leu Leu Ile Leu Asp Asp Val Trp Asp Ser Trp Val Leu
225                 230                 235                 240

Lys Ala Phe Asp Ser Gln Cys Gln Ile Leu Leu Thr Thr Arg Asp Lys
                245                 250                 255

Ser Val Thr Asp Ser Val Met Gly Pro Lys Tyr Val Pro Val Glu
                260                 265                 270

Ser Ser Leu Gly Lys Glu Lys Gly Leu Glu Ile Leu Ser Leu Phe Val
            275                 280                 285

Asn Met Lys Lys Ala Asp Leu Pro Glu Gln Ala His Ser Ile Ile Lys
        290                 295                 300

Glu Cys Lys Gly Ser Pro Leu Val Val Ser Leu Ile Gly Ala Leu Leu
305                 310                 315                 320

Arg Asp Phe Pro Asn Arg Trp Glu Tyr Tyr Leu Lys Gln Leu Gln Asn
                325                 330                 335

Lys Gln Phe Lys Arg Ile Arg Lys Ser Ser Ser Tyr Asp Tyr Glu Ala
            340                 345                 350

Leu Asp Glu Ala Met Ser Ile Ser Val Glu Met Leu Arg Glu Asp Ile
        355                 360                 365

Lys Asp Tyr Tyr Thr Asp Leu Ser Ile Leu Gln Lys Asp Val Lys Val
    370                 375                 380

Pro Thr Lys Val Leu Cys Ile Leu Trp Asp Met Glu Thr Glu Glu Val
385                 390                 395                 400
```

```
Glu Asp Ile Leu Gln Glu Phe Val Asn Lys Ser Leu Leu Phe Cys Asp
                405                 410                 415
Arg Asn Gly Lys Ser Phe Arg Tyr Tyr Leu His Asp Leu Gln Val Asp
            420                 425                 430
Phe Leu Thr Glu Lys Asn Cys Ser Gln Leu Gln Asp Leu His Lys Lys
        435                 440                 445
Ile Ile Thr Gln Phe Gln Arg Tyr His Gln Pro His Thr Leu Ser Pro
    450                 455                 460
Asp Gln Glu Asp Cys Met Tyr Trp Tyr Asn Phe Leu Ala Tyr His Met
465                 470                 475                 480
Ala Ser Ala Lys Met His Lys Glu Leu Cys Ala Leu Met Phe Ser Leu
                485                 490                 495
Asp Trp Ile Lys Ala Lys Thr Glu Leu Val Gly Pro Ala His Leu Ile
            500                 505                 510
His Glu Phe Val Glu Tyr Arg His Ile Leu Asp Glu Lys Asp Cys Ala
        515                 520                 525
Val Ser Glu Asn Phe Gln Glu Phe Leu Ser Leu Asn Gly His Leu Leu
    530                 535                 540
Gly Arg Gln Pro Phe Pro Asn Ile Val Gln Leu Gly Leu Cys Glu Pro
545                 550                 555                 560
Glu Thr Ser Glu Val Tyr Gln Gln Ala Lys Leu Gln Ala Lys Gln Glu
                565                 570                 575
Val Asp Asn Gly Met Leu Tyr Leu Glu Trp Ile Asn Lys Lys Asn Ile
            580                 585                 590
Thr Asn Leu Ser Arg Leu Val Val Arg Pro His Thr Asp Ala Val Tyr
        595                 600                 605
His Ala Cys Phe Ser Glu Asp Gly Gln Arg Ile Ala Ser Cys Gly Ala
    610                 615                 620
Asp Lys Thr Leu Gln Val Phe Lys Ala Glu Thr Gly Glu Lys Leu Leu
625                 630                 635                 640
Glu Ile Lys Ala His Glu Asp Glu Val Leu Cys Cys Ala Phe Ser Thr
                645                 650                 655
Asp Asp Arg Phe Ile Ala Thr Cys Ser Val Asp Lys Lys Val Lys Ile
            660                 665                 670
Trp Asn Ser Met Thr Gly Glu Leu Val His Thr Tyr Asp Glu His Ser
        675                 680                 685
Glu Gln Val Asn Cys Cys His Phe Thr Asn Ser Ser His His Leu Leu
    690                 695                 700
Leu Ala Thr Gly Ser Ser Asp Cys Phe Leu Lys Leu Trp Asp Leu Asn
705                 710                 715                 720
Gln Lys Glu Cys Arg Asn Thr Met Phe Gly His Thr Asn Ser Val Asn
                725                 730                 735
His Cys Arg Phe Ser Pro Asp Asp Lys Leu Leu Ala Ser Cys Ser Ala
            740                 745                 750
Asp Gly Thr Leu Lys Leu Trp Asp Ala Thr Ser Ala Asn Glu Arg Lys
        755                 760                 765
Ser Ile Asn Val Lys Gln Phe Phe Leu Asn Leu Glu Asp Pro Gln Glu
    770                 775                 780
Asp Met Glu Val Ile Val Lys Cys Cys Ser Trp Ser Ala Asp Gly Ala
785                 790                 795                 800
Arg Ile Met Val Ala Ala Lys Asn Lys Ile Phe Leu Trp Asn Thr Asp
                805                 810                 815
Ser Arg Ser Lys Val Ala Asp Cys Arg Gly His Leu Ser Trp Val His
```

```
                       820                 825                 830
Gly Val Met Phe Ser Pro Asp Gly Ser Ser Phe Leu Thr Ser Ser Asp
            835                 840                 845
Asp Gln Thr Ile Arg Leu Trp Glu Thr Lys Lys Val Cys Lys Asn Ser
    850                 855                 860
Ala Val Met Leu Lys Gln Glu Val Asp Val Val Phe Gln Glu Asn Glu
865                 870                 875                 880
Val Met Val Leu Ala Val Asp His Ile Arg Arg Leu Gln Leu Ile Asn
                885                 890                 895
Gly Arg Thr Gly Gln Ile Asp Tyr Leu Thr Glu Ala Gln Val Ser Cys
            900                 905                 910
Cys Cys Leu Ser Pro His Leu Gln Tyr Ile Ala Phe Gly Asp Glu Asn
        915                 920                 925
Gly Ala Ile Glu Ile Leu Glu Leu Val Asn Asn Arg Ile Phe Gln Ser
        930                 935                 940
Arg Phe Gln His Lys Lys Thr Val Trp His Ile Gln Phe Thr Ala Asp
945                 950                 955                 960
Glu Lys Thr Leu Ile Ser Ser Ser Asp Asp Ala Glu Ile Gln Val Trp
                965                 970                 975
Asn Trp Gln Leu Asp Lys Cys Ile Phe Leu Arg Gly His Gln Glu Thr
            980                 985                 990
Val Lys Asp Phe Arg Leu Leu Lys Asn Ser Arg Leu Leu Ser Trp Ser
        995                 1000                1005
Phe Asp Gly Thr Val Lys Val Trp Asn Ile Ile Thr Gly Asn Lys Glu
    1010                1015                1020
Lys Asp Phe Val Cys His Gln Gly Thr Val Leu Ser Cys Asp Ile Ser
1025                1030                1035                1040
His Asp Ala Thr Lys Phe Ser Ser Thr Ser Ala Asp Lys Thr Ala Lys
                1045                1050                1055
Ile Trp Ser Phe Asp Leu Leu Leu Pro Leu His Glu Leu Arg Gly His
            1060                1065                1070
Asn Gly Cys Val Arg Cys Ser Ala Phe Ser Val Asp Ser Thr Leu Leu
        1075                1080                1085
Ala Thr Gly Asp Asp Asn Gly Glu Ile Arg Ile Trp Asn Val Ser Asn
        1090                1095                1100
Gly Glu Leu Leu His Leu Cys Ala Pro Leu Ser Glu Glu Gly Ala Ala
1105                1110                1115                1120
Thr His Gly Gly Trp Val Thr Asp Leu Cys Phe Ser Pro Asp Gly Lys
                1125                1130                1135
Met Leu Ile Ser Ala Gly Gly Tyr Ile Lys Trp Trp Asn Val Val Thr
            1140                1145                1150
Gly Glu Ser Ser Gln Thr Phe Tyr Thr Asn Gly Thr Asn Leu Lys Lys
        1155                1160                1165
Ile His Val Ser Pro Asp Phe Lys Thr Tyr Val Thr Val Asp Asn Leu
        1170                1175                1180
Gly Ile Leu Tyr Ile Leu Gln Thr Leu Glu
1185                1190

<210> SEQ ID NO 51
<211> LENGTH: 1248
<212> TYPE: PRT
<213> ORGANISM: Homo sapiens

<400> SEQUENCE: 51

Met Asp Ala Lys Ala Arg Asn Cys Leu Leu Gln His Arg Glu Ala Leu
```

-continued

```
  1               5               10              15
Glu Lys Asp Ile Lys Thr Ser Tyr Ile Met Asp His Met Ile Ser Asp
            20                  25                  30

Gly Phe Leu Thr Ile Ser Glu Glu Lys Val Arg Asn Glu Pro Thr
            35                  40                  45

Gln Gln Gln Arg Ala Ala Met Leu Ile Lys Met Ile Leu Lys Lys Asp
            50                  55                  60

Asn Asp Ser Tyr Val Ser Phe Tyr Asn Ala Leu Leu His Glu Gly Tyr
 65                  70                  75                  80

Lys Asp Leu Ala Ala Leu Leu His Asp Gly Ile Pro Val Val Ser Ser
                85                  90                  95

Ser Ser Gly Lys Asp Ser Val Ser Gly Ile Thr Ser Tyr Val Arg Thr
            100                 105                 110

Val Leu Cys Glu Gly Gly Val Pro Gln Arg Pro Val Val Phe Val Thr
            115                 120                 125

Arg Lys Lys Leu Val Asn Ala Ile Gln Gln Lys Leu Ser Lys Leu Lys
            130                 135                 140

Gly Glu Pro Gly Trp Val Thr Ile His Gly Met Ala Gly Cys Gly Lys
145                 150                 155                 160

Ser Val Leu Ala Ala Glu Ala Val Arg Asp His Ser Leu Leu Glu Gly
            165                 170                 175

Cys Phe Pro Gly Gly Val His Trp Val Ser Val Gly Lys Gln Asp Lys
            180                 185                 190

Ser Gly Leu Leu Met Lys Leu Gln Asn Leu Cys Thr Arg Leu Asp Gln
            195                 200                 205

Asp Glu Ser Phe Ser Gln Arg Leu Pro Leu Asn Ile Glu Glu Ala Lys
            210                 215                 220

Asp Arg Leu Arg Ile Leu Met Leu Arg Lys His Pro Arg Ser Leu Leu
225                 230                 235                 240

Ile Leu Asp Asp Val Trp Asp Ser Trp Val Leu Lys Ala Phe Asp Ser
            245                 250                 255

Gln Cys Gln Ile Leu Leu Thr Thr Arg Asp Lys Ser Val Thr Asp Ser
            260                 265                 270

Val Met Gly Pro Lys Tyr Val Pro Val Glu Ser Ser Leu Gly Lys
            275                 280                 285

Glu Lys Gly Leu Glu Ile Leu Ser Leu Phe Val Asn Met Lys Lys Ala
            290                 295                 300

Asp Leu Pro Glu Gln Ala His Ser Ile Ile Lys Glu Cys Lys Gly Ser
305                 310                 315                 320

Pro Leu Val Val Ser Leu Ile Gly Ala Leu Leu Arg Asp Phe Pro Asn
            325                 330                 335

Arg Trp Glu Tyr Tyr Leu Lys Gln Leu Gln Asn Lys Gln Phe Lys Arg
            340                 345                 350

Ile Arg Lys Ser Ser Ser Tyr Asp Tyr Glu Ala Leu Asp Glu Ala Met
            355                 360                 365

Ser Ile Ser Val Glu Met Leu Arg Glu Asp Ile Lys Asp Tyr Tyr Thr
370                 375                 380

Asp Leu Ser Ile Leu Gln Lys Asp Val Lys Val Pro Thr Lys Val Leu
385                 390                 395                 400

Cys Ile Leu Trp Asp Met Glu Thr Glu Glu Val Glu Asp Ile Leu Gln
            405                 410                 415

Glu Phe Val Asn Lys Ser Leu Leu Phe Cys Asp Arg Asn Gly Lys Ser
            420                 425                 430
```

-continued

```
Phe Arg Tyr Tyr Leu His Asp Leu Gln Val Asp Phe Leu Thr Glu Lys
        435                 440                 445
Asn Cys Ser Gln Leu Gln Asp Leu His Lys Lys Ile Ile Thr Gln Phe
450                 455                 460
Gln Arg Tyr His Gln Pro His Thr Leu Ser Pro Asp Gln Glu Asp Cys
465                 470                 475                 480
Met Tyr Trp Tyr Asn Phe Leu Ala Tyr His Met Ala Ser Ala Lys Met
                485                 490                 495
His Lys Glu Leu Cys Ala Leu Met Phe Ser Leu Asp Trp Ile Lys Ala
            500                 505                 510
Lys Thr Glu Leu Val Gly Pro Ala His Leu Ile His Glu Phe Val Glu
            515                 520                 525
Tyr Arg His Ile Leu Asp Glu Lys Asp Cys Ala Val Ser Glu Asn Phe
        530                 535                 540
Gln Glu Phe Leu Ser Leu Asn Gly His Leu Leu Gly Arg Gln Pro Phe
545                 550                 555                 560
Pro Asn Ile Val Gln Leu Gly Leu Cys Glu Pro Glu Thr Ser Glu Val
                565                 570                 575
Tyr Gln Gln Ala Lys Leu Gln Ala Lys Gln Glu Val Asp Asn Gly Met
            580                 585                 590
Leu Tyr Leu Glu Trp Ile Asn Lys Lys Asn Ile Thr Asn Leu Ser Arg
        595                 600                 605
Leu Val Val Arg Pro His Thr Asp Ala Val Tyr His Ala Cys Phe Ser
610                 615                 620
Glu Asp Gly Gln Arg Ile Ala Ser Cys Gly Ala Asp Lys Thr Leu Gln
625                 630                 635                 640
Val Phe Lys Ala Glu Thr Gly Glu Lys Leu Leu Glu Ile Lys Ala His
                645                 650                 655
Glu Asp Glu Val Leu Cys Cys Ala Phe Ser Thr Asp Asp Arg Phe Ile
            660                 665                 670
Ala Thr Cys Ser Val Asp Lys Lys Val Lys Ile Trp Asn Ser Met Thr
        675                 680                 685
Gly Glu Leu Val His Thr Tyr Asp Glu His Ser Glu Gln Val Asn Cys
        690                 695                 700
Cys His Phe Thr Asn Ser Ser His His Leu Leu Leu Ala Thr Gly Ser
705                 710                 715                 720
Ser Asp Cys Phe Leu Lys Leu Trp Asp Leu Asn Gln Lys Glu Cys Arg
                725                 730                 735
Asn Thr Met Phe Gly His Thr Asn Ser Val Asn His Cys Arg Phe Ser
            740                 745                 750
Pro Asp Asp Lys Leu Leu Ala Ser Cys Ser Ala Asp Gly Thr Leu Lys
        755                 760                 765
Leu Trp Asp Ala Thr Ser Ala Asn Glu Arg Lys Ser Ile Asn Val Lys
        770                 775                 780
Gln Phe Phe Leu Asn Leu Glu Asp Pro Gln Glu Asp Met Glu Val Ile
785                 790                 795                 800
Val Lys Cys Cys Ser Trp Ser Ala Asp Gly Ala Arg Ile Met Val Ala
                805                 810                 815
Ala Lys Asn Lys Ile Phe Leu Phe Asp Ile His Thr Ser Gly Leu Leu
            820                 825                 830
Gly Glu Ile His Thr Gly His His Ser Thr Ile Gln Tyr Cys Asp Phe
        835                 840                 845
Ser Pro Gln Asn His Leu Ala Val Val Ala Leu Ser Gln Tyr Cys Val
850                 855                 860
```

Glu Leu Trp Asn Thr Asp Ser Arg Ser Lys Val Ala Asp Cys Arg Gly
865                 870                 875                 880

His Leu Ser Trp Val His Gly Val Met Phe Ser Pro Asp Gly Ser Ser
            885                 890                 895

Phe Leu Thr Ser Ser Asp Gln Thr Ile Arg Leu Trp Glu Thr Lys
        900                 905                 910

Lys Val Cys Lys Asn Ser Ala Val Met Leu Lys Gln Glu Val Asp Val
            915                 920                 925

Val Phe Gln Glu Asn Glu Val Met Val Leu Ala Val Asp His Ile Arg
930                 935                 940

Arg Leu Gln Leu Ile Asn Gly Arg Thr Gly Gln Ile Asp Tyr Leu Thr
945                 950                 955                 960

Glu Ala Gln Val Ser Cys Cys Cys Leu Ser Pro His Leu Gln Tyr Ile
                965                 970                 975

Ala Phe Gly Asp Glu Asn Gly Ala Ile Glu Ile Leu Glu Leu Val Asn
            980                 985                 990

Asn Arg Ile Phe Gln Ser Arg Phe Gln His Lys Lys Thr Val Trp His
        995                 1000                1005

Ile Gln Phe Thr Ala Asp Glu Lys Thr Leu Ile Ser Ser Ser Asp Asp
    1010                1015                1020

Ala Glu Ile Gln Val Trp Asn Trp Gln Leu Asp Lys Cys Ile Phe Leu
1025                1030                1035                1040

Arg Gly His Gln Glu Thr Val Lys Asp Phe Arg Leu Leu Lys Asn Ser
                1045                1050                1055

Arg Leu Leu Ser Trp Ser Phe Asp Gly Thr Val Lys Val Trp Asn Ile
            1060                1065                1070

Ile Thr Gly Asn Lys Glu Lys Asp Phe Val Cys His Gln Gly Thr Val
        1075                1080                1085

Leu Ser Cys Asp Ile Ser His Asp Ala Thr Lys Phe Ser Ser Thr Ser
    1090                1095                1100

Ala Asp Lys Thr Ala Lys Ile Trp Ser Phe Asp Leu Leu Leu Pro Leu
1105                1110                1115                1120

His Glu Leu Arg Gly His Asn Gly Cys Val Arg Cys Ser Ala Phe Ser
                1125                1130                1135

Val Asp Ser Thr Leu Leu Ala Thr Gly Asp Asp Asn Gly Glu Ile Arg
            1140                1145                1150

Ile Trp Asn Val Ser Asn Gly Glu Leu Leu His Leu Cys Ala Pro Leu
        1155                1160                1165

Ser Glu Glu Gly Ala Ala Thr His Gly Gly Trp Val Thr Asp Leu Cys
    1170                1175                1180

Phe Ser Pro Asp Gly Lys Met Leu Ile Ser Ala Gly Gly Tyr Ile Lys
1185                1190                1195                1200

Trp Trp Asn Val Val Thr Gly Glu Ser Ser Gln Thr Phe Tyr Thr Asn
                1205                1210                1215

Gly Thr Asn Leu Lys Lys Ile His Val Ser Pro Asp Phe Lys Thr Tyr
            1220                1225                1230

Val Thr Val Asp Asn Leu Gly Ile Leu Tyr Ile Leu Gln Thr Leu Glu
        1235                1240                1245

<210> SEQ ID NO 52
<211> LENGTH: 1205
<212> TYPE: PRT
<213> ORGANISM: Homo sapiens

<400> SEQUENCE: 52

```
Met Asp Ala Lys Ala Arg Asn Cys Leu Leu Gln His Arg Glu Ala Leu
 1               5                  10                  15
Glu Lys Asp Ile Lys Thr Ser Tyr Ile Met Asp His Met Ile Ser Asp
             20                  25                  30
Gly Phe Leu Thr Ile Ser Glu Glu Lys Val Arg Asn Glu Pro Thr
         35                  40                  45
Gln Gln Gln Arg Ala Ala Met Leu Ile Lys Met Ile Leu Lys Lys Asp
 50                  55                  60
Asn Asp Ser Tyr Val Ser Phe Tyr Asn Ala Leu Leu His Glu Gly Tyr
 65                  70                  75                  80
Lys Asp Leu Ala Ala Leu Leu His Asp Gly Ile Pro Val Val Ser Ser
                 85                  90                  95
Ser Ser Gly Lys Asp Ser Val Ser Gly Ile Thr Ser Tyr Val Arg Thr
             100                 105                 110
Val Leu Cys Glu Gly Gly Val Pro Gln Arg Pro Val Val Phe Val Thr
         115                 120                 125
Arg Lys Lys Leu Val Asn Ala Ile Gln Gln Lys Leu Ser Lys Leu Lys
 130                 135                 140
Gly Glu Pro Gly Trp Val Thr Ile His Gly Met Ala Gly Cys Gly Lys
 145                 150                 155                 160
Ser Val Leu Ala Ala Glu Ala Val Arg Asp His Ser Leu Leu Glu Gly
                 165                 170                 175
Cys Phe Pro Gly Gly Val His Trp Val Ser Val Gly Lys Gln Asp Lys
             180                 185                 190
Ser Gly Leu Leu Met Lys Leu Gln Asn Leu Cys Thr Arg Leu Asp Gln
         195                 200                 205
Asp Glu Ser Phe Ser Gln Arg Leu Pro Leu Asn Ile Glu Glu Ala Lys
 210                 215                 220
Asp Arg Leu Arg Ile Leu Met Leu Arg Lys His Pro Arg Ser Leu Leu
 225                 230                 235                 240
Ile Leu Asp Asp Val Trp Asp Ser Trp Val Leu Lys Ala Phe Asp Ser
                 245                 250                 255
Gln Cys Gln Ile Leu Leu Thr Thr Arg Asp Lys Ser Val Thr Asp Ser
             260                 265                 270
Val Met Gly Pro Lys Tyr Val Val Pro Val Glu Ser Ser Leu Gly Lys
         275                 280                 285
Glu Lys Gly Leu Glu Ile Leu Ser Leu Phe Val Asn Met Lys Lys Ala
 290                 295                 300
Asp Leu Pro Glu Gln Ala His Ser Ile Ile Lys Glu Cys Lys Gly Ser
 305                 310                 315                 320
Pro Leu Val Val Ser Leu Ile Gly Ala Leu Leu Arg Asp Phe Pro Asn
                 325                 330                 335
Arg Trp Glu Tyr Tyr Leu Lys Gln Leu Gln Asn Lys Gln Phe Lys Arg
             340                 345                 350
Ile Arg Lys Ser Ser Ser Tyr Asp Tyr Glu Ala Leu Asp Glu Ala Met
             355                 360                 365
Ser Ile Ser Val Glu Met Leu Arg Glu Asp Ile Lys Asp Tyr Tyr Thr
 370                 375                 380
Asp Leu Ser Ile Leu Gln Lys Asp Val Lys Val Pro Thr Lys Val Leu
 385                 390                 395                 400
Cys Ile Leu Trp Asp Met Glu Thr Glu Glu Val Glu Asp Ile Leu Gln
                 405                 410                 415
Glu Phe Val Asn Lys Ser Leu Leu Phe Cys Asp Arg Asn Gly Lys Ser
```

-continued

```
                420             425             430
Phe Arg Tyr Tyr Leu His Asp Leu Gln Val Asp Phe Leu Thr Glu Lys
            435                 440                 445
Asn Cys Ser Gln Leu Gln Asp Leu His Lys Lys Ile Ile Thr Gln Phe
        450                 455                 460
Gln Arg Tyr His Gln Pro His Thr Leu Ser Pro Asp Gln Glu Asp Cys
465                 470                 475                 480
Met Tyr Trp Tyr Asn Phe Leu Ala Tyr His Met Ala Ser Ala Lys Met
                485                 490                 495
His Lys Glu Leu Cys Ala Leu Met Phe Ser Leu Asp Trp Ile Lys Ala
            500                 505                 510
Lys Thr Glu Leu Val Gly Pro Ala His Leu Ile His Glu Phe Val Glu
        515                 520                 525
Tyr Arg His Ile Leu Asp Glu Lys Asp Cys Ala Val Ser Glu Asn Phe
            530                 535                 540
Gln Glu Phe Leu Ser Leu Asn Gly His Leu Leu Gly Arg Gln Pro Phe
545                 550                 555                 560
Pro Asn Ile Val Gln Leu Gly Leu Cys Glu Pro Glu Thr Ser Glu Val
                565                 570                 575
Tyr Gln Gln Ala Lys Leu Gln Ala Lys Gln Glu Val Asp Asn Gly Met
            580                 585                 590
Leu Tyr Leu Glu Trp Ile Asn Lys Lys Asn Ile Thr Asn Leu Ser Arg
        595                 600                 605
Leu Val Val Arg Pro His Thr Asp Ala Val Tyr His Ala Cys Phe Ser
    610                 615                 620
Glu Asp Gly Gln Arg Ile Ala Ser Cys Gly Ala Asp Lys Thr Leu Gln
625                 630                 635                 640
Val Phe Lys Ala Glu Thr Gly Glu Lys Leu Leu Glu Ile Lys Ala His
                645                 650                 655
Glu Asp Glu Val Leu Cys Cys Ala Phe Ser Thr Asp Arg Phe Ile
            660                 665                 670
Ala Thr Cys Ser Val Asp Lys Lys Val Lys Ile Trp Asn Ser Met Thr
        675                 680                 685
Gly Glu Leu Val His Thr Tyr Asp Glu His Ser Glu Gln Val Asn Cys
    690                 695                 700
Cys His Phe Thr Asn Ser Ser His His Leu Leu Ala Thr Gly Ser
705                 710                 715                 720
Ser Asp Cys Phe Leu Lys Leu Trp Asp Leu Asn Gln Lys Glu Cys Arg
                725                 730                 735
Asn Thr Met Phe Gly His Thr Asn Ser Val Asn His Cys Arg Phe Ser
            740                 745                 750
Pro Asp Asp Lys Leu Leu Ala Ser Cys Ser Ala Asp Gly Thr Leu Lys
        755                 760                 765
Leu Trp Asp Ala Thr Ser Ala Asn Glu Arg Lys Ser Ile Asn Val Lys
    770                 775                 780
Gln Phe Phe Leu Asn Leu Glu Asp Pro Gln Glu Asp Met Glu Val Ile
785                 790                 795                 800
Val Lys Cys Cys Ser Trp Ser Ala Asp Gly Ala Arg Ile Met Val Ala
                805                 810                 815
Ala Lys Asn Lys Ile Phe Leu Trp Asn Thr Asp Ser Arg Ser Lys Val
            820                 825                 830
Ala Asp Cys Arg Gly His Leu Ser Trp Val His Gly Val Met Phe Ser
        835                 840                 845
```

```
Pro Asp Gly Ser Ser Phe Leu Thr Ser Ser Asp Asp Gln Thr Ile Arg
850                 855                 860

Leu Trp Glu Thr Lys Lys Val Cys Lys Asn Ser Ala Val Met Leu Lys
865                 870                 875                 880

Gln Glu Val Asp Val Val Phe Gln Glu Asn Glu Val Met Val Leu Ala
                885                 890                 895

Val Asp His Ile Arg Arg Leu Gln Leu Ile Asn Gly Arg Thr Gly Gln
            900                 905                 910

Ile Asp Tyr Leu Thr Glu Ala Gln Val Ser Cys Cys Leu Ser Pro
        915                 920                 925

His Leu Gln Tyr Ile Ala Phe Gly Asp Glu Asn Gly Ala Ile Glu Ile
    930                 935                 940

Leu Glu Leu Val Asn Asn Arg Ile Phe Gln Ser Arg Phe Gln His Lys
945                 950                 955                 960

Lys Thr Val Trp His Ile Gln Phe Thr Ala Asp Glu Lys Thr Leu Ile
                965                 970                 975

Ser Ser Ser Asp Asp Ala Glu Ile Gln Val Trp Asn Trp Gln Leu Asp
            980                 985                 990

Lys Cys Ile Phe Leu Arg Gly His Gln Glu Thr Val Lys Asp Phe Arg
        995                 1000                1005

Leu Leu Lys Asn Ser Arg Leu Leu Ser Trp Ser Phe Asp Gly Thr Val
    1010                1015                1020

Lys Val Trp Asn Ile Ile Thr Gly Asn Lys Glu Lys Asp Phe Val Cys
1025                1030                1035                1040

His Gln Gly Thr Val Leu Ser Cys Asp Ile Ser His Asp Ala Thr Lys
                1045                1050                1055

Phe Ser Ser Thr Ser Ala Asp Lys Thr Ala Lys Ile Trp Ser Phe Asp
            1060                1065                1070

Leu Leu Leu Pro Leu His Glu Leu Arg Gly His Asn Gly Cys Val Arg
        1075                1080                1085

Cys Ser Ala Phe Ser Val Asp Ser Thr Leu Leu Ala Thr Gly Asp Asp
    1090                1095                1100

Asn Gly Glu Ile Arg Ile Trp Asn Val Ser Asn Gly Glu Leu Leu His
1105                1110                1115                1120

Leu Cys Ala Pro Leu Ser Glu Glu Gly Ala Ala Thr His Gly Gly Trp
                1125                1130                1135

Val Thr Asp Leu Cys Phe Ser Pro Asp Gly Lys Met Leu Ile Ser Ala
            1140                1145                1150

Gly Gly Tyr Ile Lys Trp Trp Asn Val Val Thr Gly Glu Ser Ser Gln
        1155                1160                1165

Thr Phe Tyr Thr Asn Gly Thr Asn Leu Lys Lys Ile His Val Ser Pro
    1170                1175                1180

Asp Phe Lys Thr Tyr Val Thr Val Asp Asn Leu Gly Ile Leu Tyr Ile
1185                1190                1195                1200

Leu Gln Thr Leu Glu
                1205

<210> SEQ ID NO 53
<211> LENGTH: 338
<212> TYPE: PRT
<213> ORGANISM: Homo sapiens

<400> SEQUENCE: 53

Met Asp Ala Lys Ala Arg Asn Cys Leu Leu Gln His Arg Glu Ala Leu
1               5                   10                  15
```

```
Glu Lys Asp Ile Lys Thr Ser Tyr Ile Met Asp His Met Ile Ser Asp
             20                  25                  30

Gly Phe Leu Thr Ile Ser Glu Glu Lys Val Arg Asn Glu Pro Thr
         35                  40                  45

Gln Gln Gln Arg Ala Ala Met Leu Ile Lys Met Ile Leu Lys Lys Asp
     50                  55                  60

Asn Asp Ser Tyr Val Ser Phe Tyr Asn Ala Leu Leu His Glu Gly Tyr
 65                  70                  75                  80

Lys Asp Leu Ala Ala Leu Leu His Asp Gly Ile Pro Val Val Ser Ser
                 85                  90                  95

Ser Ser Gly Lys Asp Ser Val Gly Ile Thr Ser Tyr Val Arg Thr
            100                 105                 110

Val Leu Cys Glu Gly Gly Val Pro Gln Arg Pro Val Val Phe Val Thr
        115                 120                 125

Arg Lys Lys Leu Val Asn Ala Ile Gln Gln Lys Leu Ser Lys Leu Lys
        130                 135                 140

Gly Glu Pro Gly Trp Val Thr Ile His Gly Met Ala Gly Cys Gly Lys
145                 150                 155                 160

Ser Val Leu Ala Ala Glu Ala Val Arg Asp His Ser Leu Leu Glu Gly
                165                 170                 175

Cys Phe Pro Gly Gly Val His Trp Val Ser Val Gly Lys Gln Asp Lys
                180                 185                 190

Ser Gly Leu Leu Met Lys Leu Gln Asn Leu Cys Thr Arg Leu Asp Gln
            195                 200                 205

Asp Glu Ser Phe Ser Gln Arg Leu Pro Leu Asn Ile Glu Glu Ala Lys
        210                 215                 220

Asp Arg Leu Arg Ile Leu Met Leu Arg Lys His Pro Arg Ser Leu Leu
225                 230                 235                 240

Ile Leu Asp Asp Val Trp Asp Ser Trp Val Leu Lys Ala Phe Asp Ser
                245                 250                 255

Gln Cys Gln Ile Leu Leu Thr Thr Arg Asp Lys Ser Val Thr Asp Ser
            260                 265                 270

Val Met Gly Pro Lys Tyr Val Val Pro Val Glu Ser Ser Leu Gly Lys
        275                 280                 285

Glu Lys Gly Leu Glu Ile Leu Ser Leu Phe Val Asn Met Lys Lys Ala
    290                 295                 300

Asp Leu Pro Glu Gln Ala His Ser Ile Ile Lys Glu Cys Lys Val Val
305                 310                 315                 320

Glu Arg Cys His Trp Gly Ile Leu Thr Asp Leu Leu His Lys Trp Asn
                325                 330                 335

Gln Ser

<210> SEQ ID NO 54
<211> LENGTH: 281
<212> TYPE: PRT
<213> ORGANISM: Homo sapiens

<400> SEQUENCE: 54

Met Ala Met Met Glu Val Gln Gly Gly Pro Ser Leu Gly Gln Thr Cys
 1               5                  10                  15

Val Leu Ile Val Ile Phe Thr Val Leu Leu Gln Ser Leu Cys Val Ala
                 20                  25                  30

Val Thr Tyr Val Tyr Phe Thr Asn Glu Leu Lys Gln Met Gln Asp Lys
             35                  40                  45

Tyr Ser Lys Ser Gly Ile Ala Cys Phe Leu Lys Glu Asp Asp Ser Tyr
```

```
                50                   55                   60
Trp Asp Pro Asn Asp Glu Glu Ser Met Asn Ser Pro Cys Trp Gln Val
 65                   70                   75                   80

Lys Trp Gln Leu Arg Gln Leu Val Arg Lys Met Ile Leu Arg Thr Ser
                 85                   90                   95

Glu Glu Thr Ile Ser Thr Val Gln Glu Lys Gln Gln Asn Ile Ser Pro
            100                  105                  110

Leu Val Arg Glu Arg Gly Pro Gln Arg Val Ala Ala His Ile Thr Gly
             115                 120                  125

Thr Arg Gly Arg Ser Asn Thr Leu Ser Ser Pro Asn Ser Lys Asn Glu
130                  135                  140

Lys Ala Leu Gly Arg Lys Ile Asn Ser Trp Glu Ser Ser Arg Ser Gly
145                  150                  155                  160

His Ser Phe Leu Ser Asn Leu His Leu Arg Asn Gly Glu Leu Val Ile
                 165                  170                  175

His Glu Lys Gly Phe Tyr Tyr Ile Tyr Ser Gln Thr Tyr Phe Arg Phe
             180                  185                  190

Gln Glu Glu Ile Lys Glu Asn Thr Lys Asn Asp Lys Gln Met Val Gln
            195                  200                  205

Tyr Ile Tyr Lys Tyr Thr Ser Tyr Pro Asp Pro Ile Leu Leu Met Lys
210                  215                  220

Ser Ala Arg Asn Ser Cys Trp Ser Lys Asp Ala Glu Tyr Gly Leu Tyr
225                  230                  235                  240

Ser Ile Tyr Gln Gly Gly Ile Phe Glu Leu Lys Glu Asn Asp Arg Ile
                 245                  250                  255

Phe Val Ser Val Thr Asn Glu His Leu Ile Asp Met Asp His Glu Ala
             260                  265                  270

Ser Phe Phe Gly Ala Phe Leu Val Gly
             275                  280

<210> SEQ ID NO 55
<211> LENGTH: 277
<212> TYPE: PRT
<213> ORGANISM: Homo sapiens

<400> SEQUENCE: 55

Met Glu Asn Thr Glu Asn Ser Val Asp Ser Lys Ser Ile Lys Asn Leu
 1               5                   10                  15

Glu Pro Lys Ile Ile His Gly Ser Glu Ser Met Asp Ser Gly Ile Ser
                 20                  25                  30

Leu Asp Asn Ser Tyr Lys Met Asp Tyr Pro Glu Met Gly Leu Cys Ile
             35                  40                  45

Ile Ile Asn Asn Lys Asn Phe His Lys Ser Thr Gly Met Thr Ser Arg
 50                  55                  60

Ser Gly Thr Asp Val Asp Ala Ala Asn Leu Arg Glu Thr Phe Arg Asn
 65                  70                  75                  80

Leu Lys Tyr Glu Val Arg Asn Lys Asn Asp Leu Thr Arg Glu Glu Ile
                 85                  90                  95

Val Glu Leu Met Arg Asp Val Ser Lys Glu Asp His Ser Lys Arg Ser
            100                  105                  110

Ser Phe Val Cys Val Leu Leu Ser His Gly Glu Glu Gly Ile Ile Phe
             115                  120                  125

Gly Thr Asn Gly Pro Val Asp Leu Lys Lys Ile Thr Asn Phe Phe Arg
130                  135                  140

Gly Asp Arg Cys Arg Ser Leu Thr Gly Lys Pro Lys Leu Phe Ile Ile
```

```
                145                 150                 155                 160
Gln Ala Cys Arg Gly Thr Glu Leu Asp Cys Gly Ile Glu Thr Asp Ser
                    165                 170                 175

Gly Val Asp Asp Met Ala Cys His Lys Ile Pro Val Glu Ala Asp
                180                 185                 190

Phe Leu Tyr Ala Tyr Ser Thr Ala Pro Gly Tyr Tyr Ser Trp Arg Asn
                195                 200                 205

Ser Lys Asp Gly Ser Trp Phe Ile Gln Ser Leu Cys Ala Met Leu Lys
                210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                    245                 250                 255

His Ala Lys Lys Gln Ile Pro Cys Ile Val Ser Met Leu Thr Lys Glu
                260                 265                 270

Leu Tyr Phe Tyr His
                275

<210> SEQ ID NO 56
<211> LENGTH: 192
<212> TYPE: PRT
<213> ORGANISM: Homo sapiens

<400> SEQUENCE: 56

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
                20                  25                  30

Asp Arg Ala Gly Arg Met Gly Gly Glu Ala Pro Glu Leu Ala Leu Asp
                35                  40                  45

Pro Val Pro Gln Asp Ala Ser Thr Lys Lys Leu Ser Glu Cys Leu Lys
            50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                    85                  90                  95

Ala Asp Met Phe Ser Asp Gly Asn Phe Asn Trp Gly Arg Val Val Ala
                100                 105                 110

Leu Phe Tyr Phe Ala Ser Lys Leu Val Leu Lys Ala Leu Cys Thr Lys
                115                 120                 125

Val Pro Glu Leu Ile Arg Thr Ile Met Gly Trp Thr Leu Asp Phe Leu
            130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
                180                 185                 190

<210> SEQ ID NO 57
<211> LENGTH: 168
<212> TYPE: PRT
<213> ORGANISM: Homo sapiens

<400> SEQUENCE: 57

Met Phe Gln Ile Pro Glu Phe Glu Pro Ser Glu Gln Glu Asp Ser Ser
1               5                   10                  15
```

```
Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser His His Gly Gly Ala
    50                  55                  60

Gly Ala Val Glu Ile Arg Ser Arg His Ser Ser Tyr Pro Ala Gly Thr
65                  70                  75                  80

Glu Asp Asp Glu Gly Met Gly Glu Gly Pro Ser Pro Phe Arg Gly Arg
                85                  90                  95

Ser Arg Ser Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 58
<211> LENGTH: 208
<212> TYPE: PRT
<213> ORGANISM: Homo sapiens

<400> SEQUENCE: 58

Met Asp Pro Phe Leu Val Leu Leu His Ser Val Ser Ser Ser Leu Ser
1               5                   10                  15

Ser Ser Glu Leu Thr Glu Leu Lys Phe Leu Cys Leu Gly Arg Val Gly
            20                  25                  30

Lys Arg Lys Leu Glu Arg Val Gln Ser Gly Leu Asp Leu Phe Ser Met
        35                  40                  45

Leu Leu Glu Gln Asn Asp Leu Glu Pro Gly His Thr Glu Leu Leu Arg
    50                  55                  60

Glu Leu Leu Ala Ser Leu Arg Arg His Asp Leu Leu Arg Arg Val Asp
65                  70                  75                  80

Asp Phe Glu Ala Gly Ala Ala Ala Gly Ala Ala Pro Gly Glu Glu Asp
                85                  90                  95

Leu Cys Ala Ala Phe Asn Val Ile Cys Asp Asn Val Gly Lys Asp Trp
            100                 105                 110

Arg Arg Leu Ala Arg Gln Leu Lys Val Ser Asp Thr Lys Ile Asp Ser
        115                 120                 125

Ile Glu Asp Arg Tyr Pro Arg Asn Leu Thr Glu Arg Val Arg Glu Ser
130                 135                 140

Leu Arg Ile Trp Lys Asn Thr Glu Lys Glu Asn Ala Thr Val Ala His
145                 150                 155                 160

Leu Val Gly Ala Leu Arg Ser Cys Gln Met Asn Leu Val Ala Asp Leu
                165                 170                 175

Val Gln Glu Val Gln Gln Ala Arg Asp Leu Gln Asn Arg Ser Gly Ala
            180                 185                 190

Met Ser Pro Met Ser Trp Asn Ser Asp Ala Ser Thr Ser Glu Ala Ser
        195                 200                 205

<210> SEQ ID NO 59
```

```
<211> LENGTH: 384
<212> TYPE: PRT
<213> ORGANISM: Homo sapiens

<400> SEQUENCE: 59

Met Ser Arg Ser Lys Arg Asp Asn Asn Phe Tyr Ser Val Glu Ile Gly
  1               5                  10                  15

Asp Ser Thr Phe Thr Val Leu Lys Arg Tyr Gln Asn Leu Lys Pro Ile
             20                  25                  30

Gly Ser Gly Ala Gln Gly Ile Val Cys Ala Ala Tyr Asp Ala Ile Leu
         35                  40                  45

Glu Arg Asn Val Ala Ile Lys Lys Leu Ser Arg Pro Phe Gln Asn Gln
 50                  55                  60

Thr His Ala Lys Arg Ala Tyr Arg Glu Leu Val Leu Met Lys Cys Val
 65                  70                  75                  80

Asn His Lys Asn Ile Ile Gly Leu Leu Asn Val Phe Thr Pro Gln Lys
                 85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
        195                 200                 205

Trp Ser Val Gly Cys Ile Met Gly Glu Met Val Cys His Lys Ile Leu
    210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
        275                 280                 285

Leu Lys Ala Ser Gln Ala Arg Asp Leu Leu Ser Lys Met Leu Val Ile
    290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
        355                 360                 365

Asn Gly Val Ile Arg Gly Gln Pro Ser Pro Leu Ala Gln Val Gln Gln
    370                 375                 380

<210> SEQ ID NO 60
```

```
<211> LENGTH: 427
<212> TYPE: PRT
<213> ORGANISM: Homo sapiens

<400> SEQUENCE: 60

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
        195                 200                 205

Trp Ser Val Gly Cys Ile Met Gly Glu Met Val Cys His Lys Ile Leu
210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
        275                 280                 285

Leu Lys Ala Ser Gln Ala Arg Asp Leu Leu Ser Lys Met Leu Val Ile
290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
        355                 360                 365

Asn Gly Val Ile Arg Gly Gln Pro Ser Pro Leu Gly Ala Ala Val Ile
370                 375                 380

Asn Gly Ser Gln His Pro Ser Ser Ser Ser Val Asn Asp Val Ser
385                 390                 395                 400
```

```
Ser Met Ser Thr Asp Pro Thr Leu Ala Ser Asp Thr Asp Ser Ser Leu
            405                 410                 415

Glu Ala Ala Ala Gly Pro Leu Gly Cys Cys Arg
            420                 425

<210> SEQ ID NO 61
<211> LENGTH: 384
<212> TYPE: PRT
<213> ORGANISM: Homo sapiens

<400> SEQUENCE: 61

Met Ser Arg Ser Lys Arg Asp Asn Asn Phe Tyr Ser Val Glu Ile Gly
  1               5                  10                  15

Asp Ser Thr Phe Thr Val Leu Lys Arg Tyr Gln Asn Leu Lys Pro Ile
             20                  25                  30

Gly Ser Gly Ala Gln Gly Ile Val Cys Ala Ala Tyr Asp Ala Ile Leu
         35                  40                  45

Glu Arg Asn Val Ala Ile Lys Lys Leu Ser Arg Pro Phe Gln Asn Gln
     50                  55                  60

Thr His Ala Lys Arg Ala Tyr Arg Glu Leu Val Leu Met Lys Cys Val
 65                  70                  75                  80

Asn His Lys Asn Ile Ile Gly Leu Leu Asn Val Phe Thr Pro Gln Lys
                 85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205

Trp Ser Val Gly Cys Ile Met Gly Glu Met Ile Lys Gly Gly Val Leu
    210                 215                 220

Phe Pro Gly Thr Asp His Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
        275                 280                 285

Leu Lys Ala Ser Gln Ala Arg Asp Leu Leu Ser Lys Met Leu Val Ile
    290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350
```

```
Lys Glu Leu Ile Tyr Lys Glu Val Met Asp Leu Glu Glu Arg Thr Lys
            355                 360                 365

Asn Gly Val Ile Arg Gly Gln Pro Ser Pro Leu Ala Gln Val Gln Gln
        370                 375                 380
```

<210> SEQ ID NO 62
<211> LENGTH: 427
<212> TYPE: PRT
<213> ORGANISM: Homo sapiens

<400> SEQUENCE: 62

```
Met Ser Arg Ser Lys Arg Asp Asn Asn Phe Tyr Ser Val Glu Ile Gly
  1               5                  10                  15

Asp Ser Thr Phe Thr Val Leu Lys Arg Tyr Gln Asn Leu Lys Pro Ile
                 20                  25                  30

Gly Ser Gly Ala Gln Gly Ile Val Cys Ala Ala Tyr Asp Ala Ile Leu
             35                  40                  45

Glu Arg Asn Val Ala Ile Lys Lys Leu Ser Arg Pro Phe Gln Asn Gln
         50                  55                  60

Thr His Ala Lys Arg Ala Tyr Arg Glu Leu Val Leu Met Lys Cys Val
 65                  70                  75                  80

Asn His Lys Asn Ile Ile Gly Leu Leu Asn Val Phe Thr Pro Gln Lys
                 85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205

Trp Ser Val Gly Cys Ile Met Gly Glu Met Ile Lys Gly Gly Val Leu
    210                 215                 220

Phe Pro Gly Thr Asp His Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
        275                 280                 285

Leu Lys Ala Ser Gln Ala Arg Asp Leu Leu Ser Lys Met Leu Val Ile
    290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350
```

```
Lys Glu Leu Ile Tyr Lys Glu Val Met Asp Leu Glu Glu Arg Thr Lys
            355                 360                 365

Asn Gly Val Ile Arg Gly Gln Pro Ser Pro Leu Gly Ala Ala Val Ile
370                 375                 380

Asn Gly Ser Gln His Pro Ser Ser Ser Ser Val Asn Asp Val Ser
385                 390                 395                 400

Ser Met Ser Thr Asp Pro Thr Leu Ala Ser Asp Thr Asp Ser Ser Leu
                    405                 410                 415

Glu Ala Ala Ala Gly Pro Leu Gly Cys Cys Arg
            420                 425

<210> SEQ ID NO 63
<211> LENGTH: 360
<212> TYPE: PRT
<213> ORGANISM: Homo sapiens

<400> SEQUENCE: 63

Met Ser Gln Glu Arg Pro Thr Phe Tyr Arg Gln Glu Leu Asn Lys Thr
  1               5                  10                  15

Ile Trp Glu Val Pro Glu Arg Tyr Gln Asn Leu Ser Pro Val Gly Ser
             20                  25                  30

Gly Ala Tyr Gly Ser Val Cys Ala Ala Phe Asp Thr Lys Thr Gly Leu
         35                  40                  45

Arg Val Ala Val Lys Lys Leu Ser Arg Pro Phe Gln Ser Ile Ile His
     50                  55                  60

Ala Lys Arg Thr Tyr Arg Glu Leu Arg Leu Leu Lys His Met Lys His
 65                  70                  75                  80

Glu Asn Val Ile Gly Leu Leu Asp Val Phe Thr Pro Ala Arg Ser Leu
                 85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asn Gln Leu Gln Gln Ile Met Arg Leu Thr Gly
225                 230                 235                 240

Thr Pro Pro Ala Tyr Leu Ile Asn Arg Met Pro Ser His Glu Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
    290                 295                 300
```

```
His Ala Tyr Phe Ala Gln Tyr His Asp Pro Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser
        355                 360

<210> SEQ ID NO 64
<211> LENGTH: 240
<212> TYPE: PRT
<213> ORGANISM: Homo sapiens

<400> SEQUENCE: 64

Met Glu Asp Tyr Thr Lys Ile Glu Lys Ile Gly Glu Gly Thr Tyr Gly
1               5                   10                  15

Val Val Tyr Lys Gly Arg His Lys Thr Thr Gly Gln Val Val Ala Met
            20                  25                  30

Lys Lys Ile Arg Leu Glu Ser Glu Glu Glu Gly Val Pro Ser Thr Ala
        35                  40                  45

Ile Arg Glu Ile Ser Leu Leu Lys Glu Leu Arg His Pro Asn Ile Val
    50                  55                  60

Ser Leu Gln Asp Val Leu Met Gln Asp Ser Arg Leu Tyr Leu Ile Phe
65                  70                  75                  80

Glu Phe Leu Ser Met Asp Leu Lys Lys Tyr Leu Asp Ser Ile Pro Pro
                85                  90                  95

Gly Gln Tyr Met Asp Ser Ser Leu Val Lys Val Val Thr Leu Trp Tyr
            100                 105                 110

Arg Ser Pro Glu Val Leu Leu Gly Ser Ala Arg Tyr Ser Thr Pro Val
        115                 120                 125

Asp Ile Trp Ser Ile Gly Thr Ile Phe Ala Glu Leu Ala Thr Lys Lys
    130                 135                 140

Pro Leu Phe His Gly Asp Ser Glu Ile Asp Gln Leu Phe Arg Ile Phe
145                 150                 155                 160

Arg Ala Leu Gly Thr Pro Asn Asn Glu Val Trp Pro Glu Val Glu Ser
                165                 170                 175

Leu Gln Asp Tyr Lys Asn Thr Phe Pro Lys Trp Lys Pro Gly Ser Leu
            180                 185                 190

Ala Ser His Val Lys Asn Leu Asp Glu Asn Gly Leu Asp Leu Leu Ser
        195                 200                 205

Lys Met Leu Ile Tyr Asp Pro Ala Lys Arg Ile Ser Gly Lys Met Ala
    210                 215                 220

Leu Asn His Pro Tyr Phe Asn Asp Leu Asp Asn Gln Ile Lys Lys Met
225                 230                 235                 240

<210> SEQ ID NO 65
<211> LENGTH: 432
<212> TYPE: PRT
<213> ORGANISM: Homo sapiens

<400> SEQUENCE: 65

Met Leu Gly Asn Ser Ala Pro Gly Pro Ala Thr Arg Glu Ala Gly Ser
1               5                   10                  15

Ala Leu Leu Ala Leu Gln Gln Thr Ala Leu Gln Glu Asp Gln Glu Asn
            20                  25                  30
```

```
Ile Asn Pro Glu Lys Ala Ala Pro Val Gln Gln Pro Arg Thr Arg Ala
         35                  40                  45

Ala Leu Ala Val Leu Lys Ser Gly Asn Pro Arg Gly Leu Ala Gln Gln
 50                  55                  60

Gln Arg Pro Lys Thr Arg Arg Val Ala Pro Leu Lys Asp Leu Pro Val
 65                  70                  75                  80

Asn Asp Glu His Val Thr Val Pro Pro Trp Lys Ala Asn Ser Lys Gln
                 85                  90                  95

Pro Ala Phe Thr Ile His Val Asp Glu Ala Lys Glu Ala Gln Lys
            100                 105                 110

Lys Pro Ala Glu Ser Gln Lys Ile Glu Arg Glu Asp Ala Leu Ala Phe
            115                 120                 125

Asn Ser Ala Ile Ser Leu Pro Gly Pro Arg Lys Pro Leu Val Pro Leu
130                 135                 140

Asp Tyr Pro Met Asp Gly Ser Phe Glu Ser Pro His Thr Met Asp Met
145                 150                 155                 160

Ser Ile Val Leu Glu Asp Glu Lys Pro Val Ser Val Asn Glu Val Pro
                165                 170                 175

Asp Tyr His Glu Asp Ile His Thr Tyr Leu Arg Glu Met Glu Val Lys
            180                 185                 190

Cys Lys Pro Lys Val Gly Tyr Met Lys Lys Gln Pro Asp Ile Thr Asn
            195                 200                 205

Ser Met Arg Ala Ile Leu Val Asp Trp Leu Val Glu Val Gly Glu Glu
210                 215                 220

Tyr Lys Leu Gln Asn Glu Thr Leu His Leu Ala Val Asn Tyr Ile Asp
225                 230                 235                 240

Arg Phe Leu Ser Ser Met Ser Val Leu Arg Gly Lys Leu Gln Leu Val
                245                 250                 255

Gly Thr Ala Ala Met Leu Leu Ala Ser Lys Phe Glu Glu Ile Tyr Pro
            260                 265                 270

Pro Glu Val Ala Glu Phe Val Tyr Ile Thr Asp Asp Thr Tyr Thr Lys
            275                 280                 285

Lys Gln Val Leu Arg Met Glu His Leu Val Leu Lys Val Leu Thr Phe
290                 295                 300

Asp Leu Ala Ala Pro Thr Val Asn Gln Phe Leu Thr Gln Tyr Phe Leu
305                 310                 315                 320

His Gln Gln Pro Ala Asn Cys Lys Val Glu Ser Leu Ala Met Phe Leu
                325                 330                 335

Gly Glu Leu Ser Leu Ile Asp Ala Asp Pro Tyr Leu Lys Tyr Leu Pro
            340                 345                 350

Ser Val Ile Ala Gly Ala Ala Phe His Leu Ala Leu Tyr Thr Val Thr
            355                 360                 365

Gly Gln Ser Trp Pro Glu Ser Leu Ile Arg Lys Thr Gly Tyr Thr Leu
370                 375                 380

Glu Ser Leu Lys Pro Cys Leu Met Asp Leu His Gln Thr Tyr Leu Lys
385                 390                 395                 400

Ala Pro Gln His Ala Gln Gln Ser Ile Arg Glu Lys Tyr Lys Asn Ser
                405                 410                 415

Lys Tyr His Gly Val Ser Leu Leu Asn Pro Pro Glu Thr Leu Asn Leu
            420                 425                 430

<210> SEQ ID NO 66
<211> LENGTH: 289
<212> TYPE: PRT
<213> ORGANISM: Homo sapiens
```

<400> SEQUENCE: 66

```
Met Glu Leu Leu Cys His Glu Val Asp Pro Val Arg Arg Ala Val Arg
 1               5                  10                  15

Asp Arg Asn Leu Leu Arg Asp Asp Arg Val Leu Gln Asn Leu Leu Thr
            20                  25                  30

Ile Glu Glu Arg Tyr Leu Pro Gln Cys Ser Tyr Phe Lys Cys Val Gln
        35                  40                  45

Lys Asp Ile Gln Pro Tyr Met Arg Arg Met Val Ala Thr Trp Met Leu
 50                  55                  60

Glu Val Cys Glu Glu Gln Lys Cys Glu Glu Val Phe Pro Leu Ala
 65                  70                  75                  80

Met Asn Tyr Leu Asp Arg Phe Leu Ala Gly Val Pro Thr Pro Lys Ser
                85                  90                  95

His Leu Gln Leu Leu Gly Ala Val Cys Met Phe Leu Ala Ser Lys Leu
            100                 105                 110

Lys Glu Thr Ser Pro Leu Thr Ala Glu Lys Leu Cys Ile Tyr Thr Asp
        115                 120                 125

Asn Ser Ile Lys Pro Gln Glu Leu Leu Glu Trp Glu Leu Val Val Leu
130                 135                 140

Gly Lys Leu Lys Trp Asn Leu Ala Ala Val Thr Pro His Asp Phe Ile
145                 150                 155                 160

Glu His Ile Leu Arg Lys Leu Pro Gln Gln Arg Glu Lys Leu Ser Leu
                165                 170                 175

Ile Arg Lys His Ala Gln Thr Phe Ile Ala Leu Cys Ala Thr Asp Phe
            180                 185                 190

Lys Phe Ala Met Tyr Pro Pro Ser Met Ile Ala Thr Gly Ser Val Gly
        195                 200                 205

Ala Ala Ile Cys Gly Leu Gln Gln Asp Glu Glu Val Ser Ser Leu Thr
    210                 215                 220

Cys Asp Ala Leu Thr Glu Leu Leu Ala Lys Ile Thr Asn Thr Asp Val
225                 230                 235                 240

Asp Cys Leu Lys Ala Cys Gln Glu Gln Ile Glu Ala Val Leu Leu Asn
                245                 250                 255

Ser Leu Gln Gln Tyr Arg Gln Asp Gln Arg Asp Gly Ser Lys Ser Glu
            260                 265                 270

Asp Glu Leu Asp Gln Ala Ser Thr Pro Thr Asp Val Arg Asp Ile Asp
        275                 280                 285

Leu
```

<210> SEQ ID NO 67
<211> LENGTH: 292
<212> TYPE: PRT
<213> ORGANISM: Homo sapiens

<400> SEQUENCE: 67

```
Met Glu Leu Leu Cys Cys Glu Gly Thr Arg His Ala Pro Arg Ala Gly
 1               5                  10                  15

Pro Asp Pro Arg Leu Leu Gly Asp Gln Arg Val Leu Gln Ser Leu Leu
            20                  25                  30

Arg Leu Glu Glu Arg Tyr Val Pro Arg Ala Ser Tyr Phe Gln Cys Val
        35                  40                  45

Gln Arg Glu Ile Lys Pro His Met Arg Lys Met Leu Ala Tyr Trp Met
 50                  55                  60

Leu Glu Val Cys Glu Glu Gln Arg Cys Glu Glu Glu Val Phe Pro Leu
```

```
            65                  70                  75                  80
Ala Met Asn Tyr Leu Asp Arg Tyr Leu Ser Cys Val Pro Thr Arg Lys
                    85                  90                  95

Ala Gln Leu Gln Leu Leu Gly Ala Val Cys Met Leu Leu Ala Ser Lys
                100                 105                 110

Leu Arg Glu Thr Thr Pro Leu Thr Ile Glu Lys Leu Cys Ile Tyr Thr
            115                 120                 125

Asp His Ala Val Ser Pro Arg Gln Leu Arg Asp Trp Glu Val Leu Val
        130                 135                 140

Leu Gly Lys Leu Lys Trp Asp Leu Ala Ala Val Ile Ala His Asp Phe
145                 150                 155                 160

Leu Ala Phe Ile Leu His Arg Leu Ser Leu Pro Arg Asp Arg Gln Ala
                165                 170                 175

Leu Val Lys Lys His Ala Gln Thr Phe Leu Ala Leu Cys Ala Thr Asp
                180                 185                 190

Tyr Thr Phe Ala Met Tyr Pro Pro Ser Met Ile Ala Thr Gly Ser Ile
            195                 200                 205

Gly Ala Ala Val Gln Gly Leu Gly Ala Cys Ser Met Ser Gly Asp Glu
        210                 215                 220

Leu Thr Glu Leu Leu Ala Gly Ile Thr Gly Thr Glu Val Asp Cys Leu
225                 230                 235                 240

Arg Ala Cys Gln Glu Gln Ile Glu Ala Ala Leu Arg Glu Ser Leu Arg
                245                 250                 255

Glu Ala Ser Gln Thr Ser Ser Ser Pro Ala Pro Lys Ala Pro Arg Gly
                260                 265                 270

Ser Ser Ser Gln Gly Pro Ser Gln Thr Ser Thr Pro Thr Asp Val Thr
            275                 280                 285

Ala Ile His Leu
            290

<210> SEQ ID NO 68
<211> LENGTH: 410
<212> TYPE: PRT
<213> ORGANISM: Homo sapiens

<400> SEQUENCE: 68

Met Pro Arg Glu Arg Arg Glu Arg Asp Ala Lys Glu Arg Asp Thr Met
1               5                   10                  15

Lys Glu Asp Gly Gly Ala Glu Phe Ser Ala Arg Ser Arg Lys Arg Lys
                20                  25                  30

Ala Asn Val Thr Val Phe Leu Gln Asp Pro Asp Glu Glu Met Ala Lys
            35                  40                  45

Ile Asp Arg Thr Ala Arg Asp Gln Cys Gly Ser Gln Pro Trp Asp Asn
        50                  55                  60

Asn Ala Val Cys Ala Asp Pro Cys Ser Leu Ile Pro Thr Pro Asp Lys
65                  70                  75                  80

Glu Asp Asp Asp Arg Val Tyr Pro Asn Ser Thr Cys Lys Pro Arg Ile
                85                  90                  95

Ile Ala Pro Ser Arg Gly Ser Pro Leu Pro Val Leu Ser Trp Ala Asn
                100                 105                 110

Arg Glu Glu Val Trp Lys Ile Met Leu Asn Lys Glu Lys Thr Tyr Leu
            115                 120                 125

Arg Asp Gln His Phe Leu Glu Gln His Pro Leu Leu Gln Pro Lys Met
        130                 135                 140

Arg Ala Ile Leu Leu Asp Trp Leu Met Glu Val Cys Glu Val Tyr Lys
```

```
                145                 150                 155                 160
Leu His Arg Glu Thr Phe Tyr Leu Ala Gln Asp Phe Asp Arg Tyr
                    165                 170                 175

Met Ala Thr Gln Glu Asn Val Val Lys Thr Leu Leu Gln Leu Ile Gly
                    180                 185                 190

Ile Ser Ser Leu Phe Ile Ala Ala Lys Leu Glu Glu Ile Tyr Pro Pro
                    195                 200                 205

Lys Leu His Gln Phe Ala Tyr Val Thr Asp Gly Ala Cys Ser Gly Asp
                    210                 215                 220

Glu Ile Leu Thr Met Glu Leu Met Ile Met Lys Ala Leu Lys Trp Arg
225                 230                 235                 240

Leu Ser Pro Leu Thr Ile Val Ser Trp Leu Asn Val Tyr Met Gln Val
                    245                 250                 255

Ala Tyr Leu Asn Asp Leu His Glu Val Leu Leu Pro Gln Tyr Pro Gln
                    260                 265                 270

Gln Ile Phe Ile Gln Ile Ala Glu Leu Leu Asp Leu Cys Val Leu Asp
                    275                 280                 285

Val Asp Cys Leu Glu Phe Pro Tyr Gly Ile Leu Ala Ala Ser Ala Leu
                    290                 295                 300

Tyr His Phe Ser Ser Ser Glu Leu Met Gln Lys Val Ser Gly Tyr Gln
305                 310                 315                 320

Trp Cys Asp Ile Glu Asn Cys Val Lys Trp Met Val Pro Phe Ala Met
                    325                 330                 335

Val Ile Arg Glu Thr Gly Ser Ser Lys Leu Lys His Phe Arg Gly Val
                    340                 345                 350

Ala Asp Glu Asp Ala His Asn Ile Gln Thr His Arg Asp Ser Leu Asp
                    355                 360                 365

Leu Leu Asp Lys Ala Arg Ala Lys Lys Ala Met Leu Ser Glu Gln Asn
                    370                 375                 380

Arg Ala Ser Pro Leu Pro Ser Gly Leu Leu Thr Pro Pro Gln Ser Gly
385                 390                 395                 400

Lys Lys Gln Ser Ser Gly Pro Glu Met Ala
                    405                 410

<210> SEQ ID NO 69
<211> LENGTH: 473
<212> TYPE: PRT
<213> ORGANISM: Homo sapiens

<400> SEQUENCE: 69

Met Ser Thr Glu Leu Phe Ser Ser Thr Arg Glu Gly Ser Ser Gly
1               5                   10                  15

Ser Gly Pro Ser Phe Arg Ser Asn Gln Arg Lys Met Leu Asn Leu Leu
                    20                  25                  30

Leu Glu Arg Asp Thr Ser Phe Thr Val Cys Pro Asp Val Pro Arg Thr
                35                  40                  45

Pro Val Gly Lys Phe Leu Gly Asp Ser Ala Asn Leu Ser Ile Leu Ser
            50                  55                  60

Gly Gly Thr Pro Lys Arg Cys Leu Asp Leu Ser Asn Leu Ser Ser Gly
65                  70                  75                  80

Glu Ile Thr Ala Thr Gln Leu Thr Thr Ser Ala Asp Leu Asp Glu Thr
                    85                  90                  95

Gly His Leu Asp Ser Ser Gly Leu Gln Glu Val His Leu Ala Gly Met
                100                 105                 110

Asn His Asp Gln His Leu Met Lys Cys Ser Pro Ala Gln Leu Leu Cys
```

```
                    115                 120                 125
Ser Thr Pro Asn Gly Leu Asp Arg Gly His Arg Lys Arg Asp Ala Met
            130                 135                 140

Cys Ser Ser Ala Asn Lys Glu Asn Asp Asn Gly Asn Leu Val Asp
145                 150                 155                 160

Ser Glu Met Lys Tyr Leu Gly Ser Pro Ile Thr Thr Val Pro Lys Leu
                165                 170                 175

Asp Lys Asn Pro Asn Leu Gly Glu Asp Gln Ala Glu Ile Ser Asp
            180                 185                 190

Glu Leu Met Glu Phe Ser Leu Lys Asp Gln Glu Ala Lys Val Ser Arg
                195                 200                 205

Ser Gly Leu Tyr Arg Ser Pro Ser Met Pro Glu Asn Leu Asn Arg Pro
            210                 215                 220

Arg Leu Lys Gln Val Glu Lys Phe Lys Asp Asn Thr Ile Pro Asp Lys
225                 230                 235                 240

Val Lys Lys Lys Tyr Phe Ser Gly Gln Gly Lys Leu Arg Lys Gly Leu
                245                 250                 255

Cys Leu Lys Lys Thr Val Ser Leu Cys Asp Ile Thr Ile Thr Gln Met
            260                 265                 270

Leu Glu Glu Asp Ser Asn Gln Gly His Leu Ile Gly Asp Phe Ser Lys
                275                 280                 285

Val Cys Ala Leu Pro Thr Val Ser Gly Lys His Gln Asp Leu Lys Tyr
            290                 295                 300

Val Asn Pro Glu Thr Val Ala Ala Leu Leu Ser Gly Lys Phe Gln Gly
305                 310                 315                 320

Leu Ile Glu Lys Phe Tyr Val Ile Asp Cys Arg Tyr Pro Tyr Glu Tyr
                325                 330                 335

Leu Gly Gly His Ile Gln Gly Ala Leu Asn Leu Tyr Ser Gln Glu Glu
            340                 345                 350

Leu Phe Asn Phe Phe Leu Lys Lys Pro Ile Val Pro Leu Asp Thr Gln
                355                 360                 365

Lys Arg Ile Ile Ile Val Phe His Cys Glu Phe Ser Ser Glu Arg Gly
370                 375                 380

Pro Arg Met Cys Arg Cys Leu Arg Glu Glu Asp Arg Ser Leu Asn Gln
385                 390                 395                 400

Tyr Pro Ala Leu Tyr Tyr Pro Glu Leu Tyr Ile Leu Lys Gly Gly Tyr
                405                 410                 415

Arg Asp Phe Phe Pro Glu Tyr Met Glu Leu Cys Glu Pro Gln Ser Tyr
            420                 425                 430

Cys Pro Met His His Gln Asp His Lys Thr Glu Leu Leu Arg Cys Arg
                435                 440                 445

Ser Gln Ser Lys Val Gln Glu Gly Glu Arg Gln Leu Arg Glu Gln Ile
            450                 455                 460

Ala Leu Leu Val Lys Asp Met Ser Pro
465                 470

<210> SEQ ID NO 70
<211> LENGTH: 400
<212> TYPE: PRT
<213> ORGANISM: Homo sapiens

<400> SEQUENCE: 70

Met Ser Thr Glu Leu Phe Ser Ser Thr Arg Glu Glu Gly Ser Ser Gly
  1               5                  10                  15

Ser Gly Pro Ser Phe Arg Ser Asn Gln Arg Lys Met Leu Asn Leu Leu
```

```
                20                  25                  30
Leu Glu Arg Asp Thr Ser Phe Thr Val Cys Pro Asp Val Pro Arg Thr
                35                  40                  45

Pro Val Gly Lys Phe Leu Gly Asp Ser Ala Asn Leu Ser Ile Leu Ser
    50                  55                  60

Gly Ser Pro Gly Phe Phe Arg Thr Ser Gly Ser Ala Phe Ser Trp Asp
65                  70                  75                  80

Asp Asn Gly Asn Leu Val Asp Ser Glu Met Lys Tyr Leu Gly Ser Pro
                85                  90                  95

Ile Thr Thr Val Pro Lys Leu Asp Lys Asn Pro Asn Leu Gly Glu Asp
            100                 105                 110

Gln Ala Glu Glu Ile Ser Asp Glu Leu Met Glu Phe Ser Leu Lys Asp
            115                 120                 125

Gln Glu Ala Lys Val Ser Arg Ser Gly Leu Tyr Arg Ser Pro Ser Met
            130                 135                 140

Pro Glu Asn Leu Asn Arg Pro Arg Leu Lys Gln Val Glu Lys Phe Lys
145                 150                 155                 160

Asp Asn Thr Ile Pro Asp Lys Val Lys Lys Tyr Phe Ser Gly Gln
                165                 170                 175

Gly Lys Leu Arg Lys Gly Leu Cys Leu Lys Lys Thr Val Ser Leu Cys
                180                 185                 190

Asp Ile Thr Ile Thr Gln Met Leu Glu Glu Asp Ser Asn Gln Gly His
                195                 200                 205

Leu Ile Gly Asp Phe Ser Lys Val Cys Ala Leu Pro Thr Val Ser Gly
            210                 215                 220

Lys His Gln Asp Leu Lys Tyr Val Asn Pro Glu Thr Val Ala Ala Leu
225                 230                 235                 240

Leu Ser Gly Lys Phe Gln Gly Leu Ile Glu Lys Phe Tyr Val Ile Asp
                245                 250                 255

Cys Arg Tyr Pro Tyr Glu Tyr Leu Gly Gly His Ile Gln Gly Ala Leu
                260                 265                 270

Asn Leu Tyr Ser Gln Glu Glu Leu Phe Asn Phe Phe Leu Lys Lys Pro
                275                 280                 285

Ile Val Pro Leu Asp Thr Gln Lys Arg Ile Ile Ile Val Phe His Cys
            290                 295                 300

Glu Phe Ser Ser Glu Arg Gly Pro Arg Met Cys Arg Cys Leu Arg Glu
305                 310                 315                 320

Glu Asp Arg Ser Leu Asn Gln Tyr Pro Ala Leu Tyr Tyr Pro Glu Leu
                325                 330                 335

Tyr Ile Leu Lys Gly Gly Tyr Arg Asp Phe Phe Pro Glu Tyr Met Glu
                340                 345                 350

Leu Cys Glu Pro Gln Ser Tyr Cys Pro Met His His Gln Asp His Lys
            355                 360                 365

Thr Glu Leu Leu Arg Cys Arg Ser Gln Ser Lys Val Gln Glu Gly Glu
            370                 375                 380

Arg Gln Leu Arg Glu Gln Ile Ala Leu Leu Val Lys Asp Met Ser Pro
385                 390                 395                 400

<210> SEQ ID NO 71
<211> LENGTH: 164
<212> TYPE: PRT
<213> ORGANISM: Homo sapiens

<400> SEQUENCE: 71

Met Ser Glu Pro Ala Gly Asp Val Arg Gln Asn Pro Cys Gly Ser Lys
```

```
                1               5                  10                 15
Ala Cys Arg Arg Leu Phe Gly Pro Val Asp Ser Glu Gln Leu Ser Arg
                    20                 25                 30

Asp Cys Asp Ala Leu Met Ala Gly Cys Ile Gln Glu Ala Arg Glu Arg
            35                 40                 45

Trp Asn Phe Asp Phe Val Thr Glu Thr Pro Leu Glu Gly Asp Phe Ala
        50                 55                 60

Trp Glu Arg Val Arg Gly Leu Gly Leu Pro Lys Leu Tyr Leu Pro Thr
65                  70                 75                 80

Gly Pro Arg Arg Gly Arg Asp Glu Leu Gly Gly Arg Arg Pro Gly
                85                 90                 95

Thr Ser Pro Ala Leu Leu Gln Gly Thr Ala Glu Glu Asp His Val Asp
                100                105                110

Leu Ser Leu Ser Cys Thr Leu Val Pro Arg Ser Gly Glu Gln Ala Glu
                115                120                125

Gly Ser Pro Gly Gly Pro Gly Asp Ser Gln Gly Arg Lys Arg Arg Gln
            130                135                140

Thr Ser Met Thr Asp Phe Tyr His Ser Lys Arg Arg Leu Ile Phe Ser
145                 150                155                160

Lys Arg Lys Pro

<210> SEQ ID NO 72
<211> LENGTH: 156
<212> TYPE: PRT
<213> ORGANISM: Homo sapiens

<400> SEQUENCE: 72

Met Glu Pro Ala Ala Gly Ser Ser Met Glu Pro Ser Ala Asp Trp Leu
1               5                  10                 15

Ala Thr Ala Ala Ala Arg Gly Arg Val Glu Glu Val Arg Ala Leu Leu
                20                 25                 30

Glu Ala Gly Ala Leu Pro Asn Ala Pro Asn Ser Tyr Gly Arg Arg Pro
            35                 40                 45

Ile Gln Val Met Met Met Gly Ser Ala Arg Val Ala Glu Leu Leu Leu
        50                 55                 60

Leu His Gly Ala Glu Pro Asn Cys Ala Asp Pro Ala Thr Leu Thr Arg
65                  70                 75                 80

Pro Val His Asp Ala Ala Arg Glu Gly Phe Leu Asp Thr Leu Val Val
                85                 90                 95

Leu His Arg Ala Gly Ala Arg Leu Asp Val Arg Asp Ala Trp Gly Arg
                100                105                110

Leu Pro Val Asp Leu Ala Glu Glu Leu Gly His Arg Asp Val Ala Arg
            115                120                125

Tyr Leu Arg Ala Ala Gly Gly Thr Arg Gly Ser Asn His Ala Arg
                130                135                140

Ile Asp Ala Ala Glu Gly Pro Ser Asp Ile Pro Asp
145                 150                155

<210> SEQ ID NO 73
<211> LENGTH: 116
<212> TYPE: PRT
<213> ORGANISM: Homo sapiens

<400> SEQUENCE: 73

Met Glu Pro Ala Ala Gly Ser Ser Met Glu Pro Ser Ala Asp Trp Leu
1               5                  10                 15
```

```
Ala Thr Ala Ala Ala Arg Gly Arg Val Glu Val Arg Ala Leu Leu
            20                  25                  30

Glu Ala Gly Ala Leu Pro Asn Ala Pro Asn Ser Tyr Gly Arg Pro
            35                  40                  45

Ile Gln Val Gly Arg Gly Ser Ala Ala Gly Ala Gly Asp Gly Arg
 50                  55                  60

Leu Trp Arg Thr Lys Phe Ala Gly Glu Leu Glu Ser Gly Ser Ala Ser
 65                  70                  75                  80

Ile Leu Arg Lys Lys Gly Arg Leu Pro Gly Glu Phe Ser Glu Gly Val
                 85                  90                  95

Cys Asn His Arg Pro Pro Pro Gly Asp Ala Leu Gly Ala Trp Glu Ala
                100                 105                 110

Lys Glu Glu Glu
        115

<210> SEQ ID NO 74
<211> LENGTH: 173
<212> TYPE: PRT
<213> ORGANISM: Homo sapiens

<400> SEQUENCE: 74

Met Gly Arg Gly Arg Cys Val Gly Pro Ser Leu Gln Leu Arg Gly Gln
 1               5                  10                  15

Glu Trp Arg Cys Ser Pro Leu Val Pro Lys Gly Ala Ala Ala
             20                  25                  30

Glu Leu Gly Pro Gly Gly Gly Glu Asn Met Val Arg Arg Phe Leu Val
             35                  40                  45

Thr Leu Arg Ile Arg Arg Ala Cys Gly Pro Pro Arg Val Arg Val Phe
 50                  55                  60

Val Val His Ile Pro Arg Leu Thr Gly Glu Trp Ala Ala Pro Gly Ala
 65                  70                  75                  80

Pro Ala Ala Val Ala Leu Val Leu Met Leu Leu Arg Ser Gln Arg Leu
                 85                  90                  95

Gly Gln Gln Pro Leu Pro Arg Arg Pro Gly His Asp Asp Gly Gln Arg
                100                 105                 110

Pro Ser Gly Gly Ala Ala Ala Pro Arg Arg Gly Ala Gln Leu Arg
             115                 120                 125

Arg Pro Arg His Ser His Pro Thr Arg Ala Arg Cys Pro Gly Gly
             130                 135                 140

Leu Pro Gly His Ala Gly Gly Ala Ala Pro Gly Arg Gly Ala Ala Gly
145                 150                 155                 160

Arg Ala Arg Cys Leu Gly Pro Ser Ala Arg Gly Pro Gly
                165                 170

<210> SEQ ID NO 75
<211> LENGTH: 298
<212> TYPE: PRT
<213> ORGANISM: Homo sapiens

<400> SEQUENCE: 75

Met Glu Asn Phe Gln Lys Val Glu Lys Ile Gly Glu Gly Thr Tyr Gly
 1               5                  10                  15

Val Val Tyr Lys Ala Arg Asn Lys Leu Thr Gly Glu Val Val Ala Leu
             20                  25                  30

Lys Lys Ile Arg Leu Asp Thr Glu Thr Glu Gly Val Pro Ser Thr Ala
         35                  40                  45

Ile Arg Glu Ile Ser Leu Leu Lys Glu Leu Asn His Pro Asn Ile Val
```

```
            50                  55                  60
Lys Leu Leu Asp Val Ile His Thr Glu Asn Lys Leu Tyr Leu Val Phe
 65                  70                  75                  80

Glu Phe Leu His Gln Asp Leu Lys Lys Phe Met Asp Ala Ser Ala Leu
                 85                  90                  95

Thr Gly Ile Pro Leu Pro Leu Ile Lys Ser Tyr Leu Phe Gln Leu Leu
                100                 105                 110

Gln Gly Leu Ala Phe Cys His Ser His Arg Val Leu His Arg Asp Leu
                115                 120                 125

Lys Pro Gln Asn Leu Leu Ile Asn Thr Glu Gly Ala Ile Lys Leu Ala
            130                 135                 140

Asp Phe Gly Leu Ala Arg Ala Phe Gly Val Pro Val Arg Thr Tyr Thr
145                 150                 155                 160

His Glu Val Val Thr Leu Trp Tyr Arg Ala Pro Glu Ile Leu Leu Gly
                165                 170                 175

Cys Lys Tyr Tyr Ser Thr Ala Val Asp Ile Trp Ser Leu Gly Cys Ile
                180                 185                 190

Phe Ala Glu Met Val Thr Arg Arg Ala Leu Phe Pro Gly Asp Ser Glu
                195                 200                 205

Ile Asp Gln Leu Phe Arg Ile Phe Arg Thr Leu Gly Thr Pro Asp Glu
            210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
                245                 250                 255

Glu Asp Gly Arg Ser Leu Leu Ser Gln Met Leu His Tyr Asp Pro Asn
                260                 265                 270

Lys Arg Ile Ser Ala Lys Ala Ala Leu Ala His Pro Phe Phe Gln Asp
            275                 280                 285

Val Thr Lys Pro Val Pro His Leu Arg Leu
            290                 295

<210> SEQ ID NO 76
<211> LENGTH: 264
<212> TYPE: PRT
<213> ORGANISM: Homo sapiens

<400> SEQUENCE: 76

Met Glu Asn Phe Gln Lys Val Glu Lys Ile Gly Glu Gly Thr Tyr Gly
  1               5                  10                  15

Val Val Tyr Lys Ala Arg Asn Lys Leu Thr Gly Glu Val Val Ala Leu
                 20                  25                  30

Lys Lys Ile Arg Leu Asp Thr Glu Thr Glu Gly Val Pro Ser Thr Ala
             35                  40                  45

Ile Arg Glu Ile Ser Leu Leu Lys Glu Leu Asn His Pro Asn Ile Val
 50                  55                  60

Lys Leu Leu Asp Val Ile His Thr Glu Asn Lys Leu Tyr Leu Val Phe
 65                  70                  75                  80

Glu Phe Leu His Gln Asp Leu Lys Lys Phe Met Asp Ala Ser Ala Leu
                 85                  90                  95

Thr Gly Ile Pro Leu Pro Leu Ile Lys Ser Tyr Leu Phe Gln Leu Leu
                100                 105                 110

Gln Gly Leu Ala Phe Cys His Ser His Arg Val Leu His Arg Asp Leu
                115                 120                 125

Lys Pro Gln Asn Leu Leu Ile Asn Thr Glu Gly Ala Ile Lys Leu Ala
```

```
                130                 135                 140
Asp Phe Gly Leu Ala Arg Ala Phe Gly Val Pro Val Arg Thr Tyr Thr
145                 150                 155                 160

His Glu Val Thr Arg Arg Ala Leu Phe Pro Gly Asp Ser Glu Ile Asp
                165                 170                 175

Gln Leu Phe Arg Ile Phe Arg Thr Leu Gly Thr Pro Asp Glu Val Val
                180                 185                 190

Trp Pro Gly Val Thr Ser Met Pro Asp Tyr Lys Pro Ser Phe Pro Lys
                195                 200                 205

Trp Ala Arg Gln Asp Phe Ser Lys Val Val Pro Pro Leu Asp Glu Asp
                210                 215                 220

Gly Arg Ser Leu Leu Ser Gln Met Leu His Tyr Asp Pro Asn Lys Arg
225                 230                 235                 240

Ile Ser Ala Lys Ala Ala Leu Ala His Pro Phe Phe Gln Asp Val Thr
                245                 250                 255

Lys Pro Val Pro His Leu Arg Leu
                260

<210> SEQ ID NO 77
<211> LENGTH: 303
<212> TYPE: PRT
<213> ORGANISM: Homo sapiens

<400> SEQUENCE: 77

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
                20                  25                  30

Ala Leu Lys Ser Val Arg Val Pro Asn Gly Gly Gly Gly Gly Gly Gly
            35                  40                  45

Leu Pro Ile Ser Thr Val Arg Glu Val Ala Leu Leu Arg Arg Leu Glu
        50                  55                  60

Ala Phe Glu His Pro Asn Val Val Arg Leu Met Asp Val Cys Ala Thr
65                  70                  75                  80

Ser Arg Thr Asp Arg Glu Ile Lys Val Thr Leu Val Phe Glu His Val
                85                  90                  95

Asp Gln Asp Leu Arg Thr Tyr Leu Asp Lys Ala Pro Pro Pro Gly Leu
                100                 105                 110

Pro Ala Glu Thr Ile Lys Asp Leu Met Arg Gln Phe Leu Arg Gly Leu
            115                 120                 125

Asp Phe Leu His Ala Asn Cys Ile Val His Arg Asp Leu Lys Pro Glu
        130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
                180                 185                 190

Thr Pro Val Asp Met Trp Ser Val Gly Cys Ile Phe Ala Glu Met Phe
                195                 200                 205

Arg Arg Lys Pro Leu Phe Cys Gly Asn Ser Glu Ala Asp Gln Leu Gly
            210                 215                 220

Lys Ile Phe Asp Leu Ile Gly Leu Pro Pro Glu Asp Asp Trp Pro Arg
225                 230                 235                 240

Asp Val Ser Leu Pro Arg Gly Ala Phe Pro Pro Arg Gly Pro Arg Pro
```

```
                       245                 250                 255
Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Phe Arg
            275                 280                 285

Ala Leu Gln His Ser Tyr Leu His Lys Asp Glu Gly Asn Pro Glu
            290                 295                 300

<210> SEQ ID NO 78
<211> LENGTH: 326
<212> TYPE: PRT
<213> ORGANISM: Homo sapiens

<400> SEQUENCE: 78

Met Glu Lys Asp Gly Leu Cys Arg Ala Asp Gln Gln Tyr Glu Cys Val
 1               5                  10                  15

Ala Glu Ile Gly Glu Gly Ala Tyr Gly Lys Val Phe Lys Ala Arg Asp
            20                  25                  30

Leu Lys Asn Gly Gly Arg Phe Val Ala Leu Lys Arg Val Arg Val Gln
         35                  40                  45

Thr Gly Glu Glu Gly Met Pro Leu Ser Thr Ile Arg Glu Val Ala Val
     50                  55                  60

Leu Arg His Leu Glu Thr Phe Glu His Pro Asn Val Val Arg Leu Phe
 65                  70                  75                  80

Asp Val Cys Thr Val Ser Arg Thr Asp Arg Glu Thr Lys Leu Thr Leu
                 85                  90                  95

Val Phe Glu His Val Asp Gln Asp Leu Thr Thr Tyr Leu Asp Lys Val
            100                 105                 110

Pro Glu Pro Gly Val Pro Thr Glu Thr Ile Lys Asp Met Met Phe Gln
        115                 120                 125

Leu Leu Arg Gly Leu Asp Phe Leu His Ser His Arg Val Val His Arg
    130                 135                 140

Asp Leu Lys Pro Gln Asn Ile Leu Val Thr Ser Ser Gly Gln Ile Lys
145                 150                 155                 160

Leu Ala Asp Phe Gly Leu Ala Arg Ile Tyr Ser Phe Gln Met Ala Leu
                165                 170                 175

Thr Ser Val Val Thr Leu Trp Tyr Arg Ala Pro Glu Val Leu Leu
            180                 185                 190

Gln Ser Ser Tyr Ala Thr Pro Val Asp Leu Trp Ser Val Gly Cys Ile
        195                 200                 205

Phe Ala Glu Met Phe Arg Arg Lys Pro Leu Phe Arg Gly Ser Ser Asp
    210                 215                 220

Val Asp Gln Leu Gly Lys Ile Leu Asp Val Ile Gly Leu Pro Gly Glu
225                 230                 235                 240

Glu Asp Trp Pro Arg Asp Val Ala Leu Pro Arg Gln Ala Phe His Ser
                245                 250                 255

Lys Ser Ala Gln Pro Ile Glu Lys Phe Val Thr Asp Ile Asp Glu Leu
                260                 265                 270

Gly Lys Asp Leu Leu Leu Lys Cys Leu Thr Phe Asn Pro Ala Lys Arg
            275                 280                 285

Ile Ser Ala Tyr Ser Ala Leu Ser His Pro Tyr Phe Gln Asp Leu Glu
        290                 295                 300

Arg Cys Lys Glu Asn Leu Asp Ser His Leu Pro Pro Ser Gln Asn Thr
305                 310                 315                 320

Ser Glu Leu Asn Thr Ala
```

-continued

325

<210> SEQ ID NO 79
<211> LENGTH: 437
<212> TYPE: PRT
<213> ORGANISM: Homo sapiens

<400> SEQUENCE: 79

Met Ala Leu Ala Gly Ala Pro Ala Gly Gly Pro Cys Ala Pro Ala Leu
1               5                   10                  15

Glu Ala Leu Leu Gly Ala Gly Ala Leu Arg Leu Leu Asp Ser Ser Gln
            20                  25                  30

Ile Val Ile Ile Ser Ala Ala Gln Asp Ala Ser Ala Pro Pro Ala Pro
        35                  40                  45

Thr Gly Pro Ala Ala Pro Ala Ala Gly Pro Cys Asp Pro Asp Leu Leu
    50                  55                  60

Leu Phe Ala Thr Pro Gln Ala Pro Arg Pro Thr Pro Ser Ala Pro Arg
65                  70                  75                  80

Pro Ala Leu Gly Arg Pro Pro Val Lys Arg Arg Leu Asp Leu Glu Thr
                85                  90                  95

Asp His Gln Tyr Leu Ala Glu Ser Ser Gly Pro Ala Arg Gly Arg Gly
            100                 105                 110

Arg His Pro Gly Lys Gly Val Lys Ser Pro Gly Glu Lys Ser Arg Tyr
        115                 120                 125

Glu Thr Ser Leu Asn Leu Thr Thr Lys Arg Phe Leu Glu Leu Leu Ser
    130                 135                 140

His Ser Ala Asp Gly Val Val Asp Leu Asn Trp Ala Ala Glu Val Leu
145                 150                 155                 160

Lys Val Gln Lys Arg Arg Ile Tyr Asp Ile Thr Asn Val Leu Glu Gly
                165                 170                 175

Ile Gln Leu Ile Ala Lys Lys Ser Lys Asn His Ile Gln Trp Leu Gly
            180                 185                 190

Ser His Thr Thr Val Gly Val Gly Gly Arg Leu Glu Gly Leu Thr Gln
        195                 200                 205

Asp Leu Arg Gln Leu Gln Glu Ser Glu Gln Gln Leu Asp His Leu Met
    210                 215                 220

Asn Ile Cys Thr Thr Gln Leu Arg Leu Leu Ser Glu Asp Thr Asp Ser
225                 230                 235                 240

Gln Arg Leu Ala Tyr Val Thr Cys Gln Asp Leu Arg Ser Ile Ala Asp
                245                 250                 255

Pro Ala Glu Gln Met Val Met Val Ile Lys Ala Pro Pro Glu Thr Gln
            260                 265                 270

Leu Gln Ala Val Asp Ser Ser Glu Asn Phe Gln Ile Ser Leu Lys Ser
        275                 280                 285

Lys Gln Gly Pro Ile Asp Val Phe Leu Cys Pro Glu Glu Thr Val Gly
    290                 295                 300

Gly Ile Ser Pro Gly Lys Thr Pro Ser Gln Glu Val Thr Ser Glu Glu
305                 310                 315                 320

Glu Asn Arg Ala Thr Asp Ser Ala Thr Ile Val Ser Pro Pro Pro Ser
                325                 330                 335

Ser Pro Pro Ser Ser Leu Thr Thr Asp Pro Ser Gln Ser Leu Leu Ser
            340                 345                 350

Leu Glu Gln Glu Pro Leu Leu Ser Arg Met Gly Ser Leu Arg Ala Pro
        355                 360                 365

Val Asp Glu Asp Arg Leu Ser Pro Leu Val Ala Ala Asp Ser Leu Leu

```
                        370                 375                 380
Glu His Val Arg Glu Asp Phe Ser Gly Leu Leu Pro Glu Phe Ile
385                 390                 395                 400

Ser Leu Ser Pro Pro His Glu Ala Leu Asp Tyr His Phe Gly Leu Glu
                    405                 410                 415

Glu Gly Glu Gly Ile Arg Asp Leu Phe Asp Cys Asp Phe Gly Asp Leu
                420                 425                 430

Thr Pro Leu Asp Phe
            435

<210> SEQ ID NO 80
<211> LENGTH: 1170
<212> TYPE: PRT
<213> ORGANISM: Homo sapiens

<400> SEQUENCE: 80

Met Gly Leu Ala Trp Gly Leu Gly Val Leu Phe Leu Met His Val Cys
  1               5                  10                  15

Gly Thr Asn Arg Ile Pro Glu Ser Gly Gly Asp Asn Ser Val Phe Asp
                 20                  25                  30

Ile Phe Glu Leu Thr Gly Ala Ala Arg Lys Gly Ser Gly Arg Arg Leu
             35                  40                  45

Val Lys Gly Pro Asp Pro Ser Ser Pro Ala Phe Arg Ile Glu Asp Ala
 50                  55                  60

Asn Leu Ile Pro Pro Val Pro Asp Asp Lys Phe Gln Asp Leu Val Asp
 65                  70                  75                  80

Ala Val Arg Ala Glu Lys Gly Phe Leu Leu Leu Ala Ser Leu Arg Gln
                 85                  90                  95

Met Lys Lys Thr Arg Gly Thr Leu Leu Ala Leu Glu Arg Lys Asp His
                100                 105                 110

Ser Gly Gln Val Phe Ser Val Val Ser Asn Gly Lys Ala Gly Thr Leu
            115                 120                 125

Asp Leu Ser Leu Thr Val Gln Gly Lys Gln His Val Val Ser Val Glu
130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
            180                 185                 190

Ser Ile Ala Arg Leu Arg Ile Ala Lys Gly Gly Val Asn Asp Asn Phe
        195                 200                 205

Gln Gly Val Leu Gln Asn Val Arg Phe Val Phe Gly Thr Thr Pro Glu
    210                 215                 220

Asp Ile Leu Arg Asn Lys Gly Cys Ser Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
            260                 265                 270

Ser Cys Asp Glu Leu Ser Ser Met Val Leu Glu Leu Arg Gly Leu Arg
        275                 280                 285

Thr Ile Val Thr Thr Leu Gln Asp Ser Ile Arg Lys Val Thr Glu Glu
    290                 295                 300

Asn Lys Glu Leu Ala Asn Glu Leu Arg Arg Pro Pro Leu Cys Tyr His
```

```
                305                 310                 315                 320
Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
                340                 345                 350

Cys Pro Ile Met Pro Cys Ser Asn Ala Thr Val Pro Asp Gly Glu Cys
                355                 360                 365

Cys Pro Arg Cys Trp Pro Ser Asp Ser Ala Asp Gly Trp Ser Pro
                370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
                420                 425                 430

Lys Gln Asp Gly Gly Trp Ser His Trp Ser Pro Trp Ser Ser Cys Ser
                435                 440                 445

Val Thr Cys Gly Asp Gly Val Ile Thr Arg Ile Arg Leu Cys Asn Ser
450                 455                 460

Pro Ser Pro Gln Met Asn Gly Lys Pro Cys Glu Gly Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
                500                 505                 510

Gln Lys Arg Ser Arg Leu Cys Asn Asn Pro Thr Pro Gln Phe Gly Gly
                515                 520                 525

Lys Asp Cys Val Gly Asp Val Thr Glu Asn Gln Ile Cys Asn Lys Gln
                530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Thr Asp Val Asp Glu Cys
                580                 585                 590

Lys Glu Val Pro Asp Ala Cys Phe Asn His Asn Gly Glu His Arg Cys
                595                 600                 605

Glu Asn Thr Asp Pro Gly Tyr Asn Cys Leu Pro Cys Pro Pro Arg Phe
                610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
                660                 665                 670

Met Tyr Arg Cys Glu Cys Lys Pro Gly Tyr Ala Gly Asn Gly Ile Ile
                675                 680                 685

Cys Gly Glu Asp Thr Asp Leu Asp Gly Trp Pro Asn Glu Asn Leu Val
                690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735
```

```
Ala Cys Asp Asp Asp Asp Asn Asp Lys Ile Pro Asp Asp Arg Asp
            740                 745                 750

Asn Cys Pro Phe His Tyr Asn Pro Ala Gln Tyr Asp Tyr Asp Arg Asp
            755                 760                 765

Asp Val Gly Asp Arg Cys Asp Asn Cys Pro Tyr Asn His Asn Pro Asp
        770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
            820                 825                 830

Cys Asp Asn Cys Pro Leu Glu His Asn Pro Asp Gln Leu Asp Ser Asp
            835                 840                 845

Ser Asp Arg Ile Gly Asp Thr Cys Asp Asn Asn Gln Asp Ile Asp Glu
        850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Lys Asp Asn Cys Arg Leu
            900                 905                 910

Val Pro Asn Pro Asp Gln Lys Asp Ser Asp Gly Asp Gly Arg Gly Asp
        915                 920                 925

Ala Cys Lys Asp Asp Phe Asp His Asp Ser Val Pro Ile Asp Asp
930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
            965                 970                 975

Trp Val Val Arg His Gln Gly Lys Glu Leu Val Gln Thr Val Asn Cys
            980                 985                 990

Asp Pro Gly Leu Ala Val Gly Tyr Asp Glu Phe Asn Ala Val Asp Phe
        995                 1000                1005

Ser Gly Thr Phe Phe Ile Asn Thr Glu Arg Asp Asp Asp Tyr Ala Gly
    1010                1015                1020

Phe Val Phe Gly Tyr Gln Ser Ser Ser Arg Pro Tyr Val Val Met Trp
1025                1030                1035                1040

Lys Gln Val Thr Gln Ser Tyr Trp Asp Thr Asn Pro Thr Arg Ala Gln
                1045                1050                1055

Gly Tyr Ser Gly Leu Ser Val Lys Val Val Asn Ser Thr Thr Gly Pro
        1060                1065                1070

Gly Glu His Leu Arg Asn Ala Leu Trp His Thr Gly Asn Thr Pro Gly
    1075                1080                1085

Gln Val Arg Thr Leu Trp His Asp Pro Arg His Ile Gly Trp Lys Asp
    1090                1095                1100

Phe Thr Ala Tyr Arg Trp Arg Leu Ser His Arg Pro Lys Thr Gly Phe
1105                1110                1115                1120

Ile Arg Val Val Met Tyr Glu Gly Lys Lys Ile Met Ala Asp Ser Gly
                1125                1130                1135

Pro Ile Tyr Asp Lys Thr Tyr Ala Gly Gly Arg Leu Gly Leu Phe Val
        1140                1145                1150

Phe Ser Gln Glu Met Val Phe Phe Ser Asp Leu Lys Tyr Glu Cys Arg
    1155                1160                1165
```

Asp Pro
1170

<210> SEQ ID NO 81
<211> LENGTH: 1516
<212> TYPE: PRT
<213> ORGANISM: Homo sapiens

<400> SEQUENCE: 81

Met Ala Pro Tyr Pro Cys Gly Cys His Ile Leu Leu Leu Phe Cys
1               5                   10                  15

Cys Leu Ala Ala Ala Arg Ala Asn Leu Leu Asn Leu Asn Trp Leu Trp
            20                  25                  30

Phe Asn Asn Glu Asp Thr Ser His Ala Ala Thr Thr Ile Pro Glu Pro
        35                  40                  45

Gln Gly Pro Leu Pro Val Gln Pro Thr Ala Asp Thr Thr His Val
    50                  55                  60

Thr Pro Arg Asn Gly Ser Thr Glu Pro Ala Thr Ala Pro Gly Ser Pro
65                  70                  75                  80

Glu Pro Pro Ser Glu Leu Leu Glu Asp Gly Gln Asp Thr Pro Thr Ser
                85                  90                  95

Ala Glu Ser Pro Asp Ala Pro Glu Glu Asn Ile Ala Gly Val Gly Ala
            100                 105                 110

Glu Ile Leu Asn Val Ala Lys Gly Ile Arg Ser Phe Val Gln Leu Trp
        115                 120                 125

Asn Asp Thr Val Pro Thr Glu Ser Leu Ala Arg Ala Glu Thr Leu Val
    130                 135                 140

Leu Glu Thr Pro Val Gly Pro Leu Ala Leu Ala Gly Pro Ser Ser Thr
145                 150                 155                 160

Pro Gln Glu Asn Gly Thr Thr Leu Trp Pro Ser Arg Gly Ile Pro Ser
                165                 170                 175

Ser Pro Gly Ala His Thr Thr Glu Ala Gly Thr Leu Pro Ala Pro Thr
            180                 185                 190

Pro Ser Pro Pro Ser Leu Gly Arg Pro Trp Ala Pro Leu Thr Gly Pro
        195                 200                 205

Ser Val Pro Pro Pro Ser Ser Glu Arg Ile Ser Glu Glu Val Gly Leu
    210                 215                 220

Leu Gln Leu Leu Gly Asp Pro Pro Gln Gln Val Thr Gln Thr Asp
225                 230                 235                 240

Asp Pro Asp Val Gly Leu Ala Tyr Val Phe Gly Pro Asp Ala Asn Ser
                245                 250                 255

Gly Gln Val Ala Arg Tyr His Phe Pro Ser Leu Phe Phe Arg Asp Phe
            260                 265                 270

Ser Leu Leu Phe His Ile Arg Pro Ala Thr Glu Gly Pro Gly Val Leu
        275                 280                 285

Phe Ala Ile Thr Asp Ser Ala Gln Ala Met Val Leu Leu Gly Val Lys
    290                 295                 300

Leu Ser Gly Val Gln Asp Gly His Gln Asp Ile Ser Leu Leu Tyr Thr
305                 310                 315                 320

Glu Pro Gly Ala Gly Gln Thr His Thr Ala Ala Ser Phe Arg Leu Pro
                325                 330                 335

Ala Phe Val Gly Gln Trp Thr His Leu Ala Leu Ser Val Ala Gly Gly
            340                 345                 350

Phe Val Ala Leu Tyr Val Asp Cys Glu Glu Phe Gln Arg Met Pro Leu
        355                 360                 365

-continued

```
Ala Arg Ser Ser Arg Gly Leu Glu Leu Glu Pro Gly Ala Gly Leu Phe
    370                 375                 380

Val Ala Gln Ala Gly Gly Ala Asp Pro Asp Lys Phe Gln Gly Val Ile
385                 390                 395                 400

Ala Glu Leu Lys Val Arg Arg Asp Pro Gln Val Ser Pro Met His Cys
                405                 410                 415

Leu Asp Glu Glu Gly Asp Asp Ser Asp Gly Ala Ser Gly Asp Ser Gly
            420                 425                 430

Ser Gly Leu Gly Asp Ala Arg Glu Leu Leu Arg Glu Thr Gly Ala
            435                 440                 445

Ala Leu Lys Pro Arg Leu Pro Ala Pro Pro Val Thr Thr Pro Pro
    450                 455                 460

Leu Ala Gly Gly Ser Ser Thr Glu Asp Ser Arg Ser Glu Glu Val Glu
465                 470                 475                 480

Glu Gln Thr Thr Val Ala Ser Leu Gly Ala Gln Thr Leu Pro Gly Ser
                485                 490                 495

Asp Ser Val Ser Thr Trp Asp Gly Ser Val Arg Thr Pro Gly Gly Arg
            500                 505                 510

Val Lys Glu Gly Gly Leu Lys Gly Gln Lys Gly Glu Pro Gly Val Pro
    515                 520                 525

Gly Pro Pro Gly Arg Ala Gly Pro Pro Gly Ser Pro Cys Leu Pro Gly
    530                 535                 540

Pro Pro Gly Leu Pro Cys Pro Val Ser Pro Leu Gly Pro Ala Gly Pro
545                 550                 555                 560

Ala Leu Gln Thr Val Pro Gly Pro Gln Gly Pro Gly Pro Pro Gly
                565                 570                 575

Arg Asp Gly Thr Pro Gly Arg Asp Gly Glu Pro Gly Asp Pro Gly Glu
            580                 585                 590

Asp Gly Lys Pro Gly Asp Thr Gly Pro Gln Gly Phe Pro Gly Thr Pro
            595                 600                 605

Gly Asp Val Gly Pro Lys Gly Asp Lys Gly Asp Pro Gly Val Gly Glu
    610                 615                 620

Arg Gly Pro Pro Gly Pro Gln Gly Pro Pro Gly Pro Pro Gly Pro Ser
625                 630                 635                 640

Phe Arg His Asp Lys Leu Thr Phe Ile Asp Met Glu Gly Ser Gly Phe
                645                 650                 655

Gly Gly Asp Leu Glu Ala Leu Arg Gly Pro Arg Gly Phe Pro Gly Pro
            660                 665                 670

Pro Gly Pro Pro Gly Val Pro Gly Leu Pro Gly Glu Pro Gly Arg Phe
            675                 680                 685

Gly Val Asn Ser Ser Asp Val Pro Gly Pro Ala Gly Leu Pro Gly Val
    690                 695                 700

Pro Gly Arg Glu Gly Pro Pro Gly Phe Pro Gly Leu Pro Gly Pro Pro
705                 710                 715                 720

Gly Pro Pro Gly Arg Glu Gly Pro Pro Gly Arg Thr Gly Gln Lys Gly
                725                 730                 735

Ser Leu Gly Glu Ala Gly Ala Pro Gly His Lys Gly Ser Lys Gly Ala
            740                 745                 750

Pro Gly Pro Ala Gly Ala Arg Gly Glu Ser Gly Leu Ala Gly Ala Pro
            755                 760                 765

Gly Pro Ala Gly Pro Pro Gly Pro Gly Pro Gly Pro Gly
    770                 775                 780

Pro Gly Leu Pro Ala Gly Phe Asp Asp Met Glu Gly Ser Gly Gly Pro
```

-continued

```
            785                 790                 795                 800
Phe Trp Ser Thr Ala Arg Ser Ala Asp Gly Pro Gln Gly Pro Pro Gly
                    805                 810                 815
Leu Pro Gly Leu Lys Gly Asp Pro Gly Val Pro Gly Leu Pro Gly Ala
                820                 825                 830
Lys Gly Glu Val Gly Ala Asp Gly Val Pro Gly Phe Pro Gly Leu Pro
            835                 840                 845
Gly Arg Glu Gly Ile Ala Gly Pro Gln Gly Pro Lys Gly Asp Arg Gly
        850                 855                 860
Ser Arg Gly Glu Lys Gly Asp Pro Gly Lys Asp Gly Val Gly Gln Pro
865                 870                 875                 880
Gly Leu Pro Gly Pro Pro Gly Pro Gly Pro Val Val Tyr Val Ser
                    885                 890                 895
Glu Gln Asp Gly Ser Val Leu Ser Val Pro Gly Pro Glu Gly Arg Pro
                900                 905                 910
Gly Phe Ala Gly Phe Pro Gly Pro Ala Gly Pro Lys Gly Asn Leu Gly
            915                 920                 925
Ser Lys Gly Glu Arg Gly Ser Pro Gly Pro Lys Gly Glu Lys Gly Glu
        930                 935                 940
Pro Gly Ser Ile Phe Ser Pro Asp Gly Gly Ala Leu Gly Pro Ala Gln
945                 950                 955                 960
Lys Gly Ala Lys Gly Glu Pro Gly Phe Arg Gly Pro Pro Gly Pro Tyr
                    965                 970                 975
Gly Arg Pro Gly Tyr Lys Gly Glu Ile Gly Phe Pro Gly Arg Pro Gly
                980                 985                 990
Arg Pro Gly Met Asn Gly Leu Lys Gly Glu Lys Gly Glu Pro Gly Asp
            995                 1000                1005
Ala Ser Leu Gly Phe Gly Met Arg Gly Met Pro Gly Pro Pro Gly Pro
        1010                1015                1020
Pro Gly Pro Pro Gly Pro Pro Gly Thr Pro Val Tyr Asp Ser Asn Val
1025                1030                1035                1040
Phe Ala Glu Ser Ser Arg Pro Gly Pro Pro Gly Leu Pro Gly Asn Gln
                    1045                1050                1055
Gly Pro Pro Gly Pro Lys Gly Ala Lys Gly Glu Val Gly Pro Pro Gly
                1060                1065                1070
Pro Pro Gly Gln Phe Pro Phe Asp Phe Leu Gln Leu Glu Ala Glu Met
            1075                1080                1085
Lys Gly Glu Lys Gly Asp Arg Gly Asp Ala Gly Gln Lys Gly Glu Arg
        1090                1095                1100
Gly Glu Pro Gly Gly Gly Gly Phe Phe Gly Ser Ser Leu Pro Gly Pro
1105                1110                1115                1120
Pro Gly Pro Pro Gly Pro Arg Gly Tyr Pro Gly Ile Pro Gly Pro Lys
                    1125                1130                1135
Gly Glu Ser Ile Arg Gly Gln Pro Gly Pro Pro Gly Gln Gly Pro
                1140                1145                1150
Pro Gly Ile Gly Tyr Glu Gly Arg Gln Gly Pro Pro Gly Pro Pro Gly
            1155                1160                1165
Pro Pro Gly Pro Pro Ser Phe Pro Gly Pro His Arg Gln Thr Ile Ser
        1170                1175                1180
Val Pro Gly Pro Pro Gly Pro Pro Gly Pro Pro Gly Pro Pro Gly Thr
1185                1190                1195                1200
Met Gly Ala Ser Ser Gly Val Arg Leu Trp Ala Thr Arg Gln Ala Met
                    1205                1210                1215
```

-continued

```
Leu Gly Gln Val His Glu Val Pro Glu Gly Trp Leu Ile Phe Val Ala
            1220                1225                1230

Glu Gln Glu Glu Leu Tyr Val Arg Val Gln Asn Gly Phe Arg Lys Val
        1235                1240                1245

Gln Leu Glu Ala Arg Thr Pro Leu Pro Arg Gly Thr Asp Asn Glu Val
    1250                1255                1260

Ala Ala Leu Gln Pro Pro Val Val Gln Leu His Asp Ser Asn Pro Tyr
1265                1270                1275                1280

Pro Arg Arg Glu His Pro His Pro Thr Ala Arg Pro Trp Arg Ala Asp
                1285                1290                1295

Asp Ile Leu Ala Ser Pro Pro Arg Leu Pro Glu Pro Gln Pro Tyr Pro
            1300                1305                1310

Gly Ala Pro His His Ser Ser Tyr Val His Leu Arg Pro Ala Arg Pro
        1315                1320                1325

Thr Ser Pro Pro Ala His Ser His Arg Asp Phe Gln Pro Val Leu His
    1330                1335                1340

Leu Val Ala Leu Asn Ser Pro Leu Ser Gly Gly Met Arg Gly Ile Arg
1345                1350                1355                1360

Gly Ala Asp Phe Gln Cys Phe Gln Gln Ala Arg Ala Val Gly Leu Ala
                1365                1370                1375

Gly Thr Phe Arg Ala Phe Leu Ser Ser Arg Leu Gln Asp Leu Tyr Ser
        1380                1385                1390

Ile Val Arg Arg Ala Asp Arg Ala Ala Val Pro Ile Val Asn Leu Lys
    1395                1400                1405

Asp Glu Leu Leu Phe Pro Ser Trp Glu Ala Leu Phe Ser Gly Ser Glu
1410                1415                1420

Gly Pro Leu Lys Pro Gly Ala Arg Ile Phe Ser Phe Asp Gly Lys Asp
1425                1430                1435                1440

Val Leu Arg His Pro Thr Trp Pro Gln Lys Ser Val Trp His Gly Ser
                1445                1450                1455

Asp Pro Asn Gly Arg Arg Leu Thr Glu Ser Tyr Cys Glu Thr Trp Arg
        1460                1465                1470

Thr Glu Ala Pro Ser Ala Thr Gly Gln Ala Ser Ser Leu Leu Gly Gly
    1475                1480                1485

Arg Leu Leu Gly Gln Ser Ala Ala Ser Cys His His Ala Tyr Ile Val
1490                1495                1500

Leu Cys Ile Glu Asn Ser Phe Met Thr Ala Ser Lys
1505                1510                1515

<210> SEQ ID NO 82
<211> LENGTH: 1336
<212> TYPE: PRT
<213> ORGANISM: Homo sapiens

<400> SEQUENCE: 82

Met Ala Pro Arg Cys Pro Trp Pro Trp Pro Arg Arg Arg Leu Leu
  1               5                  10                  15

Asp Val Leu Ala Pro Leu Val Leu Leu Gly Val Arg Ala Ala Ser
            20                  25                  30

Ala Glu Pro Glu Arg Ile Ser Glu Glu Val Gly Leu Leu Gln Leu Leu
        35                  40                  45

Gly Asp Pro Pro Gln Gln Val Thr Gln Thr Asp Pro Asp Val
    50                  55                  60

Gly Leu Ala Tyr Val Phe Gly Pro Asp Ala Asn Ser Gly Gln Val Ala
65                  70                  75                  80
```

-continued

```
Arg Tyr His Phe Pro Ser Leu Phe Phe Arg Asp Phe Ser Leu Leu Phe
                85                  90                  95
His Ile Arg Pro Ala Thr Glu Gly Pro Gly Val Leu Phe Ala Ile Thr
            100                 105                 110
Asp Ser Ala Gln Ala Met Val Leu Leu Gly Val Lys Leu Ser Gly Val
        115                 120                 125
Gln Asp Gly His Gln Asp Ile Ser Leu Leu Tyr Thr Glu Pro Gly Ala
    130                 135                 140
Gly Gln Thr His Thr Ala Ala Ser Phe Arg Leu Pro Ala Phe Val Gly
145                 150                 155                 160
Gln Trp Thr His Leu Ala Leu Ser Val Ala Gly Gly Phe Val Ala Leu
                165                 170                 175
Tyr Val Asp Cys Glu Glu Phe Gln Arg Met Pro Leu Ala Arg Ser Ser
            180                 185                 190
Arg Gly Leu Glu Leu Glu Pro Gly Ala Gly Leu Phe Val Ala Gln Ala
        195                 200                 205
Gly Gly Ala Asp Pro Asp Lys Phe Gln Gly Val Ile Ala Glu Leu Lys
    210                 215                 220
Val Arg Arg Asp Pro Gln Val Ser Pro Met His Cys Leu Asp Glu Glu
225                 230                 235                 240
Gly Asp Asp Ser Asp Gly Ala Ser Gly Asp Ser Gly Ser Gly Leu Gly
                245                 250                 255
Asp Ala Arg Glu Leu Leu Arg Glu Glu Thr Gly Ala Ala Leu Lys Pro
            260                 265                 270
Arg Leu Pro Ala Pro Pro Val Thr Thr Pro Leu Ala Gly Gly
        275                 280                 285
Ser Ser Thr Glu Asp Ser Arg Ser Glu Glu Val Glu Glu Gln Thr Thr
    290                 295                 300
Val Ala Ser Leu Gly Ala Gln Thr Leu Pro Gly Ser Asp Ser Val Ser
305                 310                 315                 320
Thr Trp Asp Gly Ser Val Arg Thr Pro Gly Gly Arg Val Lys Glu Gly
                325                 330                 335
Gly Leu Lys Gly Gln Lys Gly Glu Pro Gly Val Pro Gly Pro Pro Gly
            340                 345                 350
Arg Ala Gly Pro Pro Gly Ser Pro Cys Leu Pro Gly Pro Pro Gly Leu
        355                 360                 365
Pro Cys Pro Val Ser Pro Leu Gly Pro Ala Gly Pro Ala Leu Gln Thr
    370                 375                 380
Val Pro Gly Pro Gln Gly Pro Pro Gly Pro Pro Gly Arg Asp Gly Thr
385                 390                 395                 400
Pro Gly Arg Asp Gly Glu Pro Gly Asp Pro Gly Glu Asp Gly Lys Pro
                405                 410                 415
Gly Asp Thr Gly Pro Gln Gly Phe Pro Gly Thr Pro Gly Asp Val Gly
            420                 425                 430
Pro Lys Gly Asp Lys Gly Asp Pro Gly Val Gly Glu Arg Gly Pro Pro
        435                 440                 445
Gly Pro Gln Gly Pro Pro Gly Pro Gly Pro Ser Phe Arg His Asp
    450                 455                 460
Lys Leu Thr Phe Ile Asp Met Glu Gly Ser Gly Phe Gly Gly Asp Leu
465                 470                 475                 480
Glu Ala Leu Arg Gly Pro Arg Gly Phe Pro Gly Pro Pro Gly Pro Pro
                485                 490                 495
Gly Val Pro Gly Leu Pro Gly Glu Pro Gly Arg Phe Gly Val Asn Ser
            500                 505                 510
```

```
Ser Asp Val Pro Gly Pro Ala Gly Leu Pro Gly Val Pro Gly Arg Glu
        515                 520                 525

Gly Pro Pro Gly Phe Pro Gly Leu Pro Gly Pro Pro Gly Pro Pro Gly
        530                 535                 540

Arg Glu Gly Pro Pro Gly Arg Thr Gly Gln Lys Gly Ser Leu Gly Glu
545                 550                 555                 560

Ala Gly Ala Pro Gly His Lys Gly Ser Lys Gly Ala Pro Gly Pro Ala
        565                 570                 575

Gly Ala Arg Gly Glu Ser Gly Leu Ala Gly Ala Pro Gly Pro Ala Gly
        580                 585                 590

Pro Pro Gly Pro Pro Gly Pro Pro Gly Pro Pro Gly Pro Gly Leu Pro
        595                 600                 605

Ala Gly Phe Asp Asp Met Glu Gly Ser Gly Gly Pro Phe Trp Ser Thr
        610                 615                 620

Ala Arg Ser Ala Asp Gly Pro Gln Gly Pro Pro Gly Leu Pro Gly Leu
625                 630                 635                 640

Lys Gly Asp Pro Gly Val Pro Gly Leu Pro Gly Ala Lys Gly Glu Val
        645                 650                 655

Gly Ala Asp Gly Val Pro Gly Phe Pro Gly Leu Pro Gly Arg Glu Gly
        660                 665                 670

Ile Ala Gly Pro Gln Gly Pro Lys Gly Asp Arg Gly Ser Arg Gly Glu
        675                 680                 685

Lys Gly Asp Pro Gly Lys Asp Gly Val Gly Gln Pro Gly Leu Pro Gly
        690                 695                 700

Pro Pro Gly Pro Pro Gly Pro Val Val Tyr Val Ser Glu Gln Asp Gly
705                 710                 715                 720

Ser Val Leu Ser Val Pro Gly Pro Glu Gly Arg Pro Gly Phe Ala Gly
        725                 730                 735

Phe Pro Gly Pro Ala Gly Pro Lys Gly Asn Leu Gly Ser Lys Gly Glu
        740                 745                 750

Arg Gly Ser Pro Gly Pro Lys Gly Glu Lys Gly Glu Pro Gly Ser Ile
        755                 760                 765

Phe Ser Pro Asp Gly Gly Ala Leu Gly Pro Ala Gln Lys Gly Ala Lys
        770                 775                 780

Gly Glu Pro Gly Phe Arg Gly Pro Pro Gly Pro Tyr Gly Arg Pro Gly
785                 790                 795                 800

Tyr Lys Gly Glu Ile Gly Phe Pro Gly Arg Pro Gly Arg Pro Gly Met
        805                 810                 815

Asn Gly Leu Lys Gly Glu Lys Gly Glu Pro Gly Asp Ala Ser Leu Gly
        820                 825                 830

Phe Gly Met Arg Gly Met Pro Gly Pro Pro Gly Pro Pro Gly Pro Pro
        835                 840                 845

Gly Pro Pro Gly Thr Pro Val Tyr Asp Ser Asn Val Phe Ala Glu Ser
850                 855                 860

Ser Arg Pro Gly Pro Pro Gly Leu Pro Gly Asn Gln Gly Pro Pro Gly
865                 870                 875                 880

Pro Lys Gly Ala Lys Gly Glu Val Gly Pro Pro Gly Pro Pro Gly Gln
        885                 890                 895

Phe Pro Phe Asp Phe Leu Gln Leu Glu Ala Glu Met Lys Gly Glu Lys
        900                 905                 910

Gly Asp Arg Gly Asp Ala Gly Gln Lys Gly Glu Arg Gly Glu Pro Gly
        915                 920                 925

Gly Gly Gly Phe Phe Gly Ser Ser Leu Pro Gly Pro Pro Gly Pro Pro
```

```
                930              935              940
Gly Pro Arg Gly Tyr Pro Gly Ile Pro Gly Pro Lys Gly Glu Ser Ile
945                  950              955                  960

Arg Gly Gln Pro Gly Pro Pro Gly Pro Gln Gly Pro Pro Gly Ile Gly
                965              970                  975

Tyr Glu Gly Arg Gln Gly Pro Pro Gly Pro Pro Gly Pro Pro Gly Pro
            980              985                  990

Pro Ser Phe Pro Gly Pro His Arg Gln Thr Ile Ser Val Pro Gly Pro
            995              1000                 1005

Pro Gly Pro Gly Pro Pro Gly Pro Pro Gly Thr Met Gly Ala Ser
    1010             1015             1020

Ser Gly Val Arg Leu Trp Ala Thr Arg Gln Ala Met Leu Gly Gln Val
1025             1030             1035                 1040

His Glu Val Pro Glu Gly Trp Leu Ile Phe Val Ala Glu Gln Glu Glu
                1045             1050                 1055

Leu Tyr Val Arg Val Gln Asn Gly Phe Arg Lys Val Gln Leu Glu Ala
                1060             1065             1070

Arg Thr Pro Leu Pro Arg Gly Thr Asp Asn Glu Val Ala Ala Leu Gln
            1075             1080             1085

Pro Pro Val Val Gln Leu His Asp Ser Asn Pro Tyr Pro Arg Arg Glu
            1090             1095             1100

His Pro His Pro Thr Ala Arg Pro Trp Arg Ala Asp Asp Ile Leu Ala
1105             1110             1115                 1120

Ser Pro Pro Arg Leu Pro Glu Pro Gln Pro Tyr Pro Gly Ala Pro His
                1125             1130             1135

His Ser Ser Tyr Val His Leu Arg Pro Ala Arg Pro Thr Ser Pro Pro
            1140             1145             1150

Ala His Ser His Arg Asp Phe Gln Pro Val Leu His Leu Val Ala Leu
            1155             1160             1165

Asn Ser Pro Leu Ser Gly Gly Met Arg Gly Ile Arg Gly Ala Asp Phe
            1170             1175             1180

Gln Cys Phe Gln Gln Ala Arg Ala Val Gly Leu Ala Gly Thr Phe Arg
1185             1190             1195                 1200

Ala Phe Leu Ser Ser Arg Leu Gln Asp Leu Tyr Ser Ile Val Arg Arg
                1205             1210             1215

Ala Asp Arg Ala Ala Val Pro Ile Val Asn Leu Lys Asp Glu Leu Leu
            1220             1225             1230

Phe Pro Ser Trp Glu Ala Leu Phe Ser Gly Ser Glu Gly Pro Leu Lys
            1235             1240             1245

Pro Gly Ala Arg Ile Phe Ser Phe Asp Gly Lys Asp Val Leu Arg His
1250             1255             1260

Pro Thr Trp Pro Gln Lys Ser Val Trp His Gly Ser Asp Pro Asn Gly
1265             1270             1275                 1280

Arg Arg Leu Thr Glu Ser Tyr Cys Glu Thr Trp Arg Thr Glu Ala Pro
            1285             1290             1295

Ser Ala Thr Gly Gln Ala Ser Ser Leu Leu Gly Gly Arg Leu Leu Gly
            1300             1305             1310

Gln Ser Ala Ala Ser Cys His His Ala Tyr Ile Val Leu Cys Ile Glu
            1315             1320             1325

Asn Ser Phe Met Thr Ala Ser Lys
            1330             1335

<210> SEQ ID NO 83
<211> LENGTH: 1670
```

```
<212> TYPE: PRT
<213> ORGANISM: Homo sapiens

<400> SEQUENCE: 83

Met Ser Ala Arg Thr Ala Pro Arg Pro Gln Val Leu Leu Pro Leu
  1               5                  10                  15

Leu Leu Val Leu Leu Ala Ala Pro Ala Ala Ser Lys Gly Cys Val
             20                  25                  30

Cys Lys Asp Lys Gly Gln Cys Phe Cys Asp Gly Ala Lys Gly Glu Lys
         35                  40                  45

Gly Glu Lys Gly Phe Pro Gly Pro Pro Gly Ser Pro Gly Gln Lys Gly
     50                  55                  60

Phe Thr Gly Pro Glu Gly Leu Pro Gly Pro Gln Gly Pro Lys Gly Phe
 65                  70                  75                  80

Pro Gly Leu Pro Gly Leu Thr Gly Ser Lys Gly Val Arg Gly Ile Ser
                 85                  90                  95

Gly Leu Pro Gly Phe Ser Gly Ser Pro Gly Leu Pro Gly Thr Pro Gly
            100                 105                 110

Asn Thr Gly Pro Tyr Gly Leu Val Gly Val Pro Gly Cys Ser Gly Ser
            115                 120                 125

Lys Gly Glu Gln Gly Phe Pro Gly Leu Pro Gly Thr Leu Gly Tyr Pro
        130                 135                 140

Gly Ile Pro Gly Ala Ala Gly Leu Lys Gly Gln Lys Gly Ala Pro Ala
145                 150                 155                 160

Lys Glu Glu Asp Ile Glu Leu Asp Ala Lys Gly Asp Pro Gly Leu Pro
                165                 170                 175

Gly Ala Pro Gly Pro Gln Gly Leu Pro Gly Pro Gly Phe Pro Gly
            180                 185                 190

Pro Val Gly Pro Pro Gly Pro Pro Gly Phe Phe Gly Phe Pro Gly Ala
            195                 200                 205

Met Gly Pro Arg Gly Pro Lys Gly His Met Gly Glu Arg Val Ile Gly
        210                 215                 220

His Lys Gly Glu Arg Gly Val Lys Gly Leu Thr Gly Pro Pro Gly Pro
225                 230                 235                 240

Pro Gly Thr Val Ile Val Thr Leu Thr Gly Pro Asp Asn Arg Thr Asp
                245                 250                 255

Leu Lys Gly Glu Lys Gly Asp Lys Gly Ala Met Gly Glu Pro Gly Pro
            260                 265                 270

Pro Gly Pro Ser Gly Leu Pro Gly Glu Ser Tyr Gly Ser Glu Lys Gly
        275                 280                 285

Ala Pro Gly Asp Pro Gly Leu Gln Gly Lys Pro Gly Lys Asp Gly Val
    290                 295                 300

Pro Gly Phe Pro Gly Ser Glu Gly Val Lys Gly Asn Arg Gly Phe Pro
305                 310                 315                 320

Gly Leu Met Gly Glu Asp Gly Ile Lys Gly Gln Lys Gly Asp Ile Gly
                325                 330                 335

Pro Pro Gly Phe Arg Gly Pro Thr Glu Tyr Tyr Asp Thr Tyr Gln Glu
            340                 345                 350

Lys Gly Asp Glu Gly Thr Pro Gly Pro Pro Gly Pro Arg Gly Ala Arg
        355                 360                 365

Gly Pro Gln Gly Pro Ser Gly Pro Pro Gly Val Pro Gly Ser Pro Gly
    370                 375                 380

Ser Ser Arg Pro Gly Leu Arg Gly Ala Pro Gly Trp Pro Gly Leu Lys
385                 390                 395                 400
```

-continued

```
Gly Ser Lys Gly Glu Arg Gly Pro Lys Asp Ala Met Gly Thr
            405                 410                 415
Pro Gly Ser Pro Gly Cys Ala Gly Ser Pro Gly Leu Pro Gly Ser Pro
        420                 425                 430
Gly Pro Pro Gly Pro Pro Gly Asp Ile Val Phe Arg Lys Gly Pro Pro
            435                 440                 445
Gly Asp His Gly Leu Pro Gly Tyr Leu Gly Ser Pro Gly Ile Pro Gly
        450                 455                 460
Val Asp Gly Pro Lys Gly Glu Pro Gly Leu Leu Cys Thr Gln Cys Pro
465                 470                 475                 480
Tyr Ile Pro Gly Pro Pro Gly Leu Pro Gly Leu Pro Gly Leu His Gly
                485                 490                 495
Val Lys Gly Ile Pro Gly Arg Gln Gly Ala Ala Gly Leu Lys Gly Ser
            500                 505                 510
Pro Gly Ser Pro Gly Asn Thr Gly Leu Pro Gly Phe Pro Gly Phe Pro
        515                 520                 525
Gly Ala Gln Gly Asp Pro Gly Leu Lys Gly Glu Lys Gly Glu Thr Leu
    530                 535                 540
Gln Pro Glu Gly Gln Val Gly Val Pro Gly Asp Pro Gly Leu Arg Gly
545                 550                 555                 560
Gln Pro Gly Arg Lys Gly Leu Asp Gly Ile Pro Gly Thr Pro Gly Val
                565                 570                 575
Lys Gly Leu Pro Gly Pro Lys Gly Glu Leu Ala Leu Ser Gly Glu Lys
            580                 585                 590
Gly Asp Gln Gly Pro Pro Gly Asp Pro Gly Ser Pro Gly Ser Pro Gly
    595                 600                 605
Pro Ala Gly Pro Ala Gly Pro Pro Gly Tyr Gly Pro Gln Gly Glu Pro
    610                 615                 620
Gly Leu Gln Gly Thr Gln Gly Val Pro Gly Ala Pro Gly Pro Pro Gly
625                 630                 635                 640
Glu Ala Gly Pro Arg Gly Glu Leu Ser Val Ser Thr Pro Val Pro Gly
                645                 650                 655
Pro Pro Gly Pro Pro Gly Pro Pro Gly His Pro Gly Pro Gln Gly Pro
            660                 665                 670
Pro Gly Ile Pro Gly Ser Leu Gly Lys Cys Gly Asp Pro Gly Leu Pro
        675                 680                 685
Gly Pro Asp Gly Glu Pro Gly Ile Pro Gly Ile Gly Phe Pro Gly Pro
    690                 695                 700
Pro Gly Pro Lys Gly Asp Gln Gly Phe Pro Gly Thr Lys Gly Ser Leu
705                 710                 715                 720
Gly Cys Pro Gly Lys Met Gly Glu Pro Gly Leu Pro Gly Lys Pro Gly
                725                 730                 735
Leu Pro Gly Ala Lys Gly Glu Pro Ala Val Ala Met Pro Gly Gly Pro
            740                 745                 750
Gly Thr Pro Gly Phe Pro Gly Glu Arg Gly Asn Ser Gly Glu His Gly
        755                 760                 765
Glu Ile Gly Leu Pro Gly Leu Pro Gly Leu Pro Gly Thr Pro Gly Asn
    770                 775                 780
Glu Gly Leu Asp Gly Pro Arg Gly Asp Pro Gly Gln Pro Gly Pro Pro
785                 790                 795                 800
Gly Glu Gln Gly Pro Pro Gly Arg Cys Ile Glu Gly Pro Arg Gly Ala
                805                 810                 815
Gln Gly Leu Pro Gly Leu Asn Gly Leu Lys Gly Gln Gln Gly Arg Arg
            820                 825                 830
```

```
Gly Lys Thr Gly Pro Lys Gly Asp Pro Gly Ile Pro Gly Leu Asp Arg
        835                 840                 845

Ser Gly Phe Pro Gly Glu Thr Gly Ser Pro Gly Ile Pro Gly His Gln
    850                 855                 860

Gly Glu Met Gly Pro Leu Gly Gln Arg Gly Tyr Pro Gly Asn Pro Gly
865                 870                 875                 880

Ile Leu Gly Pro Pro Gly Glu Asp Gly Val Ile Gly Met Met Gly Phe
                885                 890                 895

Pro Gly Ala Ile Gly Pro Pro Gly Pro Pro Gly Asn Pro Gly Thr Pro
            900                 905                 910

Gly Gln Arg Gly Ser Pro Gly Ile Pro Gly Val Lys Gly Gln Arg Gly
        915                 920                 925

Thr Pro Gly Ala Lys Gly Glu Gln Gly Asp Lys Gly Asn Pro Gly Pro
    930                 935                 940

Ser Glu Ile Ser His Val Ile Gly Asp Lys Gly Glu Pro Gly Leu Lys
945                 950                 955                 960

Gly Phe Ala Gly Asn Pro Gly Glu Lys Gly Asn Arg Gly Val Pro Gly
                965                 970                 975

Met Pro Gly Leu Lys Gly Leu Lys Gly Leu Pro Gly Pro Ala Gly Pro
            980                 985                 990

Pro Gly Pro Arg Gly Asp Leu Gly Ser Thr Gly Asn Pro Gly Glu Pro
        995                 1000                1005

Gly Leu Arg Gly Ile Pro Gly Ser Met Gly Asn Met Gly Met Pro Gly
    1010                1015                1020

Ser Lys Gly Lys Arg Gly Thr Leu Gly Phe Pro Gly Arg Ala Gly Arg
1025                1030                1035                1040

Pro Gly Leu Pro Gly Ile His Gly Leu Gln Gly Asp Lys Gly Glu Pro
                1045                1050                1055

Gly Tyr Ser Glu Gly Thr Arg Pro Gly Pro Pro Gly Pro Thr Gly Asp
            1060                1065                1070

Pro Gly Leu Pro Gly Asp Met Gly Lys Lys Gly Glu Met Gly Gln Pro
        1075                1080                1085

Gly Pro Pro Gly His Leu Gly Pro Ala Gly Pro Glu Gly Ala Pro Gly
    1090                1095                1100

Ser Pro Gly Ser Pro Gly Leu Pro Gly Lys Pro Gly Pro His Gly Asp
1105                1110                1115                1120

Leu Gly Phe Lys Gly Ile Lys Gly Leu Leu Gly Pro Pro Gly Ile Arg
                1125                1130                1135

Gly Pro Pro Gly Leu Pro Gly Phe Pro Gly Ser Pro Gly Pro Met Gly
            1140                1145                1150

Ile Arg Gly Asp Gln Gly Arg Asp Gly Ile Pro Gly Pro Ala Gly Glu
        1155                1160                1165

Lys Gly Glu Thr Gly Leu Leu Arg Ala Pro Gly Pro Arg Gly Asn
    1170                1175                1180

Pro Gly Ala Gln Gly Ala Lys Gly Asp Arg Gly Ala Pro Gly Phe Pro
1185                1190                1195                1200

Gly Leu Pro Gly Arg Lys Gly Ala Met Gly Asp Ala Gly Pro Arg Gly
                1205                1210                1215

Pro Thr Gly Ile Glu Gly Phe Pro Gly Pro Gly Leu Pro Gly Ala
            1220                1225                1230

Ile Ile Pro Gly Gln Thr Gly Asn Arg Gly Pro Pro Gly Ser Arg Gly
        1235                1240                1245

Ser Pro Gly Ala Pro Gly Pro Pro Gly Pro Pro Gly Ser His Val Ile
```

```
                  1250           1255           1260
Gly Ile Lys Gly Asp Lys Gly Ser Met Gly His Pro Gly Pro Lys Gly
1265           1270           1275           1280

Pro Pro Gly Thr Ala Gly Asp Met Gly Pro Pro Gly Arg Leu Gly Ala
            1285           1290           1295

Pro Gly Thr Pro Gly Leu Pro Gly Pro Arg Gly Asp Pro Gly Phe Gln
        1300           1305           1310

Gly Phe Pro Gly Val Lys Gly Glu Lys Gly Asn Pro Gly Phe Leu Gly
    1315           1320           1325

Ser Ile Gly Pro Pro Gly Pro Ile Gly Lys Gly Pro Pro Gly Val
    1330           1335           1340

Arg Gly Asp Pro Gly Thr Leu Lys Ile Ile Ser Leu Pro Gly Ser Pro
1345           1350           1355           1360

Gly Pro Pro Gly Thr Pro Gly Glu Pro Gly Met Gln Gly Glu Pro Gly
            1365           1370           1375

Pro Pro Gly Pro Pro Gly Asn Leu Gly Pro Cys Gly Pro Arg Gly Lys
        1380           1385           1390

Pro Gly Lys Asp Gly Lys Pro Gly Thr Pro Gly Pro Ala Gly Glu Lys
    1395           1400           1405

Gly Asn Lys Gly Ser Lys Gly Glu Pro Gly Pro Ala Gly Ser Asp Gly
    1410           1415           1420

Leu Pro Gly Leu Lys Gly Lys Arg Gly Asp Ser Gly Ser Pro Ala Thr
1425           1430           1435           1440

Trp Thr Thr Arg Gly Phe Val Phe Thr Arg His Ser Gln Thr Thr Ala
            1445           1450           1455

Ile Pro Ser Cys Pro Glu Gly Thr Val Pro Leu Tyr Ser Gly Phe Ser
        1460           1465           1470

Phe Leu Phe Val Gln Gly Asn Gln Arg Ala His Gly Gln Asp Leu Gly
    1475           1480           1485

Thr Leu Gly Ser Cys Leu Gln Arg Phe Thr Thr Met Pro Phe Leu Phe
    1490           1495           1500

Cys Asn Val Asn Asp Val Cys Asn Phe Ala Ser Arg Asn Asp Tyr Ser
1505           1510           1515           1520

Tyr Trp Leu Ser Thr Pro Ala Leu Met Pro Met Asn Met Ala Pro Ile
            1525           1530           1535

Thr Gly Arg Ala Leu Glu Pro Tyr Ile Ser Arg Cys Thr Val Cys Glu
            1540           1545           1550

Gly Pro Ala Ile Ala Ile Ala Val His Ser Gln Thr Thr Asp Ile Pro
        1555           1560           1565

Pro Cys Pro His Gly Trp Ile Ser Leu Trp Lys Gly Phe Ser Phe Ile
    1570           1575           1580

Met Phe Thr Ser Ala Gly Ser Glu Gly Thr Gly Gln Ala Leu Ala Ser
1585           1590           1595           1600

Pro Gly Ser Cys Leu Glu Glu Phe Arg Ala Ser Pro Phe Leu Glu Cys
            1605           1610           1615

His Gly Arg Gly Thr Cys Asn Tyr Tyr Ser Asn Ser Tyr Ser Phe Trp
            1620           1625           1630

Leu Ala Ser Leu Asn Pro Glu Arg Met Phe Arg Lys Pro Ile Pro Ser
        1635           1640           1645

Thr Val Lys Ala Gly Glu Leu Glu Lys Ile Ile Ser Arg Cys Gln Val
    1650           1655           1660

Cys Met Lys Lys Arg His
1665           1670
```

```
<210> SEQ ID NO 84
<211> LENGTH: 1712
<212> TYPE: PRT
<213> ORGANISM: Homo sapiens

<400> SEQUENCE: 84

Met Gly Arg Asp Gln Arg Ala Val Ala Gly Pro Ala Leu Arg Arg Trp
  1               5                  10                  15

Leu Leu Leu Gly Thr Val Thr Val Gly Phe Leu Ala Gln Ser Val Leu
             20                  25                  30

Ala Gly Val Lys Lys Phe Asp Val Pro Cys Gly Gly Arg Asp Cys Ser
         35                  40                  45

Gly Gly Cys Gln Cys Tyr Pro Glu Lys Gly Arg Gly Gln Pro Gly Gly
     50                  55                  60

Pro Val Gly Pro Gln Gly Tyr Asn Gly Pro Pro Gly Leu Gln Gly Phe
 65                  70                  75                  80

Pro Gly Leu Gln Gly Arg Lys Gly Asp Lys Gly Glu Arg Gly Ala Pro
                 85                  90                  95

Gly Val Thr Gly Pro Lys Gly Asp Val Gly Ala Arg Gly Val Ser Gly
            100                 105                 110

Phe Pro Gly Ala Asp Gly Ile Pro Gly His Pro Gly Gln Gly Gly Pro
        115                 120                 125

Arg Gly Arg Pro Gly Tyr Asp Gly Cys Asn Gly Thr Gln Gly Asp Ser
    130                 135                 140

Gly Pro Gln Gly Pro Pro Gly Ser Glu Gly Phe Thr Gly Pro Pro Gly
145                 150                 155                 160

Pro Gln Gly Pro Lys Gly Gln Lys Gly Glu Pro Tyr Ala Leu Pro Lys
                165                 170                 175

Glu Glu Arg Asp Arg Tyr Arg Gly Glu Pro Gly Glu Pro Gly Leu Val
            180                 185                 190

Gly Phe Gln Gly Pro Pro Gly Arg Pro Gly His Val Gly Gln Met Gly
        195                 200                 205

Pro Val Gly Ala Pro Gly Arg Pro Gly Pro Pro Gly Pro Pro Gly Pro
    210                 215                 220

Lys Gly Gln Gln Gly Asn Arg Gly Leu Gly Phe Tyr Gly Val Lys Gly
225                 230                 235                 240

Glu Lys Gly Asp Val Gly Gln Pro Gly Pro Asn Gly Ile Pro Ser Asp
                245                 250                 255

Thr Leu His Pro Ile Ile Ala Pro Thr Gly Val Thr Phe His Pro Asp
            260                 265                 270

Gln Tyr Lys Gly Glu Lys Gly Ser Glu Gly Glu Pro Gly Ile Arg Gly
        275                 280                 285

Ile Ser Leu Lys Gly Glu Glu Gly Ile Met Gly Phe Pro Gly Leu Arg
    290                 295                 300

Gly Tyr Pro Gly Leu Ser Gly Glu Lys Gly Ser Pro Gly Gln Lys Gly
305                 310                 315                 320

Ser Arg Gly Leu Asp Gly Tyr Gln Gly Pro Asp Gly Pro Arg Gly Pro
                325                 330                 335

Lys Gly Glu Ala Gly Asp Pro Gly Pro Pro Gly Leu Pro Ala Tyr Ser
            340                 345                 350

Pro His Pro Ser Leu Ala Lys Gly Ala Arg Gly Asp Pro Gly Phe Pro
        355                 360                 365

Gly Ala Gln Gly Glu Pro Gly Ser Gln Gly Glu Pro Gly Asp Pro Gly
    370                 375                 380
```

-continued

```
Leu Pro Gly Pro Pro Gly Leu Ser Ile Gly Asp Gly Gln Arg Arg
385                 390                 395                 400

Gly Leu Pro Gly Glu Met Gly Pro Lys Gly Phe Ile Gly Asp Pro Gly
            405                 410                 415

Ile Pro Ala Leu Tyr Gly Gly Pro Pro Gly Asp Gly Lys Arg Gly
            420                 425                 430

Pro Pro Gly Pro Pro Gly Leu Pro Gly Pro Pro Gly Pro Asp Gly Phe
            435                 440                 445

Leu Phe Gly Leu Lys Gly Ala Lys Gly Arg Ala Gly Phe Pro Gly Leu
450                 455                 460

Pro Gly Ser Pro Gly Ala Arg Gly Pro Lys Gly Trp Lys Gly Asp Ala
465                 470                 475                 480

Gly Glu Cys Arg Cys Thr Glu Gly Asp Glu Ala Ile Lys Gly Leu Pro
            485                 490                 495

Gly Leu Pro Gly Pro Lys Gly Phe Ala Gly Ile Asn Gly Glu Pro Gly
            500                 505                 510

Arg Lys Gly Asp Arg Gly Asp Pro Gly Gln His Gly Leu Pro Gly Phe
            515                 520                 525

Pro Gly Leu Lys Gly Val Pro Gly Asn Ile Gly Ala Pro Gly Pro Lys
            530                 535                 540

Gly Ala Lys Gly Asp Ser Arg Thr Ile Thr Thr Lys Gly Glu Arg Gly
545                 550                 555                 560

Gln Pro Gly Val Pro Gly Val Pro Gly Met Lys Gly Asp Asp Gly Ser
            565                 570                 575

Pro Gly Arg Asp Gly Leu Asp Gly Phe Pro Gly Leu Pro Gly Pro Pro
            580                 585                 590

Gly Asp Gly Ile Lys Gly Pro Pro Gly Asp Pro Gly Tyr Pro Gly Ile
            595                 600                 605

Pro Gly Thr Lys Gly Thr Pro Gly Glu Met Gly Pro Pro Gly Leu Gly
            610                 615                 620

Leu Pro Gly Leu Lys Gly Gln Arg Gly Phe Pro Gly Asp Ala Gly Leu
625                 630                 635                 640

Pro Gly Pro Pro Gly Phe Leu Gly Pro Pro Gly Pro Ala Gly Thr Pro
            645                 650                 655

Gly Gln Ile Asp Cys Asp Thr Asp Val Lys Arg Ala Val Gly Gly Asp
            660                 665                 670

Arg Gln Glu Ala Ile Gln Pro Gly Cys Ile Gly Gly Pro Lys Gly Leu
            675                 680                 685

Pro Gly Leu Pro Gly Pro Gly Pro Thr Gly Ala Lys Gly Leu Arg
            690                 695                 700

Gly Ile Pro Gly Phe Ala Gly Ala Asp Gly Gly Pro Gly Pro Arg Gly
705                 710                 715                 720

Leu Pro Gly Asp Ala Gly Arg Glu Gly Phe Pro Gly Pro Gly Phe
            725                 730                 735

Ile Gly Pro Arg Gly Ser Lys Gly Ala Val Gly Leu Pro Gly Pro Asp
            740                 745                 750

Gly Ser Pro Gly Pro Ile Gly Leu Pro Gly Pro Asp Gly Pro Gly
            755                 760                 765

Glu Arg Gly Leu Pro Gly Glu Val Leu Gly Ala Gln Pro Gly Pro Arg
            770                 775                 780

Gly Asp Ala Gly Val Pro Gly Gln Pro Gly Leu Lys Gly Leu Pro Gly
785                 790                 795                 800

Asp Arg Gly Pro Pro Gly Phe Arg Gly Ser Gln Gly Met Pro Gly Met
            805                 810                 815
```

Pro Gly Leu Lys Gly Gln Pro Gly Leu Pro Gly Pro Ser Gly Gln Pro
            820                 825                 830

Gly Leu Tyr Gly Pro Pro Gly Leu His Gly Phe Pro Gly Ala Pro Gly
        835                 840                 845

Gln Glu Gly Pro Leu Gly Leu Pro Gly Ile Pro Gly Arg Glu Gly Leu
850                 855                 860

Pro Gly Asp Arg Gly Asp Pro Gly Asp Thr Gly Ala Pro Gly Pro Val
865                 870                 875                 880

Gly Met Lys Gly Leu Ser Gly Asp Arg Gly Asp Ala Gly Phe Thr Gly
            885                 890                 895

Glu Gln Gly His Pro Gly Ser Pro Gly Phe Lys Gly Ile Asp Gly Met
                900                 905                 910

Pro Gly Thr Pro Gly Leu Lys Gly Asp Arg Gly Ser Pro Gly Met Asp
        915                 920                 925

Gly Phe Gln Gly Met Pro Gly Leu Lys Gly Arg Pro Gly Phe Pro Gly
    930                 935                 940

Ser Lys Gly Glu Ala Gly Phe Phe Gly Ile Pro Gly Leu Lys Gly Leu
945                 950                 955                 960

Ala Gly Glu Pro Gly Phe Lys Gly Ser Arg Gly Asp Pro Gly Pro Pro
            965                 970                 975

Gly Pro Pro Val Ile Leu Pro Gly Met Lys Asp Ile Lys Gly Glu
                980                 985                 990

Lys Gly Asp Glu Gly Pro Met Gly Leu Lys Gly Tyr Leu Gly Ala Lys
        995                 1000                1005

Gly Ile Gln Gly Met Pro Gly Ile Pro Gly Leu Ser Gly Ile Pro Gly
    1010                1015                1020

Leu Pro Gly Arg Pro Gly His Ile Lys Gly Val Lys Gly Asp Ile Gly
1025                1030                1035                1040

Val Pro Gly Ile Pro Gly Leu Pro Gly Phe Pro Gly Val Ala Gly Pro
            1045                1050                1055

Pro Gly Ile Thr Gly Phe Pro Gly Phe Ile Gly Ser Arg Gly Asp Lys
                1060                1065                1070

Gly Ala Pro Gly Arg Ala Gly Leu Tyr Gly Glu Ile Gly Ala Thr Gly
        1075                1080                1085

Asp Phe Gly Asp Ile Gly Asp Thr Ile Asn Leu Pro Gly Arg Pro Gly
    1090                1095                1100

Leu Lys Gly Glu Arg Gly Thr Thr Gly Ile Pro Gly Leu Lys Gly Phe
1105                1110                1115                1120

Phe Gly Glu Lys Gly Thr Glu Gly Asp Ile Gly Phe Pro Gly Ile Thr
            1125                1130                1135

Gly Val Thr Gly Val Gln Gly Pro Pro Gly Leu Lys Gly Gln Thr Gly
                1140                1145                1150

Phe Pro Gly Leu Thr Gly Pro Pro Gly Ser Gln Gly Glu Leu Gly Arg
        1155                1160                1165

Ile Gly Leu Pro Gly Gly Lys Gly Asp Asp Gly Trp Pro Gly Ala Pro
    1170                1175                1180

Gly Leu Pro Gly Phe Pro Gly Leu Arg Gly Ile Arg Gly Leu His Gly
1185                1190                1195                1200

Leu Pro Gly Thr Lys Gly Phe Pro Gly Ser Pro Gly Ser Asp Ile His
            1205                1210                1215

Gly Asp Pro Gly Phe Pro Gly Pro Pro Gly Glu Arg Gly Asp Pro Gly
                1220                1225                1230

Glu Ala Asn Thr Leu Pro Gly Pro Val Gly Val Pro Gly Gln Lys Gly

-continued

```
            1235                1240                1245
Asp Gln Gly Ala Pro Gly Glu Arg Gly Pro Pro Gly Ser Pro Gly Leu
        1250                1255                1260
Gln Gly Phe Pro Gly Ile Thr Pro Pro Ser Asn Ile Ser Gly Ala Pro
1265                1270                1275                1280
Gly Asp Lys Gly Ala Pro Gly Ile Phe Gly Leu Lys Gly Tyr Arg Gly
            1285                1290                1295
Pro Pro Gly Pro Pro Gly Ser Ala Ala Leu Pro Gly Ser Lys Gly Asp
        1300                1305                1310
Thr Gly Asn Pro Gly Ala Pro Gly Thr Pro Gly Thr Lys Gly Trp Ala
            1315                1320                1325
Gly Asp Ser Gly Pro Gln Gly Arg Pro Gly Val Phe Gly Leu Pro Gly
        1330                1335                1340
Glu Lys Gly Pro Arg Gly Glu Gln Gly Phe Met Gly Asn Thr Gly Pro
1345                1350                1355                1360
Thr Gly Ala Val Gly Asp Arg Gly Pro Lys Gly Pro Lys Gly Asp Pro
            1365                1370                1375
Gly Phe Pro Gly Ala Pro Gly Thr Val Gly Ala Pro Gly Ile Ala Gly
        1380                1385                1390
Ile Pro Gln Lys Ile Ala Val Gln Pro Gly Thr Val Gly Pro Gln Gly
            1395                1400                1405
Arg Arg Gly Pro Pro Gly Ala Pro Gly Glu Met Gly Pro Gln Gly Pro
        1410                1415                1420
Pro Gly Glu Pro Gly Phe Arg Gly Ala Pro Gly Lys Ala Gly Pro Gln
1425                1430                1435                1440
Gly Arg Gly Gly Val Ser Ala Val Pro Gly Phe Arg Gly Asp Glu Gly
            1445                1450                1455
Pro Ile Gly His Gln Gly Pro Ile Gly Gln Glu Gly Ala Pro Gly Arg
        1460                1465                1470
Pro Gly Ser Pro Gly Leu Pro Gly Met Pro Gly Arg Ser Val Ser Ile
            1475                1480                1485
Gly Tyr Leu Leu Val Lys His Ser Gln Thr Asp Gln Glu Pro Met Cys
        1490                1495                1500
Pro Val Gly Met Asn Lys Leu Trp Ser Gly Tyr Ser Leu Leu Tyr Phe
1505                1510                1515                1520
Glu Gly Gln Glu Lys Ala His Asn Gln Asp Leu Gly Leu Ala Gly Ser
            1525                1530                1535
Cys Leu Ala Arg Phe Ser Thr Met Pro Phe Leu Tyr Cys Asn Pro Gly
            1540                1545                1550
Asp Val Cys Tyr Tyr Ala Ser Arg Asn Asp Lys Ser Tyr Trp Leu Ser
        1555                1560                1565
Thr Thr Ala Pro Leu Pro Met Met Pro Val Ala Glu Asp Glu Ile Lys
        1570                1575                1580
Pro Tyr Ile Ser Arg Cys Ser Val Cys Glu Ala Pro Ala Ile Ala Ile
1585                1590                1595                1600
Ala Val His Ser Gln Asp Val Ser Ile Pro His Cys Pro Ala Gly Trp
            1605                1610                1615
Arg Ser Leu Trp Ile Gly Tyr Ser Phe Leu Met His Thr Ala Ala Gly
            1620                1625                1630
Asp Glu Gly Gly Gly Gln Ser Leu Val Ser Pro Gly Ser Cys Leu Glu
        1635                1640                1645
Asp Phe Arg Ala Thr Pro Phe Ile Glu Cys Asn Gly Gly Arg Gly Thr
        1650                1655                1660
```

```
Cys His Tyr Tyr Ala Asn Lys Tyr Ser Phe Trp Leu Thr Thr Ile Pro
1665                1670                1675                1680

Glu Gln Ser Phe Gln Gly Ser Pro Ser Ala Asp Thr Leu Lys Ala Gly
            1685                1690                1695

Leu Ile Arg Thr His Ile Ser Arg Cys Gln Val Cys Met Lys Asn Leu
        1700                1705                1710

<210> SEQ ID NO 85
<211> LENGTH: 1427
<212> TYPE: PRT
<213> ORGANISM: Homo sapiens

<400> SEQUENCE: 85

Met Ser Met Leu Lys Pro Ser Gly Leu Lys Ala Pro Thr Lys Ile Leu
1               5                   10                  15

Lys Pro Gly Ser Thr Ala Leu Lys Thr Pro Thr Ala Val Val Ala Pro
            20                  25                  30

Val Glu Lys Thr Ile Ser Ser Glu Lys Ala Ser Ser Thr Pro Ser Ser
        35                  40                  45

Glu Thr Gln Glu Glu Phe Val Asp Asp Phe Arg Val Gly Glu Arg Val
    50                  55                  60

Trp Val Asn Gly Asn Lys Pro Gly Phe Ile Gln Phe Leu Gly Glu Thr
65                  70                  75                  80

Gln Phe Ala Pro Gly Gln Trp Ala Gly Ile Val Leu Asp Glu Pro Ile
                85                  90                  95

Gly Lys Asn Asp Gly Ser Val Ala Gly Val Arg Tyr Phe Gln Cys Glu
            100                 105                 110

Pro Leu Lys Gly Ile Phe Thr Arg Pro Ser Lys Leu Thr Arg Lys Val
        115                 120                 125

Gln Ala Glu Asp Glu Ala Asn Gly Leu Gln Thr Thr Pro Ala Ser Arg
    130                 135                 140

Ala Thr Ser Pro Leu Cys Thr Ser Thr Ala Ser Met Val Ser Ser Ser
145                 150                 155                 160

Pro Ser Thr Pro Ser Asn Ile Pro Gln Lys Pro Ser Gln Pro Ala Ala
                165                 170                 175

Lys Glu Pro Ser Ala Thr Pro Pro Ile Ser Asn Leu Thr Lys Thr Ala
            180                 185                 190

Ser Glu Ser Ile Ser Asn Leu Ser Glu Ala Gly Ser Ile Lys Lys Gly
        195                 200                 205

Glu Arg Glu Leu Lys Ile Gly Asp Arg Val Leu Val Gly Gly Thr Lys
    210                 215                 220

Ala Gly Val Val Arg Phe Leu Gly Glu Thr Asp Phe Ala Lys Gly Glu
225                 230                 235                 240

Trp Cys Gly Val Glu Leu Asp Glu Pro Leu Gly Lys Asn Asp Gly Ala
                245                 250                 255

Val Ala Gly Thr Arg Tyr Phe Gln Cys Gln Pro Lys Tyr Gly Leu Phe
            260                 265                 270

Ala Pro Val His Lys Val Thr Lys Ile Gly Phe Pro Ser Thr Thr Pro
        275                 280                 285

Ala Lys Ala Lys Ala Asn Ala Val Arg Arg Val Met Ala Thr Thr Ser
    290                 295                 300

Ala Ser Leu Lys Arg Ser Pro Ser Ala Ser Ser Leu Ser Ser Met Ser
305                 310                 315                 320

Ser Val Ala Ser Ser Val Ser Ser Arg Pro Ser Arg Thr Gly Leu Leu
                325                 330                 335
```

-continued

```
Thr Glu Thr Ser Ser Arg Tyr Ala Arg Lys Ile Ser Gly Thr Thr Ala
            340                 345                 350

Leu Gln Glu Ala Leu Lys Glu Gln Gln His Ile Glu Gln Leu Leu
            355                 360                 365

Ala Glu Arg Asp Leu Glu Arg Ala Glu Val Ala Lys Ala Thr Ser His
370                 375                 380

Val Gly Glu Ile Glu Gln Glu Leu Ala Leu Ala Arg Asp Gly His Asp
385                 390                 395                 400

Gln His Val Leu Glu Leu Glu Ala Lys Met Asp Gln Leu Arg Thr Met
                405                 410                 415

Val Glu Ala Ala Asp Arg Glu Lys Val Glu Leu Leu Asn Gln Leu Glu
            420                 425                 430

Glu Glu Lys Arg Lys Val Glu Asp Leu Gln Phe Arg Val Glu Glu Glu
            435                 440                 445

Ser Ile Thr Lys Gly Asp Leu Glu Thr Gln Thr Lys Leu Glu His Ala
            450                 455                 460

Arg Ile Lys Glu Leu Glu Gln Ser Leu Leu Phe Glu Lys Thr Lys Ala
465                 470                 475                 480

Asp Lys Leu Gln Arg Glu Leu Glu Asp Thr Arg Val Ala Thr Val Ser
                485                 490                 495

Glu Lys Ser Arg Ile Met Glu Leu Glu Lys Asp Leu Ala Leu Arg Val
            500                 505                 510

Gln Glu Val Ala Glu Leu Arg Arg Arg Leu Glu Ser Asn Lys Pro Ala
            515                 520                 525

Gly Asp Val Asp Met Ser Leu Ser Leu Leu Gln Glu Ile Ser Ser Leu
            530                 535                 540

Gln Glu Lys Leu Glu Val Thr Arg Thr Asp His Gln Arg Glu Ile Thr
545                 550                 555                 560

Ser Leu Lys Glu His Phe Gly Ala Arg Glu Glu Thr His Gln Lys Glu
                565                 570                 575

Ile Lys Ala Leu Tyr Thr Ala Thr Glu Lys Leu Ser Lys Glu Asn Glu
            580                 585                 590

Ser Leu Lys Ser Lys Leu Glu His Ala Asn Lys Glu Asn Ser Asp Val
            595                 600                 605

Ile Ala Leu Trp Lys Ser Lys Leu Glu Thr Ala Ile Ala Ser His Gln
            610                 615                 620

Gln Ala Met Glu Glu Leu Lys Val Ser Phe Ser Lys Gly Leu Gly Thr
625                 630                 635                 640

Glu Thr Ala Glu Phe Ala Glu Leu Lys Thr Gln Ile Glu Lys Met Arg
                645                 650                 655

Leu Asp Tyr Gln His Glu Ile Glu Asn Leu Gln Asn Gln Gln Asp Ser
            660                 665                 670

Glu Arg Ala Ala His Ala Lys Glu Met Glu Ala Leu Arg Ala Lys Leu
            675                 680                 685

Met Lys Val Ile Lys Glu Lys Glu Asn Ser Leu Glu Ala Ile Arg Ser
690                 695                 700

Lys Leu Asp Lys Ala Glu Asp Gln His Leu Val Glu Met Glu Asp Thr
705                 710                 715                 720

Leu Asn Lys Leu Gln Glu Ala Glu Ile Lys Val Lys Glu Leu Glu Val
                725                 730                 735

Leu Gln Ala Lys Cys Asn Glu Gln Thr Lys Val Ile Asp Asn Phe Thr
            740                 745                 750

Ser Gln Leu Lys Ala Thr Glu Glu Lys Leu Leu Asp Leu Asp Ala Leu
            755                 760                 765
```

```
Arg Lys Ala Ser Ser Glu Gly Lys Ser Glu Met Lys Lys Leu Arg Gln
    770                 775                 780

Gln Leu Glu Ala Ala Glu Lys Gln Ile Lys His Leu Glu Ile Glu Lys
785                 790                 795                 800

Asn Ala Glu Ser Ser Lys Ala Ser Ser Ile Thr Arg Glu Leu Gln Gly
                805                 810                 815

Arg Glu Leu Lys Leu Thr Asn Leu Gln Glu Asn Leu Ser Glu Val Ser
            820                 825                 830

Gln Val Lys Glu Thr Leu Glu Lys Glu Leu Gln Ile Leu Lys Glu Lys
        835                 840                 845

Phe Ala Glu Ala Ser Glu Glu Ala Val Ser Val Gln Arg Ser Met Gln
    850                 855                 860

Glu Thr Val Asn Lys Leu His Gln Lys Glu Glu Gln Phe Asn Met Leu
865                 870                 875                 880

Ser Ser Asp Leu Glu Lys Leu Arg Glu Asn Leu Ala Asp Met Glu Ala
                885                 890                 895

Lys Phe Arg Glu Lys Asp Glu Arg Glu Glu Gln Leu Ile Lys Ala Lys
            900                 905                 910

Glu Lys Leu Glu Asn Asp Ile Ala Glu Ile Met Lys Met Ser Gly Asp
        915                 920                 925

Asn Ser Ser Gln Leu Thr Lys Met Asn Asp Glu Leu Arg Leu Lys Glu
930                 935                 940

Arg Asp Val Glu Glu Leu Gln Leu Lys Leu Thr Lys Ala Asn Glu Asn
945                 950                 955                 960

Ala Ser Phe Leu Gln Lys Ser Ile Glu Asp Met Thr Val Lys Ala Glu
                965                 970                 975

Gln Ser Gln Gln Glu Ala Ala Lys Lys His Glu Glu Glu Lys Lys Glu
            980                 985                 990

Leu Glu Arg Lys Leu Ser Asp Leu Glu Lys Lys Met Glu Thr Ser His
        995                 1000                1005

Asn Gln Cys Gln Glu Leu Lys Ala Arg Tyr Glu Arg Ala Thr Ser Glu
    1010                1015                1020

Thr Lys Thr Lys His Glu Glu Ile Leu Gln Asn Leu Gln Lys Thr Leu
1025                1030                1035                1040

Leu Asp Thr Glu Asp Lys Leu Lys Gly Ala Arg Glu Glu Asn Ser Gly
                1045                1050                1055

Leu Leu Gln Glu Leu Glu Glu Leu Arg Lys Gln Ala Asp Lys Ala Lys
            1060                1065                1070

Ala Ala Gln Thr Ala Glu Asp Ala Met Gln Ile Met Glu Gln Met Thr
        1075                1080                1085

Lys Glu Lys Thr Glu Thr Leu Ala Ser Leu Glu Asp Thr Lys Gln Thr
    1090                1095                1100

Asn Ala Lys Leu Gln Asn Glu Leu Asp Thr Leu Lys Glu Asn Asn Leu
1105                1110                1115                1120

Lys Asn Val Glu Glu Leu Asn Lys Ser Lys Glu Leu Leu Thr Val Glu
                1125                1130                1135

Asn Gln Lys Met Glu Glu Phe Arg Lys Glu Ile Glu Thr Leu Lys Gln
            1140                1145                1150

Ala Ala Ala Gln Lys Ser Gln Gln Leu Ser Ala Leu Gln Glu Glu Asn
        1155                1160                1165

Val Lys Leu Ala Glu Glu Leu Gly Arg Ser Arg Asp Glu Val Thr Ser
    1170                1175                1180

His Gln Lys Leu Glu Glu Glu Arg Ser Val Leu Asn Asn Gln Leu Leu
```

```
                1185                1190                1195                1200
Glu Met Lys Lys Arg Glu Ser Lys Phe Ile Lys Asp Ala Asp Glu Glu
                    1205                1210                1215
Lys Ala Ser Leu Gln Lys Ser Ile Ser Ile Thr Ser Ala Leu Leu Thr
                    1220                1225                1230
Glu Lys Asp Ala Glu Leu Glu Lys Leu Arg Asn Glu Val Thr Val Leu
                    1235                1240                1245
Arg Gly Glu Asn Ala Ser Ala Lys Ser Leu His Ser Val Val Gln Thr
                    1250                1255                1260
Leu Glu Ser Asp Lys Val Lys Leu Glu Leu Lys Val Lys Asn Leu Glu
1265                1270                1275                1280
Leu Gln Leu Lys Glu Asn Lys Arg Gln Leu Ser Ser Ser Gly Asn
                    1285                1290                1295
Thr Asp Thr Gln Ala Asp Glu Asp Glu Arg Ala Gln Glu Ser Gln Ile
                    1300                1305                1310
Asp Phe Leu Asn Ser Val Ile Val Asp Leu Gln Arg Lys Asn Gln Asp
                    1315                1320                1325
Leu Lys Met Lys Val Glu Met Met Ser Glu Ala Ala Leu Asn Gly Asn
                    1330                1335                1340
Gly Asp Asp Leu Asn Asn Tyr Asp Ser Asp Asp Gln Glu Lys Gln Ser
1345                1350                1355                1360
Lys Lys Lys Pro Arg Leu Phe Cys Asp Ile Cys Asp Cys Phe Asp Leu
                    1365                1370                1375
His Asp Thr Glu Asp Cys Pro Thr Gln Ala Gln Met Ser Glu Asp Pro
                    1380                1385                1390
Pro His Ser Thr His His Gly Ser Arg Gly Glu Glu Arg Pro Tyr Cys
                    1395                1400                1405
Glu Ile Cys Glu Met Phe Gly His Trp Ala Thr Asn Cys Asn Asp Asp
                    1410                1415                1420
Glu Thr Phe
1425

<210> SEQ ID NO 86
<211> LENGTH: 251
<212> TYPE: PRT
<213> ORGANISM: Homo sapiens

<400> SEQUENCE: 86

Met Ala Glu Asp Leu Gly Leu Ser Phe Gly Glu Thr Ala Ser Val Glu
1               5                   10                  15
Met Leu Pro Glu His Gly Ser Cys Arg Pro Lys Ala Arg Ser Ser Ser
                20                  25                  30
Ala Arg Trp Ala Leu Thr Cys Cys Leu Val Leu Leu Pro Phe Leu Ala
            35                  40                  45
Gly Leu Thr Thr Tyr Leu Leu Val Ser Gln Leu Arg Ala Gln Gly Glu
        50                  55                  60
Ala Cys Val Gln Phe Gln Ala Leu Lys Gly Gln Glu Phe Ala Pro Ser
65                  70                  75                  80
His Gln Gln Val Tyr Ala Pro Leu Arg Ala Asp Gly Asp Lys Pro Arg
                85                  90                  95
Ala His Leu Thr Val Val Arg Gln Thr Pro Thr Gln His Phe Lys Asn
                100                 105                 110
Gln Phe Pro Ala Leu His Trp Glu His Glu Leu Gly Leu Ala Phe Thr
            115                 120                 125
Lys Asn Arg Met Asn Tyr Thr Asn Lys Phe Leu Leu Ile Pro Glu Ser
```

```
                 130                 135                 140
Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
                    180                 185                 190

Gln Leu Leu Met Gly Thr Lys Ser Val Cys Glu Val Gly Ser Asn Trp
                195                 200                 205

Phe Gln Pro Ile Tyr Leu Gly Ala Met Phe Ser Leu Gln Glu Gly Asp
                210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 87
<211> LENGTH: 498
<212> TYPE: PRT
<213> ORGANISM: Homo sapiens

<400> SEQUENCE: 87

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
                20                  25                  30

Tyr Asn Arg Ile Gln His Gly Gln Cys Ala Tyr Thr Phe Ile Leu Pro
            35                  40                  45

Glu His Asp Gly Asn Cys Arg Glu Ser Thr Thr Asp Gln Tyr Asn Thr
        50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
                100                 105                 110

Ala Gln Ile Gln Gln Asn Ala Val Gln Asn His Thr Ala Thr Met Leu
            115                 120                 125

Glu Ile Gly Thr Ser Leu Leu Ser Gln Thr Ala Glu Gln Thr Arg Lys
        130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
                180                 185                 190

Leu Leu Glu His Lys Ile Leu Glu Met Glu Gly Lys His Lys Glu Glu
            195                 200                 205

Leu Asp Thr Leu Lys Glu Glu Lys Glu Asn Leu Gln Gly Leu Val Thr
        210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
```

```
                        260                 265                 270
Lys Gly Gly Lys Arg Glu Glu Lys Pro Phe Arg Asp Cys Ala Asp
            275                 280                 285

Val Tyr Gln Ala Gly Phe Asn Lys Ser Gly Ile Tyr Thr Ile Tyr Ile
        290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
        435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 88
<211> LENGTH: 227
<212> TYPE: PRT
<213> ORGANISM: Homo sapiens

<400> SEQUENCE: 88

Met Asn Ile Lys Gly Ser Pro Trp Lys Gly Ser Leu Leu Leu Leu Leu
1               5                   10                  15

Val Ser Asn Leu Leu Cys Gln Ser Val Ala Pro Leu Pro Ile Cys
            20                  25                  30

Pro Gly Gly Ala Ala Arg Cys Gln Val Thr Leu Arg Asp Leu Phe Asp
        35                  40                  45

Arg Ala Val Val Leu Ser His Tyr Ile His Asn Leu Ser Ser Glu Met
    50                  55                  60

Phe Ser Glu Phe Asp Lys Arg Tyr Thr His Gly Arg Gly Phe Ile Thr
65                  70                  75                  80

Lys Ala Ile Asn Ser Cys His Thr Ser Ser Leu Ala Thr Pro Glu Asp
                85                  90                  95

Lys Glu Gln Ala Gln Gln Met Asn Gln Lys Asp Phe Leu Ser Leu Ile
            100                 105                 110

Val Ser Ile Leu Arg Ser Trp Asn Glu Pro Leu Tyr His Leu Val Thr
        115                 120                 125

Glu Val Arg Gly Met Gln Glu Ala Pro Glu Ala Ile Leu Ser Lys Ala
    130                 135                 140
```

```
Val Glu Ile Glu Glu Gln Thr Lys Arg Leu Leu Glu Gly Met Glu Leu
145                 150                 155                 160

Ile Val Ser Gln Val His Pro Glu Thr Lys Glu Asn Glu Ile Tyr Pro
            165                 170                 175

Val Trp Ser Gly Leu Pro Ser Leu Gln Met Ala Asp Glu Glu Ser Arg
        180                 185                 190

Leu Ser Ala Tyr Tyr Asn Leu Leu His Cys Leu Arg Arg Asp Ser His
    195                 200                 205

Lys Ile Asp Asn Tyr Leu Lys Leu Leu Lys Cys Arg Ile Ile His Asn
210                 215                 220

Asn Asn Cys
225

<210> SEQ ID NO 89
<211> LENGTH: 4391
<212> TYPE: PRT
<213> ORGANISM: Homo sapiens

<400> SEQUENCE: 89

Met Gly Trp Arg Ala Ala Gly Ala Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
        35                  40                  45

Thr His Ser Tyr Leu Ser Asp Asp Glu Met Leu Ala Asp Ser Ile
    50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
        115                 120                 125

Asp Gln Val Val Ser Val Val Phe Ile Lys Glu Leu Asp Gly Trp Val
130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Glu Phe Ala Cys His Ser
        195                 200                 205

Tyr Asn Glu Cys Val Ala Leu Glu Tyr Arg Cys Asp Arg Arg Pro Asp
    210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
                245                 250                 255

Arg Pro Glu Thr Thr Ile Met Arg Gln Pro Pro Val Thr His Ala Pro
            260                 265                 270

Gln Pro Leu Leu Pro Gly Ser Val Arg Pro Leu Pro Cys Gly Pro Gln
        275                 280                 285
```

```
Glu Ala Ala Cys Arg Asn Gly His Cys Ile Pro Arg Asp Tyr Leu Cys
    290                 295                 300

Asp Gly Gln Glu Asp Cys Glu Asp Gly Ser Asp Glu Leu Asp Cys Gly
305                 310                 315                 320

Pro Pro Pro Cys Glu Pro Asn Glu Phe Pro Cys Gly Asn Gly His
                325                 330                 335

Cys Ala Leu Lys Leu Trp Arg Cys Asp Gly Asp Phe Asp Cys Glu Asp
            340                 345                 350

Arg Thr Asp Glu Ala Asn Cys Pro Thr Lys Arg Pro Glu Glu Val Cys
        355                 360                 365

Gly Pro Thr Gln Phe Arg Cys Val Ser Thr Asn Met Cys Ile Pro Ala
    370                 375                 380

Ser Phe His Cys Asp Glu Glu Ser Asp Cys Pro Asp Arg Ser Asp Glu
385                 390                 395                 400

Phe Gly Cys Met Pro Pro Gln Val Val Thr Pro Pro Arg Glu Ser Ile
                405                 410                 415

Gln Ala Ser Arg Gly Gln Thr Val Thr Phe Thr Cys Val Ala Ile Gly
            420                 425                 430

Val Pro Thr Pro Ile Ile Asn Trp Arg Leu Asn Trp Gly His Ile Pro
        435                 440                 445

Ser His Pro Arg Val Thr Val Thr Ser Glu Gly Gly Arg Gly Thr Leu
    450                 455                 460

Ile Ile Arg Asp Val Lys Glu Ser Asp Gln Gly Ala Tyr Thr Cys Glu
465                 470                 475                 480

Ala Met Asn Ala Arg Gly Met Val Phe Gly Ile Pro Asp Gly Val Leu
                485                 490                 495

Glu Leu Val Pro Gln Arg Gly Pro Cys Pro Asp Gly His Phe Tyr Leu
            500                 505                 510

Glu His Ser Ala Ala Cys Leu Pro Cys Phe Cys Phe Gly Ile Thr Ser
        515                 520                 525

Val Cys Gln Ser Thr Arg Arg Phe Arg Asp Gln Ile Arg Leu Arg Phe
    530                 535                 540

Asp Gln Pro Asp Asp Phe Lys Gly Val Asn Val Thr Met Pro Ala Gln
545                 550                 555                 560

Pro Gly Thr Pro Pro Leu Ser Ser Thr Gln Leu Gln Ile Asp Pro Ser
                565                 570                 575

Leu His Glu Phe Gln Leu Val Asp Leu Ser Arg Arg Phe Leu Val His
            580                 585                 590

Asp Ser Phe Trp Ala Leu Pro Glu Gln Phe Leu Gly Asn Lys Val Asp
        595                 600                 605

Ser Tyr Gly Gly Ser Leu Arg Tyr Asn Val Arg Tyr Glu Leu Ala Arg
    610                 615                 620

Gly Met Leu Glu Pro Val Gln Arg Pro Asp Val Val Leu Met Gly Ala
625                 630                 635                 640

Gly Tyr Arg Leu Leu Ser Arg Gly His Thr Pro Thr Gln Pro Gly Ala
                645                 650                 655

Leu Asn Gln Arg Gln Val Gln Phe Ser Glu Glu His Trp Val His Glu
            660                 665                 670

Ser Gly Arg Pro Val Gln Arg Ala Glu Leu Leu Gln Val Leu Gln Ser
        675                 680                 685

Leu Glu Ala Val Leu Ile Gln Thr Val Tyr Asn Thr Lys Met Ala Ser
    690                 695                 700

Val Gly Leu Ser Asp Ile Ala Met Asp Thr Thr Val Thr His Ala Thr
```

```
            705                 710                 715                 720
Ser His Gly Arg Ala His Ser Val Glu Glu Cys Arg Cys Pro Ile Gly
                725                 730                 735
Tyr Ser Gly Leu Ser Cys Glu Ser Cys Asp Ala His Phe Thr Arg Val
                740                 745                 750
Pro Gly Gly Pro Tyr Leu Gly Thr Cys Ser Gly Cys Asn Cys Asn Gly
                755                 760                 765
His Ala Ser Ser Cys Asp Pro Val Tyr Gly His Cys Leu Asn Cys Gln
                770                 775                 780
His Asn Thr Glu Gly Pro Gln Cys Asn Lys Cys Lys Ala Gly Phe Phe
785                 790                 795                 800
Gly Asp Ala Met Lys Ala Thr Ala Thr Ser Cys Arg Pro Cys Pro Cys
                805                 810                 815
Pro Tyr Ile Asp Ala Ser Arg Arg Phe Ser Asp Thr Cys Phe Leu Asp
                820                 825                 830
Thr Asp Gly Gln Ala Thr Cys Asp Ala Cys Ala Pro Gly Tyr Thr Gly
                835                 840                 845
Arg Arg Cys Glu Ser Cys Ala Pro Gly Tyr Glu Gly Asn Pro Ile Gln
850                 855                 860
Pro Gly Gly Lys Cys Arg Pro Val Asn Gln Glu Ile Val Arg Cys Asp
865                 870                 875                 880
Glu Arg Gly Ser Met Gly Thr Ser Gly Glu Ala Cys Arg Cys Lys Asn
                885                 890                 895
Asn Val Val Gly Arg Leu Cys Asn Glu Cys Ala Asp Gly Ser Phe His
                900                 905                 910
Leu Ser Thr Arg Asn Pro Asp Gly Cys Leu Lys Cys Phe Cys Met Gly
                915                 920                 925
Val Ser Arg His Cys Thr Ser Ser Ser Trp Ser Arg Ala Gln Leu His
                930                 935                 940
Gly Ala Ser Glu Glu Pro Gly His Phe Ser Leu Thr Asn Ala Ala Ser
945                 950                 955                 960
Thr His Thr Thr Asn Glu Gly Ile Phe Ser Pro Thr Pro Gly Glu Leu
                965                 970                 975
Gly Phe Ser Ser Phe His Arg Leu Leu Ser Gly Pro Tyr Phe Trp Ser
                980                 985                 990
Leu Pro Ser Arg Phe Leu Gly Asp Lys Val Thr Ser Tyr Gly Gly Glu
                995                 1000                1005
Leu Arg Phe Thr Val Thr Gln Arg Ser Gln Pro Gly Ser Thr Pro Leu
                1010                1015               1020
His Gly Gln Pro Leu Val Val Leu Gly Asn Asn Ile Ile Leu Glu
1025                1030                1035               1040
His His Val Ala Gln Glu Pro Ser Pro Gly Gln Pro Ser Thr Phe Ile
1045                1050                1055
Val Pro Phe Arg Glu Gln Ala Trp Gln Arg Pro Asp Gly Gln Pro Ala
1060                1065                1070
Thr Arg Glu His Leu Leu Met Ala Leu Ala Gly Ile Asp Thr Leu Leu
1075                1080                1085
Ile Arg Ala Ser Tyr Ala Gln Gln Pro Ala Glu Ser Arg Val Ser Gly
1090                1095                1100
Ile Ser Met Asp Val Ala Val Pro Glu Glu Thr Gly Gln Asp Pro Ala
1105                1110                1115               1120
Leu Glu Val Glu Gln Cys Ser Cys Pro Pro Gly Tyr Arg Gly Pro Ser
1125                1130                1135
```

```
Cys Gln Asp Cys Asp Thr Gly Tyr Thr Arg Thr Pro Ser Gly Leu Tyr
1140                1145                1150

Leu Gly Thr Cys Glu Arg Cys Ser Cys His Gly His Ser Glu Ala Cys
1155                1160                1165

Glu Pro Glu Thr Gly Ala Cys Gln Gly Cys Gln His His Thr Glu Gly
1170                1175                1180

Pro Arg Cys Glu Gln Cys Gln Pro Gly Tyr Tyr Gly Asp Ala Gln Arg
1185                1190                1195                1200

Gly Thr Pro Gln Asp Cys Gln Leu Cys Pro Cys Tyr Gly Asp Pro Ala
1205                1210                1215

Ala Gly Gln Ala Ala His Thr Cys Phe Leu Asp Thr Asp Gly His Pro
1220                1225                1230

Thr Cys Asp Ala Cys Ser Pro Gly His Ser Gly Arg His Cys Glu Arg
1235                1240                1245

Cys Ala Pro Gly Tyr Tyr Gly Asn Pro Ser Gln Gly Gln Pro Cys Gln
1250                1255                1260

Arg Asp Ser Gln Val Pro Gly Pro Ile Gly Cys Asn Cys Asp Pro Gln
1265                1270                1275                1280

Gly Ser Val Ser Ser Gln Cys Asp Ala Ala Gly Gln Cys Gln Cys Lys
1285                1290                1295

Ala Gln Val Glu Gly Leu Thr Cys Ser His Cys Arg Pro His His Phe
1300                1305                1310

His Leu Ser Ala Ser Asn Pro Asp Gly Cys Leu Pro Cys Phe Cys Met
1315                1320                1325

Gly Ile Thr Gln Gln Cys Ala Ser Ser Ala Tyr Thr Arg His Leu Ile
1330                1335                1340

Ser Thr His Phe Ala Pro Gly Asp Phe Gln Gly Phe Ala Leu Val Asn
1345                1350                1355                1360

Pro Gln Arg Asn Ser Arg Leu Thr Gly Glu Phe Thr Val Glu Pro Val
1365                1370                1375

Pro Glu Gly Ala Gln Leu Ser Phe Gly Asn Phe Ala Gln Leu Gly His
1380                1385                1390

Glu Ser Phe Tyr Trp Gln Leu Pro Glu Thr Tyr Gln Gly Asp Lys Val
1395                1400                1405

Ala Ala Tyr Gly Gly Lys Leu Arg Tyr Thr Leu Ser Tyr Thr Ala Gly
1410                1415                1420

Pro Gln Gly Ser Pro Leu Ser Asp Pro Asp Val Gln Ile Thr Gly Asn
1425                1430                1435                1440

Asn Ile Met Leu Val Ala Ser Gln Pro Ala Leu Gln Gly Pro Glu Arg
1445                1450                1455

Arg Ser Tyr Glu Ile Met Phe Arg Glu Glu Phe Trp Arg Arg Pro Asp
1460                1465                1470

Gly Gln Pro Ala Thr Arg Glu His Leu Leu Met Ala Leu Ala Asp Leu
1475                1480                1485

Asp Glu Leu Leu Ile Arg Ala Thr Phe Ser Ser Val Pro Leu Ala Ala
1490                1495                1500

Ser Ile Ser Ala Val Ser Leu Glu Val Ala Gln Pro Gly Pro Ser Asn
1505                1510                1515                1520

Arg Pro Arg Ala Leu Glu Val Glu Glu Cys Arg Cys Pro Pro Gly Tyr
1525                1530                1535

Ile Gly Leu Ser Cys Gln Asp Cys Ala Pro Gly Tyr Thr Arg Thr Gly
1540                1545                1550

Ser Gly Leu Tyr Leu Gly His Cys Glu Leu Cys Glu Cys Asn Gly His
1555                1560                1565
```

-continued

Ser Asp Leu Cys His Pro Glu Thr Gly Ala Cys Ser Gln Cys Gln His
1570                1575                1580

Asn Ala Ala Gly Glu Phe Cys Glu Leu Cys Ala Pro Gly Tyr Tyr Gly
1585                1590                1595                1600

Asp Ala Thr Ala Gly Thr Pro Glu Asp Cys Gln Pro Cys Ala Cys Pro
1605                1610                1615

Leu Thr Asn Pro Glu Asn Met Phe Ser Arg Thr Cys Glu Ser Leu Gly
1620                1625                1630

Ala Gly Gly Tyr Arg Cys Thr Ala Cys Glu Pro Gly Tyr Thr Gly Gln
1635                1640                1645

Tyr Cys Glu Gln Cys Gly Pro Gly Tyr Val Gly Asn Pro Ser Val Gln
1650                1655                1660

Gly Gly Gln Cys Leu Pro Glu Thr Asn Gln Ala Pro Leu Val Val Glu
1665                1670                1675                1680

Val His Pro Ala Arg Ser Ile Val Pro Gln Gly Gly Ser His Ser Leu
1685                1690                1695

Arg Cys Gln Val Ser Gly Ser Pro Pro His Tyr Phe Tyr Trp Ser Arg
1700                1705                1710

Glu Asp Gly Arg Pro Val Pro Ser Gly Thr Gln Gln Arg His Gln Gly
1715                1720                1725

Ser Glu Leu His Phe Pro Ser Val Gln Pro Ser Asp Ala Gly Val Tyr
1730                1735                1740

Ile Cys Thr Cys Arg Asn Leu His Gln Ser Asn Thr Ser Arg Ala Glu
1745                1750                1755                1760

Leu Leu Val Thr Glu Ala Pro Ser Lys Pro Ile Thr Val Thr Val Glu
1765                1770                1775

Glu Gln Arg Ser Gln Ser Val Arg Pro Gly Ala Asp Val Thr Phe Ile
1780                1785                1790

Cys Thr Ala Lys Ser Lys Ser Pro Ala Tyr Thr Leu Val Trp Thr Arg
1795                1800                1805

Leu His Asn Gly Lys Leu Pro Thr Arg Ala Met Asp Phe Asn Gly Ile
1810                1815                1820

Leu Thr Ile Arg Asn Val Gln Leu Ser Asp Ala Gly Thr Tyr Val Cys
1825                1830                1835                1840

Thr Gly Ser Asn Met Phe Ala Met Asp Gln Gly Thr Ala Thr Leu His
1845                1850                1855

Val Gln Ala Ser Gly Thr Leu Ser Ala Pro Val Val Ser Ile His Pro
1860                1865                1870

Pro Gln Leu Thr Val Gln Pro Gly Gln Leu Ala Glu Phe Arg Cys Ser
1875                1880                1885

Ala Thr Gly Ser Pro Thr Pro Thr Leu Glu Trp Thr Gly Gly Pro Gly
1890                1895                1900

Gly Gln Leu Pro Ala Lys Ala Gln Ile His Gly Gly Ile Leu Arg Leu
1905                1910                1915                1920

Pro Ala Val Glu Pro Thr Asp Gln Ala Gln Tyr Leu Cys Arg Ala His
1925                1930                1935

Ser Ser Ala Gly Gln Gln Val Ala Arg Ala Val Leu His Val His Gly
1940                1945                1950

Gly Gly Gly Pro Arg Val Gln Val Ser Pro Glu Arg Thr Gln Val His
1955                1960                1965

Ala Gly Arg Thr Val Arg Leu Tyr Cys Arg Ala Ala Gly Val Pro Ser
1970                1975                1980

Ala Thr Ile Thr Trp Arg Lys Glu Gly Gly Ser Leu Pro Pro Gln Ala

-continued

```
              1985                1990                1995                2000
Arg Ser Glu Arg Thr Asp Ile Ala Thr Leu Leu Ile Pro Ala Ile Thr
2005                2010                2015

Thr Ala Asp Ala Gly Phe Tyr Leu Cys Val Ala Thr Ser Pro Ala Gly
2020                2025                2030

Thr Ala Gln Ala Arg Ile Gln Val Val Leu Ser Ala Ser Asp Ala
2035                2040                2045

Ser Pro Pro Val Lys Ile Glu Ser Ser Pro Ser Val Thr Glu
2050                2055                2060

Gly Gln Thr Leu Asp Leu Asn Cys Val Val Ala Gly Ser Ala His Ala
2065                2070                2075                2080

Gln Val Thr Trp Tyr Arg Arg Gly Gly Ser Leu Pro Pro His Thr Gln
2085                2090                2095

Val His Gly Ser Arg Leu Arg Leu Pro Gln Val Ser Pro Ala Asp Ser
2100                2105                2110

Gly Glu Tyr Val Cys Arg Val Glu Asn Gly Ser Gly Pro Lys Glu Ala
2115                2120                2125

Ser Ile Thr Val Ser Val Leu His Gly Thr His Ser Gly Pro Ser Tyr
2130                2135                2140

Thr Pro Val Pro Gly Ser Thr Arg Pro Ile Arg Ile Glu Pro Ser Ser
2145                2150                2155                2160

Ser His Val Ala Glu Gly Gln Thr Leu Asp Leu Asn Cys Val Val Pro
2165                2170                2175

Gly Gln Ala His Ala Gln Val Thr Trp His Lys Arg Gly Gly Ser Leu
2180                2185                2190

Pro Ala Arg His Gln Thr His Gly Ser Leu Leu Arg Leu His Gln Val
2195                2200                2205

Thr Pro Ala Asp Ser Gly Glu Tyr Val Cys His Val Val Gly Thr Ser
2210                2215                2220

Gly Pro Leu Glu Ala Ser Val Leu Val Thr Ile Glu Ala Ser Val Ile
2225                2230                2235                2240

Pro Gly Pro Ile Pro Pro Val Arg Ile Glu Ser Ser Ser Ser Thr Val
2245                2250                2255

Ala Glu Gly Gln Thr Leu Asp Leu Ser Cys Val Val Ala Gly Gln Ala
2260                2265                2270

His Ala Gln Val Thr Trp Tyr Lys Arg Gly Gly Ser Leu Pro Ala Arg
2275                2280                2285

His Gln Val Arg Gly Ser Arg Leu Tyr Ile Phe Gln Ala Ser Pro Ala
2290                2295                2300

Asp Ala Gly Gln Tyr Val Cys Arg Ala Ser Asn Gly Met Glu Ala Ser
2305                2310                2315                2320

Ile Thr Val Thr Val Thr Gly Thr Gln Gly Ala Asn Leu Ala Tyr Pro
2325                2330                2335

Ala Gly Ser Thr Gln Pro Ile Arg Ile Glu Pro Ser Ser Ser Gln Val
2340                2345                2350

Ala Glu Gly Gln Thr Leu Asp Leu Asn Cys Val Val Pro Gly Gln Ser
2355                2360                2365

His Ala Gln Val Thr Trp His Lys Arg Gly Gly Ser Leu Pro Val Arg
2370                2375                2380

His Gln Thr His Gly Ser Leu Leu Arg Leu Tyr Gln Ala Ser Pro Ala
2385                2390                2395                2400

Asp Ser Gly Glu Tyr Val Cys Arg Val Leu Gly Ser Ser Val Pro Leu
2405                2410                2415
```

```
Glu Ala Ser Val Leu Val Thr Ile Glu Pro Ala Gly Ser Val Pro Ala
2420                2425                2430

Leu Gly Val Thr Pro Thr Val Arg Ile Glu Ser Ser Ser Ser Gln Val
2435                2440                2445

Ala Glu Gly Gln Thr Leu Asp Leu Asn Cys Leu Val Ala Gly Gln Ala
2450                2455                2460

His Ala Gln Val Thr Trp His Lys Arg Gly Gly Ser Leu Pro Ala Arg
2465                2470                2475                2480

His Gln Val His Gly Ser Arg Leu Arg Leu Leu Gln Val Thr Pro Ala
2485                2490                2495

Asp Ser Gly Glu Tyr Val Cys Arg Val Val Gly Ser Ser Gly Thr Gln
2500                2505                2510

Glu Ala Ser Val Leu Val Thr Ile Gln Gln Arg Leu Ser Gly Ser His
2515                2520                2525

Ser Gln Gly Val Ala Tyr Pro Val Arg Ile Glu Ser Ser Ser Ala Ser
2530                2535                2540

Leu Ala Asn Gly His Thr Leu Asp Leu Asn Cys Leu Val Ala Ser Gln
2545                2550                2555                2560

Ala Pro His Thr Ile Thr Trp Tyr Lys Arg Gly Gly Ser Leu Pro Ser
2565                2570                2575

Arg His Gln Ile Val Gly Ser Arg Leu Arg Ile Pro Gln Val Thr Pro
2580                2585                2590

Ala Asp Ser Gly Glu Tyr Val Cys His Val Ser Asn Gly Ala Gly Ser
2595                2600                2605

Arg Glu Thr Ser Leu Ile Val Thr Ile Gln Gly Ser Gly Ser Ser His
2610                2615                2620

Val Pro Ser Val Ser Pro Pro Ile Arg Ile Glu Ser Ser Ser Pro Thr
2625                2630                2635                2640

Val Val Glu Gly Gln Thr Leu Asp Leu Asn Cys Val Val Ala Arg Gln
2645                2650                2655

Pro Gln Ala Ile Ile Thr Trp Tyr Lys Arg Gly Gly Ser Leu Pro Ser
2660                2665                2670

Arg His Gln Thr His Gly Ser His Leu Arg Leu His Gln Met Ser Val
2675                2680                2685

Ala Asp Ser Gly Glu Tyr Val Cys Arg Ala Asn Asn Asn Ile Asp Ala
2690                2695                2700

Leu Glu Ala Ser Ile Val Ile Ser Val Ser Pro Ser Ala Gly Ser Pro
2705                2710                2715                2720

Ser Ala Pro Gly Ser Ser Met Pro Ile Arg Ile Glu Ser Ser Ser Ser
2725                2730                2735

His Val Ala Glu Gly Glu Thr Leu Asp Leu Asn Cys Val Val Pro Gly
2740                2745                2750

Gln Ala His Ala Gln Val Thr Trp His Lys Arg Gly Gly Ser Leu Pro
2755                2760                2765

Ser His His Gln Thr Arg Gly Ser Arg Leu Arg Leu His His Val Ser
2770                2775                2780

Pro Ala Asp Ser Gly Glu Tyr Val Cys Arg Val Met Gly Ser Ser Gly
2785                2790                2795                2800

Pro Leu Glu Ala Ser Val Leu Val Thr Ile Glu Ala Ser Gly Ser Ser
2805                2810                2815

Ala Val His Val Pro Ala Pro Gly Gly Ala Pro Pro Ile Arg Ile Glu
2820                2825                2830

Pro Ser Ser Ser Arg Val Ala Glu Gly Gln Thr Leu Asp Leu Lys Cys
2835                2840                2845
```

```
Val Val Pro Gly Gln Ala His Ala Gln Val Thr Trp His Lys Arg Gly
2850                2855                2860

Gly Asn Leu Pro Ala Arg His Gln Val His Gly Pro Leu Leu Arg Leu
2865                2870                2875                2880

Asn Gln Val Ser Pro Ala Asp Ser Gly Glu Tyr Ser Cys Gln Val Thr
2885                2890                2895

Gly Ser Ser Gly Thr Leu Glu Ala Ser Val Leu Val Thr Ile Glu Pro
2900                2905                2910

Ser Ser Pro Gly Pro Ile Pro Ala Pro Gly Leu Ala Gln Pro Ile Tyr
2915                2920                2925

Ile Glu Ala Ser Ser Ser His Val Thr Glu Gly Gln Thr Leu Asp Leu
2930                2935                2940

Asn Cys Val Val Pro Gly Gln Ala His Ala Gln Val Thr Trp Tyr Lys
2945                2950                2955                2960

Arg Gly Gly Ser Leu Pro Ala Arg His Gln Thr His Gly Ser Gln Leu
2965                2970                2975

Arg Leu His Leu Val Ser Pro Ala Asp Ser Gly Glu Tyr Val Cys Arg
2980                2985                2990

Ala Ala Ser Gly Pro Gly Pro Glu Gln Glu Ala Ser Phe Thr Val Thr
2995                3000                3005

Val Pro Pro Ser Glu Gly Ser Ser Tyr Arg Leu Arg Ser Pro Val Ile
3010                3015                3020

Ser Ile Asp Pro Pro Ser Ser Thr Val Gln Gln Gly Gln Asp Ala Ser
3025                3030                3035                3040

Phe Lys Cys Leu Ile His Asp Gly Ala Ala Pro Ile Ser Leu Glu Trp
3045                3050                3055

Lys Thr Arg Asn Gln Glu Leu Glu Asp Asn Val His Ile Ser Pro Asn
3060                3065                3070

Gly Ser Ile Ile Thr Ile Val Gly Thr Arg Pro Ser Asn His Gly Thr
3075                3080                3085

Tyr Arg Cys Val Ala Ser Asn Ala Tyr Gly Val Ala Gln Ser Val Val
3090                3095                3100

Asn Leu Ser Val His Gly Pro Pro Thr Val Ser Val Leu Pro Glu Gly
3105                3110                3115                3120

Pro Val Trp Val Lys Val Gly Lys Ala Val Thr Leu Glu Cys Val Ser
3125                3130                3135

Ala Gly Glu Pro Arg Ser Ser Ala Arg Trp Thr Arg Ile Ser Ser Thr
3140                3145                3150

Pro Ala Lys Leu Glu Gln Arg Thr Tyr Gly Leu Met Asp Ser His Ala
3155                3160                3165

Val Leu Gln Ile Ser Ser Ala Lys Pro Ser Asp Ala Gly Thr Tyr Val
3170                3175                3180

Cys Leu Ala Gln Asn Ala Leu Gly Thr Ala Gln Lys Gln Val Glu Val
3185                3190                3195                3200

Ile Val Asp Thr Gly Ala Met Ala Pro Gly Ala Pro Gln Val Gln Ala
3205                3210                3215

Glu Glu Ala Glu Leu Thr Val Glu Ala Gly His Thr Ala Thr Leu Arg
3220                3225                3230

Cys Ser Ala Thr Gly Ser Pro Ala Pro Thr Ile His Trp Ser Lys Leu
3235                3240                3245

Arg Ser Pro Leu Pro Trp Gln His Arg Leu Glu Gly Asp Thr Leu Ile
3250                3255                3260

Ile Pro Arg Val Ala Gln Gln Asp Ser Gly Gln Tyr Ile Cys Asn Ala
```

-continued

```
                3265                3270                3275                3280

Thr Ser Pro Ala Gly His Ala Glu Ala Thr Ile Ile Leu His Val Glu
3285                3290                3295

Ser Pro Pro Tyr Ala Thr Thr Val Pro Glu His Ala Ser Val Gln Ala
3300                3305                3310

Gly Glu Thr Val Gln Leu Gln Cys Leu Ala His Gly Thr Pro Pro Leu
3315                3320                3325

Thr Phe Gln Trp Ser Arg Val Gly Ser Ser Leu Pro Gly Arg Ala Thr
3330                3335                3340

Ala Arg Asn Glu Leu Leu His Phe Glu Arg Ala Ala Pro Glu Asp Ser
3345                3350                3355                3360

Gly Arg Tyr Arg Cys Arg Val Thr Asn Lys Val Gly Ser Ala Glu Ala
3365                3370                3375

Phe Ala Gln Leu Leu Val Gln Gly Pro Pro Gly Ser Leu Pro Ala Thr
3380                3385                3390

Ser Ile Pro Ala Gly Ser Thr Pro Thr Val Gln Val Thr Pro Gln Leu
3395                3400                3405

Glu Thr Lys Ser Ile Gly Ala Ser Val Glu Phe His Cys Ala Val Pro
3410                3415                3420

Ser Asp Arg Gly Thr Gln Leu Arg Trp Phe Lys Glu Gly Gly Gln Leu
3425                3430                3435                3440

Pro Pro Gly His Ser Val Gln Asp Gly Val Leu Arg Ile Gln Asn Leu
3445                3450                3455

Asp Gln Ser Cys Gln Gly Thr Tyr Ile Cys Gln Ala His Gly Pro Trp
3460                3465                3470

Gly Lys Ala Gln Ala Ser Ala Gln Leu Val Ile Gln Ala Leu Pro Ser
3475                3480                3485

Val Leu Ile Asn Ile Arg Thr Ser Val Gln Thr Val Val Gly His
3490                3495                3500

Ala Val Glu Phe Glu Cys Leu Ala Leu Gly Asp Pro Lys Pro Gln Val
3505                3510                3515                3520

Thr Trp Ser Lys Val Gly Gly His Leu Arg Pro Gly Ile Val Gln Ser
3525                3530                3535

Gly Gly Val Val Arg Ile Ala His Val Glu Leu Ala Asp Ala Gly Gln
3540                3545                3550

Tyr Arg Cys Thr Ala Thr Asn Ala Ala Gly Thr Thr Gln Ser His Val
3555                3560                3565

Leu Leu Leu Val Gln Ala Leu Pro Gln Ile Ser Met Pro Gln Glu Val
3570                3575                3580

Arg Val Pro Ala Gly Ser Ala Ala Val Phe Pro Cys Ile Ala Ser Gly
3585                3590                3595                3600

Tyr Pro Thr Pro Asp Ile Ser Trp Ser Lys Leu Asp Gly Ser Leu Pro
3605                3610                3615

Pro Asp Ser Arg Leu Glu Asn Asn Met Leu Met Leu Pro Ser Val Arg
3620                3625                3630

Pro Gln Asp Ala Gly Thr Tyr Val Cys Thr Ala Thr Asn Arg Gln Gly
3635                3640                3645

Lys Val Lys Ala Phe Ala His Leu Gln Val Pro Glu Arg Val Val Pro
3650                3655                3660

Tyr Phe Thr Gln Thr Pro Tyr Ser Phe Leu Pro Leu Pro Thr Ile Lys
3665                3670                3675                3680

Asp Ala Tyr Arg Lys Phe Glu Ile Lys Ile Thr Phe Arg Pro Asp Ser
3685                3690                3695
```

-continued

```
Ala Asp Gly Met Leu Leu Tyr Asn Gly Gln Lys Arg Val Pro Gly Ser
3700                3705                3710

Pro Thr Asn Leu Ala Asn Arg Gln Pro Asp Phe Ile Ser Phe Gly Leu
3715                3720                3725

Val Gly Gly Arg Pro Glu Phe Arg Phe Asp Ala Gly Ser Gly Met Ala
3730                3735                3740

Thr Ile Arg His Pro Thr Pro Leu Ala Leu Gly His Phe His Thr Val
3745                3750                3755                3760

Thr Leu Leu Arg Ser Leu Thr Gln Gly Ser Leu Ile Val Gly Asp Leu
3765                3770                3775

Ala Pro Val Asn Gly Thr Ser Gln Gly Lys Phe Gln Gly Leu Asp Leu
3780                3785                3790

Asn Glu Glu Leu Tyr Leu Gly Gly Tyr Pro Asp Tyr Gly Ala Ile Pro
3795                3800                3805

Lys Ala Gly Leu Ser Ser Gly Phe Ile Gly Cys Val Arg Glu Leu Arg
3810                3815                3820

Ile Gln Gly Glu Glu Ile Val Phe His Asp Leu Asn Leu Thr Ala His
3825                3830                3835                3840

Gly Ile Ser His Cys Pro Thr Cys Arg Asp Arg Pro Cys Gln Asn Gly
3845                3850                3855

Gly Gln Cys His Asp Ser Glu Ser Ser Ser Tyr Val Cys Val Cys Pro
3860                3865                3870

Ala Gly Phe Thr Gly Ser Arg Cys Glu His Ser Gln Ala Leu His Cys
3875                3880                3885

His Pro Glu Ala Cys Gly Pro Asp Ala Thr Cys Val Asn Arg Pro Asp
3890                3895                3900

Gly Arg Gly Tyr Thr Cys Arg Cys His Leu Gly Arg Ser Gly Leu Arg
3905                3910                3915                3920

Cys Glu Glu Gly Val Thr Val Thr Thr Pro Ser Leu Ser Gly Ala Gly
3925                3930                3935

Ser Tyr Leu Ala Leu Pro Ala Leu Thr Asn Thr His His Glu Leu Arg
3940                3945                3950

Leu Asp Val Glu Phe Lys Pro Leu Ala Pro Asp Gly Val Leu Leu Phe
3955                3960                3965

Ser Gly Gly Lys Ser Gly Pro Val Glu Asp Phe Val Ser Leu Ala Met
3970                3975                3980

Val Gly Gly His Leu Glu Phe Arg Tyr Glu Leu Gly Ser Gly Leu Ala
3985                3990                3995                4000

Val Leu Arg Ser Ala Glu Pro Leu Ala Leu Gly Arg Trp His Arg Val
4005                4010                4015

Ser Ala Glu Arg Leu Asn Lys Asp Gly Ser Leu Arg Val Asn Gly Gly
4020                4025                4030

Arg Pro Val Leu Arg Ser Ser Pro Gly Lys Ser Gln Gly Leu Asn Leu
4035                4040                4045

His Thr Leu Leu Tyr Leu Gly Gly Val Glu Pro Ser Val Pro Leu Ser
4050                4055                4060

Pro Ala Thr Asn Met Ser Ala His Phe Arg Gly Cys Val Gly Glu Val
4065                4070                4075                4080

Ser Val Asn Gly Lys Arg Leu Asp Leu Thr Tyr Ser Phe Leu Gly Ser
4085                4090                4095

Gln Gly Ile Gly Gln Cys Tyr Asp Ser Ser Pro Cys Glu Arg Gln Pro
4100                4105                4110

Cys Gln His Gly Ala Thr Cys Met Pro Ala Gly Glu Tyr Glu Phe Gln
4115                4120                4125
```

-continued

```
Cys Leu Cys Arg Asp Gly Phe Lys Gly Asp Leu Cys Glu His Glu
4130                4135                4140

Asn Pro Cys Gln Leu Arg Glu Pro Cys Leu His Gly Thr Cys Gln
4145                4150                4155                4160

Gly Thr Arg Cys Leu Cys Leu Pro Gly Phe Ser Gly Pro Arg Cys Gln
4165                4170                4175

Gln Gly Ser Gly His Gly Ile Ala Glu Ser Asp Trp His Leu Glu Gly
4180                4185                4190

Ser Gly Gly Asn Asp Ala Pro Gly Gln Tyr Gly Ala Tyr Phe His Asp
4195                4200                4205

Asp Gly Phe Leu Ala Phe Pro Gly His Val Phe Ser Arg Ser Leu Pro
4210                4215                4220

Glu Val Pro Glu Thr Ile Glu Leu Glu Val Arg Thr Ser Thr Ala Ser
4225                4230                4235                4240

Gly Leu Leu Leu Trp Gln Gly Val Glu Val Gly Glu Ala Gly Gln Gly
4245                4250                4255

Lys Asp Phe Ile Ser Leu Gly Leu Gln Asp Gly His Leu Val Phe Arg
4260                4265                4270

Tyr Gln Leu Gly Ser Gly Glu Ala Arg Leu Val Ser Glu Asp Pro Ile
4275                4280                4285

Asn Asp Gly Glu Trp His Arg Val Thr Ala Leu Arg Glu Gly Arg Arg
4290                4295                4300

Gly Ser Ile Gln Val Asp Gly Glu Glu Leu Val Ser Gly Arg Ser Pro
4305                4310                4315                4320

Gly Pro Asn Val Ala Val Asn Ala Lys Gly Ser Val Tyr Ile Gly Gly
4325                4330                4335

Ala Pro Asp Val Ala Thr Leu Thr Gly Gly Arg Phe Ser Ser Gly Ile
4340                4345                4350

Thr Gly Cys Val Lys Asn Leu Val Leu His Ser Ala Arg Pro Gly Ala
4355                4360                4365

Pro Pro Pro Gln Pro Leu Asp Leu Gln His Arg Ala Gln Ala Gly Ala
4370                4375                4380

Asn Thr Arg Pro Cys Pro Ser
4385                4390

<210> SEQ ID NO 90
<211> LENGTH: 198
<212> TYPE: PRT
<213> ORGANISM: Homo sapiens

<400> SEQUENCE: 90

Met Asp Ser Leu Leu Met Asn Arg Arg Lys Phe Leu Tyr Gln Phe Lys
  1               5                  10                  15

Asn Val Arg Trp Ala Lys Gly Arg Arg Glu Thr Tyr Leu Cys Tyr Val
                 20                  25                  30

Val Lys Arg Arg Asp Ser Ala Thr Ser Phe Ser Leu Asp Phe Gly Tyr
             35                  40                  45

Leu Arg Asn Lys Asn Gly Cys His Val Glu Leu Leu Phe Leu Arg Tyr
         50                  55                  60

Ile Ser Asp Trp Asp Leu Asp Pro Gly Arg Cys Tyr Arg Val Thr Trp
 65                  70                  75                  80

Phe Thr Ser Trp Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
                100                 105                 110
```

```
Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                    165                 170                 175

Arg Arg Ile Leu Leu Pro Leu Tyr Glu Val Asp Asp Leu Arg Asp Ala
                180                 185                 190

Phe Arg Thr Leu Gly Leu
            195

<210> SEQ ID NO 91
<211> LENGTH: 491
<212> TYPE: PRT
<213> ORGANISM: Homo sapiens

<400> SEQUENCE: 91

Met Glu Leu Ser Val Leu Leu Phe Leu Ala Leu Leu Thr Gly Leu Leu
  1               5                  10                  15

Leu Leu Leu Val Gln Arg His Pro Asn Thr His Asp Arg Leu Pro Pro
                 20                  25                  30

Gly Pro Arg Pro Leu Pro Leu Leu Gly Asn Leu Leu Gln Met Asp Arg
             35                  40                  45

Arg Gly Leu Leu Lys Ser Phe Leu Arg Phe Arg Glu Lys Tyr Gly Asp
         50                  55                  60

Val Phe Thr Val His Leu Gly Pro Arg Pro Val Val Met Leu Cys Gly
 65                  70                  75                  80

Val Glu Ala Ile Arg Glu Ala Leu Val Asp Lys Ala Glu Ala Phe Ser
                 85                  90                  95

Gly Arg Gly Lys Ile Ala Met Val Asp Pro Phe Phe Arg Gly Tyr Gly
            100                 105                 110

Val Ile Phe Ala Asn Gly Asn Arg Trp Lys Val Leu Arg Arg Phe Ser
            115                 120                 125

Val Thr Thr Met Arg Asp Phe Gly Met Gly Lys Arg Ser Val Glu Glu
        130                 135                 140

Arg Ile Gln Glu Glu Ala Gln Cys Leu Ile Glu Glu Leu Arg Lys Ser
145                 150                 155                 160

Lys Gly Ala Leu Met Asp Pro Thr Phe Leu Phe Gln Ser Ile Thr Ala
                    165                 170                 175

Asn Ile Ile Cys Ser Ile Val Phe Gly Lys Arg Phe His Tyr Gln Asp
                180                 185                 190

Gln Glu Phe Leu Lys Met Leu Asn Leu Phe Tyr Gln Thr Phe Ser Leu
            195                 200                 205

Ile Ser Ser Val Phe Gly Gln Leu Phe Glu Leu Phe Ser Gly Phe Leu
        210                 215                 220

Lys Tyr Phe Pro Gly Ala His Arg Gln Val Tyr Lys Asn Leu Gln Glu
225                 230                 235                 240

Ile Asn Ala Tyr Ile Gly His Ser Val Glu Lys His Arg Glu Thr Leu
                    245                 250                 255

Asp Pro Ser Ala Pro Lys Asp Leu Ile Asp Thr Tyr Leu Leu His Met
                260                 265                 270

Glu Lys Glu Lys Ser Asn Ala His Ser Glu Phe Ser His Gln Asn Leu
            275                 280                 285
```

```
Asn Leu Asn Thr Leu Ser Leu Phe Phe Ala Gly Thr Glu Thr Thr Ser
    290                 295                 300

Thr Thr Leu Arg Tyr Gly Phe Leu Leu Met Leu Lys Tyr Pro His Val
305                 310                 315                 320

Ala Glu Arg Val Tyr Arg Glu Ile Glu Gln Val Ile Gly Pro His Arg
                325                 330                 335

Pro Pro Glu Leu His Asp Arg Ala Lys Met Pro Tyr Thr Glu Ala Val
            340                 345                 350

Ile Tyr Glu Ile Gln Arg Phe Ser Asp Leu Leu Pro Met Gly Val Pro
        355                 360                 365

His Ile Val Thr Gln His Thr Ser Phe Arg Gly Tyr Ile Ile Pro Lys
    370                 375                 380

Asp Thr Glu Val Phe Leu Ile Leu Ser Thr Ala Leu His Asp Pro His
385                 390                 395                 400

Tyr Phe Glu Lys Pro Asp Ala Phe Asn Pro Asp His Phe Leu Asp Ala
                405                 410                 415

Asn Gly Ala Leu Lys Lys Thr Glu Ala Phe Ile Pro Phe Ser Leu Gly
            420                 425                 430

Lys Arg Ile Cys Leu Gly Glu Gly Ile Ala Arg Ala Glu Leu Phe Leu
        435                 440                 445

Phe Phe Thr Thr Ile Leu Gln Asn Phe Ser Met Ala Ser Pro Val Ala
    450                 455                 460

Pro Glu Asp Ile Asp Leu Thr Pro Gln Glu Cys Gly Val Gly Lys Ile
465                 470                 475                 480

Pro Pro Thr Tyr Gln Ile Arg Phe Leu Pro Arg
                485                 490

<210> SEQ ID NO 92
<211> LENGTH: 454
<212> TYPE: PRT
<213> ORGANISM: Homo sapiens

<400> SEQUENCE: 92

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175
```

Pro Asn Pro Ala Arg Gly His Ser Val Cys Ser Thr Ser Ser Leu Tyr
            180                 185                 190

Leu Gln Asp Leu Ser Ala Ala Ser Glu Cys Ile Asp Pro Ser Val
        195                 200                 205

Val Phe Pro Tyr Pro Leu Asn Asp Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
                260                 265                 270

Asp Glu Glu Glu Ile Asp Val Val Ser Val Glu Lys Arg Gln Ala Pro
                275                 280                 285

Gly Lys Arg Ser Glu Ser Gly Ser Pro Ser Ala Gly Gly His Ser Lys
        290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
                340                 345                 350

Asn Asn Arg Lys Cys Thr Ser Pro Arg Ser Ser Asp Thr Glu Glu Asn
            355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
                420                 425                 430

Asp Leu Leu Arg Lys Arg Arg Glu Gln Leu Lys His Lys Leu Glu Gln
            435                 440                 445

Leu Arg Asn Ser Cys Ala
    450

<210> SEQ ID NO 93
<211> LENGTH: 894
<212> TYPE: PRT
<213> ORGANISM: Homo sapiens

<400> SEQUENCE: 93

Met Ile Leu Leu Ala Val Leu Phe Leu Cys Phe Ile Ser Ser Tyr Ser
1               5                   10                  15

Ala Ser Val Lys Gly His Thr Thr Gly Leu Ser Leu Asn Asn Asp Arg
            20                  25                  30

Leu Tyr Lys Leu Thr Tyr Ser Thr Glu Val Leu Leu Asp Arg Gly Lys
        35                  40                  45

Gly Lys Leu Gln Asp Ser Val Gly Tyr Arg Ile Ser Ser Asn Val Asp
    50                  55                  60

Val Ala Leu Leu Trp Arg Asn Pro Asp Gly Asp Asp Gln Leu Ile
65                  70                  75                  80

Gln Ile Thr Met Lys Asp Val Asn Val Glu Asn Val Asn Gln Gln Arg
                85                  90                  95

Gly Glu Lys Ser Ile Phe Lys Gly Lys Ser Pro Ser Lys Ile Met Gly
                100                 105                 110
Lys Glu Asn Leu Glu Ala Leu Gln Arg Pro Thr Leu Leu His Leu Ile
            115                 120                 125
His Gly Lys Val Lys Glu Phe Tyr Ser Tyr Gln Asn Glu Ala Val Ala
        130                 135                 140
Ile Glu Asn Ile Lys Arg Gly Leu Ala Ser Leu Phe Gln Thr Gln Leu
145                 150                 155                 160
Ser Ser Gly Thr Thr Asn Glu Val Asp Ile Ser Gly Asn Cys Lys Val
                165                 170                 175
Thr Tyr Gln Ala His Gln Asp Lys Val Ile Lys Ile Lys Ala Leu Asp
            180                 185                 190
Ser Cys Lys Ile Ala Arg Ser Gly Phe Thr Thr Pro Asn Gln Val Leu
        195                 200                 205
Gly Val Ser Ser Lys Ala Thr Ser Val Thr Thr Tyr Lys Ile Glu Asp
        210                 215                 220
Ser Phe Val Ile Ala Val Leu Ala Glu Glu Thr His Asn Phe Gly Leu
225                 230                 235                 240
Asn Phe Leu Gln Thr Ile Lys Gly Lys Ile Val Ser Lys Gln Lys Leu
                245                 250                 255
Glu Leu Lys Thr Thr Glu Ala Gly Pro Arg Leu Met Ser Gly Lys Gln
            260                 265                 270
Ala Ala Ala Ile Ile Lys Ala Val Asp Ser Lys Tyr Thr Ala Ile Pro
        275                 280                 285
Ile Val Gly Gln Val Phe Gln Ser His Cys Lys Gly Cys Pro Ser Leu
        290                 295                 300
Ser Glu Leu Trp Arg Ser Thr Arg Lys Tyr Leu Gln Pro Asp Asn Leu
305                 310                 315                 320
Ser Lys Ala Glu Ala Val Arg Asn Phe Leu Ala Phe Ile Gln His Leu
                325                 330                 335
Arg Thr Ala Lys Lys Glu Glu Ile Leu Gln Ile Leu Lys Met Glu Asn
            340                 345                 350
Lys Glu Val Leu Pro Gln Leu Val Asp Ala Val Thr Ser Ala Gln Thr
        355                 360                 365
Ser Asp Ser Leu Glu Ala Ile Leu Asp Phe Leu Asp Phe Lys Ser Asp
        370                 375                 380
Ser Ser Ile Ile Leu Gln Glu Arg Phe Leu Tyr Ala Cys Gly Phe Ala
385                 390                 395                 400
Ser His Pro Asn Glu Glu Leu Leu Arg Ala Leu Ile Ser Lys Phe Lys
                405                 410                 415
Gly Ser Ile Gly Ser Ser Asp Ile Arg Glu Thr Val Met Ile Ile Thr
            420                 425                 430
Gly Thr Leu Val Arg Lys Leu Cys Gln Asn Glu Gly Cys Lys Leu Lys
        435                 440                 445
Ala Val Val Glu Ala Lys Lys Leu Ile Leu Gly Gly Leu Glu Lys Ala
        450                 455                 460
Glu Lys Lys Glu Asp Thr Arg Met Tyr Leu Leu Ala Leu Lys Asn Ala
465                 470                 475                 480
Leu Leu Pro Glu Gly Ile Pro Ser Leu Leu Lys Tyr Ala Glu Ala Gly
                485                 490                 495
Glu Gly Pro Ile Ser His Leu Ala Thr Thr Ala Leu Gln Arg Tyr Asp
            500                 505                 510
Leu Pro Phe Ile Thr Asp Glu Val Lys Lys Thr Leu Asn Arg Ile Tyr

```
                515                 520                 525
His Gln Asn Arg Lys Val His Glu Lys Thr Val Arg Thr Ala Ala Ala
530                 535                 540

Ala Ile Ile Leu Asn Asn Pro Ser Tyr Met Asp Val Lys Asn Ile
545                 550                 555                 560

Leu Leu Ser Ile Gly Glu Leu Pro Gln Glu Met Asn Lys Tyr Met Leu
                    565                 570                 575

Ala Ile Val Gln Asp Ile Leu Arg Phe Glu Met Pro Ala Ser Lys Ile
                580                 585                 590

Val Arg Arg Val Leu Lys Glu Met Val Ala His Asn Tyr Asp Arg Phe
                595                 600                 605

Ser Arg Ser Gly Ser Ser Ala Tyr Thr Gly Tyr Ile Glu Arg Ser
610                 615                 620

Pro Arg Ser Ala Ser Thr Tyr Ser Leu Asp Ile Leu Tyr Ser Gly Ser
625                 630                 635                 640

Gly Ile Leu Arg Arg Ser Asn Leu Asn Ile Phe Gln Tyr Ile Gly Lys
                    645                 650                 655

Ala Gly Leu His Gly Ser Gln Val Val Ile Glu Ala Gln Gly Leu Glu
                660                 665                 670

Ala Leu Ile Ala Ala Thr Pro Asp Glu Gly Glu Asn Leu Asp Ser
675                 680                 685

Tyr Ala Gly Met Ser Ala Ile Leu Phe Asp Val Gln Leu Arg Pro Val
690                 695                 700

Thr Phe Phe Asn Gly Tyr Ser Asp Leu Met Ser Lys Met Leu Ser Ala
705                 710                 715                 720

Ser Gly Asp Pro Ile Ser Val Val Lys Gly Leu Ile Leu Leu Ile Asp
                    725                 730                 735

His Ser Gln Glu Leu Gln Leu Gln Ser Gly Leu Lys Ala Asn Ile Glu
                740                 745                 750

Val Gln Gly Gly Leu Ala Ile Asp Ile Ser Gly Ala Met Glu Phe Ser
                755                 760                 765

Leu Trp Tyr Arg Glu Ser Lys Thr Arg Val Lys Asn Arg Val Thr Val
770                 775                 780

Val Ile Thr Thr Asp Ile Thr Val Asp Ser Ser Phe Val Lys Ala Gly
785                 790                 795                 800

Leu Glu Thr Ser Thr Glu Thr Glu Ala Gly Leu Glu Phe Ile Ser Thr
                    805                 810                 815

Val Gln Phe Ser Gln Tyr Pro Phe Leu Val Cys Met Gln Met Asp Lys
                820                 825                 830

Asp Glu Ala Pro Phe Arg Gln Phe Glu Lys Lys Tyr Glu Arg Leu Ser
                835                 840                 845

Thr Gly Arg Gly Tyr Val Ser Gln Lys Arg Lys Glu Ser Val Leu Ala
850                 855                 860

Gly Cys Glu Phe Pro Leu His Gln Glu Asn Ser Glu Met Cys Lys Val
865                 870                 875                 880

Val Phe Ala Pro Gln Pro Asp Ser Thr Ser Ser Gly Trp Phe
                885                 890

<210> SEQ ID NO 94
<211> LENGTH: 1210
<212> TYPE: PRT
<213> ORGANISM: Homo sapiens

<400> SEQUENCE: 94

Met Arg Pro Ser Gly Thr Ala Gly Ala Ala Leu Leu Ala Leu Leu Ala
```

-continued

```
             1               5              10              15
Ala Leu Cys Pro Ala Ser Arg Ala Leu Glu Glu Lys Lys Val Cys Gln
                    20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                    100                 105                 110

Tyr Glu Asn Ser Tyr Ala Leu Ala Val Leu Ser Asn Tyr Asp Ala Asn
                115                 120                 125

Lys Thr Gly Leu Lys Glu Leu Pro Met Arg Asn Leu Gln Glu Ile Leu
            130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
                195                 200                 205

Lys Leu Thr Lys Ile Ile Cys Ala Gln Gln Cys Ser Gly Arg Cys Arg
        210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
                290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430
```

```
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
    770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
        835                 840                 845
Gln His Val Lys Ile Thr Asp Phe Gly Leu Ala Lys Leu Leu Gly Ala
    850                 855                 860
```

```
Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
        900                 905                 910

Lys Pro Tyr Asp Gly Ile Pro Ala Ser Glu Ile Ser Ser Ile Leu Glu
    915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Asp Thr Phe Leu Pro
        1075                1080                1085

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
            1140                1145                1150

Ser Pro Ala His Trp Ala Gln Lys Gly Ser His Gln Ile Ser Leu Asp
        1155                1160                1165

Asn Pro Asp Tyr Gln Gln Asp Phe Phe Pro Lys Glu Ala Lys Pro Asn
    1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
                1205                1210

<210> SEQ ID NO 95
<211> LENGTH: 705
<212> TYPE: PRT
<213> ORGANISM: Homo sapiens

<400> SEQUENCE: 95

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30
```

```
Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
    115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
    195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
    275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
    355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
    435                 440                 445

Gly Leu Arg Ser Leu Lys Glu Ile Ser Asp Gly Asp Val Ile Ile Ser
```

```
                450              455              460
Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
                515                 520                 525

Val Ser Arg Gly Arg Glu Cys Val Asp Lys Cys Asn Leu Leu Glu Gly
                530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
                595                 600                 605

Lys Tyr Ala Asp Ala Gly His Val Cys His Leu Cys His Pro Asn Cys
610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Pro Ala Ala Gln Glu Ser Cys Leu Gly Trp Ile Pro
                660                 665                 670

Ser Leu Leu Pro Ser Glu Phe Gln Leu Gly Trp Gly Gly Cys Ser His
                675                 680                 685

Leu His Ala Trp Pro Ser Ala Ser Val Ile Ile Thr Ala Ser Ser Cys
                690                 695                 700

His
705

<210> SEQ ID NO 96
<211> LENGTH: 628
<212> TYPE: PRT
<213> ORGANISM: Homo sapiens

<400> SEQUENCE: 96

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
```

```
                  115                 120                 125
Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540
```

```
Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
610                 615                 620

Thr Tyr Gly Ser
625

<210> SEQ ID NO 97
<211> LENGTH: 242
<212> TYPE: PRT
<213> ORGANISM: Homo sapiens

<400> SEQUENCE: 97

Met Ser Gly Cys Asp Ala Arg Glu Gly Asp Cys Cys Ser Arg Arg Cys
1               5                   10                  15

Gly Ala Gln Asp Lys Glu His Pro Arg Tyr Leu Ile Pro Glu Leu Cys
                20                  25                  30

Lys Gln Phe Tyr His Leu Gly Trp Val Thr Gly Thr Gly Gly Ile
            35                  40                  45

Ser Leu Lys His Gly Asp Glu Ile Tyr Ile Ala Pro Ser Gly Val Gln
    50                  55                  60

Lys Glu Arg Ile Gln Pro Glu Asp Met Phe Val Cys Asp Ile Asn Glu
65                  70                  75                  80

Lys Asp Ile Ser Gly Pro Ser Pro Ser Lys Lys Leu Lys Lys Ser Gln
                85                  90                  95

Cys Thr Pro Leu Phe Met Asn Ala Tyr Thr Met Arg Gly Ala Gly Ala
            100                 105                 110

Val Ile His Thr His Ser Lys Ala Ala Val Met Ala Thr Leu Leu Phe
            115                 120                 125

Pro Gly Arg Glu Phe Lys Ile Thr His Gln Glu Met Ile Lys Gly Ile
130                 135                 140

Lys Lys Cys Thr Ser Gly Tyr Tyr Arg Tyr Asp Asp Met Leu Val
145                 150                 155                 160

Val Pro Ile Ile Glu Asn Thr Pro Glu Glu Lys Asp Leu Lys Asp Arg
                165                 170                 175

Met Ala His Ala Met Asn Glu Tyr Pro Asp Ser Cys Ala Val Leu Val
            180                 185                 190

Arg Arg His Gly Val Tyr Val Trp Gly Glu Thr Trp Glu Lys Ala Lys
            195                 200                 205

Thr Met Cys Glu Cys Tyr Asp Tyr Leu Phe Asp Ile Ala Val Ser Met
            210                 215                 220

Lys Lys Val Gly Leu Asp Pro Ser Gln Leu Pro Val Gly Glu Asn Gly
225                 230                 235                 240

Ile Val

<210> SEQ ID NO 98
<211> LENGTH: 367
<212> TYPE: PRT
<213> ORGANISM: Homo sapiens

<400> SEQUENCE: 98
```

Met Arg Trp Phe Leu Pro Trp Thr Leu Ala Ala Val Thr Ala Ala Ala
1               5                   10                  15

Ala Ser Thr Val Leu Ala Thr Ala Leu Ser Pro Ala Pro Thr Thr Met
            20                  25                  30

Asp Phe Thr Pro Ala Pro Leu Glu Asp Thr Ser Ser Arg Pro Gln Phe
        35                  40                  45

Cys Lys Trp Pro Cys Glu Cys Pro Pro Ser Pro Pro Arg Cys Pro Leu
    50                  55                  60

Gly Val Ser Leu Ile Thr Asp Gly Cys Glu Cys Cys Lys Met Cys Ala
65                  70                  75                  80

Gln Gln Leu Gly Asp Asn Cys Thr Glu Ala Ala Ile Cys Asp Pro His
                85                  90                  95

Arg Gly Leu Tyr Cys Asp Tyr Ser Gly Asp Arg Pro Arg Tyr Ala Ile
            100                 105                 110

Gly Val Cys Ala Gln Val Val Gly Val Gly Cys Val Leu Asp Gly Val
        115                 120                 125

Arg Tyr Asn Asn Gly Gln Ser Phe Gln Pro Asn Cys Lys Tyr Asn Cys
    130                 135                 140

Thr Cys Ile Asp Gly Ala Val Gly Cys Thr Pro Leu Cys Leu Arg Val
145                 150                 155                 160

Arg Pro Pro Arg Leu Trp Cys Pro His Pro Arg Arg Val Ser Ile Pro
                165                 170                 175

Gly His Cys Cys Glu Gln Trp Val Cys Glu Asp Asp Ala Lys Arg Pro
            180                 185                 190

Arg Lys Thr Ala Pro Arg Asp Thr Gly Ala Phe Asp Ala Val Gly Glu
        195                 200                 205

Val Glu Ala Trp His Arg Asn Cys Ile Ala Tyr Thr Ser Pro Trp Ser
    210                 215                 220

Pro Cys Ser Thr Ser Cys Gly Leu Gly Val Ser Thr Arg Ile Ser Asn
225                 230                 235                 240

Val Asn Ala Gln Cys Trp Pro Glu Gln Glu Ser Arg Leu Cys Asn Leu
                245                 250                 255

Arg Pro Cys Asp Val Asp Ile His Thr Leu Ile Lys Ala Gly Lys Lys
            260                 265                 270

Cys Leu Ala Val Tyr Gln Pro Glu Ala Ser Met Asn Phe Thr Leu Ala
        275                 280                 285

Gly Cys Ile Ser Thr Arg Ser Tyr Gln Pro Lys Tyr Cys Gly Val Cys
    290                 295                 300

Met Asp Asn Arg Cys Cys Ile Pro Tyr Lys Ser Lys Thr Ile Asp Val
305                 310                 315                 320

Ser Phe Gln Cys Pro Asp Gly Leu Gly Phe Ser Arg Gln Val Leu Trp
                325                 330                 335

Ile Asn Ala Cys Phe Cys Asn Leu Ser Cys Arg Asn Pro Asn Asp Ile
            340                 345                 350

Phe Ala Asp Leu Glu Ser Tyr Pro Asp Phe Ser Glu Ile Ala Asn
        355                 360                 365

<210> SEQ ID NO 99
<211> LENGTH: 280
<212> TYPE: PRT
<213> ORGANISM: Homo sapiens

<400> SEQUENCE: 99

Met Arg Trp Phe Leu Pro Trp Thr Leu Ala Ala Val Thr Ala Ala Ala
1               5                   10                  15

Ala Ser Thr Val Leu Ala Thr Ala Leu Ser Pro Ala Pro Thr Thr Met
            20                  25                  30

Asp Phe Thr Pro Ala Pro Leu Glu Asp Thr Ser Ser Arg Pro Gln Phe
        35                  40                  45

Cys Lys Trp Pro Cys Glu Cys Pro Pro Ser Pro Pro Arg Cys Pro Leu
    50                  55                  60

Gly Val Ser Leu Ile Thr Asp Gly Cys Glu Cys Cys Lys Met Cys Ala
65                  70                  75                  80

Gln Gln Leu Gly Asp Asn Cys Thr Glu Ala Ala Ile Cys Asp Pro His
                85                  90                  95

Arg Gly Leu Tyr Cys Asp Tyr Ser Gly Asp Arg Pro Arg Tyr Ala Ile
            100                 105                 110

Gly Val Cys Ala His Ala Val Gly Glu Val Glu Ala Trp His Arg Asn
        115                 120                 125

Cys Ile Ala Tyr Thr Ser Pro Trp Ser Pro Cys Ser Thr Ser Cys Gly
    130                 135                 140

Leu Gly Val Ser Thr Arg Ile Ser Asn Val Asn Ala Gln Cys Trp Pro
145                 150                 155                 160

Glu Gln Glu Ser Arg Leu Cys Asn Leu Arg Pro Cys Asp Val Asp Ile
                165                 170                 175

His Thr Leu Ile Lys Ala Gly Lys Lys Cys Leu Ala Val Tyr Gln Pro
            180                 185                 190

Glu Ala Ser Met Asn Phe Thr Leu Ala Gly Cys Ile Ser Thr Arg Ser
        195                 200                 205

Tyr Gln Pro Lys Tyr Cys Gly Val Cys Met Asp Asn Arg Cys Cys Ile
    210                 215                 220

Pro Tyr Lys Ser Lys Thr Ile Asp Val Ser Phe Gln Cys Pro Asp Gly
225                 230                 235                 240

Leu Gly Phe Ser Arg Gln Val Leu Trp Ile Asn Ala Cys Phe Cys Asn
                245                 250                 255

Leu Ser Cys Arg Asn Pro Asn Asp Ile Phe Ala Asp Leu Glu Ser Tyr
            260                 265                 270

Pro Asp Phe Ser Glu Ile Ala Asn
        275                 280

<210> SEQ ID NO 100
<211> LENGTH: 370
<212> TYPE: PRT
<213> ORGANISM: Homo sapiens

<400> SEQUENCE: 100

Met Gly Leu Trp Ala Leu Leu Pro Gly Trp Val Ser Ala Thr Leu Leu
1               5                   10                  15

Leu Ala Leu Ala Ala Leu Pro Ala Ala Leu Ala Ala Asn Ser Ser Gly
            20                  25                  30

Arg Trp Trp Gly Ile Val Asn Val Ala Ser Ser Thr Asn Leu Leu Thr
        35                  40                  45

Asp Ser Lys Ser Leu Gln Leu Val Leu Glu Pro Ser Leu Gln Leu Leu
    50                  55                  60

Ser Arg Lys Gln Arg Arg Leu Ile Arg Gln Asn Pro Gly Ile Leu His
65                  70                  75                  80

Ser Val Ser Gly Gly Leu Gln Ser Ala Val Arg Glu Cys Lys Trp Gln
                85                  90                  95

Phe Arg Asn Arg Arg Trp Asn Cys Pro Thr Ala Pro Gly Pro His Leu
            100                 105                 110

```
Phe Gly Lys Ile Val Asn Arg Gly Cys Arg Glu Thr Ala Phe Ile Phe
            115                 120                 125
Ala Ile Thr Ser Ala Gly Val Thr His Ser Val Ala Arg Ser Cys Ser
        130                 135                 140
Glu Gly Ser Ile Glu Ser Cys Thr Cys Asp Tyr Arg Arg Arg Gly Pro
145                 150                 155                 160
Gly Gly Pro Asp Trp His Trp Gly Gly Cys Ser Asp Asn Ile Asp Phe
                165                 170                 175
Gly Arg Leu Phe Gly Arg Glu Phe Val Asp Ser Gly Glu Lys Gly Arg
            180                 185                 190
Asp Leu Arg Phe Leu Met Asn Leu His Asn Asn Glu Ala Gly Arg Thr
        195                 200                 205
Thr Val Phe Ser Glu Met Arg Gln Glu Cys Lys Cys His Gly Met Ser
    210                 215                 220
Gly Ser Cys Thr Val Arg Thr Cys Trp Met Arg Leu Pro Thr Leu Arg
225                 230                 235                 240
Ala Val Gly Asp Val Leu Arg Asp Arg Phe Asp Gly Ala Ser Arg Val
                245                 250                 255
Leu Tyr Gly Asn Arg Gly Ser Asn Arg Ala Ser Arg Ala Glu Leu Leu
            260                 265                 270
Arg Leu Glu Pro Glu Asp Pro Ala His Lys Pro Pro Ser Pro His Asp
        275                 280                 285
Leu Val Tyr Phe Glu Lys Ser Pro Asn Phe Cys Thr Tyr Ser Gly Arg
    290                 295                 300
Leu Gly Thr Ala Gly Thr Ala Gly Arg Ala Cys Asn Ser Ser Ser Pro
305                 310                 315                 320
Ala Leu Asp Gly Cys Glu Leu Leu Cys Cys Gly Arg Gly His Arg Thr
                325                 330                 335
Arg Thr Gln Arg Val Thr Glu Arg Cys Asn Cys Thr Phe His Trp Cys
            340                 345                 350
Cys His Val Ser Cys Arg Asn Cys Thr His Thr Arg Val Leu His Glu
        355                 360                 365
Cys Leu
    370

<210> SEQ ID NO 101
<211> LENGTH: 648
<212> TYPE: PRT
<213> ORGANISM: Homo sapiens

<400> SEQUENCE: 101

Met Glu His Ile Gln Gly Ala Trp Lys Thr Ile Ser Asn Gly Phe Gly
1               5                   10                  15
Phe Lys Asp Ala Val Phe Asp Gly Ser Ser Cys Ile Ser Pro Thr Ile
            20                  25                  30
Val Gln Gln Phe Gly Tyr Gln Arg Arg Ala Ser Asp Asp Gly Lys Leu
        35                  40                  45
Thr Asp Pro Ser Lys Thr Ser Asn Thr Ile Arg Val Phe Leu Pro Asn
    50                  55                  60
Lys Gln Arg Thr Val Val Asn Val Arg Asn Gly Met Ser Leu His Asp
65                  70                  75                  80
Cys Leu Met Lys Ala Leu Lys Val Arg Gly Leu Gln Pro Glu Cys Cys
                85                  90                  95
Ala Val Phe Arg Leu Leu His Glu His Lys Gly Lys Lys Ala Arg Leu
            100                 105                 110
```

```
Asp Trp Asn Thr Asp Ala Ala Ser Leu Ile Gly Glu Glu Leu Gln Val
            115                 120                 125

Asp Phe Leu Asp His Val Pro Leu Thr Thr His Asn Phe Ala Arg Lys
        130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu Pro Val
            260                 265                 270

Asp Ser Arg Met Ile Glu Asp Ala Ile Arg Ser His Ser Glu Ser Ala
        275                 280                 285

Ser Pro Ser Ala Leu Ser Ser Pro Asn Asn Leu Ser Pro Thr Gly
    290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
            340                 345                 350

Thr Arg Ile Gly Ser Gly Ser Phe Gly Thr Val Tyr Lys Gly Lys Trp
        355                 360                 365

His Gly Asp Val Ala Val Lys Ile Leu Lys Val Val Asp Pro Thr Pro
    370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
            420                 425                 430

Leu His Val Gln Glu Thr Lys Phe Gln Met Phe Gln Leu Ile Asp Ile
        435                 440                 445

Ala Arg Gln Thr Ala Gln Gly Met Asp Tyr Leu His Ala Lys Asn Ile
    450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
            500                 505                 510

Ala Pro Glu Val Ile Arg Met Gln Asp Asn Asn Pro Phe Ser Phe Gln
        515                 520                 525

Ser Asp Val Tyr Ser Tyr Gly Ile Val Leu Tyr Glu Leu Met Thr Gly
```

```
                530                 535                 540
Glu Leu Pro Tyr Ser His Ile Asn Asn Arg Asp Gln Ile Ile Phe Met
545                 550                 555                 560

Val Gly Arg Gly Tyr Ala Ser Pro Asp Leu Ser Lys Leu Tyr Lys Asn
                565                 570                 575

Cys Pro Lys Ala Met Lys Arg Leu Val Ala Asp Cys Val Lys Lys Val
            580                 585                 590

Lys Glu Glu Arg Pro Leu Phe Pro Gln Ile Leu Ser Ser Ile Glu Leu
            595                 600                 605

Leu Gln His Ser Leu Pro Lys Ile Asn Arg Ser Ala Ser Glu Pro Ser
            610                 615                 620

Leu His Arg Ala Ala His Thr Glu Asp Ile Asn Ala Cys Thr Leu Thr
625                 630                 635                 640

Thr Ser Pro Arg Leu Pro Val Phe
                645

<210> SEQ ID NO 102
<211> LENGTH: 536
<212> TYPE: PRT
<213> ORGANISM: Homo sapiens

<400> SEQUENCE: 102

Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Gly Ala Phe
            20                  25                  30

Pro Ala Ser Gln Thr Pro Ser Lys Pro Ala Ser Ala Asp Gly His Arg
        35                  40                  45

Gly Pro Ser Ala Ala Phe Ala Pro Ala Ala Ala Glu Pro Lys Leu Phe
    50                  55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
        115                 120                 125

Thr Gly Gln Thr Gly Tyr Ile Pro Ser Asn Tyr Val Ala Pro Ser Asp
    130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
        195                 200                 205

Lys Leu Asp Ser Gly Gly Phe Tyr Ile Thr Ser Arg Thr Gln Phe Asn
    210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
```

-continued

```
                260                 265                 270
Glu Val Lys Leu Gly Gln Gly Cys Phe Gly Glu Val Trp Met Gly Thr
            275                 280                 285
Trp Asn Gly Thr Thr Arg Val Ala Ile Lys Thr Leu Lys Pro Gly Thr
        290                 295                 300
Met Ser Pro Glu Ala Phe Leu Gln Glu Ala Gln Val Met Lys Lys Leu
305                 310                 315                 320
Arg His Glu Lys Leu Val Gln Leu Tyr Ala Val Val Ser Glu Glu Pro
                325                 330                 335
Ile Tyr Ile Val Thr Glu Tyr Met Ser Lys Gly Ser Leu Leu Asp Phe
            340                 345                 350
Leu Lys Gly Glu Thr Gly Lys Tyr Leu Arg Leu Pro Gln Leu Val Asp
        355                 360                 365
Met Ala Ala Gln Ile Ala Ser Gly Met Ala Tyr Val Glu Arg Met Asn
    370                 375                 380
Tyr Val His Arg Asp Leu Arg Ala Ala Asn Ile Leu Val Gly Glu Asn
385                 390                 395                 400
Leu Val Cys Lys Val Ala Asp Phe Gly Leu Ala Arg Leu Ile Glu Asp
                405                 410                 415
Asn Glu Tyr Thr Ala Arg Gln Gly Ala Lys Phe Pro Ile Lys Trp Thr
            420                 425                 430
Ala Pro Glu Ala Ala Leu Tyr Gly Arg Phe Thr Ile Lys Ser Asp Val
        435                 440                 445
Trp Ser Phe Gly Ile Leu Leu Thr Glu Leu Thr Thr Lys Gly Arg Val
    450                 455                 460
Pro Tyr Pro Gly Met Val Asn Arg Glu Val Leu Asp Gln Val Glu Arg
465                 470                 475                 480
Gly Tyr Arg Met Pro Cys Pro Pro Glu Cys Pro Glu Ser Leu His Asp
                485                 490                 495
Leu Met Cys Gln Cys Trp Arg Lys Glu Pro Glu Glu Arg Pro Thr Phe
            500                 505                 510
Glu Tyr Leu Gln Ala Phe Leu Glu Asp Tyr Phe Thr Ser Thr Glu Pro
        515                 520                 525
Gln Tyr Gln Pro Gly Glu Asn Leu
    530                 535

<210> SEQ ID NO 103
<211> LENGTH: 480
<212> TYPE: PRT
<213> ORGANISM: Homo sapiens

<400> SEQUENCE: 103

Met Ser Asp Val Ala Ile Val Lys Glu Gly Trp Leu His Lys Arg Gly
1               5                   10                  15
Glu Tyr Ile Lys Thr Trp Arg Pro Arg Tyr Phe Leu Leu Lys Asn Asp
            20                  25                  30
Gly Thr Phe Ile Gly Tyr Lys Glu Arg Pro Gln Asp Val Asp Gln Arg
        35                  40                  45
Glu Ala Pro Leu Asn Asn Phe Ser Val Ala Gln Cys Gln Leu Met Lys
    50                  55                  60
Thr Glu Arg Pro Arg Pro Asn Thr Phe Ile Ile Arg Cys Leu Gln Trp
65                  70                  75                  80
Thr Thr Val Ile Glu Arg Thr Phe His Val Glu Thr Pro Glu Glu Arg
                85                  90                  95
Glu Glu Trp Thr Thr Ala Ile Gln Thr Val Ala Asp Gly Leu Lys Lys
```

-continued

```
                100                 105                 110
Gln Glu Glu Glu Glu Met Asp Phe Arg Ser Gly Ser Pro Ser Asp Asn
            115                 120                 125

Ser Gly Ala Glu Glu Met Glu Val Ser Leu Ala Lys Pro Lys His Arg
        130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
450                 455                 460

Arg Arg Pro His Phe Pro Gln Phe Ser Tyr Ser Ala Ser Gly Thr Ala
465                 470                 475                 480
```

<210> SEQ ID NO 104
<211> LENGTH: 379
<212> TYPE: PRT
<213> ORGANISM: Homo sapiens

<400> SEQUENCE: 104

Met Ala Ala Ala Ala Ala Gln Gly Gly Gly Gly Gly Glu Pro Arg Arg

-continued

```
            1               5              10              15
Thr Glu Gly Val Gly Pro Gly Val Pro Gly Glu Val Glu Met Val Lys
                    20                  25                  30

Gly Gln Pro Phe Asp Val Gly Pro Arg Tyr Thr Gln Leu Gln Tyr Ile
                35                  40                  45

Gly Glu Gly Ala Tyr Gly Met Val Ser Ser Ala Tyr Asp His Val Arg
            50                  55                  60

Lys Thr Arg Val Ala Ile Lys Lys Ile Ser Pro Phe Glu His Gln Thr
 65                  70                  75                  80

Tyr Cys Gln Arg Thr Leu Arg Glu Ile Gln Ile Leu Leu Arg Phe Arg
                    85                  90                  95

His Glu Asn Val Ile Gly Ile Arg Asp Ile Leu Arg Ala Ser Thr Leu
                100                 105                 110

Glu Ala Met Arg Asp Val Tyr Ile Val Gln Asp Leu Met Glu Thr Asp
                115                 120                 125

Leu Tyr Lys Leu Leu Lys Ser Gln Gln Leu Ser Asn Asp His Ile Cys
                130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                    165                 170                 175

Thr Cys Asp Leu Lys Ile Cys Asp Phe Gly Leu Ala Arg Ile Ala Asp
                180                 185                 190

Pro Glu His Asp His Thr Gly Phe Leu Thr Glu Tyr Val Ala Thr Arg
                195                 200                 205

Trp Tyr Arg Ala Pro Glu Ile Met Leu Asn Ser Lys Gly Tyr Thr Lys
                210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                    245                 250                 255

Ile Leu Gly Ile Leu Gly Ser Pro Ser Gln Glu Asp Leu Asn Cys Ile
                260                 265                 270

Ile Asn Met Lys Ala Arg Asn Tyr Leu Gln Ser Leu Pro Ser Lys Thr
                275                 280                 285

Lys Val Ala Trp Ala Lys Leu Phe Pro Lys Ser Asp Ser Lys Ala Leu
                290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                    325                 330                 335

Thr Asp Glu Pro Val Ala Glu Pro Phe Thr Phe Ala Met Glu Leu
                340                 345                 350

Asp Asp Leu Pro Lys Glu Arg Leu Lys Glu Leu Ile Phe Gln Glu Thr
                355                 360                 365

Ala Arg Phe Gln Pro Gly Val Leu Glu Ala Pro
                370                 375
```

<210> SEQ ID NO 105
<211> LENGTH: 360
<212> TYPE: PRT
<213> ORGANISM: Homo sapiens

<400> SEQUENCE: 105

Met Ala Ala Ala Ala Ala Ala Gly Ala Gly Pro Glu Met Val Arg Gly

```
              1               5              10              15
Gln Val Phe Asp Val Gly Pro Arg Tyr Thr Asn Leu Ser Tyr Ile Gly
                       20                  25                  30

Glu Gly Ala Tyr Gly Met Val Cys Ser Ala Tyr Asp Asn Val Asn Lys
                       35                  40                  45

Val Arg Val Ala Ile Lys Lys Ile Ser Pro Phe Glu His Gln Thr Tyr
 50                      55                  60

Cys Gln Arg Thr Leu Arg Glu Ile Lys Ile Leu Leu Arg Phe Arg His
 65                      70                  75                  80

Glu Asn Ile Ile Gly Ile Asn Asp Ile Ile Arg Ala Pro Thr Ile Glu
                       85                  90                  95

Gln Met Lys Asp Val Tyr Ile Val Gln Asp Leu Met Glu Thr Asp Leu
                      100                 105                 110

Tyr Lys Leu Leu Lys Thr Gln His Leu Ser Asn Asp His Ile Cys Tyr
                      115                 120                 125

Phe Leu Tyr Gln Ile Leu Arg Gly Leu Lys Tyr Ile His Ser Ala Asn
                      130                 135                 140

Val Leu His Arg Asp Leu Lys Pro Ser Asn Leu Leu Leu Asn Thr Thr
145                     150                 155                 160

Cys Asp Leu Lys Ile Cys Asp Phe Gly Leu Ala Arg Val Ala Asp Pro
                      165                 170                 175

Asp His Asp His Thr Gly Phe Leu Thr Glu Tyr Val Ala Thr Arg Trp
                      180                 185                 190

Tyr Arg Ala Pro Glu Ile Met Leu Asn Ser Lys Gly Tyr Thr Lys Ser
                      195                 200                 205

Ile Asp Ile Trp Ser Val Gly Cys Ile Leu Ala Glu Met Leu Ser Asn
                      210                 215                 220

Arg Pro Ile Phe Pro Gly Lys His Tyr Leu Asp Gln Leu Asn His Ile
225                     230                 235                 240

Leu Gly Ile Leu Gly Ser Pro Ser Gln Glu Asp Leu Asn Cys Ile Ile
                      245                 250                 255

Asn Leu Lys Ala Arg Asn Tyr Leu Leu Ser Leu Pro His Lys Asn Lys
                      260                 265                 270

Val Pro Trp Asn Arg Leu Phe Pro Asn Ala Asp Ser Lys Ala Leu Asp
                      275                 280                 285

Leu Leu Asp Lys Met Leu Thr Phe Asn Pro His Lys Arg Ile Glu Val
                      290                 295                 300

Glu Gln Ala Leu Ala His Pro Tyr Leu Glu Gln Tyr Tyr Asp Pro Ser
305                     310                 315                 320

Asp Glu Pro Ile Ala Glu Ala Pro Phe Lys Phe Asp Met Glu Leu Asp
                      325                 330                 335

Asp Leu Pro Lys Glu Lys Leu Lys Glu Leu Ile Phe Glu Glu Thr Ala
                      340                 345                 350

Arg Phe Gln Pro Gly Tyr Arg Ser
                      355                 360

<210> SEQ ID NO 106
<211> LENGTH: 239
<212> TYPE: PRT
<213> ORGANISM: Homo sapiens

<400> SEQUENCE: 106

Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
```

```
                    20                  25                  30
Gly Asp Val Gly Ala Ala Pro Pro Gly Ala Ala Pro Gly Ile
            35                  40                  45

Phe Ser Ser Gln Pro Gly His Thr Pro His Pro Ala Ala Ser Arg Asp
50                      55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Val Val His Leu Thr
                85                  90                  95

Leu Arg Gln Ala Gly Asp Asp Phe Ser Arg Arg Tyr Arg Arg Asp Phe
                100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
        130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 107
<211> LENGTH: 99
<212> TYPE: PRT
<213> ORGANISM: Homo sapiens

<400> SEQUENCE: 107

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser

<210> SEQ ID NO 108
<211> LENGTH: 107
<212> TYPE: PRT
<213> ORGANISM: Homo sapiens

<400> SEQUENCE: 108

Met Ala Arg Ala Ala Leu Ser Ala Ala Pro Ser Asn Pro Arg Leu Leu
1               5                   10                  15
```

```
Arg Val Ala Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
        35                  40                  45

Leu Gln Gly Ile His Pro Lys Asn Ile Gln Ser Val Asn Val Lys Ser
    50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105
```

<210> SEQ ID NO 109
<211> LENGTH: 350
<212> TYPE: PRT
<213> ORGANISM: Homo sapiens

<400> SEQUENCE: 109

```
Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
            20                  25                  30

Glu Thr Glu Thr Leu Asn Lys Tyr Val Val Ile Ile Ala Tyr Ala Leu
        35                  40                  45

Val Phe Leu Leu Ser Leu Leu Gly Asn Ser Leu Val Met Leu Val Ile
    50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125

Ala Cys Ile Ser Val Asp Arg Tyr Leu Ala Ile Val His Ala Thr Arg
    130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
        195                 200                 205

Phe Gly Phe Ile Val Pro Leu Phe Val Met Leu Phe Cys Tyr Gly Phe
    210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
        275                 280                 285
```

```
Ala Thr Glu Ile Leu Gly Phe Leu His Ser Cys Leu Asn Pro Ile Ile
        290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335

Thr Ser Tyr Thr Ser Ser Ser Val Asn Val Ser Ser Asn Leu
                340                 345                 350

<210> SEQ ID NO 110
<211> LENGTH: 360
<212> TYPE: PRT
<213> ORGANISM: Homo sapiens

<400> SEQUENCE: 110

Met Glu Asp Phe Asn Met Glu Ser Asp Ser Phe Glu Asp Phe Trp Lys
  1               5                  10                  15

Gly Glu Asp Leu Ser Asn Tyr Ser Tyr Ser Ser Thr Leu Pro Pro Phe
                 20                  25                  30

Leu Leu Asp Ala Ala Pro Cys Glu Pro Glu Ser Leu Glu Ile Asn Lys
             35                  40                  45

Tyr Phe Val Val Ile Ile Tyr Ala Leu Val Phe Leu Leu Ser Leu Leu
 50                  55                  60

Gly Asn Ser Leu Val Met Leu Val Ile Leu Tyr Ser Arg Val Gly Arg
 65                  70                  75                  80

Ser Val Thr Asp Val Tyr Leu Leu Asn Leu Ala Leu Ala Asp Leu Leu
                 85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Ala Cys Ile Ser Val Asp Arg
    130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320
```

-continued

```
Phe Arg His Gly Leu Leu Lys Ile Leu Ala Ile His Gly Leu Ile Ser
                325                 330                 335
Lys Asp Ser Leu Pro Lys Asp Ser Arg Pro Ser Phe Val Gly Ser Ser
            340                 345                 350
Ser Gly His Thr Ser Thr Thr Leu
        355                 360
```